US012617794B2

(12) United States Patent
Toczko et al.

(10) Patent No.: US 12,617,794 B2
(45) Date of Patent: May 5, 2026

(54) GABAA POSITIVE ALLOSTERIC MODULATOR COMPOUNDS, METHODS OF MAKING, AND USES THEREOF

(71) Applicant: NEUROCYCLE THERAPEUTICS, INC., San Diego, CA (US)

(72) Inventors: Matthew Toczko, Cambridge, MA (US); Jed Hubbs, Cambridge, MA (US); YuXi Ning, Beijing (CN); Zheng Jane Li, Sherman, CT (US); Yunliang He, Shandong (CN); Xianglei Liu, Zhejiang (CN)

(73) Assignee: NEUROCYCLE THERAPEUTICS, INC., San Diego, CA (US)

( * ) Notice: Subject to any disclaimer, the term of this patent is extended or adjusted under 35 U.S.C. 154(b) by 977 days.

(21) Appl. No.: 17/770,928

(22) PCT Filed: Oct. 22, 2020

(86) PCT No.: PCT/US2020/056750
§ 371 (c)(1),
(2) Date: Apr. 21, 2022

(87) PCT Pub. No.: WO2021/081147
PCT Pub. Date: Apr. 29, 2021

(65) Prior Publication Data
US 2023/0017378 A1     Jan. 19, 2023

Related U.S. Application Data

(60) Provisional application No. 62/924,276, filed on Oct. 22, 2019.

(51) Int. Cl.
*C07D 487/04*     (2006.01)

(52) U.S. Cl.
CPC ........ *C07D 487/04* (2013.01); *C07B 2200/13* (2013.01)

(58) Field of Classification Search
CPC .......................... C07D 487/04; C07B 2200/13
See application file for complete search history.

(56) References Cited

U.S. PATENT DOCUMENTS

| | | | | |
|---|---|---|---|---|
| 11,542,263 B2 * | 1/2023 | Toczko | | C07D 487/04 |
| 12,134,619 B2 * | 11/2024 | Toczko | | C07D 487/04 |
| 2015/0313913 A1 | 11/2015 | Catterall et al. | | |
| 2017/0197965 A1 | 7/2017 | Owen et al. | | |
| 2025/0034155 A1 * | 1/2025 | Toczko | | C07D 487/04 |

FOREIGN PATENT DOCUMENTS

| | | |
|---|---|---|
| CN | 115003301 | 10/2020 |
| CN | 112384513 | 2/2021 |
| JP | 2004-513171 | 4/2004 |
| JP | 2004-536862 | 12/2004 |
| WO | 03/008418 | 1/2002 |
| WO | 02/38568 | 5/2002 |
| WO | 2019/204446 | 10/2019 |
| WO | 2021/081357 | 4/2021 |

OTHER PUBLICATIONS

Engin, Pharmacology and Therapeutics, vol. 136, Issue 2, Nov. 2012, pp. 142-152 (Year: 2012).*
Indian Office Action for Application No. 202217029173 mailed Jan. 21, 2025 (6 pages).
China Office Action for App. No. 2020800743934 mailed Dec. 7, 2023 (15 pages).
European Office Action for App. No. 20 879 254.9-1102 dated Jan. 1, 2025 (6 pages).
Singapore Office Action for App. No. 11202203761V mailed Jun. 12, 2024 (11 pages).
China Office Action for App. No. 2020800743934 mailed Apr. 30 (8 pages).
European Search Report for App. No. 20879254.9 mailed Oct. 18, 2023 (11 pages).
Donald R. Gauthier et al: "Palladium-Catalyzed Regioselective Arylation of Imidazo[1,2-b][1,2,4]triazine: Synthesis of an alpha2/3-Selective GABA Agonist", The Journal of Organic Chemistry, vol. 70, No. 15, Jul. 1, 2005, pp. 5938-5945, XP055467273, ISSN: 0022-3263, DOI: 10.1021 /jo0507035.
Aal Ton En J et al: "Solid form screening—A review", European Journal of Pharmaceutics and Biopharmaceutics, vol. 71, No. 1, Jan. 1, 2009 (Jan. 1, 2009), pp. 23-37, XP025782069,ISSN: 0939-6411, DOI: 10.1016/J.EJPB.2008.07.014.
Richard J Bastin et al: "Salt Selection and Optimisation Procedures for Pharmaceutical New Chemical Entities", Organic Process Research & Development, vol. 4, No. 5, Jul. 19, 2000, pp. 427-435, XP008154792, ISSN: 1083-6160, DOI: 10.1021/OP000018U.
Eurasian Office Action for App. No. 202291229 mailed Aug. 8, 2022 (2 pages).
Eurasian Office Action for App. No. 202291229 mailed Jul. 26 (9 pages).
Canada Office Action for App. No. 3.155.618 mailed Mar. 24, 2024 ( pages).
Japanese Office Action for App. No. 2022-523889 mailed Oct. 7, 2024 (8 pages).
The Journal of Organic Chemistr, Jun. 24, 2005, vol. 70, No. 15?pp. 5938-5945.

(Continued)

*Primary Examiner* — Andrew D Kosar
*Assistant Examiner* — Phillip Matthew Rzeczycki
(74) *Attorney, Agent, or Firm* — K&L Gates LLP

(57) ABSTRACT

Described herein are polymorphs comprising 2',6-difluoro-5'-[3-(1-hydroxy-1-methylethyl)-imidazo[1,2-b][1,2,4]triazin-7-yl]biphenyl-2-carbonitrile (TPA023B) or salts thereof. In one aspect, disclosed herein is a crystalline polymorphic salt or co-crystal of TPA023B with phosphoric acid. In another aspect, disclosed herein is a crystalline polymorphic salt or co-crystal of TPA023B with sulfuric acid. Also described herein are methods of making and using the same.

19 Claims, 94 Drawing Sheets

(56) References Cited

OTHER PUBLICATIONS

Journal of Medicinal Chemistry, Feb. 1, 2006?vol. 49, No. 4?pp. 1235-1238.

International Search Report dated Feb. 1, 2021 for PCT/US2020/56750 (2 pages).

Duke et al. "Evidence That Sedative Effects of Benzodiazepines Involve Unexpected GABAA Receptor Subtypes: Quantitative Observation Studies in Rhesus Monkeys", J Pharmacol Exp Thar. 2018. vol. 366, pp. 145-157, entire document, especially: abstract, TPA023B 6,2'-diflouro-5'-[3-(1-hydroxy-1-methylethyl)imidazo[1,2-b][1,2,4]triazin-7-yl]biphenyl-2-carbonitrile.

Russell et al. "Discovery of Imidazo[1,2-b][1,2,4]triazines as GABAA alpha-2/3 Subtype Selective Agonists for the Treatment of Anxiety", J. Med. Chem. 2006. vol. 49, pp. 1235-1238, entire document, especially: p. 1236, Table 1, compd 11.

Goodacre et al. "Imidazo[1,2-a]pyrazin-8-ones, imidazo[1,2-d)[1,2,4Jtriazin-8-ones and imidazo[2,1-f][1,2,4Jtriazin-8-ones as alpha-2/alpha-3 subtype selective GABAA agonists for the treatment of anxiety", Bioorganic and Medicinal Chemistry Letters. 2006. vol. 16, pp. 1582-1585, entire document. especially: p. 1582, Figure 1, formula 2.

Mexican Office Action for App. No. MX/a/2022/004642 dated Jul. 9, 2025 (10 pages).

Korean Office Action for App. No. 10-2022-7014893 dated Jul. 14, 2025 (7 pages).

Japanese Office Action for App. No. 2022-523889 dated Jun. 30, 2025 (2 pages).

* cited by examiner

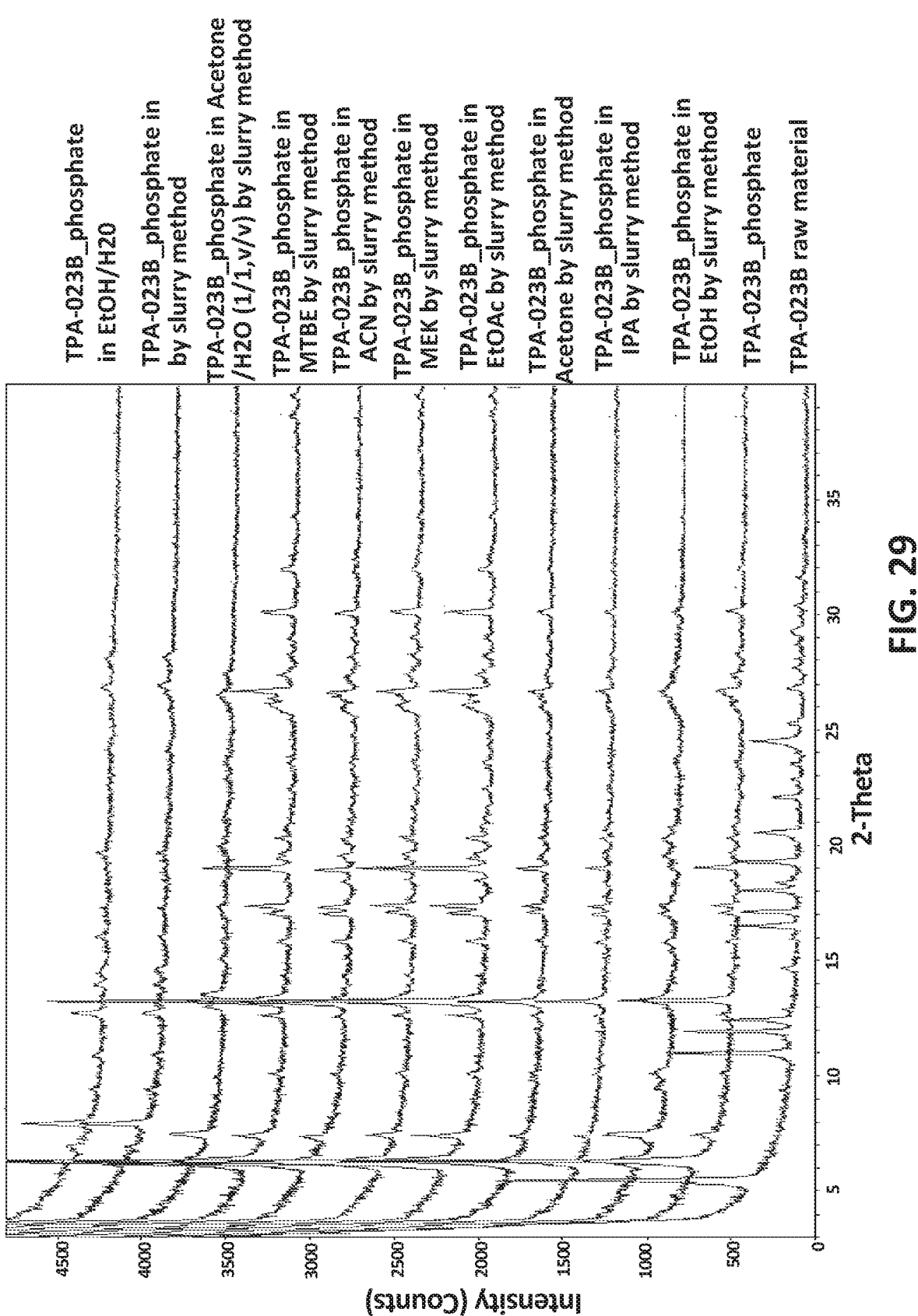

TPA-023B_phosphate in EtOH/H2O

TPA-023B_phosphate in by slurry method

TPA-023B_phosphate in Acetone /H2O (1/1,v/v) by slurry method

TPA-023B_phosphate in MTBE by slurry method

TPA-023B_phosphate in ACN by slurry method

TPA-023B_phosphate in MEK by slurry method

TPA-023B_phosphate in EtOAc by slurry method

TPA-023B_phosphate in Acetone by slurry method

TPA-023B_phosphate in IPA by slurry method

TPA-023B_phosphate in EtOH by slurry method

TPA-023B_phosphate

TPA-023B raw material

2-Theta

Intensity (Counts)

FIG. 29

TPA023B chloride Form B

HCl-THF-EtOH-1-4-dioxane

TPA023B chloride Form C

HCl-THF-EtOH-acetone

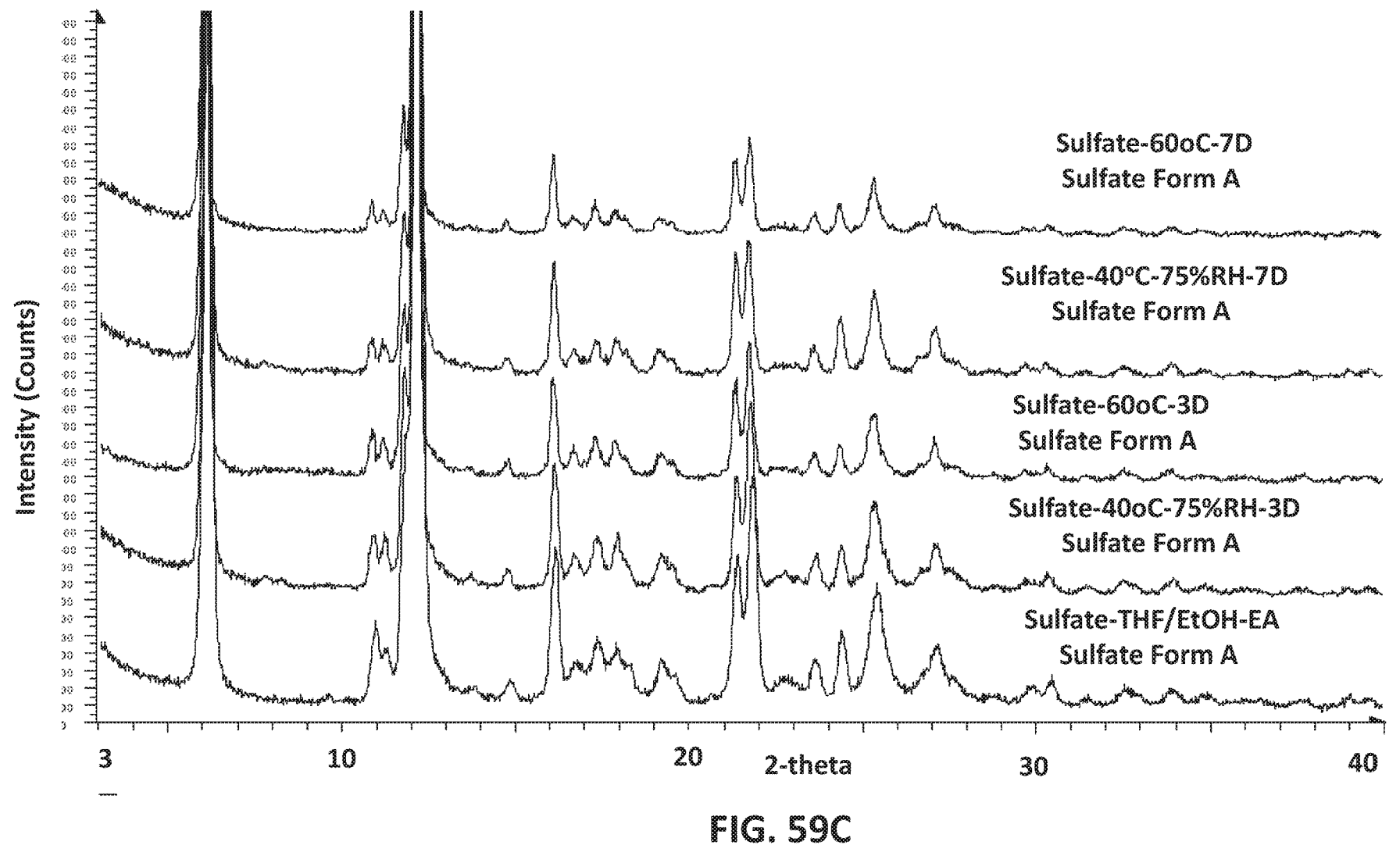

Sulfate-60oC-7D
Sulfate Form A

Sulfate-40°C-75%RH-7D
Sulfate Form A

Sulfate-60oC-3D
Sulfate Form A

Sulfate-40oC-75%RH-3D
Sulfate Form A

Sulfate-THF/EtOH-EA
Sulfate Form A 2-theta

Intensity (Counts)

FIG. 59C

Solid Form Conversion Map

Weight (%)

Heat Flow (Normalized) Q (W/g)

Temperature T (°C)

—Ramp 10 °C/min to 300.00 °C
--- Ramp 10 °C/min to 300.00 °C

Weight Percent Loss: 1.055 %
Temperature: 150 °C

Enthalpy (normalized): 77.789 J/g
Onset x: 196.98 °C
Peak temperature: 200.46 °C Phosphate Form J

GABAA POSITIVE ALLOSTERIC MODULATOR COMPOUNDS, METHODS OF MAKING, AND USES THEREOF

CROSS-REFERENCE

This application is a 371 of International Application No. PCT/US2020/056750 which claims benefit of U.S. Provisional Patent Application No. 62/924,276 filed on Oct. 22, 2019, which is hereby incorporated by reference in its entirety.

SUMMARY OF THE INVENTION

In one aspect, the present disclosure pertains to salts and polymorphs of 2',6-difluoro-5'-[3-(1-hydroxy-1-methylethyl)-imidazo[1,2-b][1,2,4]triazin-7-yl]biphenyl-2-carbonitrile (designated herein as TPA023B), including but not limited to stable polymorphs of the salt of TPA023B with sulfuric acid:

MW: 489.45 g*mol$^{-1}$

MF: $C_{21}H_{15}F_2N_5O \cdot H_2SO_4$

Polymorphs of the free base compound are also described. These polymorphs are suitable for use as the active pharmaceutical ingredient of products intended for therapeutic use in mammals, humans or animals, and also as chemical intermediates in the synthesis of active pharmaceutical ingredients.

In one aspect, described herein is a crystalline form of 2',6-difluoro-5'-[3-(1-hydroxy-1-methylethyl)-imidazo[1,2-b][1,2,4]triazin-7-yl]biphenyl-2-carbonitrile with sulfuric acid, wherein the crystalline form has at least one of the following properties: (a) an X-ray powder diffraction (XRPD) pattern substantially the same as shown in FIG. 61, when measured using the parameters described in Table 26-4; (b) an XRPD pattern having characteristic peak locations of at least three of the values selected from the group consisting of: about 6.1, 10.9, 11.3, 11.8, 12.2, 13.8, 14.8, 16.1, 16.8, 17.3, 17.9, 18.3, 19.2, 19.6, 21.4, 21.8, 22.8, 23.6, 24.4, 25.4, 27.2, 29.9, 30.5, 31.5, 32.6, 33.9, and 39.1±0.2 degrees, 2-Theta, when measured using the parameters described in Table 26-4; (c) a differential scanning calorimetry (DSC) thermogram substantially the same as shown in FIG. 53C; (d) a DSC thermogram with an endothermic peak at about 192° C.; (e) stable for at least 3 days at about 40°; and (f) stable for at least 3 days at about 60° C. In some embodiments, the crystalline form provides an XRPD pattern substantially the same as shown in FIG. 61, when measured using the parameters described in Table 26-4. In some embodiments, the crystalline form provides an XRPD pattern having characteristic peak locations of at least three of the values selected from the group consisting of: about 6.1, 10.9, 11.3, 11.8, 12.2, 13.8, 14.8, 16.1, 16.8, 17.3, 17.9, 18.3, 19.2, 19.6, 21.4, 21.8, 22.8, 23.6, 24.4, 25.4, 27.2, 29.9, 30.5, 31.5, 32.6, 33.9, and 39.1±0.2 degrees, 2-Theta, when measured using the parameters described in Table 26-4. In some embodiments, the crystalline form provides an XRPD pattern having characteristic peak locations of at least six of the values selected from the group consisting of: about 6.1, 10.9, 11.3, 11.8, 12.2, 13.8, 14.8, 16.1, 16.8, 17.3, 17.9, 18.3, 19.2, 19.6, 21.4, 21.8, 22.8, 23.6, 24.4, 25.4, 27.2, 29.9, 30.5, 31.5, 32.6, 33.9, and 39.1±0.2 degrees, 2-Theta, when measured using the parameters described in Table 26-4. In some embodiments, the crystalline form provides an XRPD pattern having characteristic peak locations of at least three of the values selected from the group consisting of; about 6.1, 10.9, 12.2, 16.1, 16.8, 21.4, 21.8, 25.4, and 27.2±0.2 degrees, 2-Theta, when measured using the parameters described in Table 26-4. In some embodiments, the crystalline form provides an XRPD pattern having characteristic peak locations of at least three of the values selected from the group consisting of: about 6.1, 12.2, 16.1, 21.8, 24.4 and 25.4±0.2 degrees, 2-Theta, when measured using the parameters described in Table 26-4. In some embodiments, the crystalline form provides an XRPD pattern having characteristic peak locations of all of the values selected from the group consisting of: about 6.1, 12.2, and 21.8±0.2 degrees, 2-Theta, when measured using the parameters described in Table 26-4. In some embodiments, the crystalline form provides a DSC thermogram substantially the same as shown in FIG. 53C. In some embodiments, the crystalline form provides a DSC thermogram with an endothermic peak at about 192° C. In some embodiments, the crystalline form is stable for at least a month at about 40° C. In some embodiments, the crystalline form is stable for at least a month at about 60° C. In some embodiments, the crystalline form provides substantially the same XRPD pattern post-storage at 40° C. and 75% RH for at least 3 days. In some embodiments, the crystalline form provides substantially the same XRPD pattern post-storage at 40° C. and 75% RH for at least 7 days. In some embodiments, the crystalline form provides substantially the same XRPD pattern post-storage at 60° C. and 75% RH for at least 3 days. In some embodiments, the crystalline form provides substantially the same XRPD pattern post-storage at 60° C. and 75% RH for at least 7 days. In some embodiments, the crystalline form is a salt. In some embodiments, the crystalline form is a co-crystal.

In one aspect, described herein is a crystalline form of 2',6-difluoro-5'-[3-(1-hydroxy-1-methylethyl)-imidazo[1,2-b][1,2,4]triazin-7-yl]biphenyl-2-carbonitrile with hydrochloric acid, wherein the crystalline form has at least one of the following properties: (a) an X-ray powder diffraction (XRPD) pattern substantially the same as shown in FIG. 63, when measured using the parameters described in Table 26-4; (b) an XRPD pattern having characteristic peak locations of at least three, at least nine, at least six, or all of the values selected from the group consisting of: about 6.3, 11.7, 12.8, 14.1, 15.1, 16.5, 17.6, 18.8, 19.3, 20.6, 21.8, 23.2, 24.3, 25.7, 26.5, 26.9, 28.5, 30.3, 32.2, 32.7, and 33.5±0.2 degrees, 2-Theta, when measured using the parameters described in Table 26-4; (c) a differential scanning calorimetry (DSC) thermogram substantially the same as one labelled Chloride Form C in FIG. 52F; (d) a DSC thermogram with an endothermic peak at about 179° C.; (e) substantially the same XRPD pattern post-storage at 40° C. and 75% RH for at least 3 days; and (f) substantially the same XRPD pattern post-storage at 60° C. and 75% RH for at least 3 days. In some embodiments, the crystalline form provides an XRPD pattern substantially the same as shown in FIG. 63, when measured using the parameters described in Table 26-4. In some embodiments, the crystalline form provides an XRPD pattern having characteristic peak locations of at least three, at least nine, at least six, or all of the values selected from the group consisting of: about 6.3, 11.7, 12.8, 14.1, 15.1, 16.5, 17.6, 18.8, 19.3, 20.6, 21.8, 23.2, 24.3, 25.7, 26.5, 26.9, 28.5, 30.3, 32.2, 32.7, and 33.5±0.2 degrees, 2-Theta, when measured using the parameters described in Table 26-4. In some embodiments, the crystalline form provides an XRPD pattern having characteristic peak locations of at least three of the values selected from the group consisting of: about 6.3, 11.7, 12.8, 16.5, 17.6, and 21.8±0.2 degrees, 2-Theta, when measured using the parameters described in Table 26-4. In some embodiments, the crystalline form provides an XRPD pattern having characteristic peak locations of all of the values selected from the group consisting of: about 11.7, 12.8, and 21.8±0.2 degrees, 2-Theta, when measured using the parameters described in Table 26-4. In some embodiments, the crystalline form provides a differential scanning calorimetry (DSC) thermogram substantially the same as one labelled Chloride Form C in FIG. 52F. In some embodiments, the crystalline form provides a DSC thermogram with an endothermic peak at about 179° C. In some embodiments, the crystalline form provides substantially the same XRPD pattern post-storage at 40° C. and 75% RH for at least 3 days. In some embodiments, the crystalline form provides substantially the same XRPD pattern post-storage at 60° C. and 75% RH for at least 3 days.

In one aspect, described herein is a crystalline polymorph of 2',6-difluoro-5'-[3-(1-hydroxy-1-methylethyl)-imidazo[1,2-b][1,2,4]triazin-7-yl]biphenyl-2-carbonitrile, of Form E, providing an X-ray Powder Diffraction (XRPD) pattern having characteristic peak locations of at least three values selected from the group consisting of: about: 6.6, 7.5, 9.6, 10.3, 13.3, 13.8, 14.5, 15.4, 15.9, 16.5, 17.3, 17.8, 19.5, 20.3, 22.3, 23.2, 23.7, 26.1, 26.9, 27.9, 29.0, 31.1, and 35.8±0.2 degrees, 2-theta, when measured using the parameters described in Table 26-4. In some embodiments, the crystalline polymorph provides an XRPD pattern substantially the same as the XRPD pattern labelled Form E in FIG. 36A. In some embodiments, the crystalline form provides an XRPD pattern having characteristic peak locations of at least three, at least six, at least nine, or all of the values selected from the group consisting of: about 6.6, 7.5, 9.6, 10.3, 13.3, 13.8, 14.5, 15.4, 15.9, 16.5, 17.3, 17.8, 19.5, 20.3, 22.3, 23.2, 23.7, 26.1, 26.9, 27.9, 29.0, 31.1, and 35.8±0.2 degrees, 2-Theta, when measured using the parameters described in Table 26-4. In some embodiments, the crystalline form provides an XRPD pattern having characteristic peak locations of at least three of the values selected from the group consisting of: about 7.5, 9.6, 10.3, 13.3, 19.5, and 20.3±0.2 degrees, 2-Theta, when measured using the parameters described in Table 26-4. In some embodiments, the crystalline form provides an XRPD pattern having characteristic peak locations of at least three of the values selected from the group consisting of: about 7.5, 9.6, and 10.3±0.2 degrees, 2-Theta, when measured using the parameters described in Table 26-4.

In one aspect, described herein is a crystalline polymorph of 2',6-difluoro-5'-[3-(1-hydroxy-1-methylethyl)-imidazo[1,2-b][1,2,4]triazin-7-yl]biphenyl-2-carbonitrile, of Form F, providing an X-ray Powder Diffraction (XRPD) pattern having characteristic peak locations of at least three values selected from the group consisting of about: 7.0, 7.7, 8.1, 9.2, 10.9, 12.3, 13.1, 14.0, 14.2, 15.2, 15.4, 15.7, 16.3, 17.2, 17.8, 19.4, 19.9, 21.0, 22.9, 26.7, and 27.6±0.2-degrees, 2-theta, when measured using the parameters described in Table 26-4. In some embodiments, the crystalline polymorph provides an XRPD pattern substantially the same as the XRPD pattern labelled Form F in FIG. 36A. In some embodiments, the crystalline form provides an XRPD pattern having characteristic peak locations of at least three, at least six, at least nine, or all of the values selected from the group consisting of: about 7.0, 7.7, 8.1, 9.2, 10.9, 12.3, 13.1, 14.0, 14.2, 15.2, 15.4, 15.7, 16.3, 17.2, 17.8, 19.4, 19.9, 21.0, 22.9, 26.7, and 27.6±0.2 degrees, 2-Theta, when measured using the parameters described in Table 26-4. In some embodiments, the crystalline form provides an XRPD pattern having characteristic peak locations of at least three of the values selected from the group consisting of: about 7.0, 7.7, 8.1, 12.3, 13.1, and 15.2±0.2 degrees, 2-Theta, when measured using the parameters described in Table 26-4. In some embodiments, the crystalline form provides an XRPD pattern having characteristic peak locations of at least three of the values selected from the group consisting of: about 7.7, 8.1, and 13.1±0.2 degrees, 2-Theta, when measured using the parameters described in Table 26-4.

In one aspect, described herein is a crystalline polymorph of 2',6-difluoro-5'-[3-(1-hydroxy-1-methylethyl)-imidazo[1,2-b][1,2,4]triazin-7-yl]biphenyl-2-carbonitrile, of Form G, providing an X-ray Powder Diffraction (XRPD) pattern having characteristic peak locations of at least three values selected from the group consisting of about: 6.3, 7.5, 8.0, 11.7, 12.0, 12.8, 13.3, 14.1, 14.8, 15.3, 17.2, 18.0, 19.2, 19.6, 21.5, 23.2, 23.8, 25.9, 26.6, 27.7, and 32.4±0.2-degrees, 2-theta, when measured using the parameters described in Table 26-4. In some embodiments, the crystalline polymorph provides an XRPD pattern substantially the same as the XRPD pattern labelled Form G in FIG. 36A. In some embodiments, the crystalline form provides an XRPD pattern having characteristic peak locations of at least three, at least six, at least nine, or all of the values selected from the group consisting of: about 6.3, 7.5, 8.0, 11.7, 12.0, 12.8, 13.3, 14.1, 14.8, 15.3, 17.2, 18.0, 19.2, 19.6, 21.5, 23.2, 23.8, 25.9, 26.6, 27.7, and 32.4±0.2 degrees, 2-Theta, when measured using the parameters described in Table 26-4. In some embodiments, the crystalline form provides an XRPD pattern having characteristic peak locations of at least three of the values selected from the group consisting of: about 6.3, 8.0, 12.0, 12.8, and 13.3±0.2 degrees, 2-Theta, when measured using the parameters described in Table 26-4. In some embodiments, the crystalline form provides an XRPD pattern having characteristic peak locations of at least three of the values selected from the group consisting of: about 6.3, 8.0, and 13.3±0.2 degrees, 2-Theta, when measured using the parameters described in Table 26-4.

In one aspect, described herein is a crystalline polymorph of 2',6-difluoro-5'-[3-(1-hydroxy-1-methylethyl)-imidazo[1,2-b][1,2,4]triazin-7-yl]biphenyl-2-carbonitrile, of Form H, providing an X-ray Powder Diffraction (XRPD) pattern having characteristic peak locations of at least three values selected from the group consisting of: about: 7.0, 7.9, 9.4, 10.9, 12.7, 13.4, 14.0, 14.3, 14.6, 16.0, 16.3, 18.0, 19.2, 19.7, 20.1, 21.2, 24.1, 25.7, 26.9, and 28.0±0.2-degrees, 2-theta, when measured using the parameters described in Table 26-4. In some embodiments, the crystalline polymorph provides an XRPD pattern substantially the same as the XRPD pattern labelled Form H in FIG. 36A. In some embodiments, the crystalline form provides an XRPD pattern having characteristic peak locations of at least three, at least six, at least nine, or all of the values selected from the group consisting of: about 7.0, 7.9, 9.4, 10.9, 12.7, 13.4, 14.0, 14.3, 14.6, 16.0, 16.3, 18.0, 19.2, 19.7, 20.1, 21.2, 24.1, 25.7, 26.9, and 28.0±0.2 degrees, 2-Theta, when measured using the parameters described in Table 26-4. In some embodiments, the crystalline form provides an XRPD pattern having characteristic peak locations of at least three of the values selected from the group consisting of: about 7.0, 7.9, 9.4, 10.9, 12.7, and 14.0±0.2 degrees, 2-Theta, when measured using the parameters described in Table 26-4. In some embodiments, the crystalline form provides an XRPD pattern having characteristic peak locations of at least three, at least six, at least nine, or all of the values selected from the group consisting of: about 7.9, 12.7, and 14.0±0.2 degrees, 2-Theta, when measured using the parameters described in Table 26-4.

In one aspect, described herein is a crystalline form of 2',6-difluoro-5'-[3-(1-hydroxy-1-methylethyl)-imidazo[1,2-b][1,2,4]triazin-7-yl]biphenyl-2-carbonitrile selected from the group consisting of: (a) chloride salt, which provides substantially the same XRPD pattern as shown in FIG. 62; and (b) besylate salt, which provides substantially the same XRPD pattern as an XRPD pattern labelled besylate Form A shown in FIG. 57A.

In one aspect, described herein is a crystalline form of 2',6-difluoro-5'-[3-(1-hydroxy-1-methylethyl)-imidazo[1,2-b][1,2,4]triazin-7-yl]biphenyl-2-carbonitrile with phosphoric acid, wherein the crystalline form has at least one of the following properties: (a) an X-ray powder diffraction (XRPD) pattern substantially the same as shown in FIG. 67, when measured using the parameters described in Table 35; (b) an XRPD pattern having characteristic peak locations of at least three of the values selected from the group consisting of: about 6.3, 7.4, 10.1, 12.6, 13.2, 14.0, 15.7, 17.0, 17.3, 18.0, 19.0, 20.2, 20.7, 26.4, 27.2, and 27.5±0.2 degrees, 2-Theta, when measured using the parameters described in Table 35; (c) a differential scanning calorimetry (DSC) thermogram substantially the same as shown in FIG. 69; (d) a DSC thermogram with an endothermic peak at about 200° C.; and (e) a DSC thermogram with an endothermic peak having an onset temperature at about 197° C. In some embodiments, the crystalline form provides an XRPD pattern substantially the same as shown in FIG. 67, when measured using the parameters described in Table 35. In some embodiments, the crystalline form provides an XRPD pattern having characteristic peak locations of at least three, at least six, or at least nine of the values selected from the group consisting of: about 6.3, 7.4, 10.1, 12.6, 13.2, 14.0, 15.7, 17.0, 17.3, 18.0, 19.0, 20.2, 20.7, 26.4, 27.2, and 27.5±0.2 degrees, 2-Theta, when measured using the parameters described in Table 35. In some embodiments, the crystalline form provides an XRPD pattern having characteristic peak locations of at least three, at least six, or at least nine of the values selected from the group consisting of: about 6.3, 13.2, 14.0, 15.7, 17.0, 17.3, 18.0, 19.0, 20.2, 20.7, and 26.4±0.2 degrees, 2-Theta, when measured using the parameters described in Table 35. In some embodiments, the crystalline form provides an XRPD pattern having charac-teristic peak locations of at least three, at least six, or at least nine of the values selected from the group consisting of: about 6.3, 13.2, 14.0, 15.7, 17.0, 17.3, 18.0, 20.2, 20.7, and 26.4±0.2 degrees, 2-Theta, when measured using the parameters described in Table 35. In some embodiments, the crystalline form provides an XRPD pattern having characteristic peak locations of at least three, at least six, or at least nine of the values selected from the group consisting of: about 6.3, 13.2, 14.0, 15.7, 17.0, 17.3, 18.0, 19.0, 20.2, 20.7, and 26.4±0.2 degrees, 2-Theta, when measured using the parameters described in Table 35. In some embodiments, the crystalline form provides an XRPD pattern having characteristic peak locations of at least three, at least six, or at least nine of the values selected from the group consisting of: about 6.3, 13.2, 14.0, 15.7, 17.0, 17.3, 18.0, and 26.4±0.2 degrees, 2-Theta, when measured using the parameters described in Table 35. In some embodiments, the crystalline form provides an XRPD pattern having characteristic peak locations of at least three, at least six, or at least nine of the values selected from the group consisting of: about 6.3, 13.2, 14.0, 15.7, 17.0, 17.3, 18.0, 19.0, and 26.4±0.2 degrees, 2-Theta, when measured using the parameters described in Table 35. In some embodiments, the crystalline form provides an XRPD pattern having characteristic peak locations of all of the values selected from the group consisting of: about 6.3, 17.0, and 19.0±0.2 degrees, 2-Theta, when measured using the parameters described in Table 35. In some embodiments, the crystalline form provides a DSC thermogram substantially the same as shown in FIG. 69. In some embodiments, the crystalline form provides a DSC thermogram with an endothermic peak at about 200° C. In some embodiments, the crystalline form provides a DSC thermogram with an endothermic peak having an onset temperature at about 197° C. In some embodiments, the crystalline form is a salt. In some embodiments, the crystalline form is a co-crystal. In some embodiments, described herein is a method of preparing the crystalline form of 2',6-difluoro-5'-[3-(1-hydroxy-1-methylethyl)-imidazo[1,2-b][1,2,4]triazin-7-yl]biphenyl-2-carbonitrile with phosphoric acid.

In one aspect, disclosed herein is a therapeutic or prophylactic composition comprising a described compound. In another aspect, disclosed herein is a method of treating a condition or a disorder in a subject in need thereof, the method comprising administering a therapeutically effective amount of a compound or a composition described herein to said subject. In one aspect, disclosed herein is a compound for use in treating a condition or a disorder in a subject in need thereof. In one aspect, disclosed herein is a composi-tion for use in treating a condition or a disorder in a subject in need thereof. In some embodiments, the condition or disorder is associated with α2/α3 GABAA receptor. In some embodiments, the condition or disorder is selected from: pain, neuropathic pain, inflammatory pain, anxiety, epilep-sies, convulsion, muscle spasms, pruritus, itch, cognitive impairment, alcohol dependence, drug addiction, schizo-phrenia, depression, autism, panic disorder, noise phobia, and generalized fear and anxiety disorders. In some embodi-ments, the condition or disorder is pain. In some embodi-ments, the pain is Fibromyalgia, Inflammatory pain, Neu-ropathic pain, Peripheral Diabetic Neuropathy, Chemotherapy induced pain, HIV associated Neuropathy, Post-herpetic neuralgia, Musculoskeletal pain, Rheumatoid arthritis, Osteoarthritis, Post-operative pain, Burn pain, Sun-burn pain, or Phantom limb pain. In some embodiments, the condition or disorder is itch. In some embodiments, the itch is Chronic Itch, Neurogenic itch, Contact Dermatitis itch, Uremic Pruritus, Neurodermatitis, Atopic Dermatitis, Atopic Eczema, Prurigo Nodularis, Notalgia Parasthetica, Psoriasis, Psychogenic itch or Aquagenic Itch. In some embodiments, the condition or disorder is epilepsy. In some embodiments, the epilepsy is Focal epilepsy, Generalized epilepsy, Dravet Syndrome, Childhood absence epilepsy (CEA), Juvenile absence epilepsy, Juvenile myoclonic epilepsy (JME), West Syndrome, Lennox-Gastaut syndrome (LGS), Sunflower Syndrome, Status epilepticus, Nerve agent induced seizures, Tremors from alcohol withdrawal, Traumatic Brain Injury, Tuberous Sclerosis Complex, Doose Syndrome, Rasmussen's Syndrome, Early myoclonic encephalopathy, Malignant migrating partial seizures of infancy, Epilepsy with continuous spike and waves during slow wave sleep, Landau-Kleffner syndrome, Benign epilepsy with centrotemporal spikes, Benign familial neonatal infantile seizures, Cortical dysplasia focal epilepsy syndrome, Generalized epilepsy with febrile seizure plus (GEFS+), Myoclonic atonic epilepsy, Malignant migrating partial seizures of infancy, Ohtahara syndrome (a.k.a. early infantile epileptic encephalopathy), or Partial epilepsy and febrile seizures plus. In some embodiments, the condition or disorder is autism. In some embodiments, the autism is an autism resulting from SCN2a mutation, fragile X syndrome, or autism related to ion-channel dysfunction.

In one aspect, disclosed herein is a method for preparing a crystalline form of 2',6-difluoro-5'-[3-(1-hydroxy-1-methylethyl)-imidazo[1,2-b][1,2,4]triazin-7-yl]biphenyl-2-carbonitrile with phosphoric acid, the method comprising crystallizing 2',6-difluoro-5'-[3-(1-hydroxy-1-methylethyl)-imidazo[1,2-b][1,2,4]triazin-7-yl]biphenyl-2-carbonitrile phosphate from a solution comprising one or more of: ethyl acetate, methyl ethyl ketone, 2-methyl butanone, dimethyl sulfoxide, dimethylformamide, dimethyl acetamide, acetone, water, tetrahydrofuran (THF), 2-methyl-THF, isopropyl acetate (IPAC), acetonitrile, and dichloromethane, wherein the crystalline form provides an X-ray Powder Diffraction (XRPD) pattern substantially the same as shown in FIG. 64, when measured using the parameters described in Table 26-4. In some embodiments, the crystalline form provides an XRPD pattern having characteristic peak locations of at least three values selected from the group consisting of: about 6.5, 7.6, 10.2, 13.4, 14.0, 14.4, 15.4, 16.0, 16.2, 17.2, 17.5, 17.8, 18.6, 19.2, 19.8, 20.4, 20.9, 21.6, 23.5, 26.2, 26.6, 27.4, 28.3, 29.0, 30.2, and 32.7±0.2 degrees, 2-theta, when measured using the parameters described in Table 26-4. In some embodiments, the crystalline form provides an XRPD pattern having characteristic peak locations of at least three values selected from the group consisting of: about 6.5, 13.4, 14.0, 15.4, 17.2, 17.5, and 26.6±0.2 degrees, 2-theta, when measured using the parameters described in Table 26-4. In some embodiments, the crystalline form provides an XRPD pattern having characteristic peak locations of all of the values selected from the group consisting of: about 6.5, 14.4, 16.0, 18.6, 19.2, 21.6, and 26.6±0.2 degrees, 2-theta, when measured using the parameters described in Table 26-4. In some embodiments, at least 500 grams of the crystalline form is prepared. In some embodiments, at least 1000 grams of the crystalline form is prepared. In some embodiments, the solution comprises THF. In some embodiments, the solution comprises 2-Me THF. In some embodiments, the solution comprises IPAC. In some embodiments, the solution comprises heptane. In some embodiments, the solution comprises acetonitrile. In some embodiments, the solution comprises methyl tert-butyl ether. In some embodiments, the solution comprises ethyl acetate. In some embodiments, the solution comprises acetone. In some embodiments, the solution comprises a mixture acetone and water. In some embodiments, the method comprises removing water through any means such as azeotropic drying, activated sieves, magnesium sulfate, sodium sulfate, or other drying agents. In some embodiments, the method comprises an azeotropic drying step to remove water. In some embodiments, the solution does not comprise water or alcohol. In some embodiments, the method comprises removing acetone by distillation for one or more times. In some embodiments, the method comprises removing acetone by distillation for one to three times. In some embodiments, the method comprises removing ethyl acetate by distillation for one or more times. In some embodiments, the method comprises removing ethyl acetate by distillation for one to three times. In some embodiments, the method comprises removing water by distillation of a solvent that has a lower boiling point than water. In some embodiments, the solvent is ethyl acetate, methyl ethyl ketone, 2-methyl butanone, acetone, tetrahydrofuran, 2-methyl-THF, isopropyl acetate, acetonitrile, or dichloromethane.

BRIEF DESCRIPTION OF THE DRAWINGS

FIG. 29 illustrates XRPD patterns of TPA023B phosphate solids obtained by polymorph screening using the slurry method

FIG. 59A-FIG. 59D illustrate the XRPD patterns of stability samples of: TPA023B free base (FIG. 59A), TPA023B chloride (FIG. 59B), TPA023B sulfate (FIG. 59C), and TPA023B besylate (FIG. 59D)

DETAILED DESCRIPTION

Described herein are novel free base polymorphs, pharmaceutical salts and salt polymorphs, and pharmaceutical co-crystals and co-crystal polymorphs having beneficial properties including improved solubility, improved oral bioavailability, more consistent oral bioavailability, improved stability, improved manufacturability, and corresponding improved formulations. Salts, co-crystals, polymorphs, salt polymorphs, and co-crystal polymorphs of TPA023B are described herein, and are useful for treating several disorders in addition to itch. Those skilled in the art will appreciate that such compounds may find use in treating any disorders reported to be treatable by α2/α3 GABAA positive allosteric modulators, as well as disorders treatable with non-selective GABAA positive allosteric modulators. These include, but are not limited to, pain, anxiety, epilepsies, muscle spasms, pruritus, itch, cognitive impairment, alcohol dependence, schizophrenia, depression, autism, and the like.

Phosphate Forms

Phosphate Form A

Figure 48:
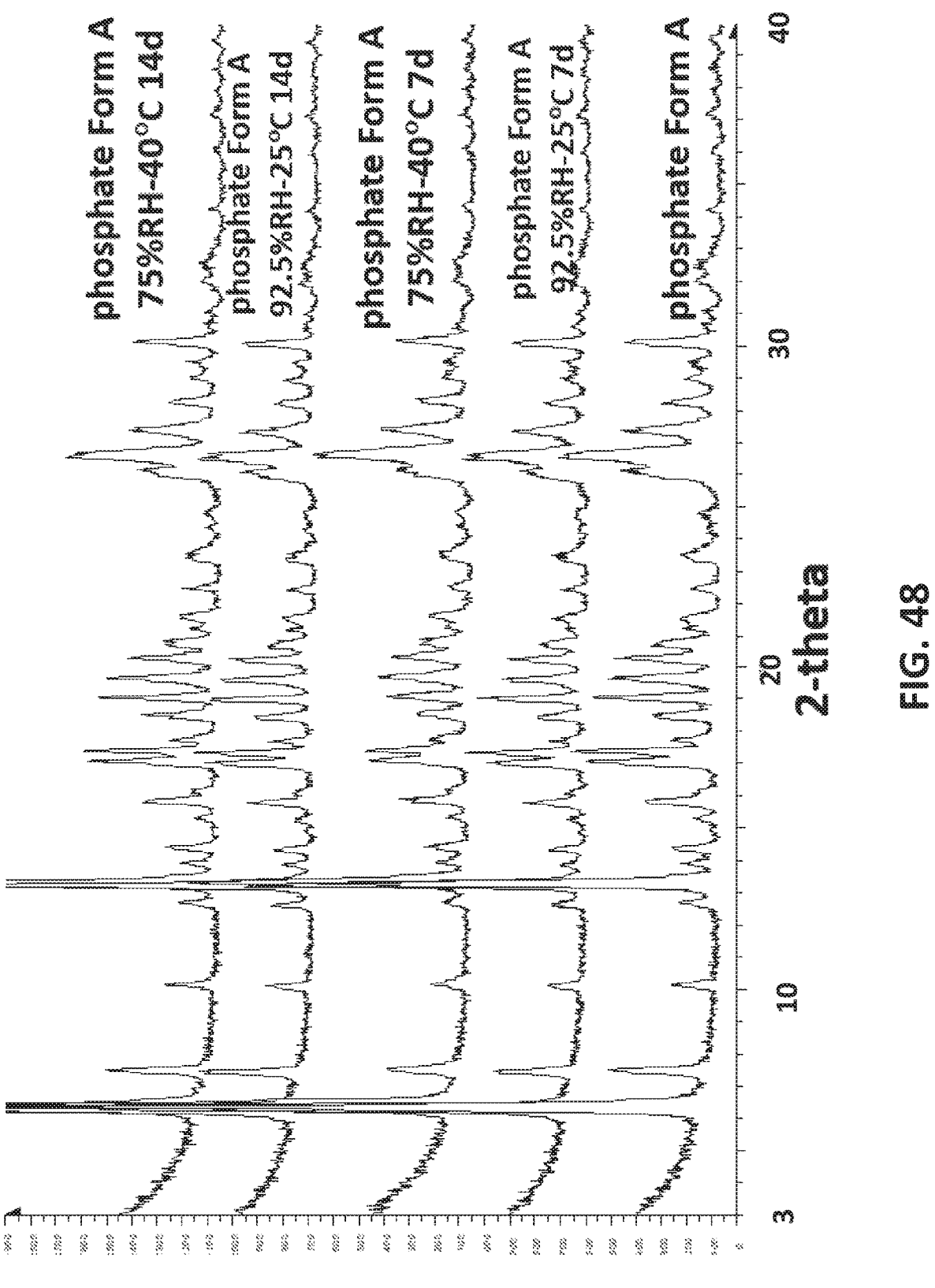
FIG. 48 illustrates the XRPD patterns of Phosphate Form A before and after thermal and humidity treatments

In one or more embodiments the present disclosure discloses a stable polymorph of the salt or co-crystal of 2',6-difluoro-5'-[3-(1-hydroxy-1-methylethyl)-imidazo[1,2-b][1,2,4]triazin-7-yl]biphenyl-2-carbonitrile with phosphoric acid. In one or more embodiments, protonated 2',6-difluoro-5'-[3-(1-hydroxy-1-methylethyl)-imidazo[1,2-b][1,2,4]triazin-7-yl]biphenyl-2-carbonitrile has a pKa of 2.19 as measured in Example 23. Phosphoric acid is reported to have a pKa of 2.16. Because the pKa's are similar, it is unexpectedly discovered that 2',6-difluoro-5'-[3-(1-hydroxy-1-methylethyl)-imidazo[1,2-b][1,2,4]triazin-7-yl]biphenyl-2-carbonitrile can form a stable crystal polymorph with phosphoric acid. In one or more embodiments, this crystal form is a salt. In one or more embodiments, this crystal form is a co-crystal. This crystalline polymorph is designated "Phosphate Polymorphic Form A" and exhibits an X-Ray Powder Diffraction (XRPD) pattern having characteristic peak locations of at least three, at least six, at least nine, at least twelve, or all values selected from the group consisting of: about 6.4, 7.5, 12.7, 13.3, 17.1, 17.4, 18.5, 19.1, 19.7, 26.7, 30.2, and 32.1±0.2 degrees, 2-theta, when measured using the parameters described in Table 1. In one or more embodiments, Phosphate Polymorphic Form A exhibits an XRPD pattern substantially the same as the XRPD pattern shown in FIG. 1. In some embodiments, "Phosphate Polymorphic Form A" (i.e., Phosphate Form A) exhibits an XRPD pattern having characteristic peak locations of at least three, at least six, at least nine, at least twelve, at least fifteen or all values selected from the group consisting of: about 6.5, 7.6, 10.2, 13.4, 14.0, 14.4, 15.4, 16.0, 16.2, 17.2, 17.5, 17.8, 18.6, 19.2, 19.8, 20.4, 20.9, 21.6, 23.5, 26.2, 26.6, 27.4, 28.3, 29.0, 30.2, and 32.7±0.2 degrees, 2-theta, when measured using the parameters described in Table 26-4. In one or more embodiments, Phosphate Polymorphic Form A exhibits an XRPD pattern substantially the same as the XRPD pattern shown in FIG. 38A. In some embodiments, Phosphate Polymorphic Form A exhibits an XRPD pattern having a characteristic peak located at about 6.5±0.2 degrees, 2-theta. In some embodiments, Phosphate Polymorphic Form A exhibits an XRPD pattern having a characteristic peak located at about 7.6±0.2 degrees, 2-theta. In some embodiments, Phosphate Polymorphic Form A exhibits an XRPD pattern having a characteristic peak located at about 13.4±0.2 degrees, 2-theta. In some embodiments, Phosphate Polymorphic Form A exhibits an XRPD pattern having a characteristic peak located at about 17.2±0.2 degrees, 2-theta. In some embodiments, Phosphate Polymorphic Form A exhibits an XRPD pattern having a characteristic peak located at about 17.8±0.2 degrees, 2-theta. In some embodiments, Phosphate Polymorphic Form A exhibits an XRPD pattern having a characteristic peak located at about 26.2±0.2 degrees, 2-theta. In some embodiments, Phosphate Polymorphic Form A exhibits an XRPD pattern having a characteristic peak located at about 30.2±0.2 degrees, 2-theta. In one or more embodiments, Phosphate Polymorphic Form A exhibits an XRPD pattern substantially the same as the XRPD pattern shown in FIG. 48A and FIG. 48B. In one or more embodiments, Phosphate Polymorphic Form A exhibits an XRPD pattern substantially the same as any XRPD pattern described herein as Phosphate Form A.

TABLE 1

| XRPD Parameters | |
| --- | --- |
| Parameters | Settings/Values |
| X-Ray wavelength | Cu: K- Alpha (λ = 1.54179Å) |
| X-Ray tube setting | Voltage: 40 kV; Current: 40 mA |
| Scan scope | 3 to 40 deg |
| Sample rotation speed | 15 rpm |
| Scanning rate | 10 deg./min |

In some embodiments, Phosphate Polymorphic Form A is a stable form. In some embodiments, Phosphate Polymorphic Form A can be stored at various temperatures and relative humidities. For example, Phosphate Polymorphic Form A can be stored at about −20° C., about −10° C., about 0° C., about 5° C., about 15° C., about 25° C., about 40° C., and about 60° C. For another example, Phosphate Polymorphic Form A can be stored at 10% RH, 20% RH, 30% RH, 40% RH, 50% RH, 60% RH, 75% RH, or 90% RH. In some embodiments, Phosphate Polymorphic Form A is stable at about 25° C. for at least 7 days, at least 14 days, at least 21 days, at least a month, at least 2 months, at least 3 months, at least 6 months, at least 9 months, at least 12 months, or at least 24 months. In some embodiments, Phosphate Polymorphic Form A is stable at about 25° C. for at least 36 months, at least 48 months, or at least 60 months. In some embodiments, Phosphate Polymorphic Form A is stable at about 40° C. for at least 3 days, at least 7 days, at least 14 days, at least 21 days, at least a month, at least 2 months, at least 3 months, at least 6 months, at least 9 months, at least 12 months, or at least 24 months. In some embodiments, Phosphate Polymorphic Form A is stable at about 60° C. for at least 3 days, at least 7 days, at least 14 days, at least 21 days, at least a month, at least two months, at least 6 months, at least 12 months, or at least 24 months. In some embodiments, a stable Phosphate Polymorphic Form A has about 80%, 85%, 90%, 91%, 92%, 93%, 94%, 95%, 96%, 97%, 98%, 99% w/w or greater of the initial phosphate salt amount at the end of the given storage period. In some embodiments, a stable Phosphate Polymorphic Form A has about 20%, 15%, 10%, 5%, 2%, 1% w/w or less total impurity or related substances at the end of the given storage period. In some embodiments, Phosphate Polymorphic Form A provides an XRPD pattern substantially the same post-storage at about 40° C. and 75% RH for at least a week. In some embodiments, Phosphate Polymorphic Form A provides an XRPD pattern substantially the same post-storage at about 40° C. and 75% RH for at least two weeks. In some embodiments, Phosphate Polymorphic Form A provides an XRPD pattern substantially the same post-storage at about 40° C. and 75% RH for at least a month. In some embodiments, Phosphate Polymorphic Form A provides an XRPD pattern substantially the same post-storage at about 40° C. and 75% RH for at least three months. In some embodiments, Phosphate Polymorphic Form A provides an XRPD pattern substantially the same post-storage at about 40° C. and 75% RH for at least six months. In some embodiments, Phosphate Polymorphic Form A provides an XRPD pattern substantially the same post-storage at about 25° C. and 92.5% RH for at least a week. In some embodiments, Phosphate Polymorphic Form A provides an XRPD pattern substantially the same post-storage at about 25° C. and 92.5% RH for at least two weeks. In some embodiments, Phosphate Polymorphic Form A provides an XRPD pattern substantially the same post-storage at about 25° C. and 92.5% RH for at least a month. In some embodiments, Phosphate Polymorphic Form A provides an XRPD pattern substantially the same post-storage at about 25° C. and 92.5% RH for at least three months. In some embodiments, Phosphate Polymorphic Form A provides an XRPD pattern substantially the same post-storage at about 25° C. and 92.5% RH for at least six months.

Figure 2A:
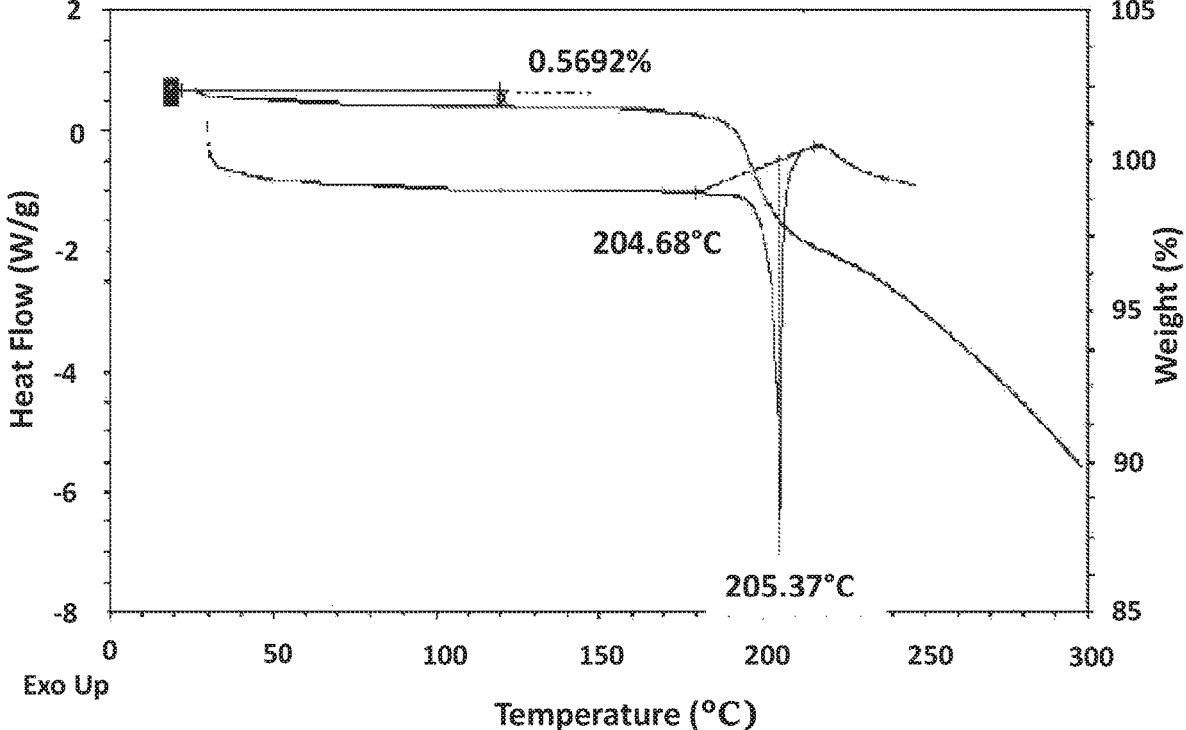
FIG. 2A-FIG. 2C illustrate a DSC/TGA thermogram for TPA023B phosphate Form A (FIG. 2A); an NMR spectrum of TPA023B phosphate Form A (FIG. 2B); and an additional DSC/TGA thermogram for TPA023B phosphate Form A (FIG. 2C)
Figure 2B:
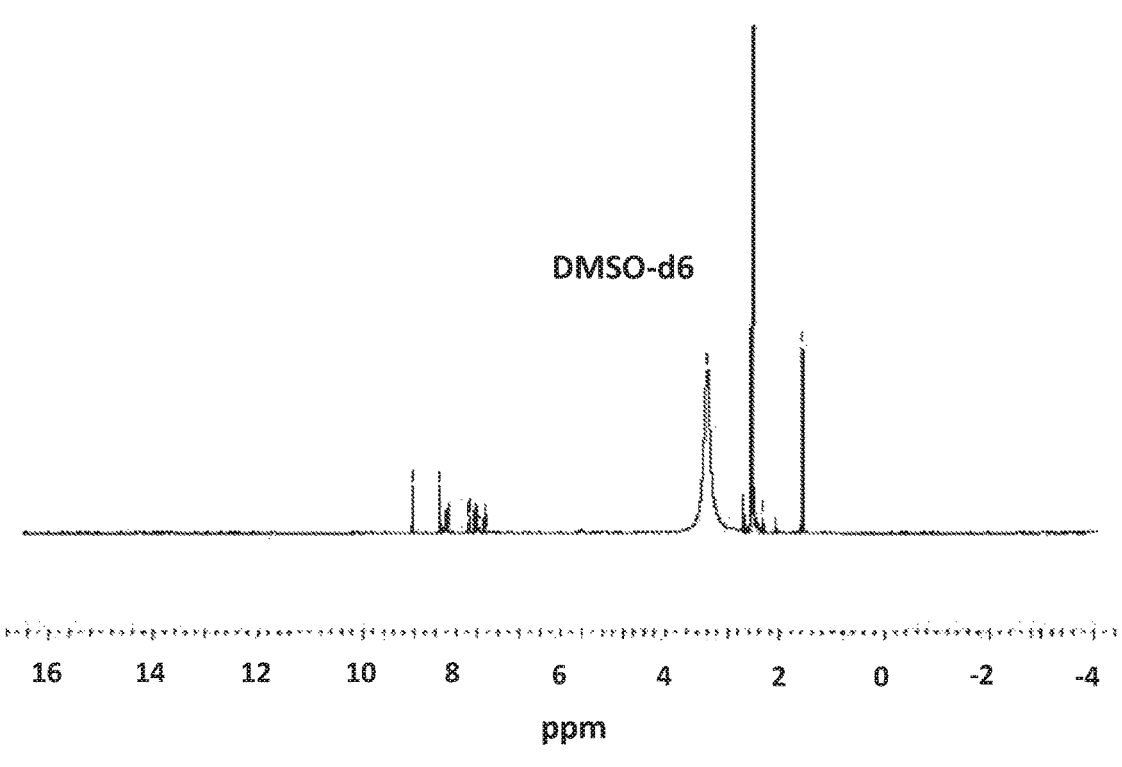
Figure 2C:
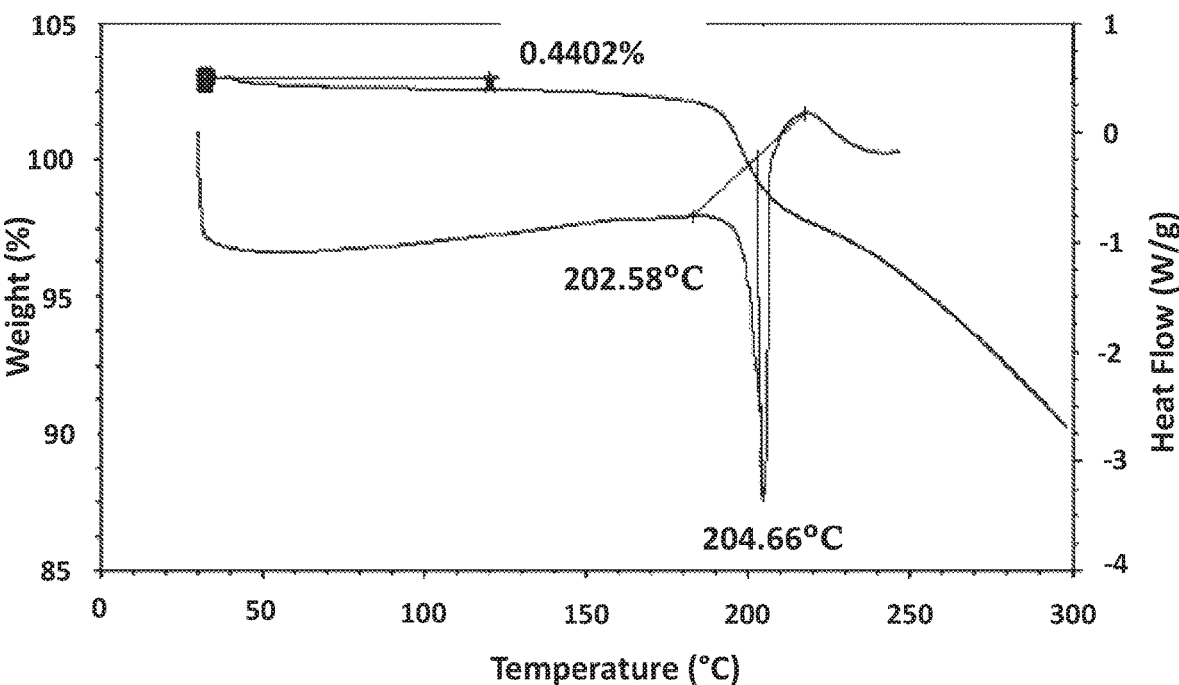

In one or more embodiments, Phosphate Polymorphic Form A has a melting range of from about 199° C. to about 209° C. In one or more embodiments, Phosphate Polymorphic Form A exhibits a differential scanning calorimetry (DSC) thermogram comprising an endothermic peak at about 205° C. In one or more embodiments, Phosphate Polymorphic Form A provides a DSC thermogram comprising an endothermic peak at about 206° C. In some embodiments, Phosphate Polymorphic Form A provides a DSC thermogram comprising a single endothermic peak with an onset temperature of 203° C. In some embodiments, Phosphate Polymorphic Form A provides a DSC thermogram comprising a single endothermic peak with an onset temperature of 204° C. In one or more embodiments, Phosphate Polymorphic Form A exhibits a DSC thermogram substantially the same as the DSC thermogram shown in FIG. 2A. In one or more embodiments, Phosphate Polymorphic Form A exhibits a DSC thermogram substantially the same as the DSC thermogram shown in FIG. 38B. In some embodiments, Phosphate Polymorphic Form A provides a DSC thermogram substantially the same as shown in FIG. 2C.

This melting point is obtained using DSC with a heating rate of 10° C./min. In some embodiments, Phosphate Polymorphic Form A displays birefringence under polarized light. Phosphate Polymorphic Form A can be synthesized using the method of Example 5, Example 33, or Example 50. In one or more embodiments, pharmaceutical compositions comprising the Phosphate Polymorphic Form A are described. In one or more embodiments, the disclosure includes purified forms of the crystalline Phosphate Polymorphic Form A.

In one or more embodiments, the Phosphate Polymorphic Form A described herein is at least 50% a, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, or at least 99.9% pure, as measured by HPLC as described herein. In some embodiment, the Phosphate Polymorphic Form A described herein comprises an impurity. In some embodiments, the impurity in Phosphate Polymorphic Form A is at most 0.1%, at most 0.5%, at most 1%, at most 2%, at most 3%, at most 4%, at most 5%, at most 6%, at most 7%, at most 8%, at most 9%, at most 10%, at most 15%, at most 20%, at most 25%, at most 30%, at most 40%, or at most 50%, as measured by HPLC as described herein.

In some embodiments, Phosphate Polymorphic Form A has a plasma half-life that is at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, or at least 15 hours in the plasma of a rat. In some embodiments, Phosphate Polymorphic Form A has a plasma half-life that is at most 5 hours, at most 6 hours, at most 7 hours, at most 8 hours, at most 9 hours, at most 10 hours, at most 11 hours, at most 12 hours, at most 13 hours, at most 14 hours, at most 15 hours, at most 20 hours, or at most 40 hours in the plasma of a rat. In some embodiments, Phosphate Polymorphic Form A has a plasma half-life that is from about 8 hours to about 15 hours in the plasma of a rat. In some embodiments, Phosphate Polymorphic Form A has a plasma half-life that is from about 10 hours to about 13 hours in the plasma of a rat.

Phosphate Polymorphic Form A can have a higher solubility than a free base form of TPA023B. For example, the solubility can be determined as described in Example 15. In some embodiments, the solubility of Phosphate Polymorphic Form A is at least 1.1 fold, 1.5 fold, 2 fold, 3 fold, 4 fold, 5 fold, 6 fold, 7 fold, or 8 fold higher than the solubility of Free Base Form A in simulated gastric fluid (SGF). In some embodiments, the solubility of Phosphate Polymorphic Form A is at least 1.1 fold, 1.5 fold, 2 fold, 3 fold, 4 fold, 5 fold, 6 fold, 7 fold, or 8 fold higher than the solubility of Free Base Form A in Fasted-state simulated intestinal fluid (FaSSIF). In some embodiments, the solubility of Phosphate Polymorphic Form A is at least 1.1 fold, 1.5 fold, 2 fold, 3 fold, 4 fold, 5 fold, 6 fold, 7 fold, or 8 fold higher than the solubility of Free Base Form A in Fed-state simulated intestinal fluid (FeSSIF) than Free Base Polymorphic Form A.

Figure 64:
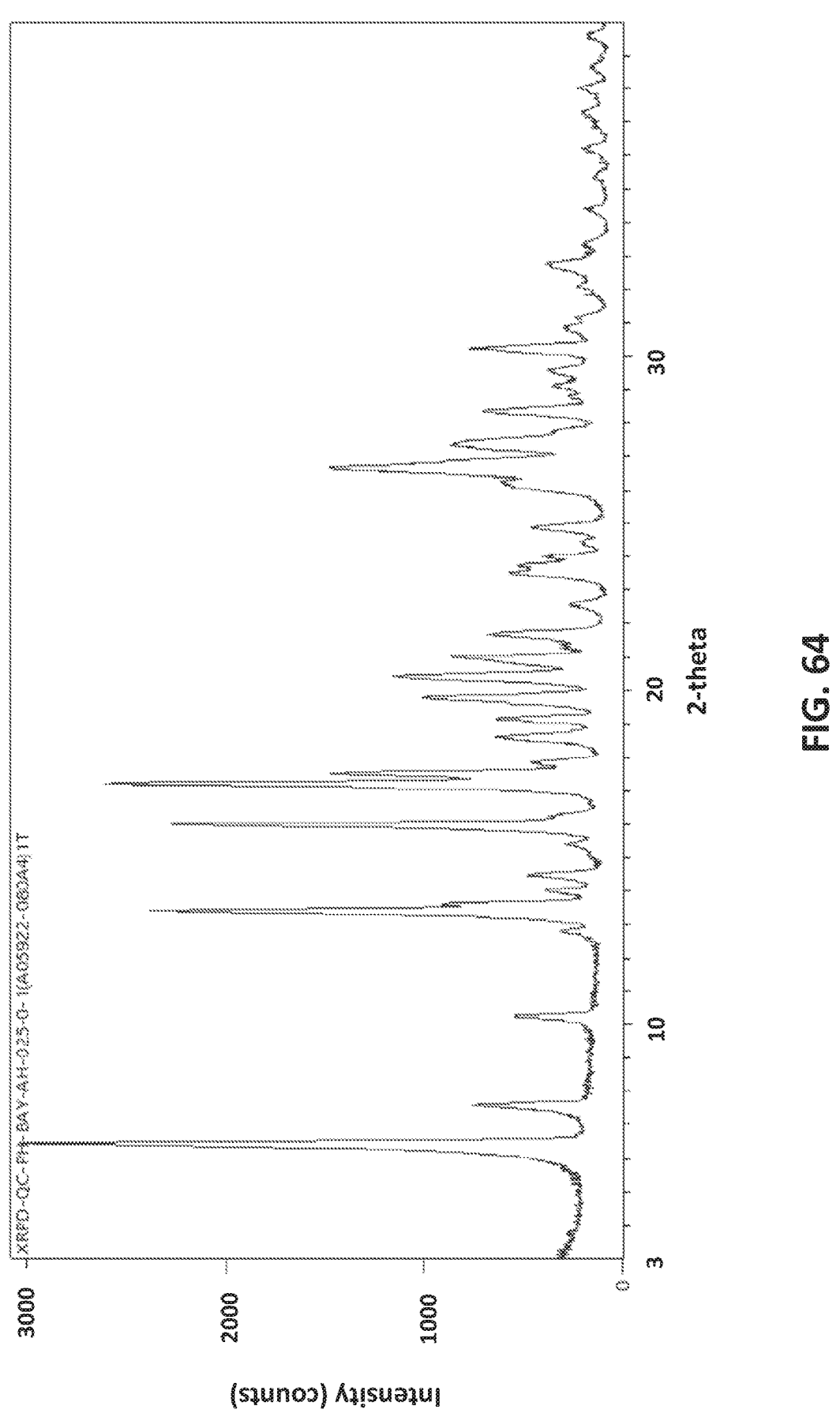
FIG. 64 illustrates the XRPD pattern of TPA023B phosphate Form A produced by the kilogram-Scale Preparation Procedure

In one aspect, disclosed herein is a method for preparing a crystalline form (e.g., salt or co-crystal) of Phosphate Polymorphic Form A from a solution. In some embodiments, the crystalline salt or co-crystal of Phosphate polymorphic form A provides an X-ray Powder Diffraction (XRPD) pattern substantially the same as shown in FIG. 64, when measured using the parameters described in Table 26-4. In some embodiments, the crystalline salt or co-crystal provides an XRPD pattern having characteristic peak locations of at least three, at least six, or at least nine values selected from the group consisting of; about 6.5, 7.6, 10.2, 13.4, 14.0, 14.4, 15.4, 16.0, 16.2, 17.2, 17.5, 17.8, 18.6, 19.2, 19.8, 20.4, 20.9, 21.6, 23.5, 26.2, 26.6, 27.4, 28.3, 29.0, 30.2, and 32.7±0.2 degrees, 2-theta, when measured using the parameters described in Table 26-4. In some embodiments, the crystalline form provides an XRPD pattern having characteristic peak locations of at least three, at least six, at least nine, or at least 12 values selected from the group consisting of: about 6.5, 7.6, 10.2, 13.4, 14.0, 14.4, 15.4, 16.0, 16.2, 17.2, 17.5, 17.8, 18.6, 19.2, 19.8, 20.4, 20.9, 21.6, 23.5, 26.2, 26.6, 27.4, 28.3, 29.0, 30.2, and 32.7±0.2 degrees, 2-theta, when measured using the parameters described in Table 26-4. In some embodiments, the crystalline form provides an XRPD pattern having characteristic peak locations of at least three values, at least six, at least nine, or at least 12 selected from the group consisting of: about 6.5, 7.6, 10.2, 13.4, 14.0, 14.4, 15.4, 16.0, 16.2, 17.2, 17.5, 17.8, 18.6, 19.2, 19.8, 20.4, 20.9, 21.6, 23.5, 26.2, 26.6, 27.4, 28.3, 29.0, 30.2, and 32.7±0.2 degrees, 2-theta, when measured using the parameters described in Table 35. In some embodiments, the method comprises crystalizing Phosphate Polymorphic Form A from a solution. In some embodiments, the solution comprises one or more of: ethyl acetate, methyl ethyl ketone, 2-methyl butanone, dimethyl sulfoxide, dimethylformamide, dimethyl acetamide, acetone, water, tetrahydrofuran (THF), 2-methyl-THF, isopropyl acetate (IPAC), acetonitrile, and dichloromethane. In some embodiments, at least 500 grams of the crystalline salt or co-crystal is prepared. In some embodiments, the solution comprises THF. In some embodiments, the solution comprises 2-Me THF. In some embodiments, the solution comprises IPAC. In some embodiments, the solution comprises heptane. In some embodiments, the solution comprises acetonitrile. In some embodiments, the solution comprises methyl tert-butyl ether. In some embodiments, the solution comprises a low level of water and/or alcohol. For example, in some embodiments, the water content in the solution is at most 10 wt %, at most 5 wt %, at most 4 wt %, at most 3 wt %, at most 2 wt %, at most 1 wt %, at most 0.5 wt %, at most 0.2 wt %, at most 0.1 wt %, or at most 0.01 wt %. In some embodiments, the water and alcohol content as combined in the solution is at most 10 wt %, at most 5 wt %, at most 4 wt %, at most 3 wt %, at most 2 wt %, at most 1 wt %, at most 0.5 wt %, at most 0.2 wt %, at most 0.1 wt %, or at most 0.01 wt %. In some embodiments, at least 1000 grams, at least 2000 grams, at least 2500 grams, or at least 5000 grams of the crystalline salt or co-crystal is prepared. In some embodiments, the solution comprises ethyl acetate. In some embodiments, the solution comprises acetone. In some embodiments, the solution comprises acetone, water, and ethyl acetate. In some embodiments, the solution comprises a mixture acetone and water. In some embodiments, the method comprises removing water through any means such as azeotropic drying, activated sieves, magnesium sulfate, sodium sulfate, or other drying agents. In some embodiments, the method comprises an azeotropic drying step to remove water. In some embodiments, the solution does not comprise water or alcohol. In some embodiments, the method comprises removing acetone by distillation for one or more times. In some embodiments, the method comprises removing acetone by distillation for one, two, three or more times. In some embodiments, the method comprises removing ethyl acetate by distillation for one or more times. In some embodiments, the method comprises removing ethyl acetate by distillation for one, two, three or more times. In some embodiments, the method comprises removing water by distillation of a solvent that has a lower boiling point than water. In some embodiments, the solvent comprises ethyl acetate, methyl ethyl ketone, 2-methyl butanone, acetone, tetrahydrofuran, 2-methyl-THF, isopropyl acetate, acetonitrile, or dichloromethane.

Phosphate Form J

Figure 66:
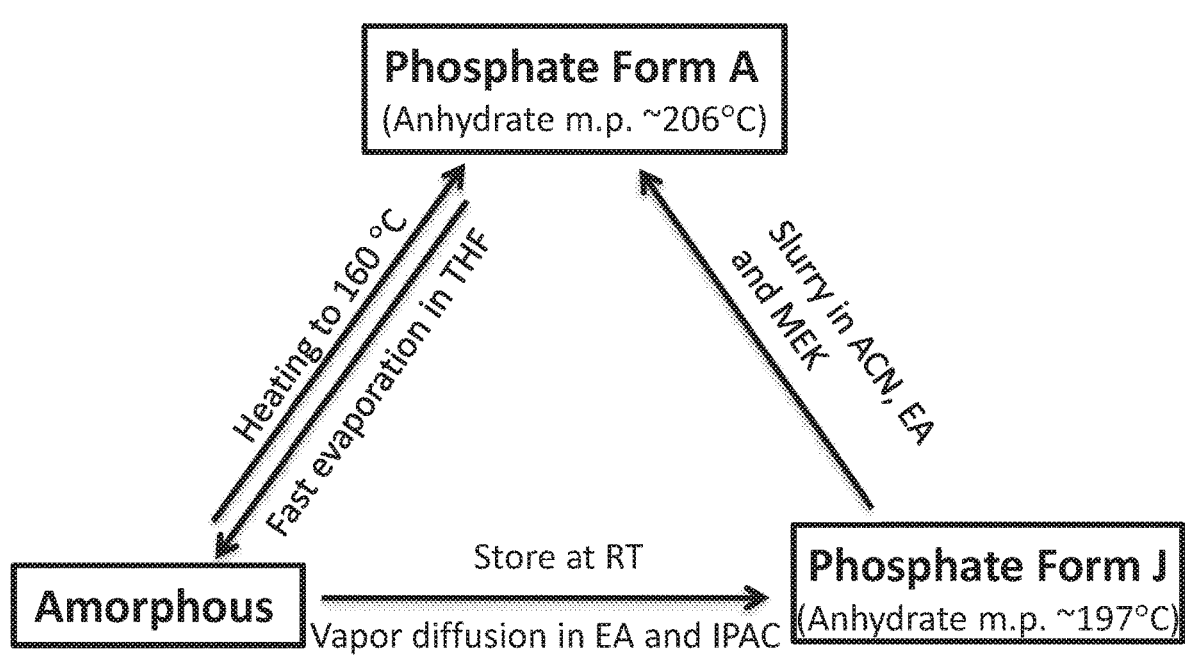
FIG. 66 illustrates the solid form conversion map between the amorphous form to Phosphate Form A and Phosphate Form J anhydrates.
Figure 67:
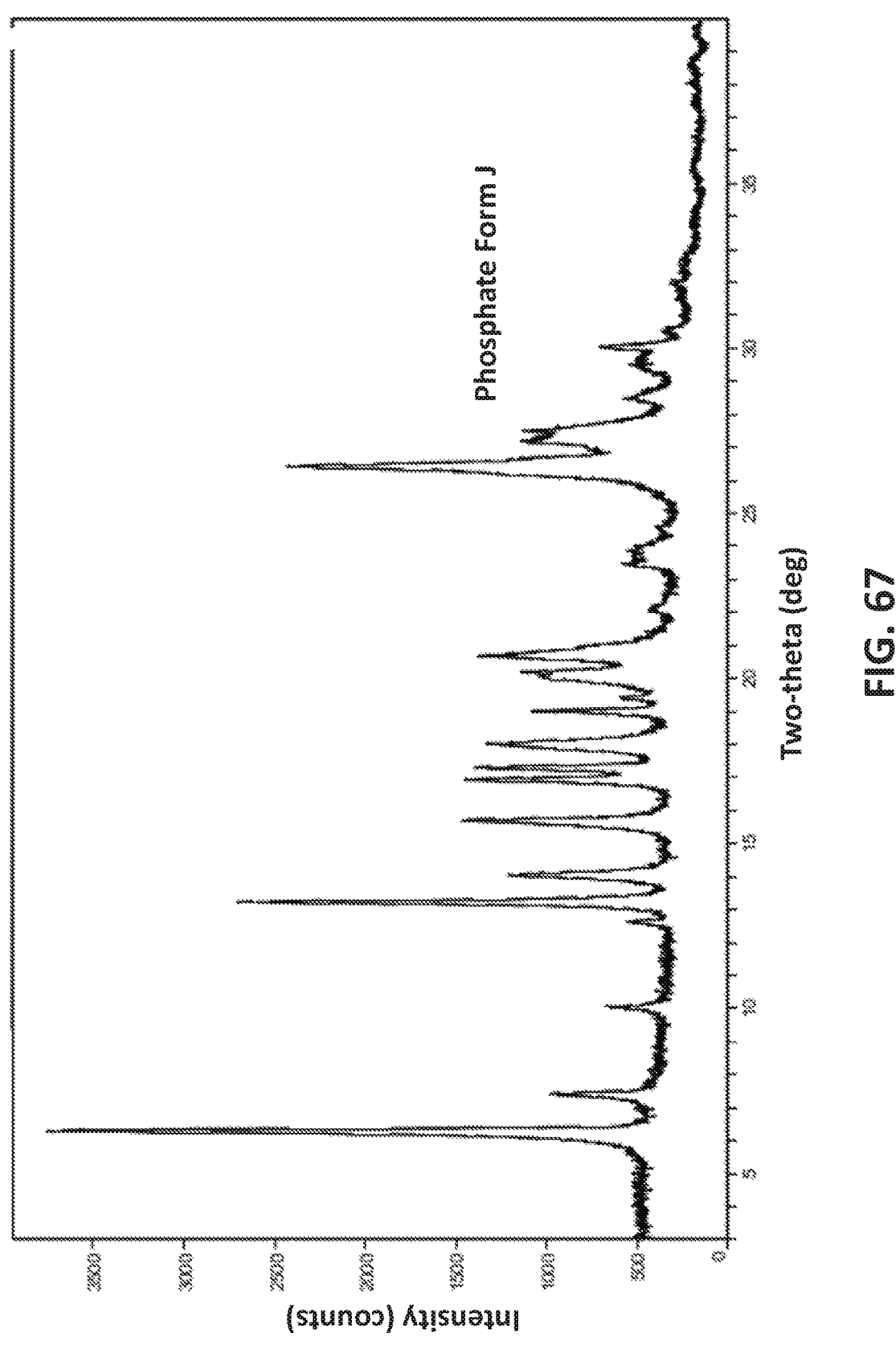
FIG. 67 illustrates the XRPD pattern of Phosphate Form J.

In one aspect, disclosed herein is a new crystalline form of the salt or co-crystal of 2',6-difluoro-5'-[3-(1-hydroxy-1-methylethyl)-imidazo[1,2-b][1,2,4]triazin-7-yl]biphenyl-2-carbonitrile with phosphoric acid ("Phosphate Polymorphic Form J"). Phosphate Polymorphic Form J can be isolated under vapor diffusion. In some embodiments, Phosphate Polymorphic Form J is an anhydrate. In some embodiments, Phosphate Polymorphic Form J comprises water and/or other solvent. In one or more embodiments, this crystal form is a salt. In one or more embodiments, this crystal form is a co-crystal. In some embodiments, the coformer is phosphoric acid. In some embodiments, Phosphate Polymorphic Form J displays birefringence under polarized light. In some embodiments, Phosphate Polymorphic Form J is isolated under vapor diffusion in ethyl acetate and/or isopropyl acetate as seen in FIG. 66. In some embodiments, Phosphate Polymorphic Form J (i.e., Phosphate Form J) exhibits an X-Ray Powder Diffraction (XRPD) pattern having characteristic peak locations of at least three, at least six, at least nine, or all values selected from the group consisting of: about 6.3, 13.2, 14.0, 15.7, 17.0, 17.3, 18.0, 20.2, 20.7, and 26.4±0.2 degrees, 2-theta, when measured using the parameters described in Table 35. In some embodiments, Phosphate Form J exhibits an XRPD pattern having characteristic peak locations of at least three, at least six, at least nine, or all values selected from the group consisting of: about 6.3, 7.4, 10.1, 12.6, 13.2, 14.0, 15.7, 17.0, 17.3, 18.0, 19.0, 20.2, 20.7, 26.4, 27.2, and 27.5±0.2 degrees, 2-theta, when measured using the parameters described in Table 35. In one or more embodiments, Phosphate Polymorphic Form J exhibits an XRPD pattern substantially the same as the XRPD pattern shown in FIG. 67.

Figure 68:
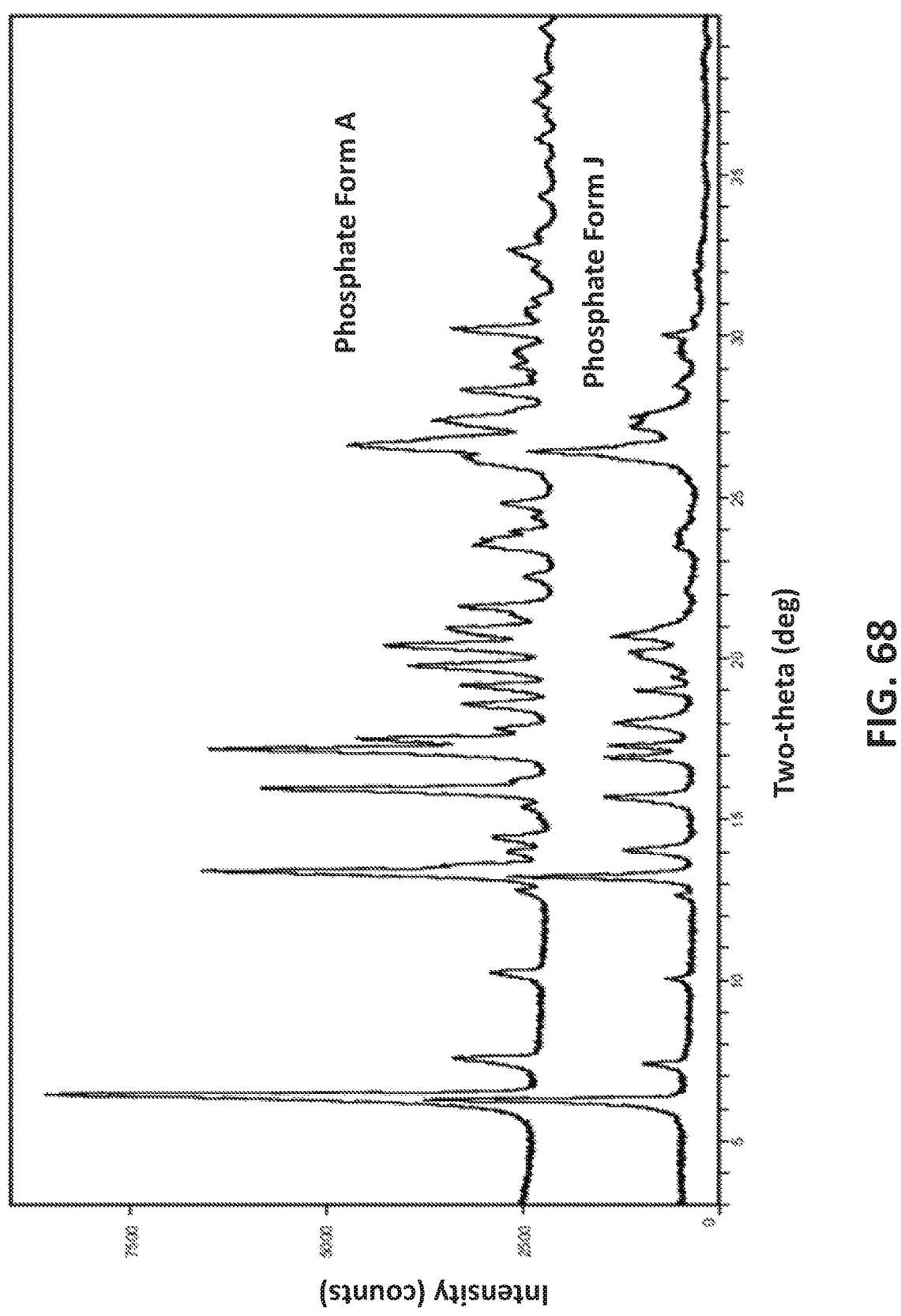
FIG. 68 illustrates the overlaid XRPD patterns of Phosphate Form A and Phosphate Form J.

In FIG. 68, the overlaid XRPD illustrates both Phosphate Forms A and J, when measured using the parameters described in Table 35. As illustrated in FIG. 68, Phosphate Forms A exhibits an XRPD pattern having characteristic peak locations of 6.5, 13.4, 16.0, 17.2, 17.5, 19.8, 20.4, 20.9, 21.6, and 26.6±0.2 degrees, 2-theta, when measured using the parameters described in Table 35. As illustrated in FIG. 68, Phosphate Forms J exhibits an XRPD pattern having characteristic peak locations of 6.3, 13.2, 14.0, 15.7, 17.0, 17.3, 18.0, 20.2, 20.7, and 26.4±0.2 degrees, 2-theta, when measured using the parameters described in Table 35.

In some embodiments, Phosphate Polymorphic Form J exhibits an XRPD pattern having a characteristic peak located at about 6.3±0.2 degrees, 2-theta. In some embodiments, Phosphate Polymorphic Form J exhibits an XRPD pattern having a characteristic peak located at about 7.4±0.2 degrees, 2-theta. In some embodiments, Phosphate Polymorphic Form J exhibits an XRPD pattern having a characteristic peak located at about 13.2±0.2 degrees, 2-theta. In some embodiments, Phosphate Polymorphic Form J exhibits an XRPD pattern having a characteristic peak located at about 14.0±0.2 degrees, 2-theta. In some embodiments, Phosphate Polymorphic Form J exhibits an XRPD pattern having a characteristic peak located at about 15.7±0.2 degrees, 2-theta. In some embodiments, Phosphate Polymorphic Form J exhibits an XRPD pattern having a characteristic peak located at about 17.0±0.2 degrees, 2-theta. In some embodiments, Phosphate Polymorphic Form J exhibits an XRPD pattern having a characteristic peak located at about 17.3±0.2 degrees, 2-theta. In some embodiments, Phosphate Polymorphic Form J exhibits an XRPD pattern having a characteristic peak located at about 18.0±0.2 degrees, 2-theta. In some embodiments, Phosphate Polymorphic Form J exhibits an XRPD pattern having a characteristic peak located at about 19.0±0.2 degrees, 2-theta. In some embodiments, Phosphate Polymorphic Form J exhibits an XRPD pattern having a characteristic peak located at about 20.2±0.2 degrees, 2-theta. In some embodiments, Phosphate Polymorphic Form J exhibits an XRPD pattern having a characteristic peak located at about 20.7±0.2 degrees, 2-theta. In some embodiments, Phosphate Polymorphic Form J exhibits an XRPD pattern having a characteristic peak located at about 26.4±0.2 degrees, 2-theta. In some embodiments, the XRPD patterns of Phosphate Polymorphic Form J is measured using the parameters described in Table 35.

In some embodiments, Phosphate Polymorphic Form J exhibits an XRPD pattern lacking a characteristic peak located at about 21.6±0.2 degrees, 2-theta. In some embodiments, Phosphate Polymorphic Form J exhibits an XRPD pattern lacking a characteristic peak located at about 17.8±0.2 degrees, 2-theta. In some embodiments, Phosphate Polymorphic Form J exhibits an XRPD pattern lacking a characteristic peak located at about 18.6±0.2 degrees, 2-theta. In some embodiments, Phosphate Polymorphic Form J exhibits an XRPD pattern lacking a characteristic peak located at about 14.4±0.2 degrees, 2-theta. In some embodiments, the XRPD patterns of Phosphate Polymorphic Form J is measured using the parameters described in Table 35.

In some embodiments, Phosphate Polymorphic Form J is a metastable form. In some embodiments, Phosphate Polymorphic Form J convert easily to Phosphate Polymorphic Form A. In some embodiments, Phosphate Polymorphic Form J can be stored at various temperatures and relative humidities. For example, Phosphate Polymorphic Form J can be stored at about −20° C., about −10° C., about 0° C., about 5° C., about 15° C., about 25° C., about 40° C., and about 60° C. For another example, Phosphate Polymorphic Form J can be stored at 10% RH, 20% RH, 30% RH, 40% RH, 50% RH, 60% RH, 75% RH, or 90% RH. In some embodiments, Phosphate Polymorphic Form J can be stored at no higher than 10% RH, 20% RH, 30% RH, or 40% RH. In some embodiments, Phosphate Polymorphic Form J is stable at about 25° C. for at least 7 days, at least 14 days, at least 21 days, at least a month, at least 2 months, at least 3 months, at least 6 months, at least 9 months, or at least 12 months. In some embodiments, Phosphate Polymorphic Form J is stable at about 25° C. for at least 1 month. In some embodiments, Phosphate Polymorphic Form J is stable at about 40° C. for at least 3 days, at least 7 days, at least 14 days, at least 21 days, at least a month, at least 2 months, at least 3 months, at least 6 months, at least 9 months, or at least 12 months. In some embodiments, Phosphate Polymorphic Form J is stable at about 60° C. for at least 3 days, at least 7 days, at least 14 days, at least 21 days, at least a month, at least two months, at least 6 months, or at least 12 months. In some embodiments, a stable Phosphate Polymorphic Form J has about 80%, 85%, 90%, 91%, 92%, 93%, 94%, 95%, 96%, 97%, 98%, 99% w/w or greater of the initial phosphate salt amount at the end of the given storage period. In some embodiments, a sample of Phosphate Polymorphic Form J has about 95% w/w or greater of the initial phosphate salt amount at the end of the given storage period. In some embodiments, a sample Phosphate Polymorphic Form J has about 20%, 15%, 10%, 5%, 2%, 1% w/w or less total impurity or related substances at the end of the given storage period. In some embodiments, Phosphate Polymorphic Form J provides an XRPD pattern substantially the same post-storage at about 25° C. and 40% RH for at least a week. In some embodiments, Phosphate Polymorphic Form J provides an XRPD pattern substantially the same post-storage at about 25° C. and 40% RH for at least two weeks. In some embodiments, Phosphate Polymorphic Form J provides an XRPD pattern substantially the same post-storage at about 25° C. and 40% RH for at least a month.

Figure 69:
FIG. 69 illustrates the TGA and DSC thermograms of Phosphate Form J.
Figure 70:
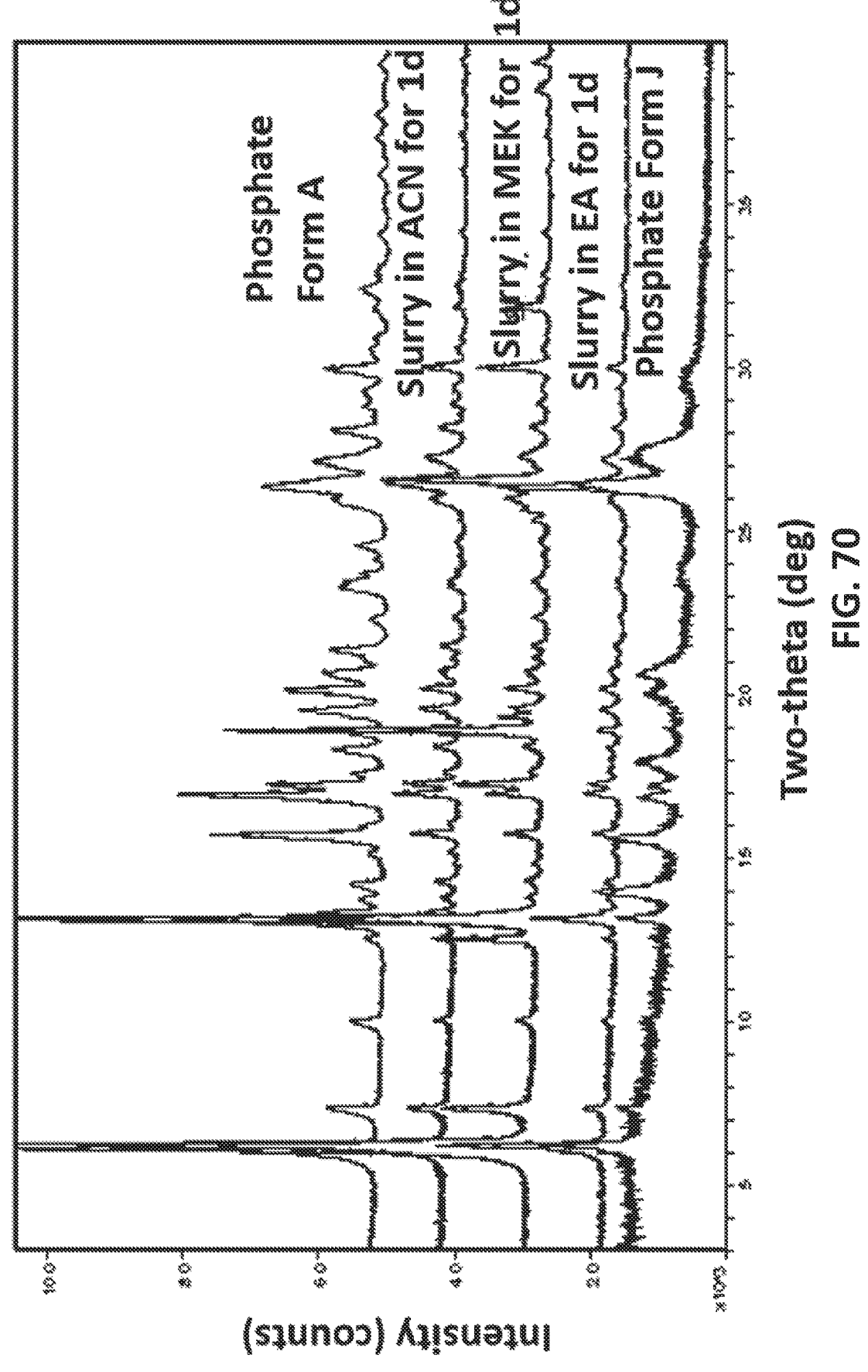
FIG. 70 illustrates the overlaid XRPD of Phosphate Form J converting to Phosphate Form A from slurry.

In one or more embodiments, Phosphate Polymorphic Form J has a melting range of from about 197 to 200° C. as seen in FIG. 69. In some embodiments, Phosphate Polymorphic Form J has a melting range of from about 195 to 202° C. In some embodiments, Phosphate Polymorphic Form J has a melting range of from about 192 to 205° C. In one or more embodiments, Phosphate Polymorphic Form J exhibits a differential scanning calorimetry (DSC) thermogram comprising an endothermic peak at about 197° C. In one or more embodiments, Phosphate Polymorphic Form J provides a DSC thermogram comprising an endothermic peak at about 198° C. In one or more embodiments, Phosphate Polymorphic Form J provides a DSC thermogram comprising an endothermic peak at about 199° C. In one or more embodiments, Phosphate Polymorphic Form J provides a DSC thermogram comprising an endothermic peak at about 200° C. In one or more embodiments, Phosphate Polymorphic Form J provides a DSC thermogram comprising an endothermic peak at about 201° C. In one or more embodiments, Phosphate Polymorphic Form J provides a DSC thermogram comprising an endothermic peak at about 202° C. In one or more embodiments, Phosphate Polymorphic Form J provides a DSC thermogram comprising an endothermic peak at about 198° C. to 202° C. In one or more embodiments, Phosphate Polymorphic Form J provides a DSC thermogram comprising an endothermic peak at about 195° C. to 205° C. In some embodiments, Phosphate Polymorphic Form J provides a DSC thermogram comprising a single endothermic peak with an onset temperature of 195° C. In some embodiments, Phosphate Polymorphic Form J provides a DSC thermogram comprising a single endothermic peak with an onset temperature of 196° C. In some embodiments, Phosphate Polymorphic Form J provides a DSC thermogram comprising a single endothermic peak with an onset temperature of 197° C. In some embodiments, Phosphate Polymorphic Form J provides a DSC thermogram comprising a single endothermic peak with an onset temperature of 198° C. In some embodiments, Phosphate Polymorphic Form J provides a DSC thermogram comprising a single endothermic peak with an onset temperature of 199° C. In some embodiments, Phosphate Polymorphic Form J provides a DSC thermogram comprising a single endothermic peak with an onset temperature of 195° C. to 199° C. In some embodiments, Phosphate Polymorphic Form J provides a DSC thermogram comprising a single endothermic peak with an onset temperature of 192° C. to 202° C. In some embodiments, Phosphate Polymorphic Form J provides a DSC thermogram comprising a single endothermic peak with an onset temperature of 197° C. and a peak temperate of 200° C. In one or more embodiments, Phosphate Polymorphic Form J exhibits a DSC thermogram substantially the same as the DSC thermogram shown in FIG. 69. This melting point is obtained using DSC with a heating rate of 10° C./min.

Phosphate Polymorphic Form J can be synthesized using the method described in Example 62 and Example 69. In one or more embodiments, pharmaceutical compositions comprising the Phosphate Polymorphic Form J are described. In one or more embodiments, the disclosure includes purified forms of the crystalline Phosphate Polymorphic Form J.

In one or more embodiments, the Phosphate Polymorphic Form J described herein is at least 500%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, or at least 99.9% pure, as measured by HPLC as described herein. In one or more embodiments, the Phosphate Polymorphic Form J described herein is at least 95% pure, as measured by HPLC as described herein. In some embodiment, the Phosphate Polymorphic Form J described herein comprises an impurity. In some embodiments, the impurity in Phosphate Polymorphic Form J is at most 0.1%, at most 0.5%, at most 1%, at most 2%, at most 3%, at most 4%, at most 5%, at most 6%, at most 7%, at most 8%, at most 9%, at most 10%, at most 15%, at most 20%, at most 25%, at most 30%, at most 40%, or at most 50%, as measured by HPLC as described herein. In some embodiments, the impurity in Phosphate Polymorphic Form J is at most 5% impurity.

Phosphate Polymorphic Form J can have a higher solubility than a free base form of TPA023B. For example, the solubility can be determined as described in Example 15. In some embodiments, the solubility of Phosphate Polymorphic Form J is at least 1.1 fold, 1.5 fold, 2 fold, 3 fold, 4 fold, 5 fold, 6 fold, 7 fold, or 8 fold higher than the solubility of Free Base Form A in simulated gastric fluid (SGF). In some embodiments, the solubility of Phosphate Polymorphic Form J is at least 1.1 fold, 1.5 fold, 2 fold, 3 fold, 4 fold, 5 fold, 6 fold, 7 fold, or 8 fold higher than the solubility of Free Base Form A in Fasted-state simulated intestinal fluid (FaSSIF). In some embodiments, the solubility of Phosphate Polymorphic Form J is at least 1.1 fold, 1.5 fold, 2 fold, 3 fold, 4 fold, 5 fold, 6 fold, 7 fold, or 8 fold higher than the solubility of Free Base Form A in Fed-state simulated intestinal fluid (FeSSIF) than Free Base Polymorphic Form A.

In one aspect, disclosed herein is a method for preparing a crystalline salt or co-crystal of Phosphate Polymorphic Form J. In some embodiments, the method for preparing a crystalline salt or co-crystal of Phosphate Polymorphic Form J comprises converting an amorphous salt of 2',6-difluoro-5'-[3-(1-hydroxy-1-methylethyl)-imidazo[1,2-b][1,2,4]triazin-7-yl]biphenyl-2-carbonitrile with phosphoric acid into Form J. In some embodiments, the conversion occurs through drying at room temperature. In some embodiments, the conversion occurs through solid-vapor diffusion. In some embodiments, the method of forming the amorphous salt of 2',6-difluoro-5'-[3-(1-hydroxy-1-methylethyl)-imidazo[1,2-b][1,2,4]triazin-7-yl]biphenyl-2-carbonitrile with phosphoric acid is rotary evaporating Polymorphic Phosphate Form A in a solvent such as THF. In some embodiments, the method of crystallizing Polymorphic Form J comprises drying an amorphous salt of 2',6-difluoro-5'-[3-(1-hydroxy-1-methylethyl)-imidazo[1,2-b][1,2,4]triazin-7-yl]biphenyl-2-carbonitrile with phosphoric acid solution. In some embodiments, the amorphous salt of 2',6-difluoro-5'-[3-(1-hydroxy-1-methylethyl)-imidazo[1,2-b][1,2,4]triazin-7-yl]biphenyl-2-carbonitrile with phosphoric acid solution comprises an amorphous salt of 2',6-difluoro-5'-[3-(1-hydroxy-1-methylethyl)-imidazo[1,2-b][1,2,4]triazin-7-yl]biphenyl-2-carbonitrile with phosphoric acid and a solvent. In some embodiments, the solvent used to dissolve the amorphous salt of 2',6-difluoro-5'-[3-(1-hydroxy-1-methylethyl)-imidazo[1,2-b][1,2,4]triazin-7-yl]biphenyl-2-carbonitrile with phosphoric acid is THF.

In some embodiments, a method of preparing a crystalline salt or co-crystal of Phosphate Polymorphic Form J comprises crystalizing Phosphate Polymorphic Form J from a solution. In some embodiments, the solution comprises one or more of: ethyl acetate, methyl ethyl ketone, water, tetrahydrofuran (THF), isopropyl acetate (IPAC), and acetonitrile. In some embodiments, the solution comprises ethyl acetate. In some embodiments, the solution comprises methyl ethyl ketone. In some embodiments, the solution comprises THF. In some embodiments, the solution comprises IPAC. In some embodiments, the solution comprises acetonitrile. In some embodiments, the solution comprises a low level of water and/or alcohol. For example, in some embodiments, the water content in the solution is at most 10 wt %, at most 5 wt %/o, at most 4 wt %, at most 3 wt %, at most 2 wt %, at most 1 wt %, at most 0.5 wt %, at most 0.2 wt %, at most 0.1 wt %, or at most 0.01 wt %. In some embodiments, the water and alcohol content as combined in the solution is at most 10 wt %, at most 5 wt %, at most 4 wt %, at most 3 wt %, at most 2 wt %, at most 1 wt %, at most 0.5 wt %, at most 0.2 wt %, at most 0.1 wt %, or at most 0.01 wt %. In some embodiments, at least 1000 grams, at least 2000 grams, at least 2500 grams, or at least 5000 grams of the crystalline salt or co-crystal is prepared. In some embodiments, the solvent comprises ethyl acetate, methyl ethyl ketone, acetone, tetrahydrofuran, isopropyl acetate, acetonitrile, or a combination thereof.

In some embodiments, a method of crystallizing Phosphate Polymorphic Form J comprises subjecting an amorphous salt of 2',6-difluoro-5'-[3-(1-hydroxy-1-methylethyl)-imidazo[1,2-b][1,2,4]triazin-7-yl]biphenyl-2-carbonitrile with phosphoric acid to solid-vapor diffusion. In some embodiments, the solid-vapor diffusion is performed at RT. In some embodiments, the solid-vapor diffusion is performed at 20° C. to 25° C. In some embodiments, the solid-vapor diffusion is performed at about 10° C., 15° C., 20° C., 25° C., or 30° C. In some embodiments, the solid-vapor diffusion is performed for a period of 2 hours to 2 weeks, or any ranges therebetween. In some embodiments, the solid-vapor diffusion is performed for a period of 12 hours to 3 days or 12 hours to 2 days. In some embodiments, the solid-vapor diffusion is performed for a period of 1 day, 2 days, 3 days, 4 days or 5 days. In some embodiments, the solid-vapor diffusion is performed for a period of 1 day. In some embodiments, the solid-vapor diffusion is performed for a period of 1 to 3 days. In some embodiments, the solid-vapor diffusion is performed according to a procedure of Example 62. In some embodiments, the solvent used for solid-vapor diffusion is IPAC or ethyl acetate. In some embodiments, the solvent used for solid-vapor diffusion is methyl acetate. In some embodiments, the solvent used for solid-vapor diffusion is MEK. In some embodiments, a method of crystallizing Phosphate Polymorphic Form J comprises storing an amorphous salt of 2',6-difluoro-5'-[3-(1-hydroxy-1-methylethyl)-imidazo[1,2-b][1,2,4]triazin-7-yl]biphenyl-2-carbonitrile with phosphoric acid in a desiccator at room temperature. In some embodiments, a method of crystallizing Phosphate Polymorphic Form J comprises mechanical grinding of an amorphous salt of 2',6-difluoro-5'-[3-(1-hydroxy-1-methylethyl)-imidazo[1,2-b][1,2,4]triazin-7-yl]biphenyl-2-carbonitrile with phosphoric acid in a solvent. In some embodiments, the solvent used for grinding is acetonitrile or ethyl acetate. In some embodiments, the solvent used of grinding is acetonitrile. In some embodiments, the solve used for grinding is ethyl acetate.

Phosphate Patterns

In some embodiments, described herein is a mixture comprising crystalline polymorph of the salt or co-crystal of 2',6-difluoro-5'-[3-(1-hydroxy-1-methylethyl)-imidazo[1,2-b][1,2,4]triazin-7-yl]biphenyl-2-carbonitrile with phosphoric acid. This crystalline polymorph mixture is designated "Phosphate Polymorphic Pattern B" (i.e., phosphate Pattern B) and exhibits an XRPD pattern having characteristic peak locations of at least three, at least six, at least nine, at least twelve, at least fifteen or all values selected from the group consisting of about: 6.3, 7.0, 8.0, 9.4, 10.9, 12.7, 13.2, 14.0, 14.7, 16.1, 17.3, 19.4, 19.7, 22.1, 24.1, 24.3, 26.6, 27.0, and 28.2±0.2-degrees, 2-theta, when measured using the parameters described in Table 1. TPA023B Phosphate Polymorphic Pattern B can comprise TPA023B phosphate Form A. Phosphate Polymorphic Pattern B can also comprise Phosphate Pattern G. In one or more embodiments, Phosphate Polymorphic Pattern B exhibits an XRPD pattern substantially the same as the XRPD pattern shown in FIG. 3. In one or more embodiments, Phosphate Polymorphic Pattern B has a melting/dehydration/desolvation range of from about 80° C. to about 205° C. In one or more embodiments, Phosphate Polymorphic Pattern B exhibits a DSC thermogram comprising endothermic peaks at about 193 and 203° C. In one or more embodiments, Phosphate Polymorphic Pattern B exhibits a DSC thermogram substantially the same as the DSC thermogram shown in FIG. 4A. In one or more embodiments, Phosphate Polymorphic Pattern B can be synthesized using the method of Example 6. In one or more embodiments, pharmaceutical compositions comprising the Phosphate Polymorphic Pattern B are described.

Figure 30:
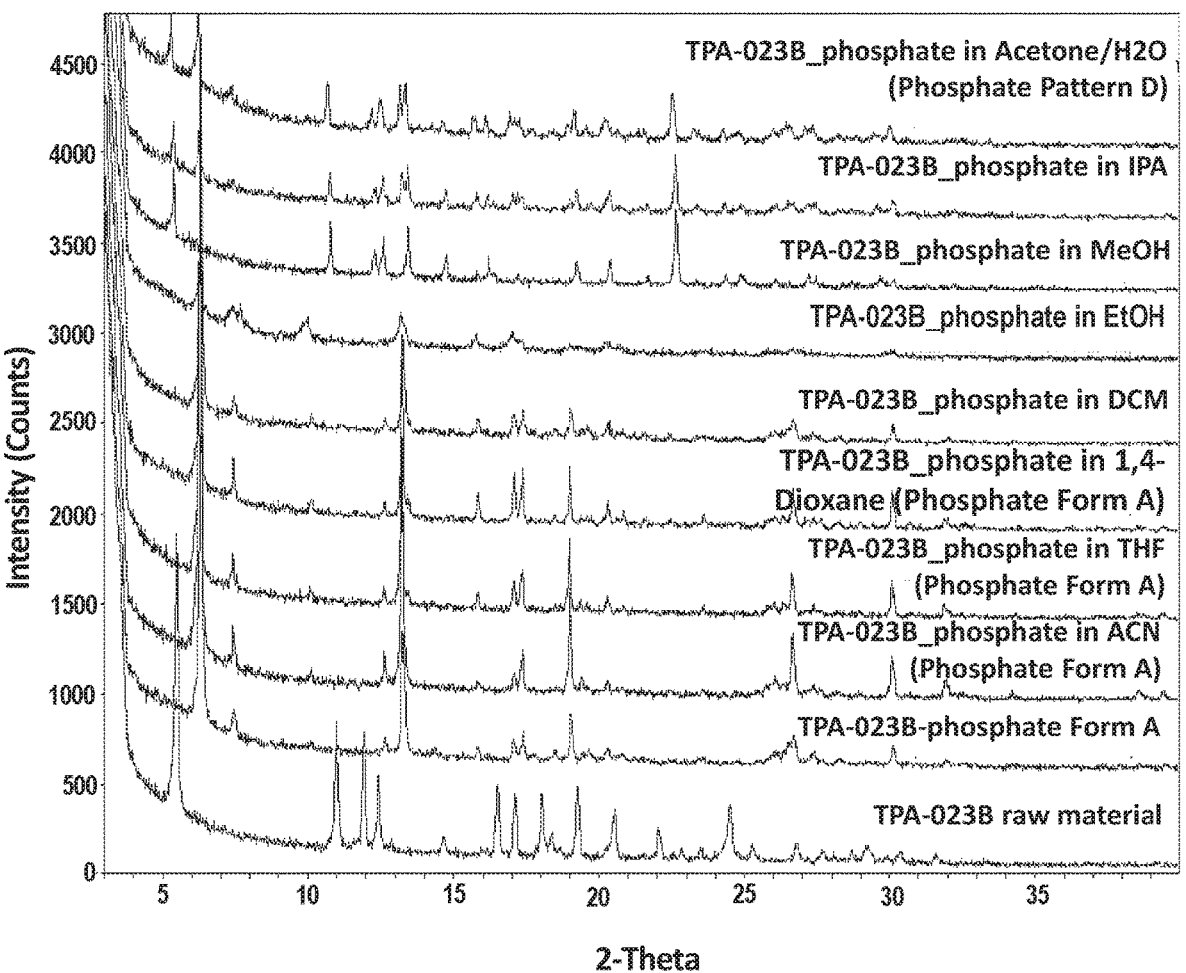
FIG. 30 illustrates XRPD patterns of TPA023B phosphate solids obtained by polymorph screening using the heat-cooling method

In some embodiments, described herein is another mixture comprising crystalline polymorph of the salt or co-crystal of 2',6-difluoro-5'-[3-(1-hydroxy-1-methylethyl)-imidazo[1,2-b][1,2,4]triazin-7-yl]biphenyl-2-carbonitrile with phosphoric acid. This crystalline polymorph mixture is designated "Phosphate Polymorphic Pattern D" (i.e., phosphate Pattern D) and exhibits an XRPD pattern having characteristic peak locations of at least three, at least six, at least nine, at least twelve, at least fifteen or all values selected from the group consisting of about: 5.3, 6.3, 7.4, 10.8, 12.2, 12.6, 13.1, 13.3, 14.6, 15.8, 16.0, 16.9, 17.1, 18.9, 19.0, 19.4, 20.1, 22.5, 23.1, 24.3, 24.9, 26.0, 26.5, 27.2, 29.5 and 30.0±0.2-degrees, 2-theta, when measured using the parameters described in Table 1. TPA023B Phosphate Polymorphic Pattern D can comprise TPA023B phosphate Form A. TPA023B Phosphate Polymorphic Pattern D can also comprise TPA023B Free Base Form C. In one or more embodiments, Phosphate Polymorphic Pattern D exhibits an XRPD pattern substantially the same as the XRPD pattern labelled Phosphate Pattern D as shown in FIG. 30. In one or more embodiments, Phosphate Polymorphic Pattern D has a melting/dehydration/desolvation range of from about 30° C. to about 150° C. In one or more embodiments, Phosphate Polymorphic Pattern D exhibits a DSC thermogram comprising an endothermic peak at about 202° C. In one or more embodiments, Phosphate Polymorphic Pattern D exhibits a DSC thermogram substantially the same as the DSC thermogram shown in FIG. 31. In one or more embodiments, Phosphate Polymorphic Pattern D can be synthesized using the method described in Example 27. In one or more embodiments, pharmaceutical compositions comprising the Phosphate Polymorphic Pattern D are described.

In one or more embodiments, a mixture comprising crystalline polymorph of the salt or co-crystal of 2',6-difluoro-5'-[3-(1-hydroxy-1-methylethyl)-imidazo[1,2-b][1,2,4]triazin-7-yl]biphenyl-2-carbonitrile with phosphoric acid is described. This crystalline polymorph mixture is designated "Phosphate Polymorphic Pattern E" and exhibits an XRPD pattern having characteristic peak locations of at least three, at least six, at least nine, at least twelve, or all values selected from the group consisting of about: 6.4, 7.6, 13.0, 13.3, 15.5, 15.8, 17.0, 17.4, 19.1, 19.5, 20.3, 20.7, 26.8, and 30.1±0.2-degrees, 2-theta, when measured using the parameters described in Table 1. TPA023B Phosphate Polymorphic Pattern E is likely a mixture comprising TPA023B phosphate Form A. In one or more embodiments, Phosphate Polymorphic Pattern E exhibits an XRPD pattern substantially the same as the XRPD pattern shown in FIG. 7. In one or more embodiments, Phosphate Polymorphic Pattern E has a melting/dehydration/desolvation range from about 60° C. to about 95° C. In one or more embodiments, Phosphate Polymorphic Pattern E exhibits a DSC thermogram comprising an endothermic peak at about 191° C. In one or more embodiments, Phosphate Polymorphic Pattern E exhibits a DSC thermogram comprising an endothermic peak at about 199° C. In one or more embodiments, Phosphate Polymorphic Pattern E exhibits a DSC thermogram substantially the same as the DSC thermogram shown in FIG. 8. This melting point is obtained using DSC with a heating rate of 10° C./min. In one or more embodiments, Phosphate Polymorphic Pattern E can be synthesized using the method of Example 8. In one or more embodiments, pharmaceutical compositions comprising the Phosphate Polymorphic Pattern E are described.

In one or more embodiments, a mixture comprising crystalline polymorph of the free base, the salt or co-crystal of 2',6-difluoro-5'-[3-(1-hydroxy-1-methylethyl)-imidazo[1,2-b][1,2,4]triazin-7-yl]biphenyl-2-carbonitrile with phosphoric acid is identified and designated as "Phosphate Polymorphic Pattern F" (i.e., Phosphate Pattern F). It is likely that Phosphate Polymorphic Pattern F mainly comprises TPA023B free base. Phosphate Polymorphic Pattern F exhibits an XRPD pattern substantially the same as the XRPD pattern labelled Pattern F in FIG. 37A. In one or more embodiments, Phosphate Polymorphic Pattern F exhibits a DSC thermogram substantially the same as FIG. 39. In one or more embodiments, Phosphate Polymorphic Pattern F has a melting/desolvation/dehydration range of about 75° C. to about 115° C. In one or more embodiments, Phosphate Polymorphic Pattern F exhibits a DSC thermogram comprising an endothermic peak at about 104° C. In one or more embodiments, Phosphate Polymorphic Pattern F exhibits a DSC thermogram comprising an endothermic peak at about 194° C. In one or more embodiments, Phosphate Polymorphic Pattern F provides a DSC thermogram comprising an endothermic peak at about 205° C. In one or more embodiments, Phosphate Polymorphic Pattern F exhibits a DSC thermogram comprising three endothermic peaks, at about 104° C., 194° C., and 205° C. Phosphate Polymorphic Pattern F can be synthesized using the method described in Example 33. In one or more embodiments, pharmaceutical compositions comprising the Phosphate Polymorphic Pattern F are described. In one or more embodiments, the disclosure includes purified forms of the crystalline Phosphate Polymorphic Pattern F.

In one or more embodiments, a mixture comprising crystalline polymorph of the free base, the salt or co-crystal of 2',6-difluoro-5'-[3-(1-hydroxy-1-methylethyl)-imidazo[1,2-b][1,2,4]triazin-7-yl]biphenyl-2-carbonitrile with phosphoric acid is identified and designated as "Phosphate Polymorphic Pattern G" (i.e., Phosphate Pattern G). It is likely that Phosphate Polymorphic Pattern G mainly comprises TPA023B free base. Phosphate Polymorphic Pattern G exhibits an XRPD pattern substantially the same as the XRPD pattern labelled Pattern G in FIG. 37A. In one or more embodiments, Phosphate Polymorphic Pattern G exhibits a DSC thermogram substantially the same as FIG. 40. In one or more embodiments, Phosphate Polymorphic Pattern G has a melting/desolvation/dehydration range of from about 95° C. to about 115° C. In one or more embodiments, Phosphate Polymorphic Pattern G exhibits a DSC thermogram comprising an endothermic peak at about 108° C. In one or more embodiments, Phosphate Polymorphic Pattern G exhibits a DSC thermogram comprising an endothermic peak at about 194° C. In one or more embodiments, Phosphate Polymorphic Pattern G exhibits a DSC thermogram comprising an endothermic peak at about 205° C. In one or more embodiments, Phosphate Polymorphic Pattern G exhibits a DSC thermogram comprising three endothermic peaks, at about 108° C., 194° C., and 205° C. Phosphate Polymorphic Pattern G can be synthesized using the method described in Example 33. In one or more embodiments, pharmaceutical compositions comprising the Phosphate Polymorphic Pattern G are described. In one or more embodiments, the disclosure includes purified forms of the crystalline Phosphate Polymorphic Pattern G.

In one or more embodiments, a mixture comprising crystalline polymorph of the free base, the salt or co-crystal of 2',6-difluoro-5'-[3-(1-hydroxy-1-methylethyl)-imidazo[1,2-b][1,2,4]triazin-7-yl]biphenyl-2-carbonitrile with phosphoric acid is identified and designated as "Phosphate Polymorphic Pattern H" (i.e., Phosphate Pattern H). It is likely that Phosphate Polymorphic Pattern H mainly comprises TPA023B free base. Phosphate Polymorphic Pattern H exhibits an XRPD pattern substantially the same as the XRPD pattern labelled Pattern H in FIG. 37A. In one or more embodiments, Phosphate Polymorphic Pattern H exhibits a DSC thermogram substantially the same as FIG. 41. In one or more embodiments, Phosphate Polymorphic Pattern H has a melting range of about 185° C. to about 210° C. In one or more embodiments, Phosphate Polymorphic Pattern H has a melting range of about 185° C. to about 195° C. In one or more embodiments, Phosphate Polymorphic Pattern H exhibits a DSC thermogram comprising an endothermic peak at about 194° C. In one or more embodiments, Phosphate Polymorphic Pattern H exhibits a DSC thermogram comprising an endothermic peak at about 205° C. In one or more embodiments, Phosphate Polymorphic Pattern H exhibits a DSC thermogram comprising two endothermic peaks, at about 194° C. and 205° C. In some embodiments, Phosphate Polymorphic Pattern H can be synthesized using the method described in Example 33. In one or more embodiments, pharmaceutical compositions comprising the Phosphate Polymorphic Pattern H are described. In one or more embodiments, the disclosure provides purified forms of the crystalline Phosphate Polymorphic Pattern H.

Tosylate

Figure 17A:
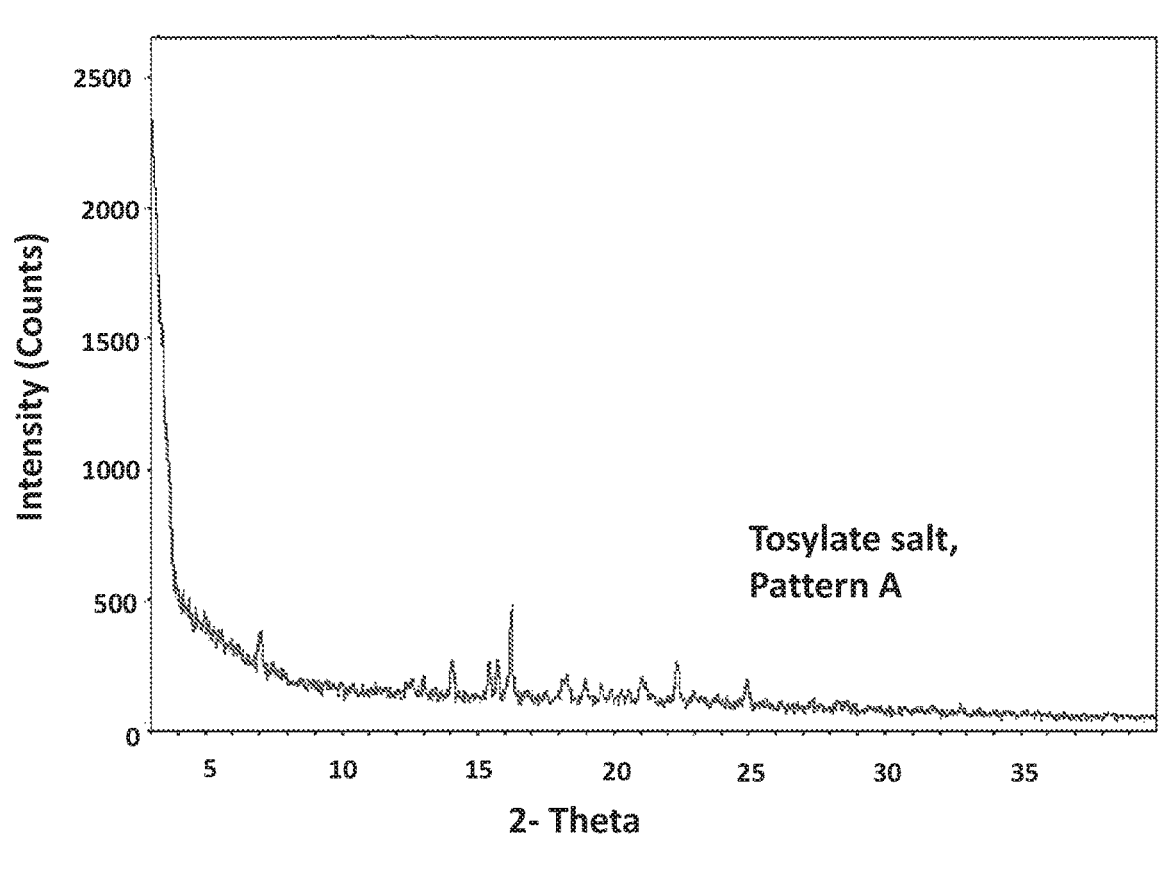
FIG. 17A and FIG. 17B illustrate an XRPD pattern for TPA023B tosylate Form A (FIG. 17A); and an NMR spectrum of TPA023B tosylate Form A (FIG. 17B)
Figure 18:
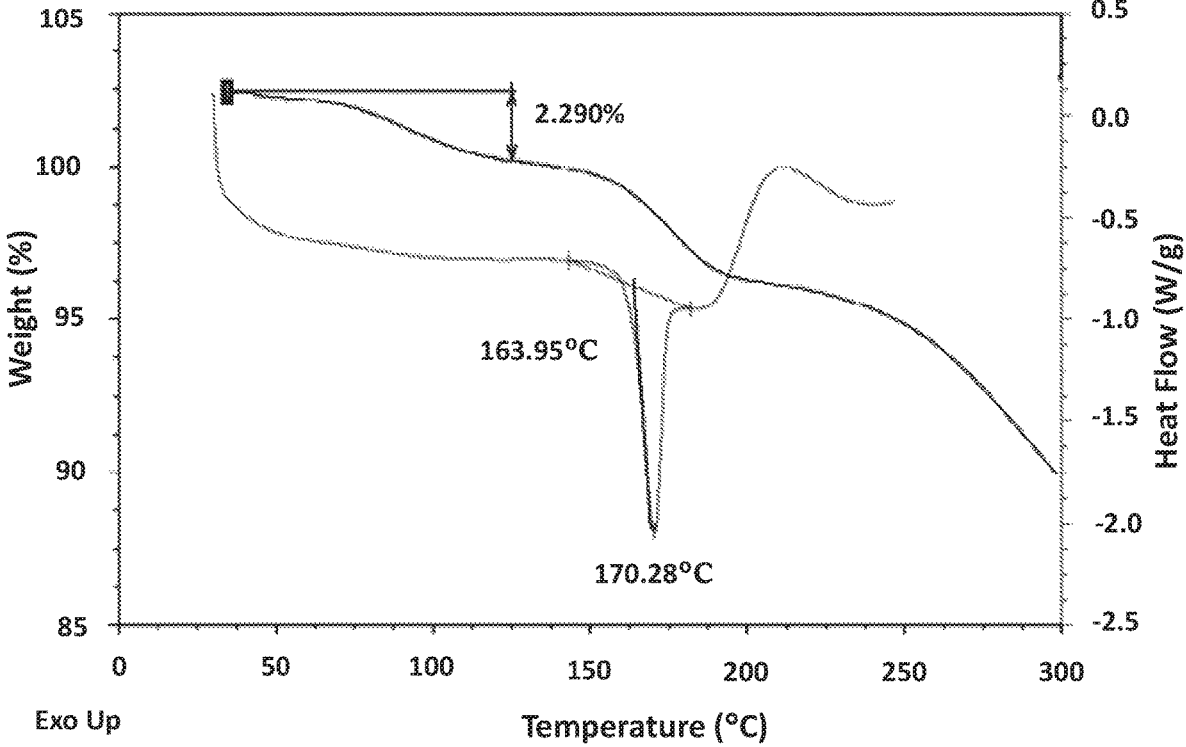
FIG. 18 illustrates a DSC/TGA thermogram for TPA023B tosylate Form A

In one or more embodiments, a crystalline polymorph of the salt of 2',6-difluoro-5'-[3-(1-hydroxy-1-methylethyl)-imidazo[1,2-b][1,2,4]triazin-7-yl]biphenyl-2-carbonitrile with p-toluenesulfonic acid is also described. This crystalline polymorph is designated "Tosylate Polymorphic Form A" (i.e., Tosylate Form A) and exhibits an XRPD pattern having characteristic peak locations of at least three, at least six, at least nine, at least twelve, at least fifteen or all values selected from the group consisting of: about: 7.0, 12.4, 12.6, 13.0, 14.1, 15.4, 15.7, 16.3, 17.5, 18.3, 19.0, 21.0, 22.3, 23.0, 24.9, and ±0.2-degrees, 2-theta, when measured using the parameters described in Table 1. In one or more embodiments, Tosylate Polymorphic Form A exhibits an XRPD pattern substantially the same as the XRPD pattern shown in FIG. 17A. In one or more embodiments, Tosylate Polymorphic Form A exhibits an XRPD pattern substantially the same as the XRPD pattern shown in FIG. 55. In one or more embodiments, Tosylate Polymorphic Form A has a melting range of from about 155° C. to about 175° C. In one or more embodiments, Tosylate Polymorphic Form A exhibits a DSC thermogram comprising an endothermic peak at about 170° C. In one or more embodiments, Tosylate Polymorphic Form A exhibits a DSC thermogram substantially the same as the DSC thermogram shown in FIG. 18. This melting point is obtained using DSC with a heating rate of 10° C./min. In some embodiments, Tosylate Polymorphic Form A can be synthesized using the method of Example 9. In one or more embodiments, pharmaceutical compositions comprising the Tosylate Polymorphic Form A are described. In one or more embodiments, the disclosure provides purified forms of the crystalline Tosylate Polymorphic Form A.

Free Base

Figure 9:
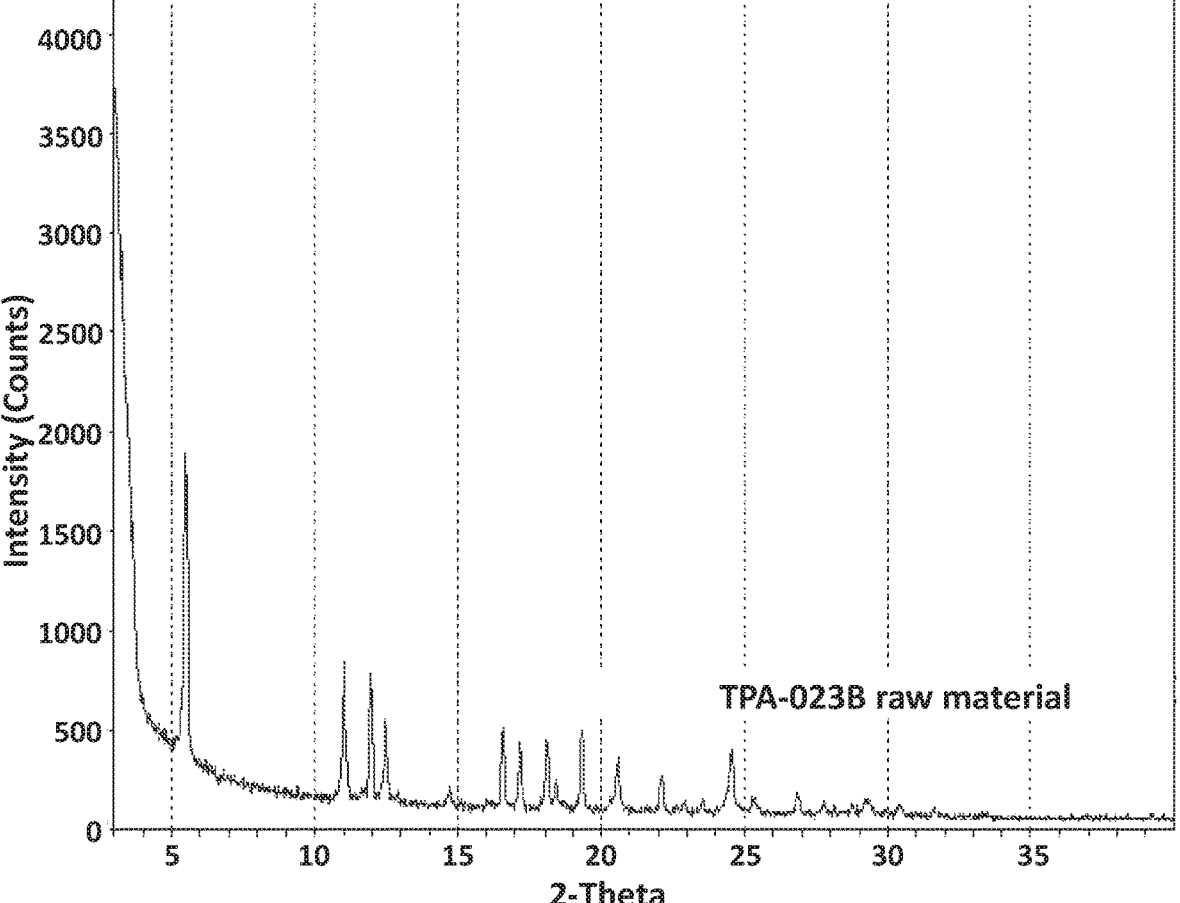
FIG. 9 illustrates an XRPD pattern for TPA023B freebase Form A
Figures 10A, 10B:
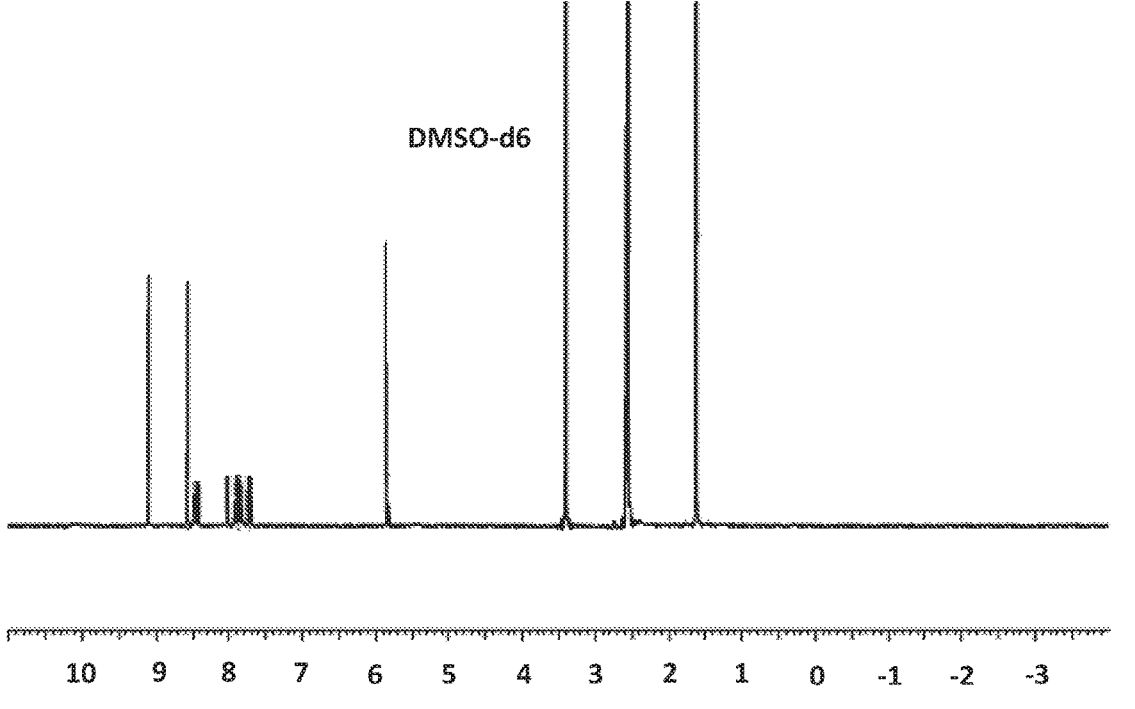
FIG. 10A and FIG. 10B illustrate a DSC/TGA thermogram for TPA023B freebase Form A (FIG. 10A); and an NMR spectrum of TPA023B freebase Form A (FIG. 10B)

In one or more embodiments, a crystalline polymorph of 2',6-difluoro-5'-[3-(1-hydroxy-1-methylethyl)-imidazo[1,2-b][1,2,4]triazin-7-yl]biphenyl-2-carbonitrile has also been identified. This crystalline polymorph is designated "Free Base Polymorphic Form A" and exhibits an XRPD pattern having characteristic peak locations of at least three, at least six, at least nine, at least twelve, at least fifteen or all values selected from the group consisting of about: 5.5, 11.0, 12.0, 12.5, 14.7, 16.5, 17.1, 18.1, 18.4, 19.3, 20.6, 22.1, 23.5, 24.6, 25.3, 26.8, 27.7, 28.1, 29.3, and 30.5±0.2-degrees, 2-theta, when measured using the parameters described in Table 1. In one or more embodiments, Free Base Polymorphic Form A exhibits an XRPD pattern substantially the same as the XRPD pattern shown in FIG. 9. In one or more embodiments, Free Base Polymorphic Form A exhibits an XRPD pattern substantially the same as the XRPD pattern shown in FIG. 36A labeled "Form A". In one or more embodiments, Free Base Polymorphic Form A has a melting range of from about 195° C. to about 210° C. In one or more embodiments, Free Base Polymorphic Form A exhibits a DSC thermogram comprising an endothermic peak at about 206° C. In one or more embodiments, Free Base Polymorphic Form A exhibits a DSC thermogram substantially the same as the DSC thermogram shown in FIG. 10A. In one or more embodiments, Free Base Polymorphic Form A exhibits a DSC thermogram substantially the same as the DSC thermogram shown in FIG. 36B. This melting point is obtained using DSC with a heating rate of 10° C./min. In some embodiments, Free Base Polymorphic Form A displays birefringence under polarized light. In some embodiments, Free Base Polymorphic Form A is anhydrate. In some embodiments, Free Base Polymorphic Form A can be synthesized using the method of Example 10. In one or more embodiments, pharmaceutical compositions comprising the Free Base Polymorphic Form A are described. In one or more embodiments, the disclosure includes purified forms of the crystalline Free Base Polymorphic Form A.

Figure 11:
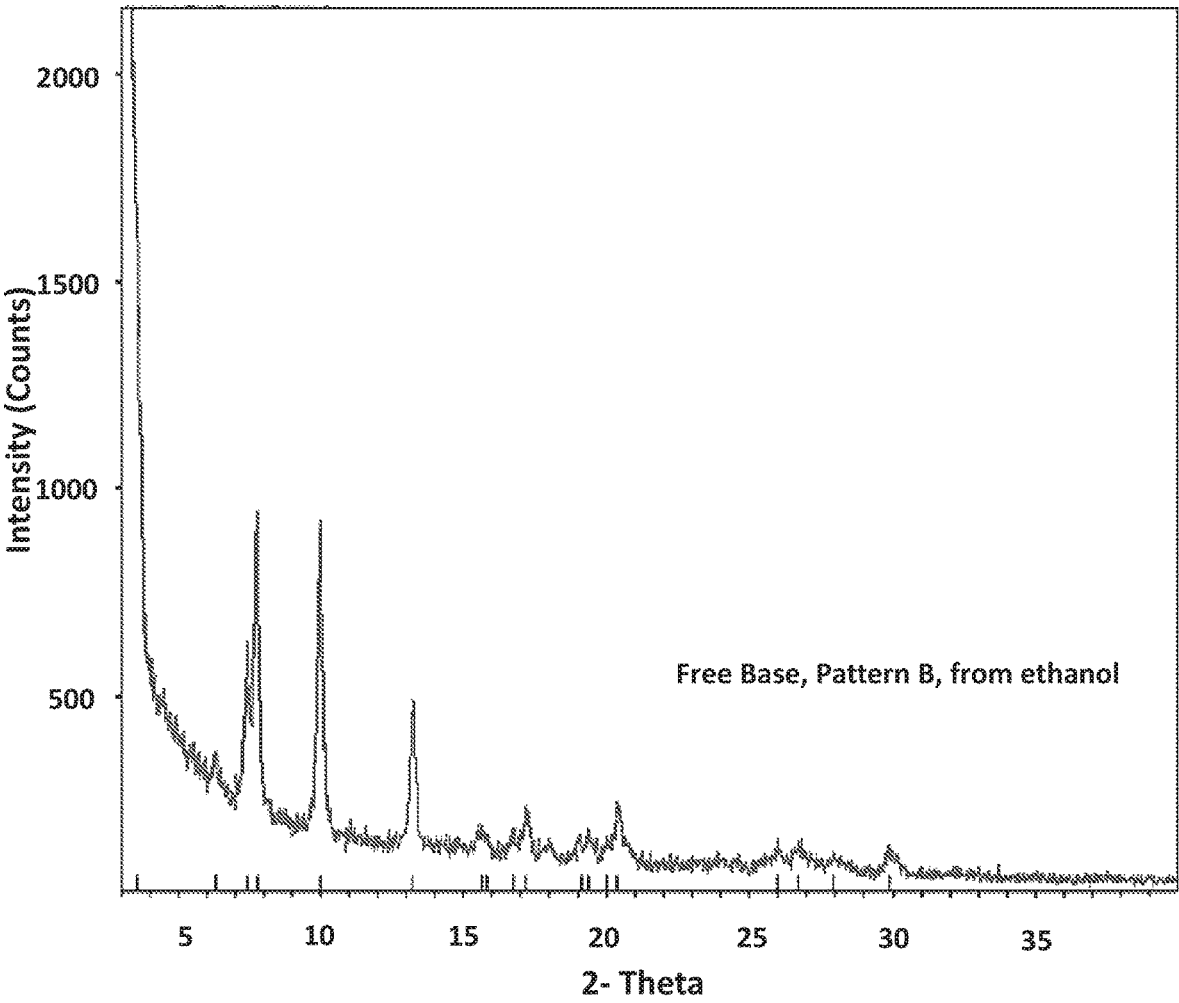
FIG. 11 illustrates an XRPD pattern for TPA023B freebase Form B

In one or more embodiments, the present disclosure further provides a crystalline polymorph of 2',6-difluoro-5'-[3-(1-hydroxy-1-methylethyl)-imidazo[1,2-b][1,2,4]triazin-7-yl]biphenyl-2-carbonitrile. This crystalline polymorph is designated "Free Base Polymorphic Form B" and exhibits an XRPD pattern having characteristic peak locations of at least three, at least six, at least nine, at least twelve, at least fifteen or all values selected from the group consisting of about: 6.3, 7.4, 7.7, 10.0, 13.2, 15.6, 15.8, 16.7, 17.2, 19.1, 19.4, 20.0, 20.4, 26.0, 26.7, 27.9, and 29.9±0.2 degrees, 2-theta, when measured using the parameters described in Table 1. In one or more embodiments, Free Base Polymorphic Form B exhibits an XRPD pattern substantially the same as the XRPD pattern shown in FIG. 11. In one or more embodiments, Free Base Polymorphic Form B has a melting/desolvation range of from about 40° C. to about 150° C. In one or more embodiments, Free Base Polymorphic Form B is synthesized using the method of Example 11. In one or more embodiments, pharmaceutical compositions comprising the Free Base Polymorphic Form B are described. In one or more embodiments, the disclosure provides an ethanol solvate. In one or more embodiments, the disclosure provides purified forms of the crystalline Free Base Polymorphic Form B.

Figure 12:
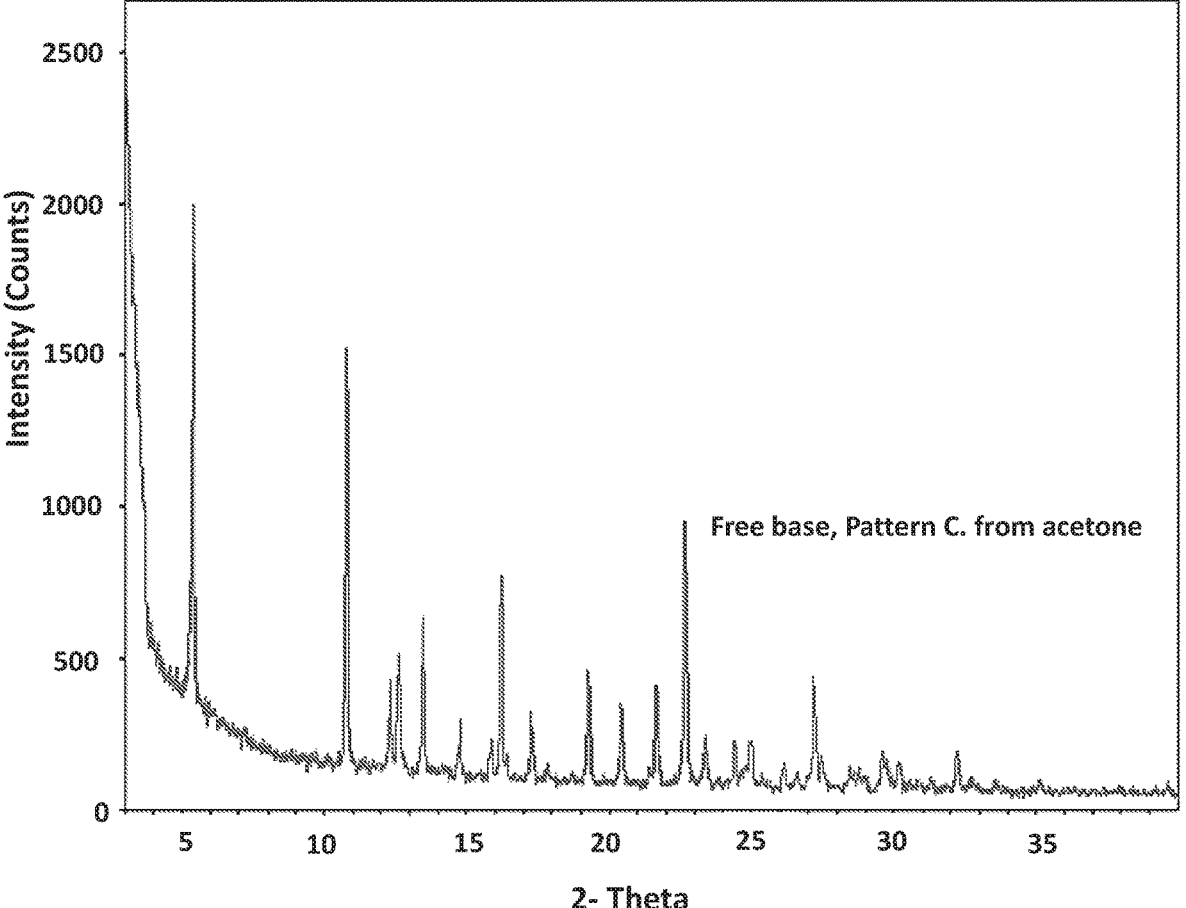
FIG. 12 illustrates an XRPD pattern for TPA023B freebase Form C

In one or more embodiments, a still further crystalline polymorph of 2',6-difluoro-5'-[3-(1-hydroxy-1-methylethyl)-imidazo[1,2-b][1,2,4]triazin-7-yl]biphenyl-2-carbonitrile is described herein. This crystalline polymorph is designated "Free Base Polymorphic Form C" (i.e., Free Base Form C) and exhibits an XRPD pattern having characteristic peak locations of at least three, at least six, at least nine, at least twelve, at least fifteen or all values selected from the group consisting of about: 5.4, 10.8, 12.3, 12.6, 13.5, 14.8, 16.2, 17.3, 19.3, 20.4, 21.7, 22.7, 23.4, 24.4, 25.0, 27.2, 29.6, and 32.2±0.2 degrees, 2-theta, when measured using the parameters described in Table 1. In some embodiments, Free Base Polymorphic Form C provides an XRPD pattern having characteristic peak locations of at least three, at least six, at least nine, at least twelve, at least fifteen or all values selected from the group consisting of about: 5.4, 10.8, 12.3, 12.6, 13.5, 14.8, 15.9, 16.3, 16.4, 17.3, 17.8, 19.3, 20.4, 21.5, 21.7, 22.7, 23.4, 24.4, 24.7, 25.0, 26.1, 26.6, 27.0, 27.2, 27.5, 28.4, 28.7, 29.0, 29.6, 30.2, and 32.3±0.2-degrees, 2-theta, when measured using the parameters described in Table 1. In some embodiments, Free Base Polymorphic Form C provides an XRPD pattern having characteristic peak locations of at least three, at least six, at least nine, at least twelve, at least fifteen or all values selected from the group consisting of about: 5.3, 7.9, 10.7, 12.3, 12.6, 13.4, 14.1, 14.7, 15.8, 16.2, 16.4, 17.2, 17.8, 18.6, 19.2, 20.4, 21.4, 21.6, 22.6, 23.3, 23.8, 24.3, 24.7, 24.9, 25.3, 26.0, 26.6, 26.9, 27.2, 27.5, 28.4, 28.7, 28.9, 29.6, 30.1, 31.7, 32.2, 33.5, 35.1, and 39.6±0.2-degrees, 2-theta, when measured using the parameters described in Table 26-4. In some embodiments, Free Base Polymorphic Form C provides an XRPD pattern having characteristic peak locations of at least three values selected from the group consisting of about: 5.3, 10.7, 12.3, 12.5, 13.4, and 14.7±0.2-degrees, 2-theta, when measured using the parameters described in Table 26-4. In one or more embodiments, TPA023B Free Base Polymorphic Form C exhibits an XRPD pattern substantially the same as the XRPD pattern shown in FIG. 5. In one or more embodiments, Free Base Polymorphic Form C exhibits an XRPD pattern substantially the same as the XRPD pattern shown in FIG. 12. In one or more embodiments, Free Base Polymorphic Form C exhibits an XRPD pattern substantially the same as the XRPD pattern shown in FIG. 36A labelled Form C. In one or more embodiments, Free Base Polymorphic Form C exhibits an XRPD pattern substantially the same as the XRPD pattern shown in FIG. 46A labelled Form C.

Figure 13:
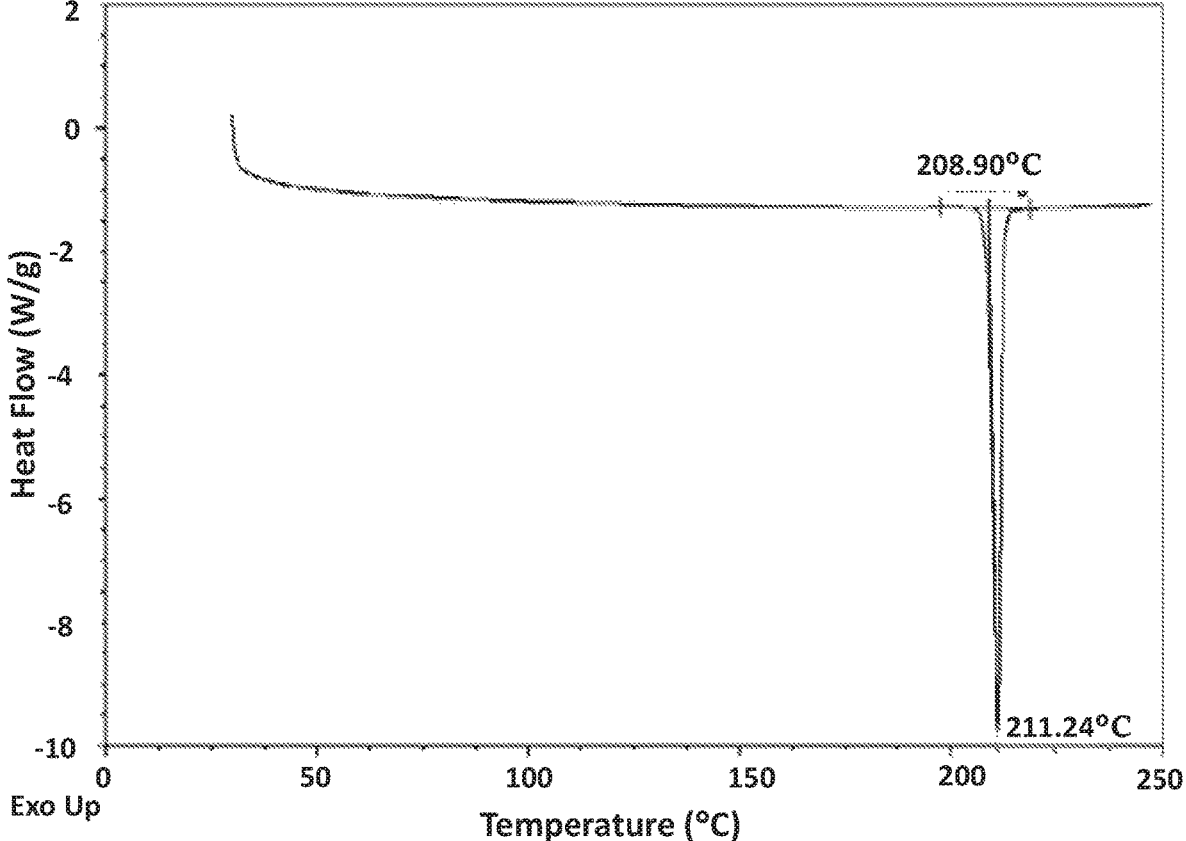
FIG. 13 illustrates a DSC thermogram for TPA023B freebase Form C

In one or more embodiments, Free Base Polymorphic Form C has a melting range of from about 205° C. to about 215° C. In one or more embodiments, Free Base Polymorphic Form C has a melting range from about 195° C. to about 215° C. In one or more embodiments, Free Base Polymorphic Form C exhibits a DSC thermogram comprising an endothermic peak at about 209, 210, or 211° C. In one or more embodiments, Free Base Polymorphic Form C exhibits a DSC thermogram substantially the same as FIG. 13. In one or more embodiments, Free Base Polymorphic Form C exhibits a DSC thermogram substantially the same as FIG. 36D. In one or more embodiments, Free Base Polymorphic Form C exhibits a DSC thermogram substantially the same as the DSC thermogram shown in FIG. 6. This melting point is obtained using DSC with a heating rate of 10° C./min. In some embodiments, Free Base Polymorphic Form C displays birefringence under polarized light. In one or more embodiments, Free Base Polymorphic Form C can be synthesized using the method of Example 12 or Example 35. In some embodiments, Free Base Polymorphic Form C is an anhydrate. In one or more embodiments, pharmaceutical compositions comprising the Free Base Polymorphic Form C are described. In one or more embodiments, the disclosure provides purified forms of the crystalline Free Base Polymorphic Form C.

In some embodiments, Free Base Polymorphic Form C is a stable form. In some embodiments, Free Base Polymorphic Form C can be stored at various temperatures and relative humidities. For example, Free Base Polymorphic Form C can be stored at about −20° C., about −10° C., about 0° C., about 5° C., about 15° C., about 25° C., about 40° C., and about 60° C. For another example, Free Base Polymorphic Form C can be stored at 10% RH, 20% RH, 30% RH, 40% RH, 50% RH, 60% RH, 75% RH, or 90% RH. In some embodiments, Free Base Polymorphic Form C is stable at about 25° C. for at least at least 7 days, at least 14 days, at least 21 days, at least a month, at least 2 months, at least 3 months, at least 6 months, at least 9 months, at least 12 months, at least 24 months, at least 36 months, at least 48 months, or at least 60 months. In some embodiments, Free Base Polymorphic Form C is stable at about 40° C. for at least 3 days, at least 7 days, at least 14 days, at least 21 days, at least a month, at least 3 months, at least 6 months, at least 9 months, at least 12 months, or at least 24 months. In some embodiments, Free Base Polymorphic Form C is stable at about 60° C. for at least 3 days, at least 7 days, at least 14 days, at least 21 days, at least a month, at least 3 months, at least 6 months, at least 9 months, at least 12 months, or at least 24 months. In some embodiments, a stable TPA023B Free Base Polymorphic Form, such as Free Base Form C, has about 80%, 85%, 90%, 91%, 92%, 93%, 94%, 95%, 96%, 97%, 98%, 99% w/w or greater of the initial free base amount at the end of the given storage period. In some embodiments, a stable TPA023B Free Base Polymorphic Form, such as Free Base Form C, has about 20%, 15%, 10%, 5%, 2%, 1% w/w or less total impurity or related substances at the end of the given storage period. In some embodiments, Free Base Polymorphic Form C provides an XRPD pattern substantially the same post-storage at about 40° C. and 75% RH for at least a week. In some embodiments, Free Base Polymorphic Form C provides an XRPD pattern substantially the same post-storage at about 40° C. and 75% RH for at least two weeks, at least a month, at least 3 months, at least 6 months, at least 9 months, at least 12 months, or at least 24 months. In some embodiments, Free Base Polymorphic Form C provides an XRPD pattern substantially the same post-storage at about 25° C. and 92.5% RH for at least a week, at least two weeks, at least a month, at least 3 months, at least 6 months, at least 9 months, at least 12 months, or at least 24 months.

In one or more embodiments, a Free Base Polymorphic Form described herein, such as Free Base Form C, is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, or at least 99.9% pure, as measured by HPLC as described herein. In some embodiment, a Free Base Polymorphic Form, such as Free Base Form C, comprises an impurity. In some embodiments, the impurity in a Free Base Form, such as in Free Base Form C is at most 0.1%, at most 0.5%, at most 1%, at most 2%, at most 3%, at most 4%, at most 5%, at most 6%, at most 7%, at most 8%, at most 9%, at most 10%, at most 15%, at most 20%, at most 25%, at most 30%, at most 40%, or at most 50%, as measured by HPLC as described herein.

Figure 14:
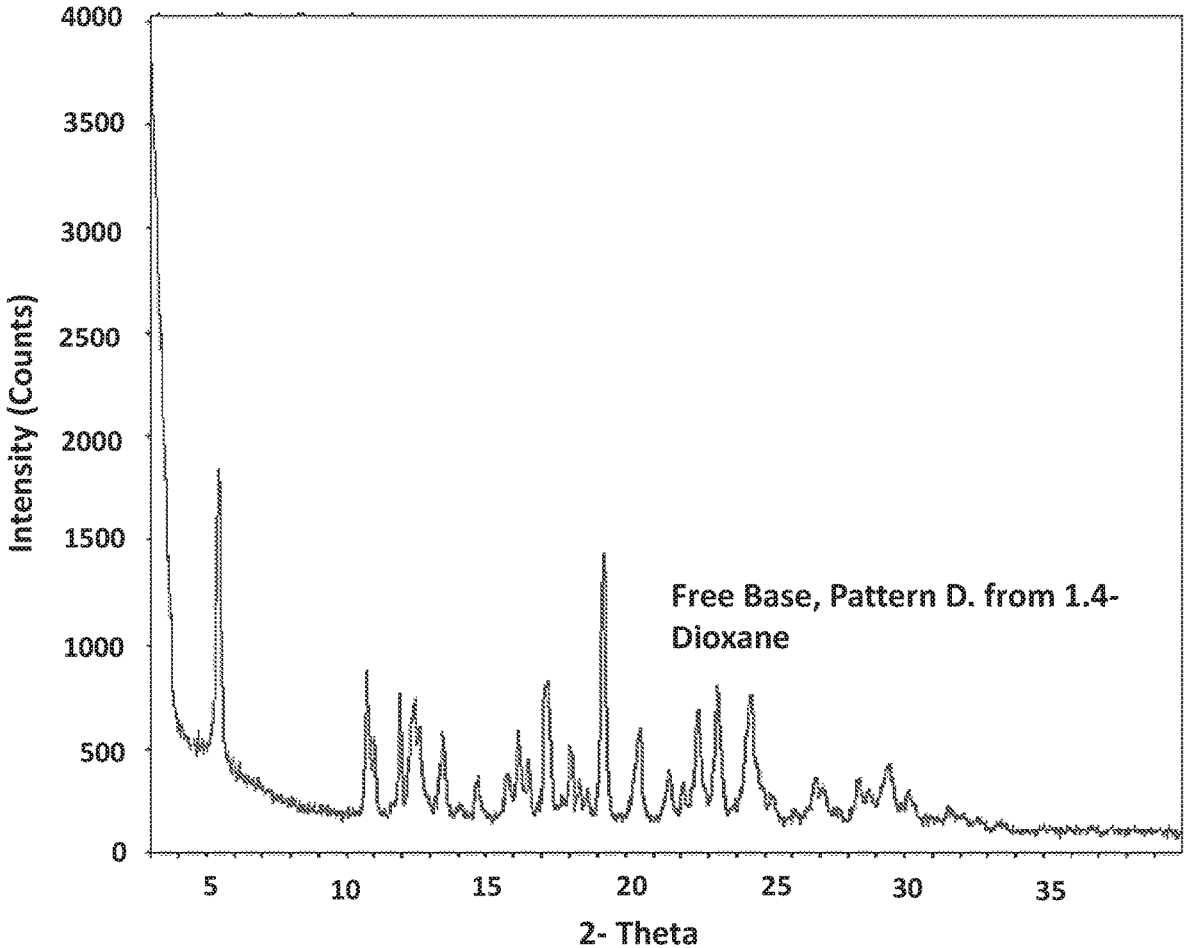
FIG. 14 illustrates an XRPD pattern for TPA023B freebase mixture comprising free base Form A

In one or more embodiments, a crystalline polymorph mixture of 2',6-difluoro-5'-[3-(1-hydroxy-1-methylethyl)-imidazo[1,2-b][1,2,4]triazin-7-yl]biphenyl-2-carbonitrile is described. This crystalline polymorph mixture is designated "Free Base Polymorphic Pattern D" and exhibits an XRPD pattern having characteristic peak locations of at least three, at least six, at least nine, at least twelve, at least fifteen or all values selected from the group consisting of about: 5.4, 10.8, 11.0, 12.0, 12.4, 13.5, 14.7, 15.8, 16.2, 16.5, 17.2, 18.0, 19.3, 20.6, 21.6, 22.6, 23.3, 24.5, 26.8, 27.1, 28.4, 29.5, and 30.2±0.2 degrees, 2-theta, when measured using the parameters described in Table 1. In one or more embodiments, TPA023B Free Base Polymorphic Pattern D can comprise Free Base Form A. In one or more embodiments, TPA023B Free Base Polymorphic Pattern D can comprise Free Base Form C. In one or more embodiments, Free Base Polymorphic Pattern D comprises a dioxane solvate. In one or more embodiments, Free Base Polymorphic Pattern D exhibits an XRPD pattern substantially the same as the XRPD pattern shown in FIG. 14. In one or more embodiments, Free Base Polymorphic Pattern D has a melting/desolvating range of from about 50° C. to about 225° C. Free Base Polymorphic Pattern D can be synthesized using the method of Example 13. In one or more embodiments, pharmaceutical compositions comprising the Free Base Polymorphic Pattern D are described. In one or more embodiments, the disclosure provides purified forms of the crystalline Free Base Polymorphic Pattern D.

In one or more embodiments, a crystalline polymorph of 2',6-difluoro-5'-[3-(1-hydroxy-1-methylethyl)-imidazo[1,2-b][1,2,4]triazin-7-yl]biphenyl-2-carbonitrile is described. This crystalline polymorph is designated "Free Base Polymorphic Form E" (i.e., Free Base Form E) and exhibits an XRPD pattern substantially the same as the XRPD pattern labelled Form E in FIG. 36A. In some embodiments, Free Base Polymorphic Form E exhibits an XRPD pattern having characteristic peak locations of at least three, at least six, at least nine, at least twelve, at least fifteen or all values selected from the group consisting of about: 6.6, 7.5, 9.6, 10.3, 13.3, 13.8, 14.5, 15.4, 15.9, 16.5, 17.3, 17.8, 19.5, 20.3, 22.3, 23.2, 23.7, 26.1, 26.9, 27.9, 29.0, 31.1, and 35.8±0.2 degrees, 2-theta, when measured using the parameters described in Table 26-4. In some embodiments, Free Base Polymorphic Form E exhibits an XRPD pattern having characteristic peak locations of at least three values selected from the group consisting of about: 6.6, 7.5, 9.6, 10.3, 13.3, and 19.5±0.2 degrees, 2-theta, when measured using the parameters described in Table 26-4. In one or more embodiments, Free Base Polymorphic Form E exhibits a DSC thermogram substantially the same as FIG. 36C. In one or more embodiments, Free Base Polymorphic Form E has a melting/desolvation/dehydration range of from about 90° C.

to about 110° C. In one or more embodiments, Free Base Polymorphic Form E exhibits a DSC thermogram comprising an endothermic peak at about 104° C. In one or more embodiments, Free Base Polymorphic Form E can be synthesized using the method described in Example 35. In some embodiments, Free Base Polymorphic Form E is a solvate. In one or more embodiments, pharmaceutical compositions comprising the Free Base Polymorphic Pattern E are described. In one or more embodiments, the disclosure provides purified forms of the crystalline Free Base Polymorphic Pattern E.

In one or more embodiments, the present disclosure further provides a crystalline polymorph of 2',6-difluoro-5'-[3-(1-hydroxy-1-methylethyl)-imidazo[1,2-b][1,2,4]triazin-7-yl]biphenyl-2-carbonitrile. This crystalline polymorph is designated "Free Base Polymorphic Form F" (i.e., Free Base Form F) and exhibits an XRPD pattern having characteristic peak locations of at least three, at least six, at least nine, at least twelve, at least fifteen or all values selected from the group consisting of about: 7.0, 7.7, 8.1, 9.2, 10.9, 12.3, 13.1, 14.0, 14.2, 15.2, 15.4, 15.7, 16.3, 17.2, 17.8, 19.4, 19.9, 21.0, 22.9, 26.7, and 27.6±0.2-degrees, 2-theta, when measured using the parameters described in Table 26-4. In some embodiments, Free Base Polymorphic Form F provides an XRPD pattern having characteristic peak locations of at least three values selected from the group consisting of about: 7.0, 7.7, 8.1, 9.2, 10.9, and 13.1±0.2-degrees, 2-theta, when measured using the parameters described in Table 26-4. In some embodiments, Free Base Form F provides an XRPD pattern substantially the same as the XRPD pattern labelled Form F in FIG. 36A. In one or more embodiments, Free Base Polymorphic Form F exhibits a DSC thermogram substantially the same as FIG. 36E. In one or more embodiments, Free Base Polymorphic Form F has a melting/desolvation/dehydration range of from about 90° C. to about 110° C. In one or more embodiments, Free Base Polymorphic Form F exhibits a DSC thermogram comprising an endothermic peak at about 104° C. In one or more embodiments, Free Base Polymorphic Form F exhibits a DSC thermogram comprising an endothermic peak at about 195° C. In one or more embodiments, Free Base Polymorphic Form F exhibits a DSC thermogram comprising an endothermic peak at about 205° C. In one or more embodiments, Free Base Polymorphic Form F exhibits a DSC thermogram comprising one or more endothermic peaks selected from peaks at 104° C., 195° C., and 205° C. In some embodiments, Free Base Polymorphic Form F is an anhydrate. In some embodiments, Free Base Polymorphic Form F is a solvate. Free Base Polymorphic Form F can be synthesized using the method described in Example 35. In one or more embodiments, pharmaceutical compositions comprising the Free Base Polymorphic Form F are described. In one or more embodiments, the disclosure provides purified forms of the crystalline Free Base Polymorphic Form F.

In one or more embodiments, a crystalline polymorph of 2',6-difluoro-5'-[3-(1-hydroxy-1-methylethyl)-imidazo[1,2-b][1,2,4]triazin-7-yl]biphenyl-2-carbonitrile is described. This crystalline polymorph is designated "Free Base Polymorphic Form G" (i.e., Free Base Form G) and exhibits an XRPD pattern having characteristic peak locations of at least three, at least six, at least nine, at least twelve, at least fifteen or all values selected from the group consisting of about: 6.3, 7.5, 8.0, 11.7, 12.0, 12.8, 13.3, 14.1, 14.8, 15.3, 17.2, 18.0, 19.2, 19.6, 21.5, 23.2, 23.8, 25.9, 26.6, 27.7, and 32.4±0.2-degrees, 2-theta, when measured using the parameters described in Table 26-4. In some embodiments, Free Base Polymorphic Form G provides an XRPD pattern having characteristic peak locations of at least three values selected from the group consisting of about: 6.3, 7.5, 11.7, 12.8, and 13.3±0.2-degrees, 2-theta, when measured using the parameters described in Table 26-4. In some embodiments, Free Base Form G provides an XRPD pattern substantially the same as the XRPD pattern labelled Form G in FIG. 36A. In one or more embodiments, Free Base Polymorphic Form G exhibits a DSC thermogram substantially the same as FIG. 36F. In one or more embodiments, Free Base Polymorphic Form G has a melting range of from about 205° C. to about 215° C. In one or more embodiments, Free Base Polymorphic Form G exhibits a DSC thermogram comprising an endothermic peak at about 210° C. In some embodiments, Free Base Polymorphic Form G is an anhydrate. In some embodiments, Free Base Polymorphic Form G is a solvate. In one or more embodiments, Free Base Polymorphic Form G can be synthesized using the method described in Example 35. In one or more embodiments, pharmaceutical compositions comprising the Free Base Polymorphic Form G are described. In one or more embodiments, the disclosure provides purified forms of the crystalline Free Base Polymorphic Form G.

In one or more embodiments, a crystalline polymorph of 2',6-difluoro-5'-[3-(1-hydroxy-1-methylethyl)-imidazo[1,2-b][1,2,4]triazin-7-yl]biphenyl-2-carbonitrile is described. This crystalline polymorph is designated "Free Base Polymorphic Form H" and exhibits an XRPD pattern having characteristic peak locations of at least three, at least six, at least nine, at least twelve, at least fifteen or all values selected from the group consisting of about: 7.0, 7.9, 9.4, 10.9, 12.7, 13.4, 14.0, 14.3, 14.6, 16.0, 16.3, 18.0, 19.2, 19.7, 20.1, 21.2, 24.1, 25.7, 26.9, and 28.0±0.2-degrees, 2-theta, when measured using the parameters described in Table 26-4. In some embodiments, Free Base Polymorphic Form H provides an XRPD pattern having characteristic peak locations of at least three values selected from the group consisting of about: 7.0, 7.9, 9.4, 10.9, 12.7, and 14.0±0.2-degrees, 2-theta, when measured using the parameters described in Table 26-4. In some embodiments, Free Base Form H provides an XRPD pattern substantially the same as the XRPD pattern labelled Form H in FIG. 36A. In one or more embodiments, Free Base Polymorphic Form H exhibits a DSC thermogram substantially the same as FIG. 36G. In one or more embodiments, Free Base Polymorphic Form H has a melting range of from about 100° C. to about 120° C. In one or more embodiments, Free Base Polymorphic Form H exhibits a DSC thermogram comprising an endothermic peak at about 108° C. In one or more embodiments, Free Base Polymorphic Form H exhibits a DSC thermogram comprising an endothermic peak at about 194° C. In one or more embodiments, Free Base Polymorphic Form H exhibits a DSC thermogram comprising an endothermic peak at about 205° C. In one or more embodiments, Free Base Polymorphic Form H exhibits a DSC thermogram comprising one or more endothermic peaks selected from peaks at 108° C., 194° C., and 205° C. In some embodiments, Free Base Polymorphic Form H is a hydrate. Free Base Polymorphic Form H can be synthesized using the method described in Example 32. In one or more embodiments, pharmaceutical compositions comprising the Free Base Polymorphic Form H are described. In one or more embodiments, the disclosure provides purified forms of the crystalline Free Base Polymorphic Form H.

In one or more embodiments, a mixture comprising a crystalline polymorph of 2',6-difluoro-5'-[3-(1-hydroxy-1-methylethyl)-imidazo[1,2-b][1,2,4]triazin-7-yl]biphenyl-2-carbonitrile is described. This crystalline polymorph mixture is designated "Free Base Polymorphic Pattern I" and provides an XRPD pattern substantially the same as the XRPD pattern labeled pattern I in FIG. 36A. In some embodiments, Free Base Pattern I provides an XRPD pattern having characteristic peak locations of at least three, at least six, at least nine, at least twelve, at least fifteen or all values selected from the group consisting of about: 5.7, 6.3, 11.0, 11.9, 12.4, 16.0, 16.5, 17.1, 18.1, 18.9, 19.3, 19.9, 20.3, 20.5, 23.5, 24.5, 24.9, and 29.3±0.2-degrees, 2-theta, when measured using the parameters described in Table 26-4. Free Base Polymorphic Pattern I can comprise Free Base Form A. Free Base Polymorphic Pattern I can also comprise a new free base form, Free Base Form J. In one or more embodiments, Free Base Polymorphic pattern I exhibits a DSC thermogram substantially the same as FIG. 36H. In one or more embodiments, Free Base Polymorphic pattern I has a melting range of from about 189° C. to about 210° C. In one or more embodiments, Free Base Polymorphic pattern I has a melting range of from about 189° C. to about 199° C. In one or more embodiments, Free Base Polymorphic pattern I has a melting range of from about 200° C. to about 210° C. In one or more embodiments, Free Base Polymorphic pattern I exhibits a DSC thermogram comprising an endothermic peak at about 194° C. In one or more embodiments, Free Base Polymorphic pattern I exhibits a DSC thermogram comprising an endothermic peak at about 205° C. In one or more embodiments, Free Base Polymorphic pattern I exhibits a DSC thermogram comprising two endothermic peaks, at about 194° C. and about 205° C. Free Base Polymorphic Pattern I can be synthesized using the method described in Example 35. In one or more embodiments, pharmaceutical compositions comprising the Free Base Polymorphic Form J are described. In one or more embodiments, the disclosure provides purified forms of the crystalline Free Base Polymorphic Form J. In some embodiments, Free Base Polymorphic Form J provides a DSC thermogram comprising an endothermic peak at about 194° C. In some embodiments, Free Base Polymorphic Form J provides an XRPD pattern having characteristic peak locations of at least three values selected from the group consisting of about: 11.9, 16.0, 18.9, 20.0, 20.3, and 23.5±0.2 degrees, 2-theta, when measured using the parameters described in Table 26-4. In one or more embodiments, pharmaceutical compositions comprising the Free Base Polymorphic Form J are described.

Figure 73:
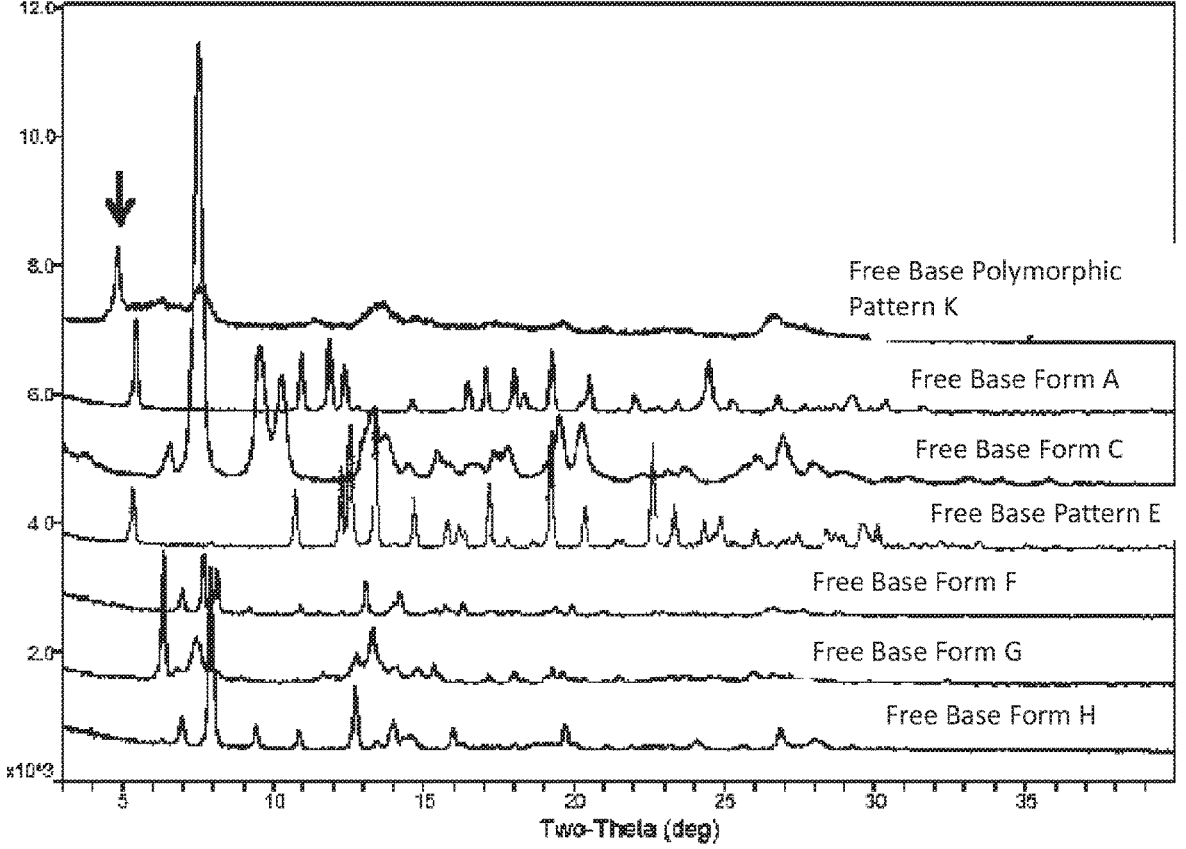
FIG. 73 illustrates the XRPD pattern of TPA023B free base pattern K

In one or more embodiments, a crystalline polymorph of 2',6-difluoro-5'-[3-(1-hydroxy-1-methylethyl)-imidazo[1,2-b][1,2,4]triazin-7-yl]biphenyl-2-carbonitrile is described. This crystalline polymorph mixture is designated "Free Base Polymorphic Pattern K" and provides an XRPD pattern substantially the same as the XRPD pattern labeled pattern K in FIG. 73, when measured using the parameters described in Table 26-4. Free Base Polymorphic Pattern K can be prepared according to Example 63.

Sulfate

Figures 53A, 53B:
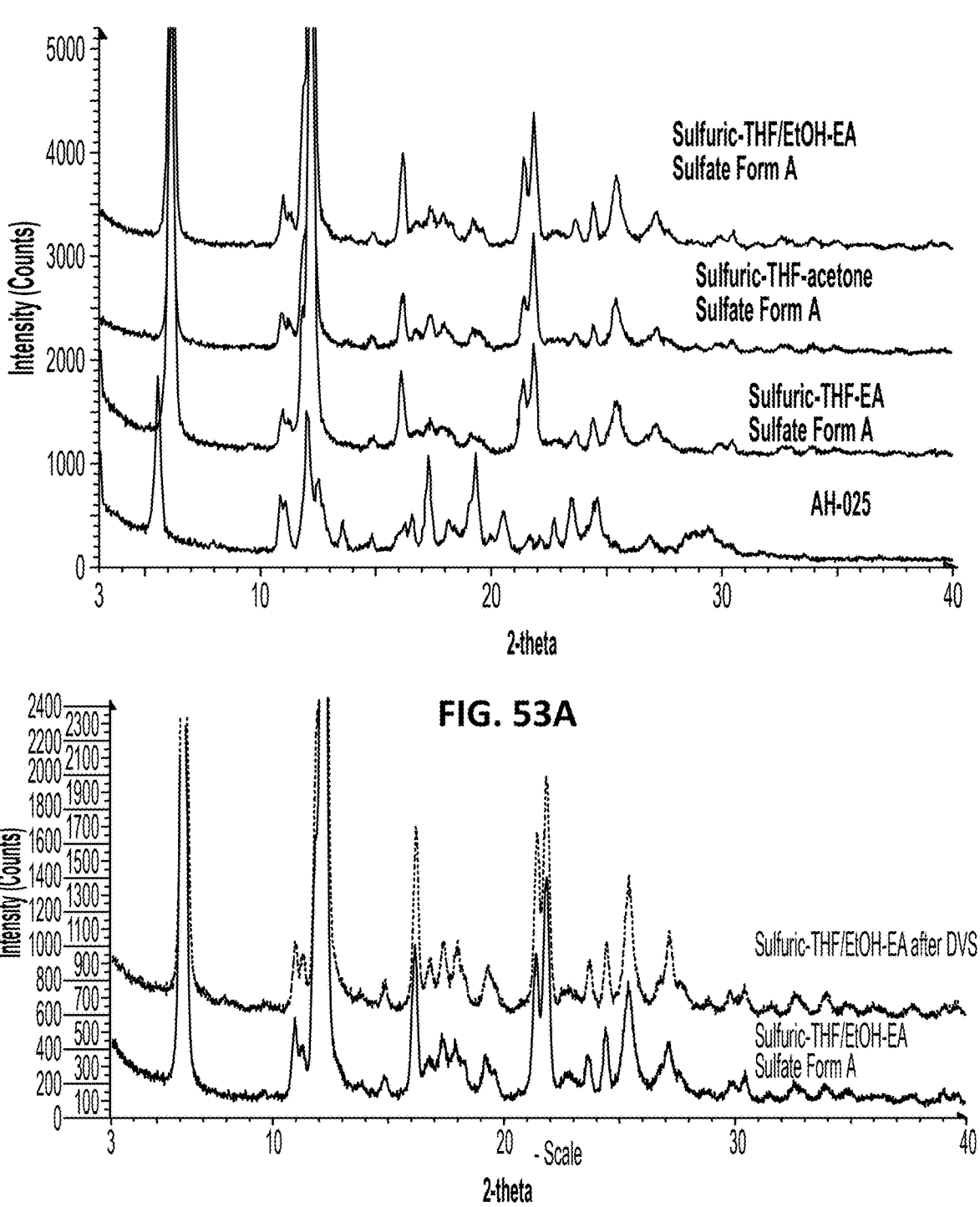
FIG. 53A-FIG. 53D illustrate the XRPD patterns (FIG. 53A), the XRPD patterns of TPA023B Sulfate after performance of DVS testing (FIG. 53B), the DSC/TGA thermogram (FIG. 53C), and the DVS profiles of TPA023B Sulfate (FIG. 53D)
Figure 59A:
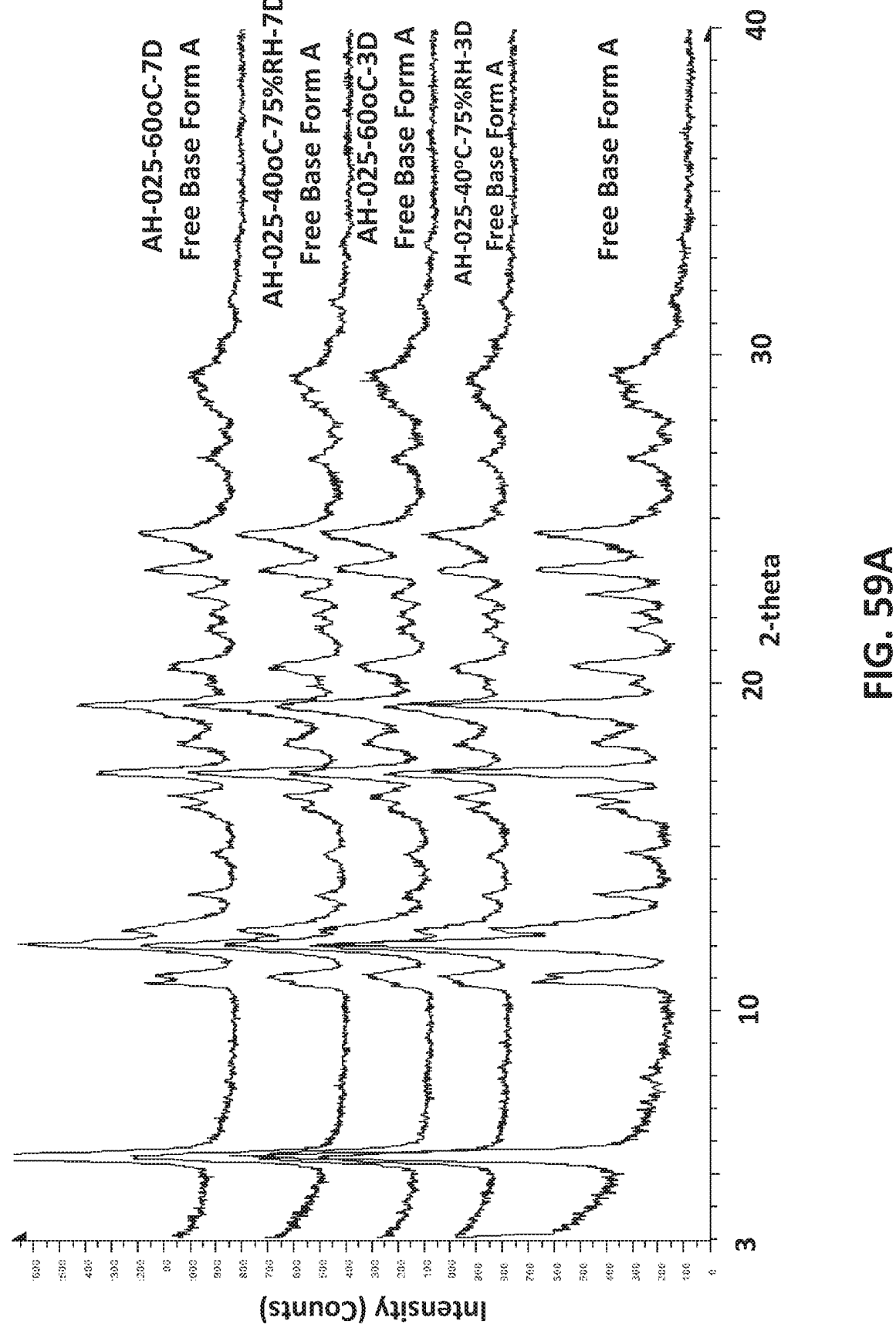
Figure 59B:
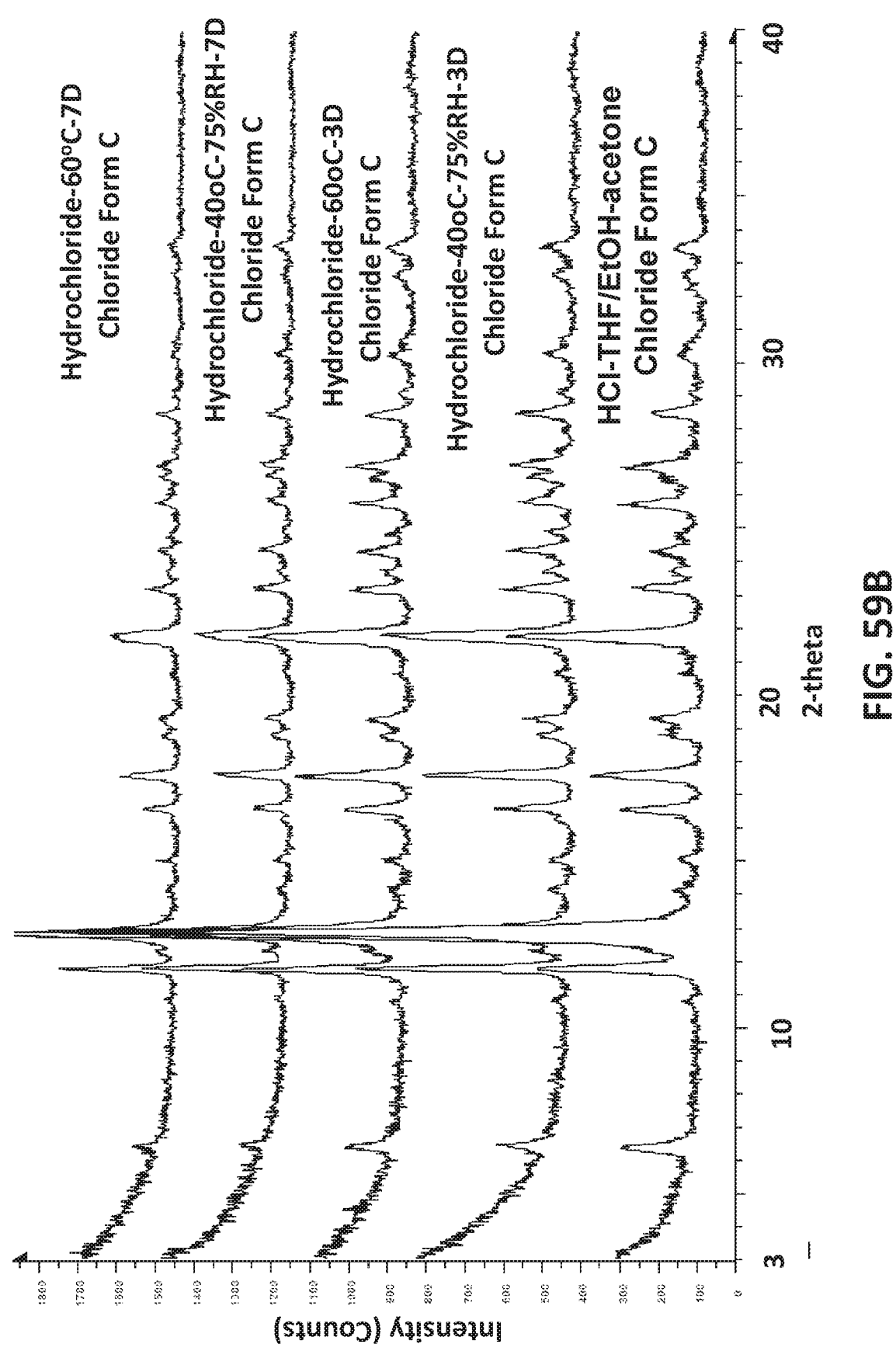

In one aspect, a crystalline form (e.g., a salt or cocrystal) of 2',6-difluoro-5'-[3-(1-hydroxy-1-methylethyl)-imidazo[1,2-b][1,2,4]triazin-7-yl]biphenyl-2-carbonitrile with sulfuric acid is described. This crystalline polymorph is designated "Sulfate Polymorphic Form A" (i.e., Sulfate Form A) and exhibits an XRPD pattern having characteristic peak locations of at least three, at least six, at least nine, at least twelve, at least fifteen or all values selected from the group consisting of about: 6.1, 10.9, 11.3, 11.8, 12.2, 13.8, 14.8, 16.1, 16.8, 17.3, 17.9, 18.3, 19.2, 19.6, 21.4, 21.8, 22.8, 23.6, 24.4, 25.4, 27.2, 29.9, 30.5, 31.5, 32.6, 33.9, and 39.1±0.2 degrees, 2-theta, when measured using the parameters described in Table 26-4. In one or more embodiments, Sulfate Polymorphic Form A exhibits an XRPD pattern having characteristic peak locations of at least three, at least six, or all values selected from the group consisting of about: 6.1, 10.9, 11.3, 11.8, 12.2, 16.1, 16.8, 21.4, 21.8, 25.4 and 27.2±0.2 degrees, 2-theta, when measured using the parameters described in Table 26-4. In one or more embodiments, Sulfate Polymorphic Form A exhibits an XRPD pattern substantially the same as the XRPD pattern labeled Sulfate Form A in FIG. 53A, when measured using the parameters described in Table 26-4. In one or more embodiments, Sulfate Polymorphic Form A exhibits an XRPD pattern substantially the same as the XRPD pattern labeled Sulfate Form A in FIG. 61, when measured using the parameters described in Table 26-4. In one or more embodiments, Sulfate Polymorphic Form A exhibits an XRPD pattern substantially the same as an XRPD pattern labelled Sulfate Form A in FIG. 59C, when measured using the parameters described in Table 26-4. In some embodiments, Sulfate Polymorphic Form A exhibits an XRPD pattern having a characteristic peak located at about 6.1±0.2 degrees, 2-theta. In some embodiments, Sulfate Polymorphic Form A exhibits an XRPD pattern having a characteristic peak located at about 12.2±0.2 degrees, 2-theta. In some embodiments, Sulfate Polymorphic Form A exhibits an XRPD pattern having a characteristic peak located at about 16.1±0.2 degrees, 2-theta. In some embodiments, Sulfate Polymorphic Form A exhibits an XRPD pattern having a characteristic peak located at about 21.4±0.2 degrees, 2-theta. In some embodiments, Sulfate Polymorphic Form A exhibits an XRPD pattern having a characteristic peak located at about 21.8±0.2 degrees, 2-theta. In some embodiments, Sulfate Polymorphic Form A exhibits an XRPD pattern having a characteristic peak located at about 25.4±0.2 degrees, 2-theta. In some embodiments, Sulfate Polymorphic Form A displays birefringence under polarized light. In one or more embodiments, Sulfate Polymorphic Form A has a melting/desolvating range of from about 175° C. to about 205° C. In one or more embodiments, Sulfate Polymorphic Form A has a melting range of from about 160° C. to about 210° C. In one or more embodiments, Sulfate Polymorphic Form A has a DSC thermograph substantially the same as the DSC curve in FIG. 53C. In one or more embodiments, Sulfate Polymorphic Form A has one endothermic peak with an onset temperature of about 184° C. In one or more embodiments, Sulfate Polymorphic Form A has one endothermic peak with an onset temperature of about 182° C. to 186° C. In one or more embodiments, Sulfate Polymorphic Form A has one endothermic peak with an onset temperature of about 179° C. to 189° C. In one or more embodiments, Sulfate Polymorphic Form A exhibits a DSC thermogram comprising an endothermic peak at about 192° C. In one or more embodiments, Sulfate Polymorphic Form A exhibits a DSC thermogram comprising an endothermic peak at about 190° C. to 194° C. In one or more embodiments, Sulfate Polymorphic Form A exhibits a DSC thermogram comprising an endothermic peak at about 187° C. to 197° C.

In some embodiments, Sulfate Polymorphic Form A is a stable form. In some embodiments, Sulfate Polymorphic Form A can be stored at various temperatures and relative humidities. For example, Sulfate Polymorphic Form A can be stored at about −20° C., about −10° C., about 0° C., about 5° C., about 15° C., about 25° C., about 40° C., and about 60° C. For another example, Sulfate Polymorphic Form A can be stored at 10% RH, 20% RH, 30% RH, 40% RH, 50% RH, 60% RH, 75% RH, or 90% RH. In some embodiments, Sulfate Polymorphic Form A is stable at about 25° C. for at least 7 days, at least 14 days, at least 21 days, at least a month, at least 2 months, at least 3 months, at least 6 months, at least 9 months, at least 12 months, or at least 24 months. In some embodiments, Sulfate Polymorphic Form A is stable at about 25° C. for at least a month. In some embodiments, Sulfate Polymorphic Form A is stable at about 25° C. for at least 36 months, at least 48 months, or at least 60 months. In some embodiments, a stable Sulfate Polymorphic Form A has about 80%, 85%, 90%, 91%, 92%, 93%, 94%, 95%, 96%, 97%, 98%, 99% w/w or greater of the initial sulfate salt amount at the end of the given storage period. In some embodiments, a stable Sulfate Polymorphic Form A has about 95% w/w or greater of the initial sulfate salt amount at the end of the given storage period. In some embodiments, a stable Sulfate Polymorphic Form A has about 20%, 15%, 10%, 5%, 2%, 1% w/w or less total impurity or related substances at the end of the given storage period. In some embodiments, Sulfate Polymorphic Form A is stable at about 40° C. for at least 3 days, at least 7 days, at least 14 days, at least 21 days, at least a month, at least 2 months, at least 3 months, at least 6 months, at least 9 months, at least 12 months, or at least 24 months. In some embodiments, Sulfate Polymorphic Form A is stable at about 60° C. for at least 3 days, at least 7 days, at least 14 days, at least 21 days, at least a month, at least 2 months, at least 3 months, at least 6 months, at least 9 months, at least 12 months, or at least 24 months. In some embodiments, Sulfate Polymorphic Form A provides an XRPD pattern substantially the same post-storage at about 40° C. and 75% RH for at least 3 days. In some embodiments, Sulfate Polymorphic Form A provides an XRPD pattern substantially the same post-storage at about 40° C. and 75% RH for at least 7 days. In some embodiments, Sulfate Polymorphic Form A provides an XRPD pattern substantially the same post-storage at about 40° C. and 75% RH for at least two weeks. In some embodiments, Sulfate Polymorphic Form A provides an XRPD pattern substantially the same post-storage at about 40° C. and 75% RH for at least one month. In some embodiments, Sulfate Polymorphic Form A provides an XRPD pattern substantially the same post-storage at about 40° C. and 75% RH for at least two months. In some embodiments, Sulfate Polymorphic Form A provides an XRPD pattern substantially the same post-storage at about 60° C. and 75% RH for at least 3 days. In some embodiments, Sulfate Polymorphic Form A provides an XRPD pattern substantially the same post-storage at about 60° C. and 75% RH for at least 7 days. In some embodiments, Sulfate Polymorphic Form A provides an XRPD pattern substantially the same post-storage at about 60° C. and 75% RH for at least two weeks. In some embodiments, Sulfate Polymorphic Form A provides an XRPD pattern substantially the same post-storage at about 60° C. and 75% RH for at least one month. In some embodiments, Sulfate Polymorphic Form A provides an XRPD pattern substantially the same post-storage at about 60° C. and 75% RH for at least two months.

Sulfate Polymorphic Form A can be synthesized using the method of Example 42. In one or more embodiments, pharmaceutical compositions comprising the Sulfate Polymorphic Form A are described. In one or more embodiments, the disclosure provides purified forms of the crystalline Sulfate Polymorphic Form A. In one or more embodiments, the Sulfate Polymorphic Form A described herein is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, or at least 99.9% pure, as measured by HPLC as described herein. In one or more embodiments, the Sulfate Polymorphic Form A described herein is at least 95% pure, as measured by HPLC as described herein. In some embodiment, the Sulfate Polymorphic Form A described herein comprises an impurity. In some embodiments, the impurity in Sulfate Polymorphic Form A is at most 0.1%, at most 0.5%, at most 1%, at most 2%, at most 3%, at most 4%, at most 5%, at most 6%, at most 7%, at most 8%, at most 9%, at most 10%, at most 15%, at most 20%, at most 25%, at most 30%, at most 40%, or at most 50%, as measured by HPLC as described herein. In one or more embodiments, the Sulfate Polymorphic Form A described herein comprises at most 5% impurity, as measured by HPLC.

In some embodiments, Sulfate Polymorphic Form A has a plasma half-life that is at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, or at least 15 hours in the plasma of a rat. In some embodiments, Sulfate Polymorphic Form A has a plasma half-life that is at most 5 hours, at most 6 hours, at most 7 hours, at most 8 hours, at most 9 hours, at most 10 hours, at most 11 hours, at most 12 hours, at most 13 hours, at most 14 hours, at most 15 hours, at most 20 hours, or at most 40 hours in the plasma of a rat. In some embodiments, Sulfate Polymorphic Form A has a plasma half-life that is from about 8 hours to about 15 hours in the plasma of a rat. In some embodiments, Sulfate Polymorphic Form A has a plasma half-life that is from about 10 hours to about 13 hours in the plasma of a rat.

Sulfate Polymorphic Form A can have a higher solubility than a free base form of TPA023B. For example, the solubility can be determined as described in example 15. In some embodiments, the solubility of Sulfate Polymorphic Form A is at least 1.1 fold, 1.5 fold, 2 fold, 3 fold, 4 fold, 5 fold, 6 fold, 7 fold, or 8 fold higher than the solubility of Free Base Form A in simulated gastric fluid (SGF). In some embodiments, the solubility of Sulfate Polymorphic Form A is at least 1.1 fold higher than the solubility of Free Base Form A in simulated gastric fluid. In some embodiments, the solubility of Sulfate Polymorphic Form A is at least 2 fold higher than the solubility of Free Base Form A in simulated gastric fluid. In some embodiments, the solubility of Sulfate Polymorphic Form A is at least 1.1 fold, 1.5 fold, 2 fold, 3 fold, 4 fold, 5 fold, 6 fold, 7 fold, or 8 fold higher than the solubility of Free Base Form A in Fasted-state simulated intestinal fluid (FaSSIF). In some embodiments, the solubility of Sulfate Polymorphic Form A is at least 1.1 fold higher than the solubility of Free Base Form A in Fasted-state simulated intestinal fluid. In some embodiments, the solubility of Sulfate Polymorphic Form A is at least 2 fold higher than the solubility of Free Base Form A in Fasted-state simulated intestinal fluid. In some embodiments, the solubility of Sulfate Polymorphic Form A is at least 1.1 fold, 1.5 fold, 2 fold, 3 fold, 4 fold, 5 fold, 6 fold, 7 fold, or 8 fold higher than the solubility of Free Base Form A in Fed-state simulated intestinal fluid (FeSSIF) than Free Base Polymorphic Form A. In some embodiments, the solubility of Sulfate Polymorphic Form A is at least 1.1 fold higher than the solubility of Free Base Form A in Fed-state simulated intestinal fluid than Free Base Polymorphic Form A. In some embodiments, the solubility of Sulfate Polymorphic Form A is at least 2 fold higher than the solubility of Free Base Form A in Fed-state simulated intestinal fluid than Free Base Polymorphic Form A.

Chloride

Figure 15:
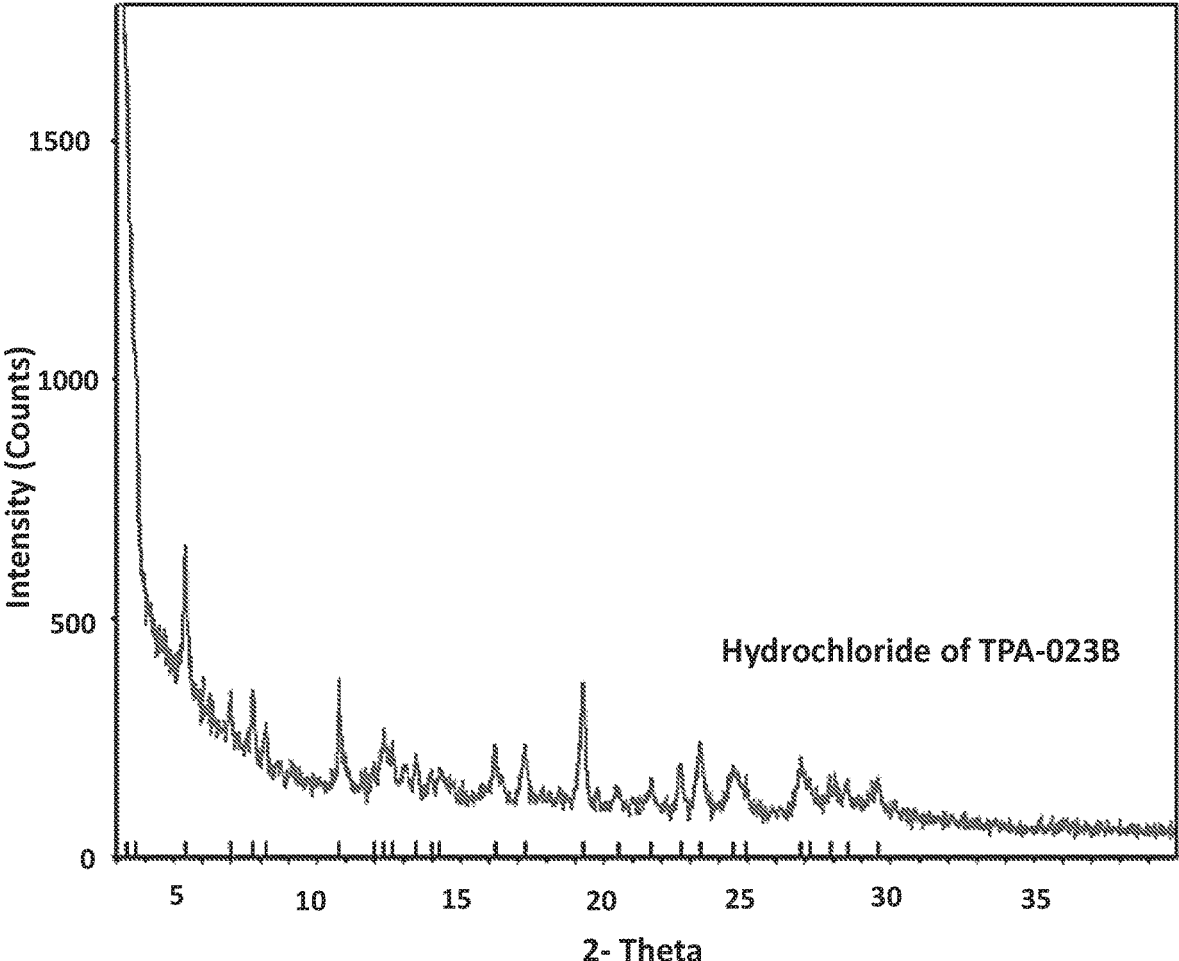
FIG. 15 illustrates an XRPD pattern for TPA023B chloride Pattern A
Figure 16:
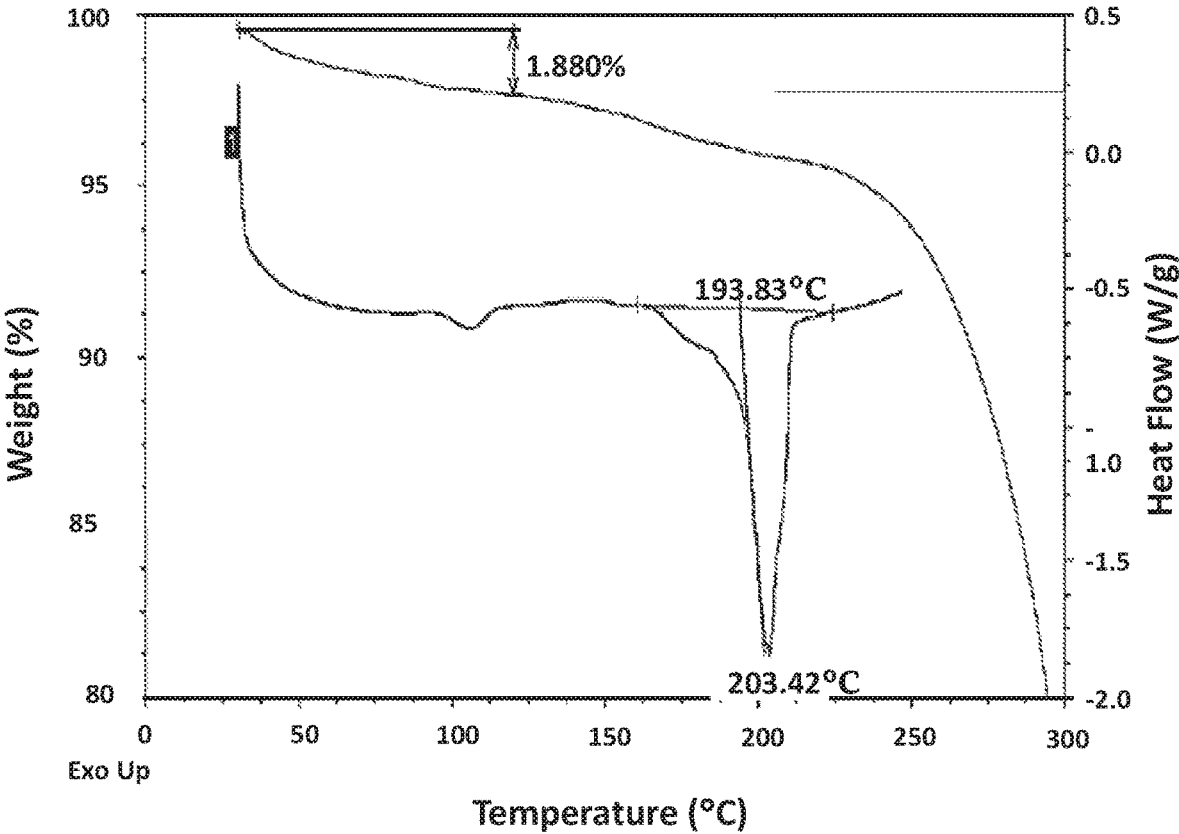
FIG. 16 illustrates a DSC/TGA thermogram for TPA023B chloride Pattern A

In one or more embodiments, a mixture comprising a crystalline polymorph of 2',6-difluoro-5'-[3-(1-hydroxy-1-methylethyl)-imidazo[1,2-b][1,2,4]triazin-7-yl]biphenyl-2-carbonitrile is described. This crystalline polymorph mixture is designated "Chloride Polymorphic Pattern A" (i.e., Chloride Pattern A) and exhibits an XRPD pattern having characteristic peak locations of at least three or all values selected from the group consisting of about: 7.0, 7.7, 8.2, 14.0, and 14.3±0.2 degrees, 2-theta, when measured using the parameters described in Table 1. Chloride Pattern A can comprise Free Base Form C. Chloride Pattern A can comprise Free Base Form F. In one or more embodiments, Chloride Polymorphic Pattern A exhibits an XRPD pattern substantially the same as the XRPD pattern shown in FIG. 15. In one or more embodiments, Chloride Polymorphic Pattern A has a melting/desolvating range of from about 150° C. to about 210° C. In one or more embodiments, Chloride Polymorphic Pattern A has a DSC thermograph substantially the same as FIG. 16. Chloride Polymorphic Pattern A can be synthesized using the method of Example 1. In one or more embodiments, pharmaceutical compositions comprising the Chloride Polymorphic Pattern A are described. In one or more embodiments, the disclosure provides purified forms of the crystalline Chloride Polymorphic Pattern A.

In one or more embodiments, a crystalline polymorph of a salt of 2',6-difluoro-5'-[3-(1-hydroxy-1-methylethyl)-imidazo[1,2-b][1,2,4]triazin-7-yl]biphenyl-2-carbonitrile with hydrochloric acid is described. This crystalline polymorph is designated "Chloride Polymorphic Form B" (i.e., Chloride Form B) and exhibits an XRPD pattern substantially the same as the XRPD pattern shown in FIG. 62, when measured using the parameters described in Table 26-4. In some embodiments, Chloride Polymorphic Form B exhibits an XRPD pattern having characteristic peak locations of at least three, at least six, at least nine or all values selected from the group consisting of about: 5.5, 7.7, 9.4, 12.2, 15.4, 16.6, 17.3, 19.5, 20.7, 23.4, 23.7 and 24.8±0.2 degrees, 2-theta, when measured using the parameters described in Table 26-4. In one or more embodiments, Chloride Polymorphic Form B exhibits an XRPD pattern substantially the same as the XRPD patterns labelled Form B in FIG. 52A. In some embodiments, Chloride Polymorphic Form B displays birefringence under polarized light. In one or more embodiments, Chloride Polymorphic Form B has a DSC thermograph substantially the same as the curves labeled Chloride Form B in FIG. 52E. In one or more embodiments, Chloride Polymorphic Form B exhibits a DSC thermogram comprising an endothermic peak at about 193° C. In one or more embodiments, Chloride Polymorphic Form B exhibits a DSC thermogram comprising an endothermic peak at about 162° C.

In one or more embodiments, still a further crystalline polymorph of a salt of 2',6-difluoro-5'-[3-(1-hydroxy-1-methylethyl)-imidazo[1,2-b][1,2,4]triazin-7-yl]biphenyl-2-carbonitrile with hydrochloric acid is described. This crystalline polymorph is designated "Chloride Polymorphic Form C" (i.e., Chloride Form C) and exhibits an XRPD pattern having characteristic peak locations of at least three, at least six, at least nine, at least twelve, at least fifteen or all values selected from the group consisting of about: 6.3, 11.7, 12.8, 14.1, 15.1, 16.5, 17.6, 18.8, 19.3, 20.6, 21.8, 23.2, 24.3, 25.7, 26.5, 26.9, 28.5, 30.3, 32.2, 32.7, and 33.5±0.2 degrees, 2-theta, when measured using the parameters described in Table 26-4. In one or more embodiments, Chloride Polymorphic Form C exhibits an XRPD pattern having characteristic peak locations of at least three, at least six, at least nine, or all values selected from the group consisting of about: 6.3, 11.7, 12.8, 15.1, 16.5, 18.8, 19.3, 21.8, 24.3, 25.7, 26.5, 26.9, 28.5, and 30.3±0.2 degrees, 2-theta, when measured using the parameters described in Table 26-4. In some embodiments, Chloride Polymorphic Form C exhibits an XRPD pattern having a characteristic peak located at 6.3±0.2 degrees, 2-theta. In some embodiments, Chloride Polymorphic Form C exhibits an XRPD pattern having a characteristic peak located at about 11.7±0.2 degrees, 2-theta. In some embodiments, Chloride Polymorphic Form C exhibits an XRPD pattern having a characteristic peak located at about 12.8±0.2 degrees, 2-theta. In some embodiments, Chloride Polymorphic Form C exhibits an XRPD pattern having a characteristic peak located at about 17.6±0.2 degrees, 2-theta. In some embodiments, Chloride Polymorphic Form C exhibits an XRPD pattern having a characteristic peak located at about 21.8±0.2 degrees, 2-theta. In some embodiments, Chloride Polymorphic Form C exhibits an XRPD pattern having a characteristic peak located at about 25.7±0.2 degrees, 2-theta. In one or more embodiments, Chloride Polymorphic Form C exhibits an XRPD pattern substantially the same as the XRPD pattern labeled Chloride Form C in FIG. 52A, when measured using the parameters described in Table 26-4. In one or more embodiments, Chloride Polymorphic Form C exhibits an XRPD pattern substantially the same as the XRPD pattern in FIG. 63, when measured using the parameters described in Table 26-4. In some embodiments, Chloride Polymorphic Form C displays birefringence under polarized light. In one or more embodiments, Chloride Polymorphic Form C has a melting/desolvating range of from about 150° C. to about 210° C. In one or more embodiments, Chloride Polymorphic Form C has a DSC thermograph substantially the same as the curves labelled Form C in FIG. 52H. In one or more embodiments, Chloride Polymorphic Form C has a DSC thermograph substantially the same as one of the curves in FIG. 52G and FIG. 52F.

In some embodiments, Chloride Polymorphic Form C is a stable form. In some embodiments, Chloride Polymorphic Form C can be stored at various temperatures and relative humidities. For example, Chloride Polymorphic Form C can be stored at about −20° C., about −10° C., about 0° C., about 5° C., about 15° C., about 25° C., about 40° C., and about 60° C. For another example, Chloride Polymorphic Form C can be stored at 10% RH, 20% RH, 30%/o RH, 40% RH, 50% RH, 60% RH, 75% RH, or 90% RH. In some embodiments, Chloride Polymorphic Form C is stable at about 25° C. for at least at least 7 days, at least 14 days, at least 21 days, at least a month, at least 2 months, at least 3 months, at least 6 months, at least 9 months, at least 12 months, at least 24 months, at least 36 months, at least 48 months, or at least 60 months. In some embodiments, Chloride Polymorphic Form C is stable at about 40° C. for at least 3 days, at least 7 days, at least 14 days, at least 21 days, at least a month, at least two months, at least 3 months, at least 6 months, at least 9 months, at least 12 months, or at least 24 months. In some embodiments, Chloride Polymorphic Form C is stable at about 60° C. for at least 3 days, at least 7 days, at least 14 days, at least 21 days, at least a month, at least two months, at least 3 months, at least 6 months, at least 9 months, at least 12 months, or at least 24 months. In some embodiments, a stable Chloride Polymorphic Form C has about 80%, 85%, 90%, 91%, 92%, 93%, 94%, 95%, 96%, 97%, 98%, 99% w/w or greater of the initial chloride salt amount at the end of the given storage period. In some embodiments, a stable Chloride Polymorphic Form C has about 20%, 15%, 100%, 5%, 2%, 1% w/w or less total impurity or related substances at the end of the given storage period. In some embodiments, Chloride Polymorphic Form C has substantially the same XRPD pattern post-storage at about 40° C. and 75% RH for at least 3 days, at least 7 days, at least 14 days, at least 21 days, at least a month, at least 2 months, at least 3 months, at least 6 months, at least 9 months, at least 12 months, at least 24 months, at least 36 months, at least 48 months, or at least 60 months. In some embodiments, Chloride Polymorphic Form C has substantially the same XRPD pattern post-storage at about 60° C. and 75% RH for at least 3 days, at least 14 days, at least 21 days, at least a month, at least 2 months, at least 3 months, at least 6 months, at least 9 months, at least 12 months, at least 24 months, at least 36 months, at least 48 months, or at least 60 months.

In one or more embodiments, Chloride Polymorphic Form C exhibits a DSC thermogram comprising an endothermic peak at about 179° C. Chloride Polymorphic Form C can be synthesized using the method of Example 41. In one or more embodiments, pharmaceutical compositions comprising the Chloride Polymorphic Form C are described. In one or more embodiments, the disclosure provides purified forms of the crystalline Chloride Polymorphic Form C.

In one or more embodiments, the Chloride Polymorphic Form C described herein is at least 50° %, at least 60%, at least 70%, at least 75%, at least 80%, at least 85%, at least 90° %, at least 91%, at least 92%, at least 93%, at least 94%, at least 95%, at least 96%, at least 97%, at least 98%, at least 99%, at least 99.5%, or at least 99.9% pure, as measured by HPLC as described herein. In some embodiment, the Chloride Polymorphic Form C described herein comprises an impurity. In some embodiments, the impurity in Chloride Polymorphic Form C is at most 0.1%, at most 0.5%, at most 1%, at most 2%, at most 3%, at most 4%, at most 5%, at most 6%, at most 7%, at most 8%, at most 9%, at most 10%, at most 15%, at most 20%, at most 25%, at most 30%, at most 40%, or at most 50%, as measured by HPLC as described herein.

Chloride Polymorphic Forms, such as Form C, can have a higher solubility than a free base form of TPA023B. For example, the solubility can be determined as described in example 15. In some embodiments, the solubility of Chloride Polymorphic Forms, such as Form C, is at least 1.1 fold, 1.5 fold, 2 fold, 3 fold, 4 fold, 5 fold, 6 fold, 7 fold, or 8 fold higher than the solubility of Free Base Form A in simulated gastric fluid (SGF). In some embodiments, the solubility of Chloride Polymorphic Forms, such as Form C, is at least 1.1 fold, 1.5 fold, 2 fold, 3 fold, 4 fold, 5 fold, 6 fold, 7 fold, or 8 fold higher than the solubility of Free Base Form A in Fasted-state simulated intestinal fluid (FaSSIF). In some embodiments, the solubility of Chloride Polymorphic Forms, such as Form C, is at least 1.1 fold, 1.5 fold, 2 fold, 3 fold, 4 fold, 5 fold, 6 fold, 7 fold, or 8 fold higher than the solubility of Free Base Form A in Fed-state simulated intestinal fluid (FeSSIF) than Free Base Polymorphic Form A.

Besylate

Figure 60:
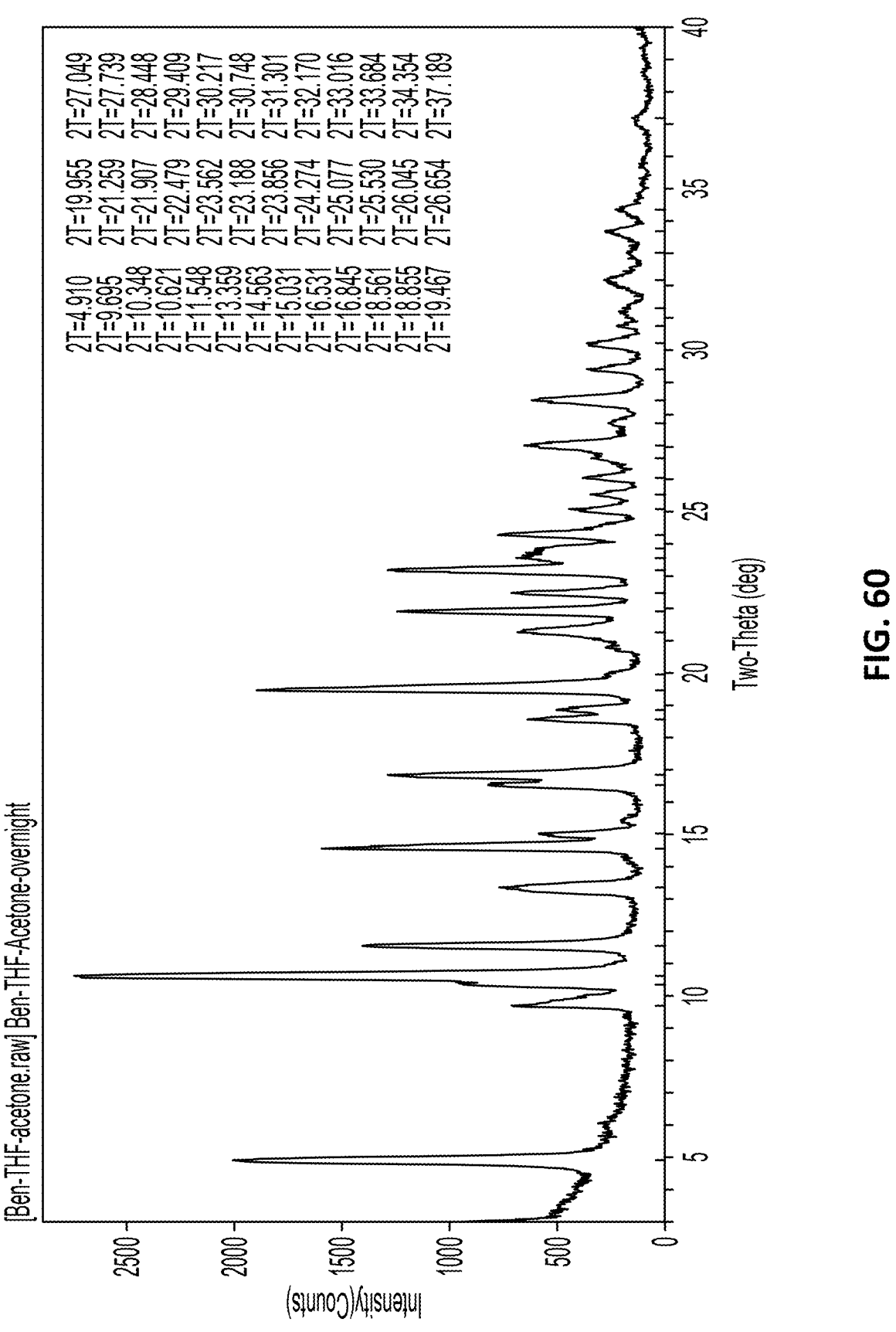
FIG. 60 illustrates an annotated XRPD pattern of TPA023B besylate Form A

In one or more embodiments, still a further crystalline polymorph of a salt of 2',6-difluoro-5'-[3-(1-hydroxy-1-methylethyl)-imidazo[1,2-b][1,2,4]triazin-7-yl]biphenyl-2-carbonitrile with benzenesulfonic acid is described. This crystalline polymorph is designated "Besylate Polymorphic Form A" (i.e., Besylate Form A) and exhibits an XRPD pattern having characteristic peak locations of at least three, at least six, at least nine, at least twelve, at least fifteen or all values selected from the group consisting of about: 4.9, 9.7, 10.3, 10.6, 11.5, 13.4, 14.6, 15.0, 16.5, 16.8, 18.6, 18.9, 19.5, 20.0, 21.3, 21.9, 22.5, 23.2, 23.6, 23.9, 24.3, 25.1, 25.5, 26.0, 26.7, 27.0, 27.7, 28.4, 29.4, 30.2, 30.7, 31.3, 32.2, 33.0, 33.7, 34.4, and 37.2±0.2 degrees, 2-theta, when measured using the parameters described in Table 26-4. In one or more embodiments, Besylate Polymorphic Form A exhibits an XRPD pattern having characteristic peak locations of at least three, at least six, at least nine, or all values selected from the group consisting of about: 4.9, 10.3, 10.6, 11.5, 13.4, 14.6, 15.0, 16.5, 16.8, 19.5, 21.3, 21.9, 23.2, 23.6, 23.9, 27.0, and 28.4±0.2 degrees, 2-theta, when measured using the parameters described in Table 26-4. In one or more embodiments, Besylate Polymorphic Form A exhibits an XRPD pattern substantially the same as the XRPD pattern in FIG. 57A, when measured using the parameters described in Table 26-4. In one or more embodiments, Besylate Polymorphic Form A exhibits an XRPD pattern substantially the same as the XRPD pattern in FIG. 60, when measured using the parameters described in Table 26-4. In some embodiments, Besylate Polymorphic Form A displays birefringence under polarized light. In one or more embodiments, Besylate Polymorphic Form A has a melting/desolvating range of from about 140° C. to about 160° C. In one or more embodiments, Besylate Polymorphic Form A has a DSC thermograph substantially the same as any one of the curves in FIG. 57D-FIG. 57F. In one or more embodiments, Besylate Polymorphic Form A exhibits a DSC thermogram comprising an endothermic peak at about 157° C. In one or more embodiments, Besylate Polymorphic Form A exhibits a DSC thermogram comprising an endothermic peak at about 148° C. Besylate Polymorphic Form A can be synthesized using the method of Example 46. In one or more embodiments, pharmaceutical compositions comprising the Besylate Polymorphic Form A are described. In one or more embodiments, the disclosure provides purified forms of the crystalline Besylate Polymorphic Form A.

In one or more embodiments, still a further anhydrous, hydrated, or solvated crystalline polymorph of a salt or co-crystal of 2',6-difluoro-5'-[3-(1-hydroxy-1-methylethyl)-imidazo[1,2-b][1,2,4]triazin-7-yl]biphenyl-2-carbonitrile with a pharmaceutically acceptable acid including, but not limited to acetic acid, benzoic acid, benzene sulfonic acid, carbonic acid, camphorsulfonic acid, citric acid, fumaric acid, gluconic acid, glucuraonic acid, hydrochloric acid, hydrobromic acid, hydroiodic acid, isethionic acid, lactic acid, lauryl sulfonic acid, malic acid, maleic acid, malonic acid, methane sulfonic acid, 1-napthylenesulfonic acid, 2-napthylenesulfonic acid, oleic acid, oxalic acid, pamoic acid, phosphoric acid, succinic acid, sulfuric acid, steric acid, tartaric acid, or para-toluene sulfonic acid in any ratio is described. Further crystalline polymorphic forms are synthesized using the method of Example 19, or any other method known to one skilled in the art. In one or more embodiments, pharmaceutical compositions comprising the Polymorphic Form are described. In one or more embodiments, the disclosure provides purified forms of the crystalline polymorphic form.

In one or more embodiments, still a further anhydrous, hydrated, or solvated crystalline polymorph of 2',6-difluoro-5'-[3-(1-hydroxy-1-methylethyl)-imidazo[1,2-b][1,2,4]triazin-7-yl]biphenyl-2-carbonitrile is described. Further crystalline polymorphic forms are synthesized using the method of Example 20. In one or more embodiments, pharmaceutical compositions comprising the Polymorphic Form are described. In one or more embodiments, the disclosure provides purified forms of the crystalline polymorphic form.

Salts

In one aspect, disclosed herein are salts of 2',6-difluoro-5'-[3-(1-hydroxy-1-methylethyl)-imidazo[1,2-b][1,2,4]triazin-7-yl]biphenyl-2-carbonitrile. In some embodiments, the disclosed salts are formed with TPA023B and an acid. The acid can be an organic or inorganic acid. In some embodiments, the acid comprises one or more of: acetic acid, benzoic acid, benzene sulfonic acid, carbonic acid, camphorsulfonic acid, citric acid, fumaric acid, gluconic acid, glucuraonic acid, hydrochloric acid, hydrobromic acid, hydroiodic acid, isethionic acid, lactic acid, lauryl sulfonic acid, malic acid, maleic acid, malonic acid, methane sulfonic acid, 1-napthylenesulfonic acid, 2-napthylenesulfonic acid, oleic acid, oxalic acid, pamoic acid, phosphoric acid, succinic acid, sulfuric acid, steric acid, tartaric acid, para-toluene sulfonic acid, and the like. In some embodiments, the acid is a pharmaceutically acceptable acid. In some embodiments, the salt comprises TPA023B free base and an acid in a certain ratio, e.g., TPA023B Free Base to acid in 5:1, 4:1, 3:1, 2:1, or 1:1 ratio by mole. In some embodiments, the ratio between the TPA023B free base and the acid could be any ratio, e.g., from 1:10 to 10:1 by mole. In some embodiments, the salt is in an anhydrate form. In some embodiments, the salt is in a hydrate form. In some embodiments, the salt is in a solvate form, e.g., an ethanol, dioxane, THF, methanol, or acetone solvate. In some embodiments, the salt is free of any solvent. In some embodiments, the salt is in a crystalline form. In some embodiments, the salt is partially crystalline. In some embodiments, the salt is in an amorphous form. In some embodiments, described herein is a salt of TPA023B with sulfuric acid in an amorphous form. In some embodiments, described herein is a salt of TPA023B with phosphoric acid in an amorphous form.

In some embodiments, the salt is TPA023B phosphate. In some embodiments, the salt is TPA023B chloride. In some embodiments, the salt is TPA023B sulfate. In some embodiments, the salt is TPA023B besylate. In some embodiments, the salt is TPA023B mesylate. In some embodiments, the salt is TPA023B tosylate. In some embodiments, the salt is TPA023B carboxylate. In some embodiments, the salt is TPA023B gluconate. In some embodiments, the salt is TPA023B maleate. In some embodiments, the salt is TPA023 benzoate.

In one aspect, disclosed herein are mixtures comprising TPA023B or a salt thereof. In some embodiments, the disclosed mixture comprises TPA023B free base. In some embodiments, the mixture comprises one or more TPA023B free base forms, e.g., Free Base Form E, Free Base Form F, or a combination of Form E and Form F. In some embodiments, the mixture comprises a salt of TPA023B, e.g., TPA023B phosphate or TPA023B sulfate. In some embodiments, the mixture comprises one or more TPA023 salt forms, e.g., TPA023B phosphate Form G and TPA023B phosphate Form F. In some embodiments, the mixture comprises a TPA023B Free Base and a TPA023B salt, e.g., Free Base Form E and Phosphate Form F.

In one or more embodiments, the TPA023B salt described herein is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, or at least 99.9% pure, as measured by HPLC as described herein. In some embodiment, the TPA023B salt described herein comprises an impurity. In some embodiments, the impurity in the TPA023B salt is at most 0.1%, at most 0.5%, at most 1%, at most 2%, at most 3%, at most 4%, at most 5%, at most 6%, at most 7%, at most 8%, at most 9%, at most 10%, at most 15%, at most 20%, at most 25%, at most 30%, at most 40%, or at most 50%, as measured by HPLC as described herein.

Co-Crystals

In one aspect, disclosed herein are co-crystals of 2',6-difluoro-5'-[3-(1-hydroxy-1-methylethyl)-imidazo[1,2-b][1,2,4]triazin-7-yl]biphenyl-2-carbonitrile. In some embodiments, the disclosed co-crystals are formed with TPA023B and an acid. The acid can be an organic or inorganic acid. In some embodiments, the acid comprises one or more of; acetic acid, benzoic acid, benzene sulfonic acid, carbonic acid, camphorsulfonic acid, citric acid, fumaric acid, gluconic acid, glucuraonic acid, hydrochloric acid, hydrobromic acid, hydroiodic acid, isethionic acid, lactic acid, lauryl sulfonic acid, malic acid, maleic acid, malonic acid, methane sulfonic acid, 1-napthylenesulfonic acid, 2-napthylenesulfonic acid, oleic acid, oxalic acid, pamoic acid, phosphoric acid, succinic acid, sulfuric acid, steric acid, tartaric acid, para-toluene sulfonic acid, and the like. In some embodiments, the acid is a pharmaceutically acceptable acid. In some embodiments, the co-crystal comprises TPA023B free base and an acid in a certain ratio, e.g., TPA023B Free Base to acid in 5:1, 4:1, 3:1, 2:1, or 1:1 ratio by mole. In some embodiments, the ratio between the TPA023B free base and the acid could be any ratio, e.g., from 1:10 to 10:1 by mole. In some embodiments, the co-crystal is in an anhydrate form. In some embodiments, the co-crystal is in a hydrate form. In some embodiments, co-crystal is in a solvate form, e.g., an ethanol, dioxane, THF, methanol, ethyl acetate, or acetone solvate. In some embodiments, the co-crystal is free of any solvent. In some embodiments, the co-crystal is in a crystalline form. In some embodiments, the co-crystal is partially crystalline.

In some embodiments, the co-crystal is TPA023B phosphate. In some embodiments, the co-crystal is TPA023B gluconate. In some embodiments, the co-crystal is TPA023B maleate. In some embodiments, the co-crystal is TPA023 benzoate.

In one aspect, disclosed herein are mixtures comprising TPA023B or co-crystal thereof. In some embodiments, the disclosed mixture comprises TPA023B free base. In some embodiments, the mixture comprises one or more TPA023B free base forms, e.g., Free Base Form E, Free Base Form F, or a combination of Form E and Form F. In some embodiments, the mixture comprises a co-crystal of TPA023B, e.g., TPA023B phosphate. In some embodiments, the mixture comprises one or more TPA023 co-crystal forms. In some embodiments, the mixture comprises a TPA023B Free Base and a TPA023B co-crystal, e.g., Free Base Form C and a co-crystal of Phosphate Form A.

In one or more embodiments, the TPA023B co-crystal described herein is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, or at least 99.9% pure, as measured by HPLC as described herein. In some embodiment, the TPA023B co-crystal described herein comprises an impurity. In some embodiments, the impurity in the TPA023B co-crystal is at most 0.1%, at most 0.5%, at most 1%, at most 2%, at most 3%, at most 4%, at most 5%, at most 6%, at most 7%, at most 8%, at most 9%, at most 10%, at most 15%, at most 20%, at most 25%, at most 30%, at most 40%, or at most 50%, as measured by HPLC as described herein.

In some embodiments, the salt or co-crystal of 2',6-difluoro-5'-[3-(1-hydroxy-1-methylethyl)-imidazo[1,2-b][1,2,4]triazin-7-yl]biphenyl-2-carbonitrile with an acid can have a higher solubility than a free base form of TPA023B. For example, the solubility can be determined as described in example 15. In some embodiments, the solubility of the salt or co-crystal is at least 1.1 fold, 1.5 fold, 2 fold, 3 fold, 4 fold, 5 fold, 6 fold, 7 fold, or 8 fold higher than the solubility of Free Base Form A in simulated gastric fluid (SGF). In some embodiments, the solubility of the salt or co-crystal is at least 1.1 fold, 1.5 fold, 2 fold, 3 fold, 4 fold, 5 fold, 6 fold, 7 fold, or 8 fold higher than the solubility of Free Base Form A in Fasted-state simulated intestinal fluid (FaSSIF). In some embodiments, the solubility of the salt or co-crystal is at least 1.1 fold, 1.5 fold, 2 fold, 3 fold, 4 fold, 5 fold, 6 fold, 7 fold, or 8 fold higher than the solubility of Free Base Form A in Fed-state simulated intestinal fluid (FeSSIF) than Free Base Polymorphic Form A.

In the context of the present application, a "polymorph" is a particular crystalline arrangement or crystal "form" of a chemical compound in the solid state. A crystal form, or polymorph, of a chemical compound contains constituent molecules arranged in an orderly, repeating, three-dimensional pattern. Some chemical compounds are able to form multiple polymorphs each having a different arrangement of atoms and or molecules in their crystal structure. When the compound is a biologically active compound, such as an active pharmaceutical ingredient, the difference in crystal structures can lead to each polymorph having different chemical, physical, and biological properties. Properties which may be affected include crystal shape, density, hardness, color, chemical stability, melting point, hygroscopicity, suspensibility, dissolution rate and biological availability. As such, a specific polymorph may have properties which make it unexpectedly advantageous in a particular application relative to another polymorph of the same parent compound. In particular, the physical, chemical, and biological properties listed above can have a significant effect on the development of production methods and formulations and the quality and efficacy of active pharmaceutical ingredients. Some chemical compounds and molecular complexes (such as solvates, co-crystals, coordination compounds) can exist in multiple polymorphs, each manifesting different physical characteristics. Furthermore, less stable polymorphs may convert or partly convert into more stable polymorphs under suitable conditions. For these reasons, it is necessary to control the particular crystalline form of an active pharmaceutical ingredient when developing products which will be used for therapeutic benefit in humans or animals. It is noted that predicting whether the solid state of a compound may form one or more polymorphs is not possible and nor is it possible to predict the properties of any of these crystal forms.

In one or more embodiments, the crystalline polymorph described herein is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, or at least 99.9% pure, as measured by HPLC as described herein. In some embodiment, the crystalline polymorph described herein comprises an impurity. In some embodiments, the impurity in the crystalline polymorph is at most 0.1%, at most 0.5%, at most 1%, at most 2%, at most 3%, at most 4%, at most 5%, at most 6%, at most 7%, at most 8%, at most 9%, at most 10%, at most 15%, at most 20%, at most 25%, at most 30%, at most 40%, or at most 50%, as measured by HPLC as described herein.

Assaying the solid phase for the presence of crystals may be carried out by conventional methods known in the art. For example, it is convenient and routine to use powder X-ray diffraction techniques. Other techniques which may be used include differential scanning calorimetry (DSC), thermogravimetric analysis (TGA) and Raman or Infra-red spectroscopy, NMR, gas chromatography or HPLC.

In one or more embodiments, the present disclosure provides prophylactic and/or therapeutic compositions comprising one or more of the compounds described herein dispersed in a pharmaceutically-acceptable carrier. The term "carrier" is used herein to refer to diluents, excipients, vehicles, and the like, in which the compound may be dispersed for administration. Suitable carriers will be pharmaceutically acceptable. As used herein, the term "pharmaceutically acceptable" means not biologically or otherwise undesirable, in that it can be administered to a subject without excessive toxicity, irritation, or allergic response, and does not cause unacceptable biological effects or interact in a deleterious manner with any of the other components of the composition in which it is contained. A pharmaceutically-acceptable carrier would naturally be selected to minimize any degradation of the compound or other agents and to minimize any adverse side effects in the subject, as would be well known to one of skill in the art. Pharmaceutically-acceptable ingredients include those acceptable for veterinary use as well as human pharmaceutical use, and will depend on the route of administration. For example, compositions suitable for administration via injection are typically solutions in sterile isotonic aqueous buffer. Exemplary carriers include aqueous solutions such as normal (n.) saline (~0.9% NaCl), phosphate buffered saline (PBS), sterile water/distilled autoclaved water (DAW), other acceptable vehicles, and the like. Other ingredients may be included in the composition, such as adjuvants, other active agents, preservatives, buffering agents, salts, other pharmaceutically-acceptable ingredients. The composition can comprise a therapeutically effective amount of the compound dispersed in the carrier.

In one or more embodiments, the present disclosure provides methods for treating a condition or disorder in subject in need thereof, wherein the method generally comprises administering a therapeutically effective amount of one or more of the compounds described herein. As used herein, a "therapeutically effective" amount refers to the amount that will elicit the biological or medical response of a tissue, system, or subject that is being sought by a researcher or clinician, and in particular elicit some desired therapeutic or prophylactic effect against the targeted disease or condition. One of skill in the art recognizes that an amount may be considered therapeutically "effective" even if the condition is not totally eradicated or prevented, but it or its symptoms and/or effects are improved or alleviated partially in the subject. In the case of certain salts or co-crystals, it will be appreciated that formulations may be administered in amounts to provide sufficient levels of the active compound.

In some embodiments, the condition or disorder is associated with α2/α3 GABAA receptor. In some embodiments, the condition or disorder is pain, anxiety, epilepsies, muscle spasms, pruritus, itch, cognitive impairment, alcohol dependence, drug addiction, schizophrenia, depression, autism, panic disorder, or generalized anxiety disorder.

In some embodiments, the condition or disorder is pain. In some embodiments, the pain is Fibromyalgia, Inflammatory pain, Neuropathic pain, Pain resulting from Peripheral Diabetic Neuropathy, Chemotherapy induced pain, pain resulting from HIV-associated Neuropathy, pain resulting from Post-herpetic neuralgia, Musculoskeletal pain, pain resulting from Rheumatoid arthritis, pain resulting from Osteoarthritis, Post-operative pain, Burn pain, Sunburn pain, or phantom limb pain. In some embodiments, the pain is an acute pain, chronic pain, neuropathic pain, nociceptive (including inflammatory) pain, somatic pain, visceral pain, or dysfunctional pain. In some embodiments, there is a brain or spinal condition underlying the pain. In some embodiments, the pain is of a neuropathic, nociceptive, and/or inflammatory nature. In some embodiments, the pain can affect either the somatic or visceral systems, or it can affect multiple systems. In some embodiments, the pain is a physiological pain. In some embodiments, the pain is an acute pain. In some embodiments, the pain is associated with a defined injury, e.g. surgery, dental work, a strain or a sprain. In some embodiments, the pain is a chronic pain. In some embodiments, the chronic pain is neuropathic pain (e.g. painful diabetic neuropathy or postherpetic neuralgia), carpal tunnel syndrome, back pain, osteoarthritis, headache, cancer pain, arthritic pain, or chronic post-surgical pain. In some embodiments, the pain is a chronic painful condition affecting any system. In some embodiments, the neuropathic pain is associated with a disease or trauma such as peripheral neuropathy, post herpetic neuralgia, diabetic neuropathy, trigeminal neuralgia, cancer neuropathy, HIV neuropathy, phantom limb pain, back pain, carpal tunnel syndrome, central post-stroke pain and pain associated with chronic alcoholism, hypothyroidism, uremia, spinal cord injury, multiple sclerosis, Parkinson's disease, epilepsy and vitamin deficiency. In some embodiments, the condition or disorder is fibromyalgia or chronic regional pain syndrome. In some embodiments, the pain is a moderate to severe acute nociceptive pain, which can be associated with post-operative pain, posttraumatic pain, cancer pain, back pain, osteoarthritis, pain associated with gout, or pains from strains, sprains, burns, myocardial infarction, or acute pancreatitis. In some embodiments, the cancer pain is a chronic pain, e.g., tumor related bone pain, headache, facial pain, or visceral pain. In some embodiments, the cancer pain is a pain associated with cancer therapy, e.g., the pain in response to chemotherapy, immunotherapy, hormonal therapy or radiotherapy. In some embodiments, the pain is a back pain. In some embodiments, the pain is associated with arthritis such as rheumatoid arthritis or osteoarthritis.

In some embodiments, the condition or disorder is Drug addiction or Alcohol dependence. In some embodiments, the condition or disorder is panic disorder, generalized anxiety disorder, anxiety, or schizophrenia. In some embodiments, the condition or disorder is a stress disorder, e.g., post-traumatic stress disorder, acute stress disorder, or substance-induced stress disorder. In some embodiments, the condition or disorder is a phobia, such as agoraphobia, social phobia, noise phobia or animal phobias. In some embodiments, the condition or disorder is an obsessive compulsive disorder. In some embodiments, the anxiety is a separation anxiety or a childhood anxiety disorder.

In some embodiments, the condition or disorder is itch, e.g., chronic or acute itch. In some embodiments, the condition or disorder is Chronic Itch, Neurogenic itch, Inflammatory itch, Uremic Pruritus, Neurodermatitis, Atopic Dermatitis, Notalgia Paresthetica, Prurigo Nodularis, Psoriasis, Psychogenic itch, or Aquagenic Itch. In some embodiments, the itch is Pruriceptive itch. Pruriceptive itch can be caused by an allergic reaction, inflammation, dryness or other skin damage. Pruriceptive itch can be associated with atopic dermatitis (eczema), urticaria (hives), psoriasis, drug reactions, mites, or dry skin. In some embodiments, the itch is neuropathic itch. Neuropathic itch can be caused by damage to the nervous system and is often accompanied by sensations of numbness and tingling. Neuropathic itch can be seen after shingles, after stroke or burn injury, and in notalgia parasthetica (an area of itchy skin, usually on the back). Neurogenic itch can be associated with chronic liver and kidney disease in response to opioid neuropeptides. In some embodiments, the itch is psychogenic itch. Psychogenic itch can be induced in response to the chemicals serotonin or norepinephrine, which influences stress, depression and delusional parasitosis (a false belief of parasite infestation). In some embodiments, the condition or disorder is Cholestatic Pruritus, Uremic Pruritus, Neurodermatitis, Atopic Dermatitis, Atopic Eczema, Contact Dermatitis, Prurigo Nodularis, Psoriasis, Bug bites, Parasites, Fungal infection, Aquagenic Itch, Uticaria, Allergic itch, or Delusional parasitosis.

In some embodiments, the condition or disorder is chronic cough or Irritable Bowel Syndrome. In some embodiments, the condition or disorder is epilepsy. In some embodiments, the epilepsy is autosomal dominant nocturnal frontal lobe epilepsy (ADNFLE), Focal epilepsy, Generalized epilepsy, Dravet Syndrome, Childhood absence epilepsy (CEA), Juvenile absence epilepsy, Juvenile myoclonic epilepsy (JME), West Syndrome, Lennox-Gastaut syndrome (LGS), Sunflower Syndrome, Status epilepticus, Nerve agent induced seizures, Tremors from alcohol withdrawal, Traumatic Brain Injury, Tuberous Sclerosis Complex, Doose Syndrome, Rasmussen's Syndrome, Early myoclonic encephalopathy, Malignant migrating partial seizures of infancy, Epilepsy with continuous spike and waves during slow wave sleep, Landau-Kleffner syndrome, Benign epilepsy with centrotemporal spikes, Benign familial neonatal infantile seizures, Benign centrotemporal lobe epilepsy of childhood, Benign occipital epilepsy of childhood (BOEC), Cortical dysplasia focal epilepsy syndrome, Generalized epilepsy with febrile seizure plus (GEFS+), Myoclonic atonic epilepsy, Malignant migrating partial seizures of infancy, Ohtahara syndrome (a.k.a. early infantile epileptic encephalopathy), primary reading epilepsy, symptomatic localization-related epilepsies, temporal lobe epilepsy (TLE), Rasmussen's encephalitis, progressive myoclonic epilepsy, or Partial epilepsy and febrile seizures plus. In some embodiments, the condition or disorder is spasticity (such as Post-stroke spasticity, or generalized and focal spasticity), Muscle spasms, convulsion, essential tremor, dystonia, or premature ejaculation. In some embodiments, the condition or disorder is autism. In some embodiments, the condition or disorder is autism resulting from a SCN2a mutation, fragile X syndrome, or any form of autism related to the dysfunction of an ion-channel. In some embodiments, the condition or disorder is depressive disorder (such as depression), bipolar disorders, or cyclothymia. In some embodiments, the condition or disorder is schizophrenia such as schizophrenia of the paranoid type, disorganized type, catatonic type, undifferentiated type, residual type, post-schizophrenic depression and simple schizophrenia.

In some embodiments, the compounds and compositions described herein can be used as an antiemetic agents, e.g., for chemotherapy or radiation induced emesis, post-operative nausea and vomiting, or motion sickness. In some embodiments, the compounds and compositions described herein can be used as a cognition-enhancing agent.

In some embodiments, the subject is afflicted with or suffering from a condition (e.g., infection, disease, or disorder) before the compounds are administered, wherein methods described herein are useful for treating the condition and/or ameliorating the effects of the condition. In one or more embodiments, the methods are useful for reversing progression of the disease or condition. In other embodiments, the subject is free of a given condition before administering the compound, wherein the methods described herein are useful for preventing the occurrence or incidence of the condition and/or preventing the observable effects of the condition. The disclosed embodiments can be formulated for various routes of administration, depending upon the particular carrier and other ingredients used. For example, the prophylactic and/or therapeutic compounds or compositions can be injected intramuscularly, subcutaneously, intradermally, or intravenously. They can also be administered via mucosa such as intranasally, intravaginally, intrarectally or orally. The compounds or compositions can also be administered topically through the skin via a transdermal patch, spot-on, pour-on or microneedles. Suspensions, solutions, powders, tablets, gel caps, etc., are contemplated herein.

In some embodiments, the compound or compositions can be provided in unit dosage form in a suitable container. The term "unit dosage form" refers to a physically discrete unit suitable as a unitary dosage for human or animal use. Each unit dosage form may contain a predetermined amount of the inventive compound (and/or other active agents) in the carrier calculated to produce a desired effect. In other embodiments, the compound can be provided separate from the carrier (e.g., in its own vial, ampule, sachet, or other suitable container) for on-site mixing before administration to a subject. A kit comprising the compound(s) is also disclosed herein. The kit further comprises instructions for administering the compound to a subject. The compound(s) can be provided as part of a dosage unit, already dispersed in a pharmaceutically-acceptable carrier, or it can be provided separately from the carrier. The kit can further comprise instructions for preparing the compounds for administration to a subject, including for example, instructions for dispersing the compounds in a suitable carrier.

It will be appreciated that therapeutic and prophylactic methods described herein are applicable to humans as well as any suitable animal, including, without limitation, dogs, cats, and other pets, as well as, rodents, primates, horses, cattle, pigs, etc. The methods can be also applied for clinical research and/or study.

In still another embodiment, described herein are methods of preparing a crystalline form of a compound described herein. The methods generally comprise one or more of the following techniques: slurrying the compound for a period of time in one or more solvents, with or without heating; dissolving the compound in a one or more solvents with or without heating and then removing some or all of the solvent(s) through a method such as evaporation or distillation; dissolving the compound in one or more solvents and adding an anti-solvent, combination of antisolvents, or a mixture of solvent and antisolvent; dissolving a compound in one or more solvents with or without heating and then allowing the solution to cool, or actively cooling any solution; heating a compound in the absence of solvent; heating a compound under atmospheric or reduced pressure until it sublimates and collecting it on a cooled surface; melting a solid and allowing it to cool; exposing the compound to water vapor or the vapor of a solvent; adding small amounts of seed material; any other method known to one skilled in the art; and combinations of any or all of the above processes.

In still another embodiment, the disclosure is concerned with use of a compound according to the various embodiments described herein to prepare a therapeutic or prophylactic medicament for the treatment or prevention of a disease or condition treatable by α2/α3 GABAA positive allosteric modulators, as well as disorders treatable with non-selective GABAA positive allosteric modulators in mammals, animals and humans.

Additional advantages of the various embodiments of the disclosure will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments but is not necessarily included. Thus, the present disclosure encompasses a variety of combinations and/or integrations of the specific embodiments described and claimed herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

As used herein, the term "about" when used in association with a measurement, or used to modify a value, a unit, a constant, or a range of values, refers to variations of no more than +/−3%.

The term "substantially the same," as used herein to define a figure is intended to mean that the figure is considered the same as a reference figure by a skilled artisan in view of deviations acceptable in the art. Such deviations may be caused by factors related to instruments, operation conditions and human factors, etc., known in the art. For example, one skilled in the art can appreciate that the endotherm onset and peak temperatures as measured by differential scanning calorimetry (DSC) may vary significantly from experiment to experiment. In some embodiments, when positions of characteristic peaks of two figures do not vary more than +/−5%, +/−4%, +/−3%, +/−2%, or +/−1%, it is deemed that the two figures are substantially the same. For example, one skilled in the art can readily identify whether two X-ray diffraction patterns or two DSC thermograms are substantially the same. In some embodiments, when characteristic peaks of two X-ray diffraction patterns do not vary more than +0.3 degrees 2-Theta, +0.2 degrees 2-Theta or 0.1 degrees 2-Theta, it is deemed that the X-ray diffraction patterns are substantially the same.

The present description also uses numerical ranges to quantify certain parameters relating to various embodiments of the disclosure. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the disclosure. It is to be understood, however, that these examples are provided by way of illustration and nothing therein should be taken as a limitation upon the overall scope of the disclosure.

Example 1

Salt Screening

Salt screening via reaction crystallization was preliminarily conducted using five acids in four solvents or solvent mixtures. For hydrochloric acid, sulfuric acid, phosphoric acid, and methanesulfonic acid, about 20 mg of TPA023B was stirred in about 0.5 mL of solvent and about 1.1 molar equivalents of the corresponding acid solutions were added. For p-toluenesulfonic acid, about 20 mg of TPA023B and about 1.1 molar equivalents of the corresponding acid were stirred in about 0.5 mL of each solvent. For controls, about 20 mg of TPA023B was stirred in about 0.5 mL of the corresponding solvent. The resulting mixture was heated to about 50° C. with continuous stirring for about 4 hrs and slowly cooled to about 20-25° C. overnight.

Because TPA023B possesses a tertiary alcohol that is also alpha to an aromatic ring it may be prone to degradation by elimination under acidic conditions. HPLC analysis was conducted on the acetone samples to determine the extent of degradation that occurred, if any. The results showed that TPA023B with $H_3PO_4$ in acetone had lower degradation than the other acids.

TABLE 2

| HPLC analysis | |
| --- | --- |
| Sample | Purity (%) |
| TPA023B control in acetone | 99.33 |
| TPA023B with $H_3PO_4$ in acetone | 98.88 |
| TPA023B with methane sulfonic acid in acetone | 98.71 |
| TPA023B with p-toluene sulfonic acid in acetone | 98.65 |
| TPA023B with HCl in acetone | 98.61 |
| TPA023B with $H_2SO_4$ in acetone | 98.33 |

Figure 25:
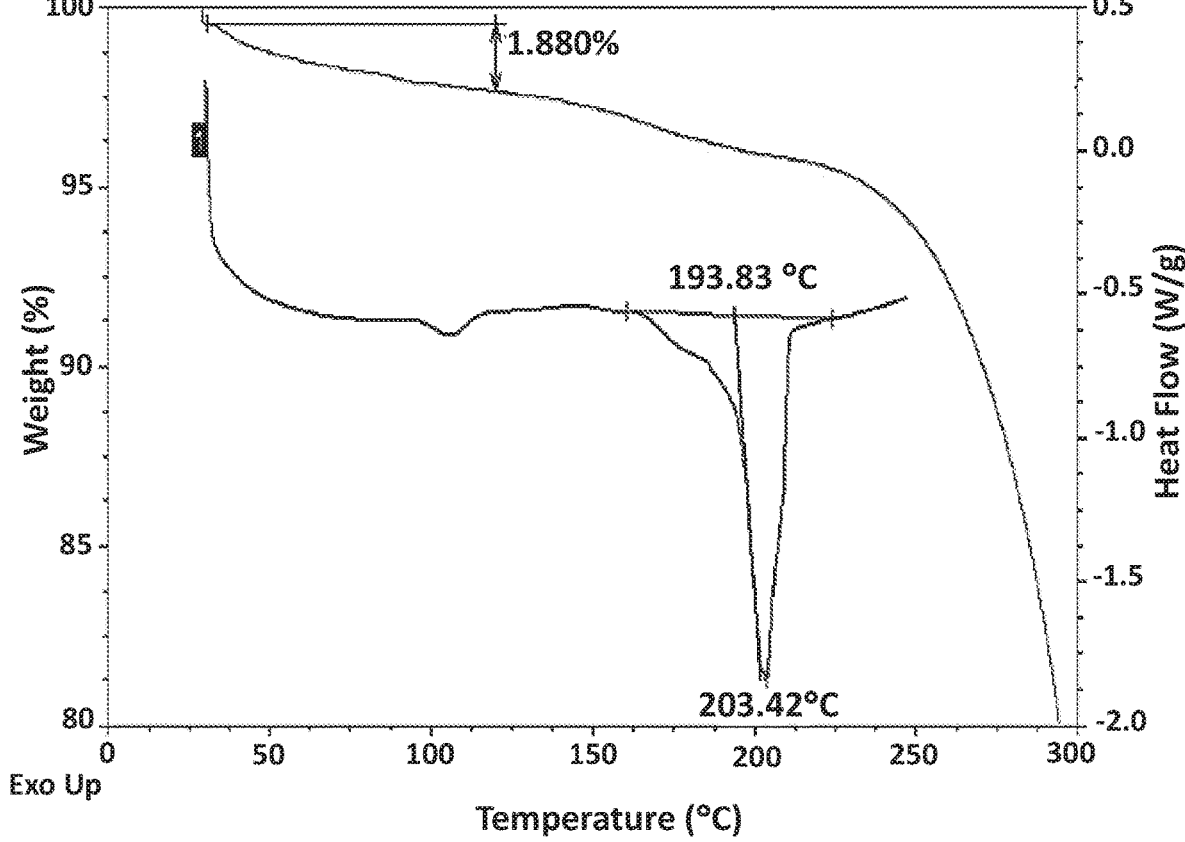
FIG. 25 illustrates the TGA and DSC results of TPA023B HCl salt in Acetone system (a mixture comprising TPA023B Free Base Form C and TPA023B Chloride Pattern A)
Figure 26:
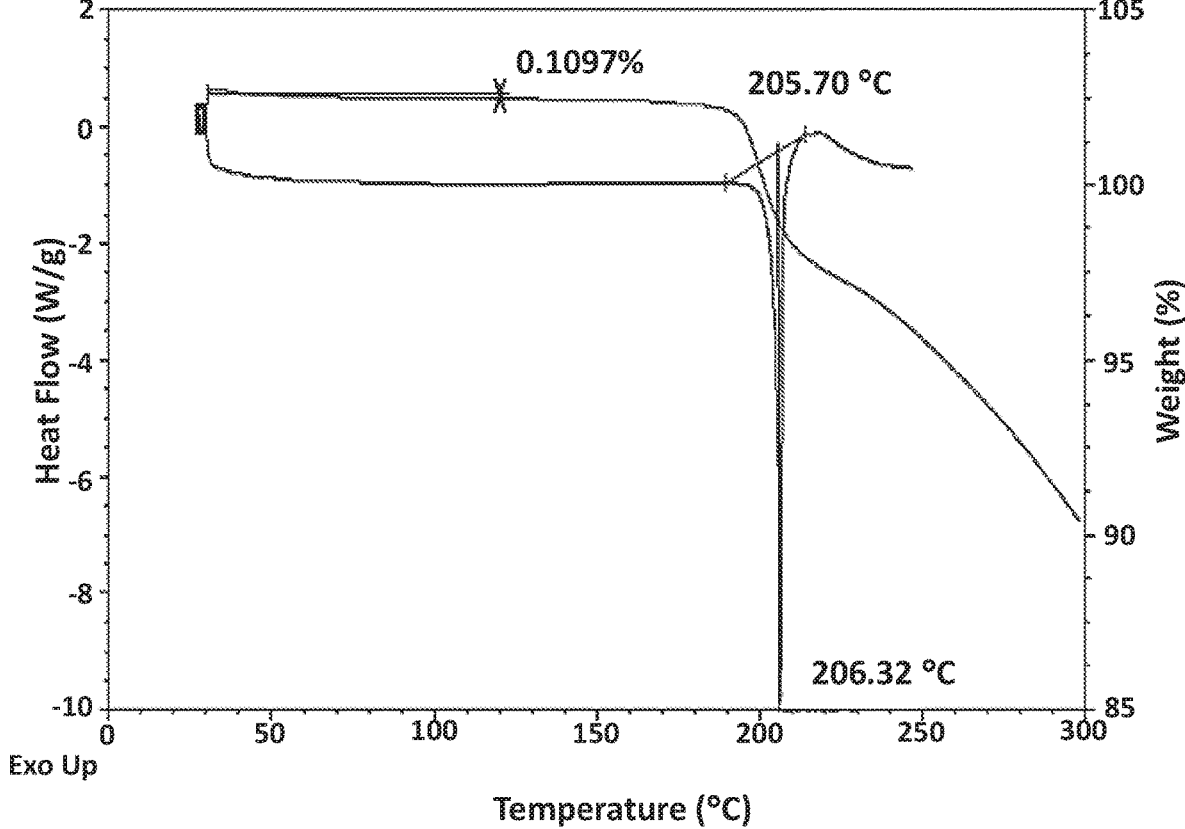
FIG. 26 illustrates the TGA and DSC results of TPA023B Phosphoric Acid Salt in ACN system (TPA023B phosphate Form A)

For any experiment which produced an observable solid, the solid was isolated by centrifugation (about 14,000 rpm for about 5 minutes) and analyzed by XRPD. For clear solutions, solids were produced via evaporation at 35° C. by drying in vacuo and checked by XRPD. TGA and DSC characterization data was collected for any solid that demonstrated novel crystallinity by XRPD. The results are shown in Table 3 and the XRPD patterns are shown in FIGS. 20 to 24. The DSC/TGA resulting solid from the "Hydrochloric Acid in Acetone" experiment is provided in FIG. 25. The DSC/TGA resulting solid from the "Phosphoric Acid in Acetonitrile" experiment is provided in FIG. 26.

TABLE 3

| | Results of Example 1. | | | |
| --- | --- | --- | --- | --- |
| | Solvent System | | | |
| Acid | Acetone | Ethyl Acetate | Acetonitrile | 95% IPA/H20 |
| Hydrochloric Acid | Mixture: Free Base Polymorphic Form C and Chloride Polymorphic Pattern A | Free Base Polymorphic Form A | Free Base Polymorphic Form A | Free Base Polymorphic Form A |

TABLE 3-continued

Results of Example 1.

| | Solvent System | | | |
| --- | --- | --- | --- | --- |
| Acid | Acetone | Ethyl Acetate | Acetonitrile | 95% IPA/H20 |
| Sulfuric Acid | Amorphous | Amorphous | Amorphous | Free Base Polymorphic Form A |
| Phosphoric acid | Phosphate Polymorphic Form A | Phosphate Polymorphic Form A | Phosphate Polymorphic Form A | Free Base Polymorphic Form A |
| p-toluene sulfonic acid | Amorphous | Amorphous | Amorphous | Free Base Polymorphic Form A |
| Methane sulfonic acid | Amorphous | Amorphous | Amorphous | Free Base Polymorphic Form A |
| API control | Free Base Polymorphic Form C | Free Base Polymorphic Form A | Free Base Polymorphic Form A | Free Base Polymorphic Form A |

The phosphate salt was found to readily form a stable new crystalline form. In addition, a trace of a new crystalline form was observed that may be a hydrochloride salt or a new polymorph of the free base. It was labeled Chloride Polymorphic Pattern A. Given the pKa of TPA023B (about 2.19) and its highly planar aromatic structure of TPA023B, it is unexpected that out of the strong acids tested under the conditions, only phosphoric acid formed highly crystalline solids with properties suitable for manufacture and use in pharmaceutical preparations, especially given that the pKa of TPA023B and Phosphoric Acid are so similar. The relative stability of TPA023B with phosphoric acid, as compared with other stronger acids, provides a significant benefit to the manufacturability of the phosphate salt or co-crystal that could not have been predicted beforehand. It is highly beneficial that the salt or co-crystal formation be the final particle forming step, because any additional purification steps after this stage add significantly to the cost of goods. Therefore, the reduced impurity formation afforded by the phosphate salt or co-crystal reduces the risk of needing additional purification and offers an advantage over other counterions.

Example 2

Crystallization Screening on Amorphous Salts of TPA023B

Additional attempts to find crystalline salt forms of TPA023B were made. The amorphous TPA023B salts formed in Example 1, and about 0.5 ml of the corresponding solvent shown (Table 4) were heated to about 50° C. with continuous stirring for about 2 days. Only in the case of p-toluene sulfonate in toluene, a crystalline solid was obtained. In all other cases, an amorphous solid was obtained. This salt was labeled Tosylate Polymorphic Form A.

TABLE 4

Results from Example 2

| | Solvent System | | |
| --- | --- | --- | --- |
| Acid | Toluene | MTBE | Heptane |
| Sulfuric acid | Amorphous | Amorphous | Amorphous |
| p-toluene sulfonic acid | Tosylate Polymorphic Form A | Amorphous | Amorphous |
| Methanesulfonic acid | Amorphous | Amorphous | Amorphous |

Example 3

Accelerated Stability Testing of Phosphate Polymorphic Form A and Free Base Polymorphic Form A The stability of Phosphate Polymorphic Form A and Free Base Polymorphic Form A were evaluated under accelerated conditions.

TABLE 5

One (1) Week Accelerated Stability Testing

| Material | Storage Conditions | Timepoint | Assay* (%) | Purity (%) |
| --- | --- | --- | --- | --- |
| Phosphate Polymorphic Form A | — | Initial | 104.60 | 98.91 |
| | 80° C. (open) | 1 week | 95.99 | 98.94 |
| | 40° C./75% RH (open) | 1 week | 97.12 | 99.02 |
| | Light | ~50 h | 95.25 | 97.55 |
| Free Base Polymorphic Form A | — | Initial | 105.51 | 98.72 |
| | 80° C. (open) | 1 week | 101.60 | 98.62 |
| | 40° C./75% RH (open) | 1 week | 102.35 | 98.64 |
| | Light | ~50 h | 104.28 | 98.60 |

*Assay criterion: 95%-105%

TABLE 6

Details of Photostability Chamber

| | Conditions | Time |
| --- | --- | --- |
| VIS (light) | 30 Kilolux | 43 hrs |
| VIS (UV) | 200 watt | 7.92 hrs |

Example 4

Figure 19:
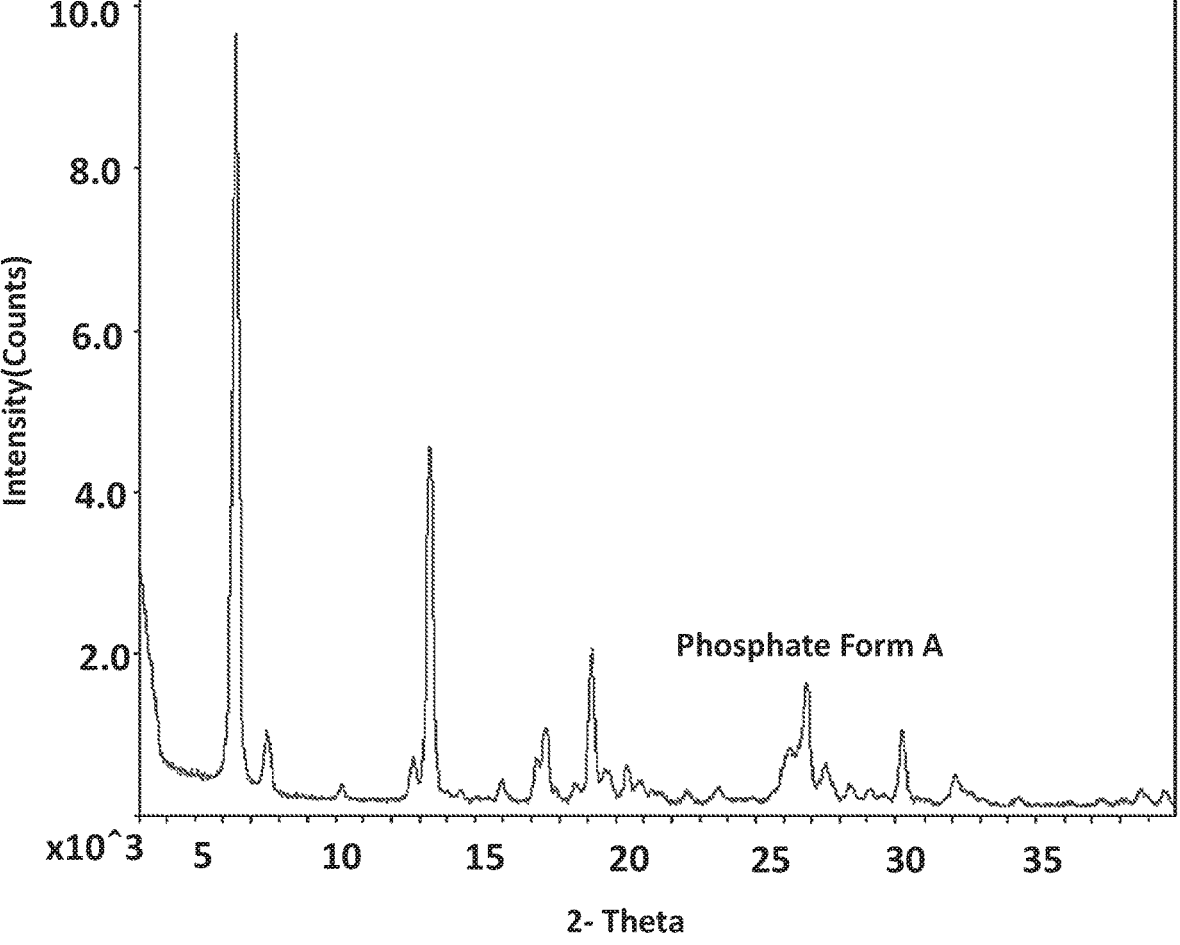
FIG. 19 illustrates an XRPD pattern for TPA023B phosphate Form A after DVS
Figure 20:
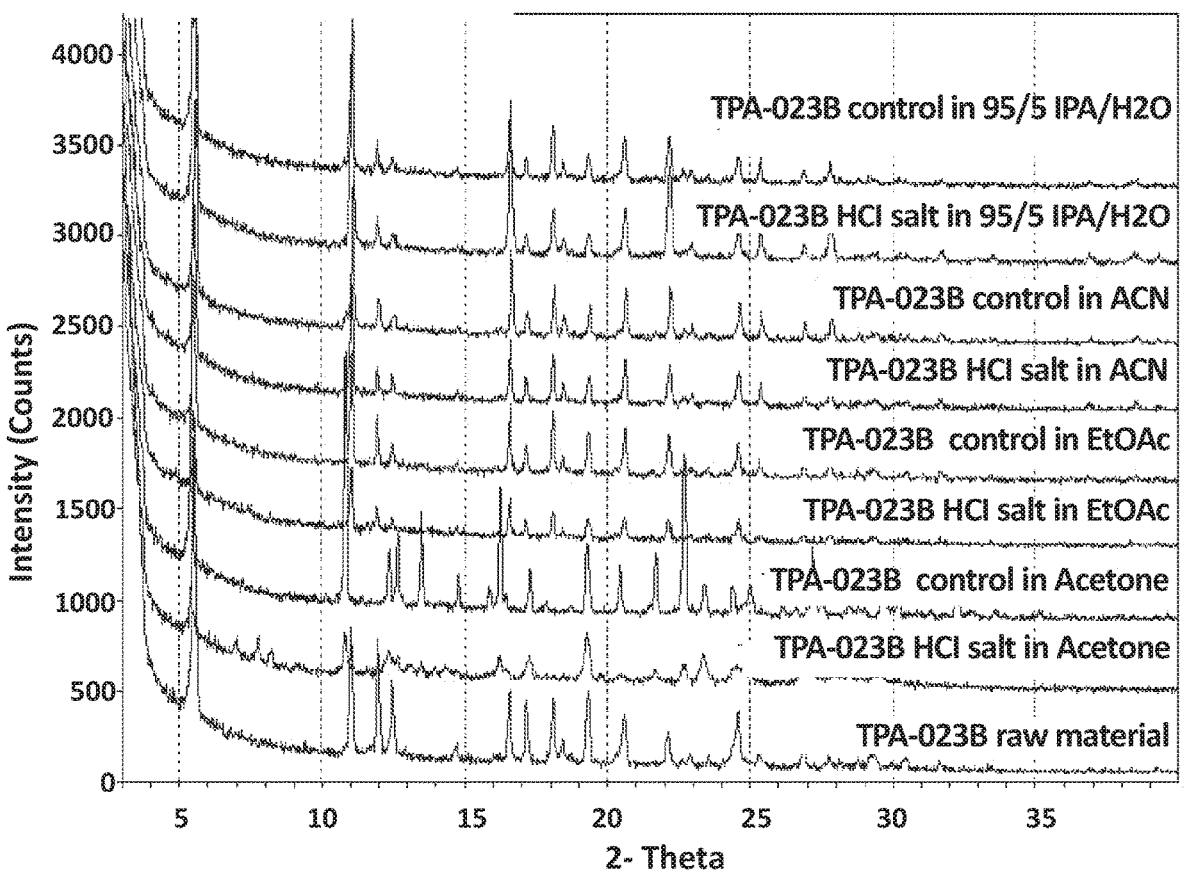
FIG. 20 illustrates XRPD patterns of TPA023B HCl Salt Screening
Figure 21:
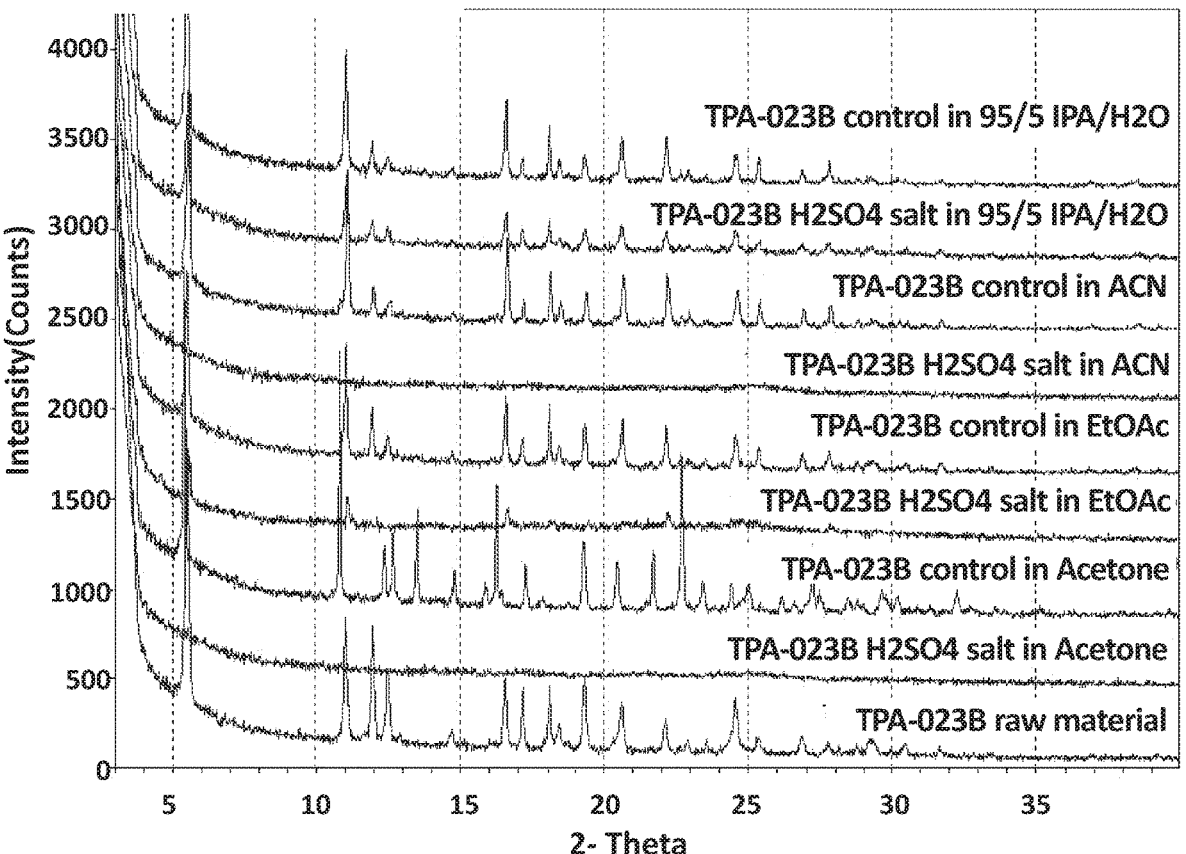
FIG. 21 illustrates XRPD patterns of TPA023B Sulfate Screening
Figure 22:
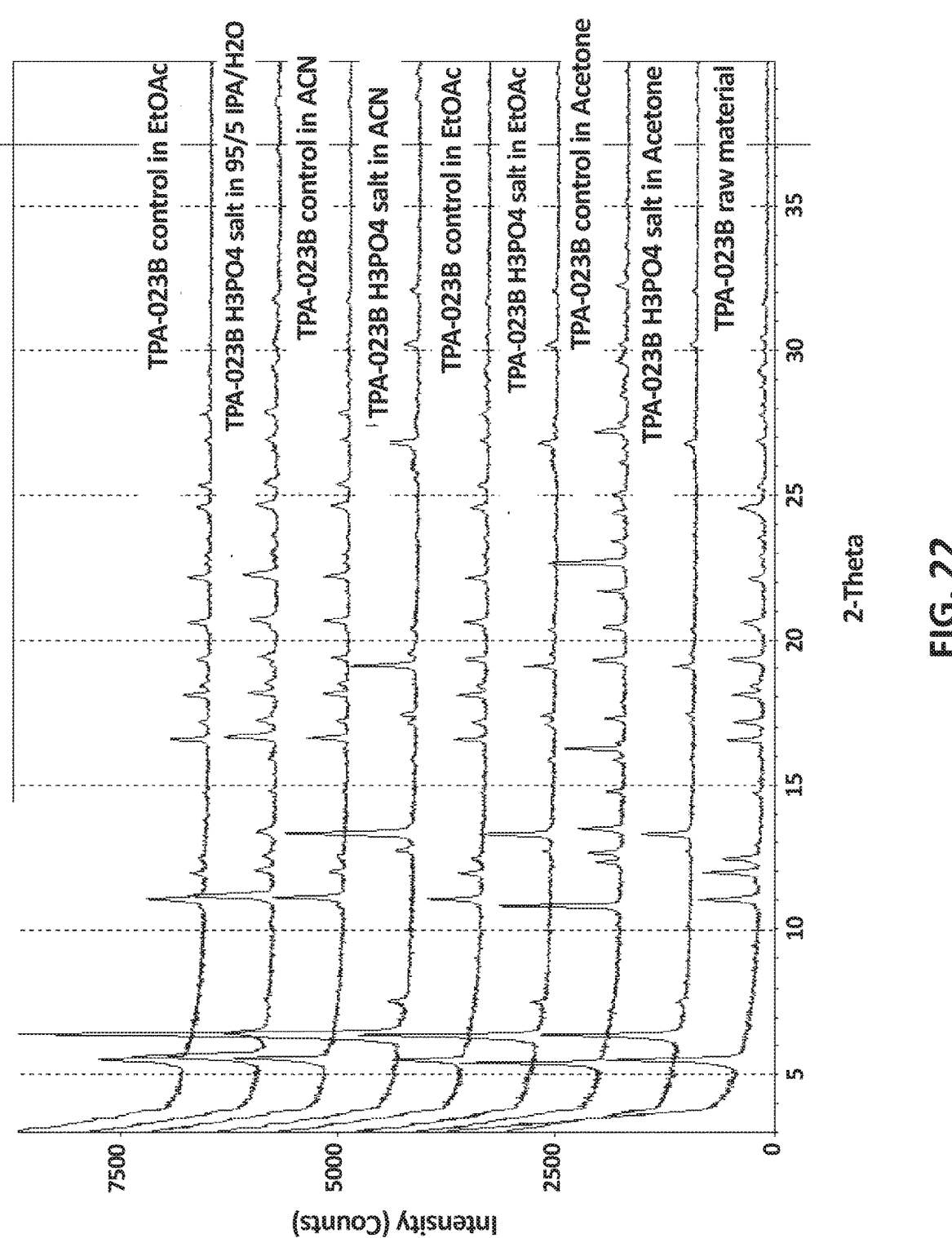
FIG. 22 illustrates XRPD patterns of TPA023B Phosphoric Acid Salt Screening
Figure 23:
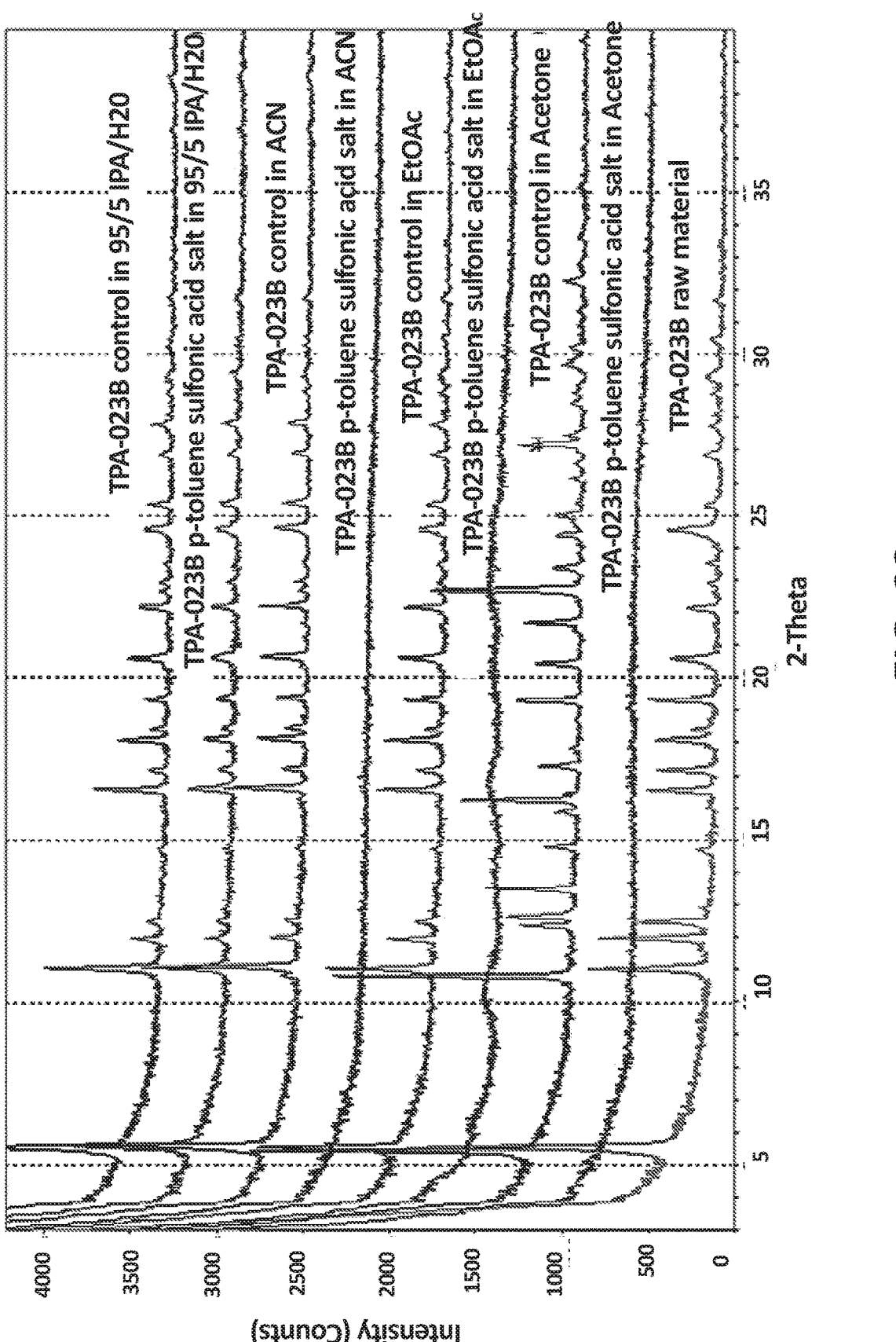
FIG. 23 illustrates XRPD patterns of TPA023B Tosylate Screening
Figure 24:
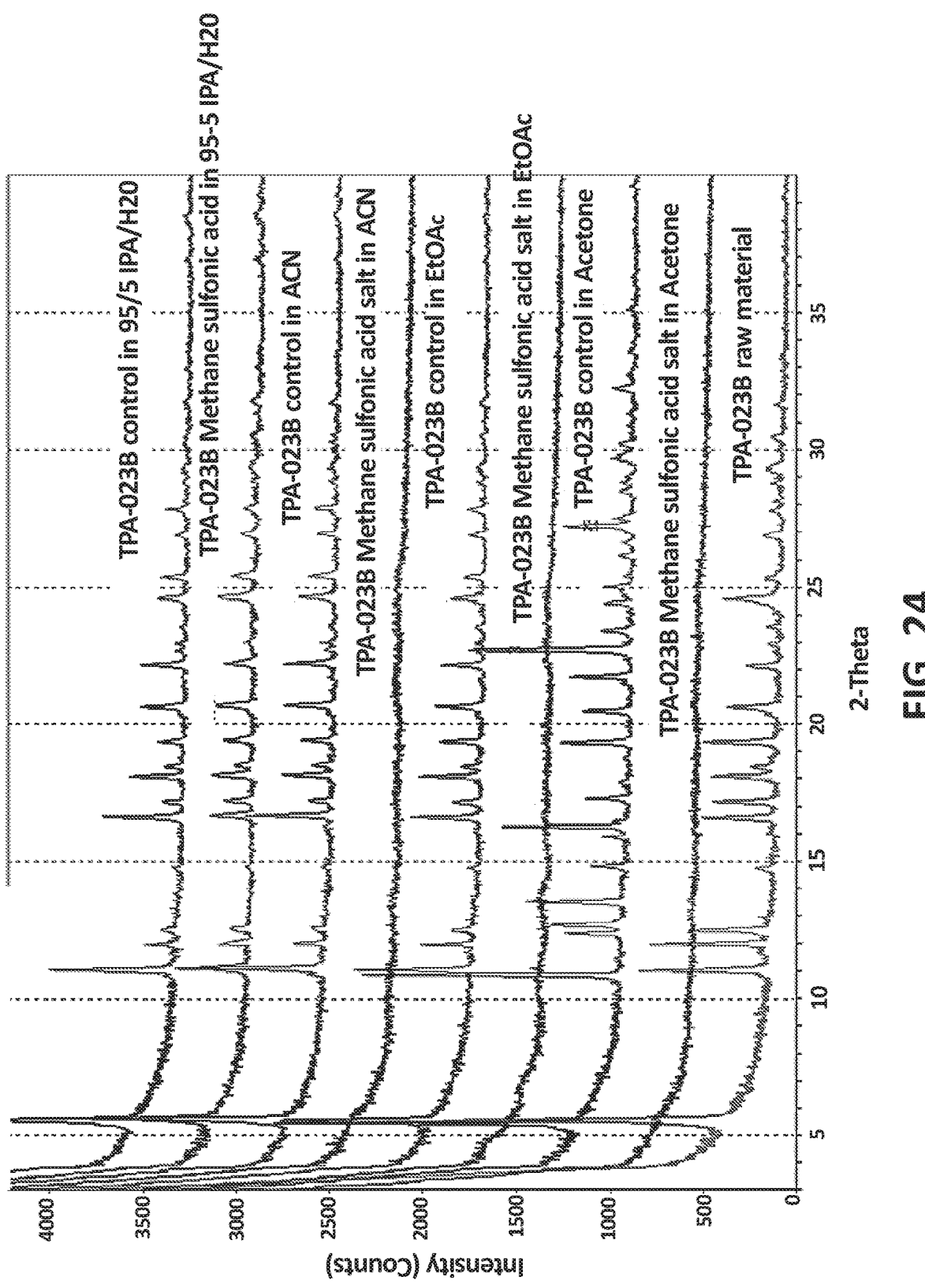
FIG. 24 illustrates XRPD patterns of TPA023B Methane Sulfonic Acid Salt Screening

The hygroscopicity of Phosphate Polymorph Form A was measured by Dynamic vapor sorption (DVS). A reversible mass increase of about 1.08% was observed. After DVS, XRPD confirmed that the crystalline form was retained (FIG. 19).

Example 5

Figure 1:
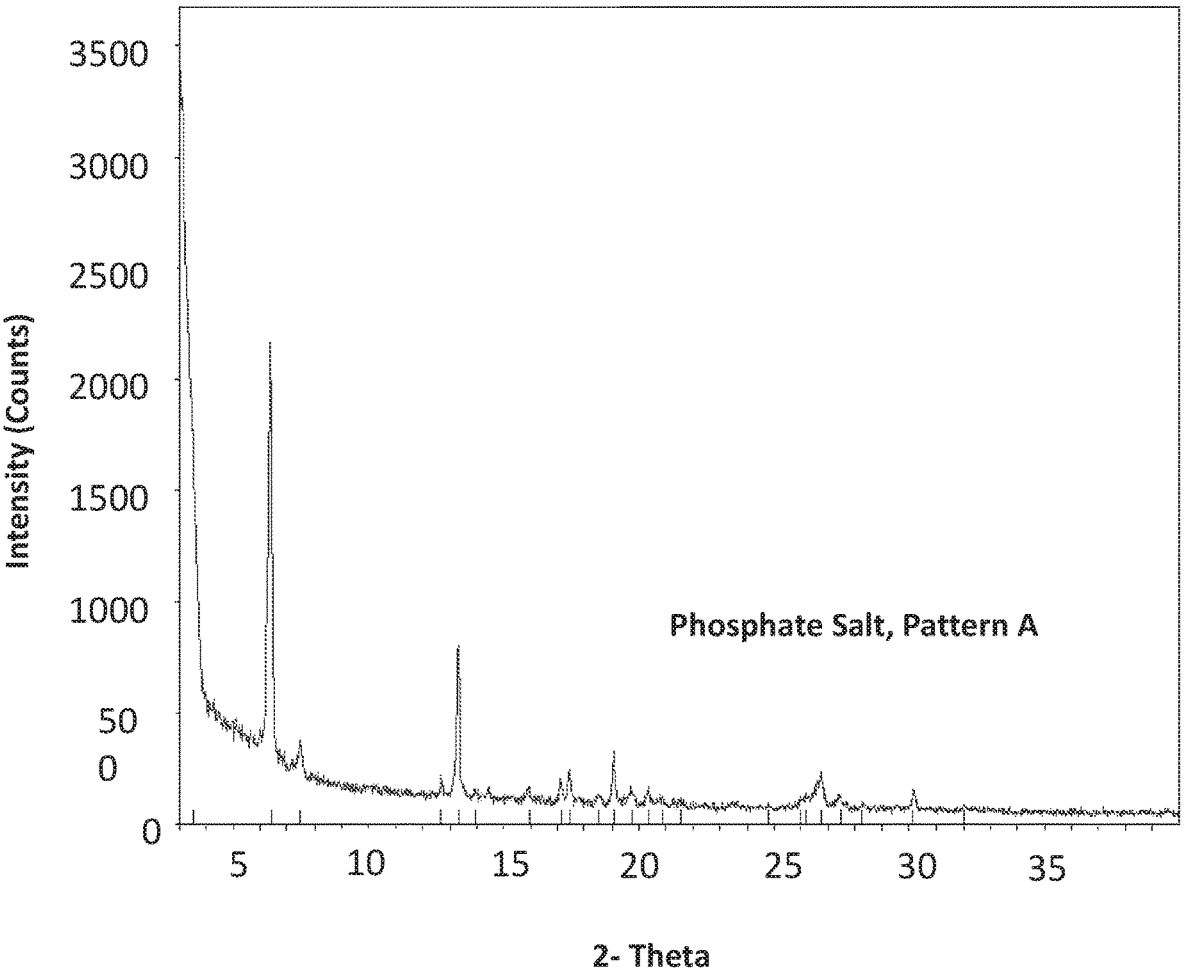
FIG. 1 illustrates an XRPD pattern for TPA023B phosphate Form A

Preparation of Polymorphic Form A of the salt or co-crystal of 2',6-difluoro-5'-[3-(1-hydroxy-1-methylethyl)-imidazo[1,2-b][1,2,4]triazin-7-yl]bi-phenyl-2-carbonitrile with phosphoric acid Phosphate Polymorphic Form A A 0.5 M solution of phosphoric acid in acetonitrile (44 mL, 22 mmol, 1.1 Eq) was added to 2',6-difluoro-5'-[3-(1- hydroxy-1-methylethyl)-imidazo[1,2-b][1,2,4]triazin-7-yl]biphenyl-2-carbonitrile (8.0 g, 20 mmol, 1.0 Eq) in acetonitrile (200 mL) and stirred at about 50° C. for about 4 hrs. The resulting mixture was cooled slowly to room temperature overnight. The resulting solid was collected and dried to provide Phosphate Polymorphic Form A (9.2 g, 92% yield). An XRPD pattern of TPA023B Phosphate Polymorphic Form A is illustrated in FIG. 1. A DSC/TGA thermogram, and an NMR spectrum of TPA023B Phosphate Polymorphic Form A are illustrated in FIG. 2A, and FIG. 2B, respectively. Additional DSC/TGA thermogram of TPA023B Phosphate Polymorphic Form A is illustrated in FIG. 2C. The Phosphate Polymorphic Form A samples for FIGS. 1, 2A, and 2B are taken from the same batch; the sample for FIG. 2C is taken from a different batch.

Example 6

Preparation of Polymorphic Pattern B of the salt or co-crystal of 2',6-difluoro-5'-[3-(1-hydroxy-1-methylethyl)-imidazo[1,2-b][1,2,4]triazin-7-yl]biphenyl-2-carbonitrile with phosphoric acid

Phosphate Polymorphic Pattern B

The salt or cocrystal of 2',6-difluoro-5'-[3-(1-hydroxy-1-methylethyl)-imidazo[1,2-b][1,2,4]triazin-7-yl]biphenyl-2-carbonitrile with phosphoric acid (20.9 mg, 0.041 mmol) was stirred for about 3 days in methanol (0.2 mL) at about 20° C. to 25° C. The resulting solid was separated by centrifuge (5 min at 14000 rpm) and dried overnight in a vacuum oven heated to about 30° C. to provide Phosphate Polymorphic Pattern B. TPA023B Phosphate Pattern B likely comprises a mixture of Phosphate Form A and Phosphate Form G.

Figure 3:
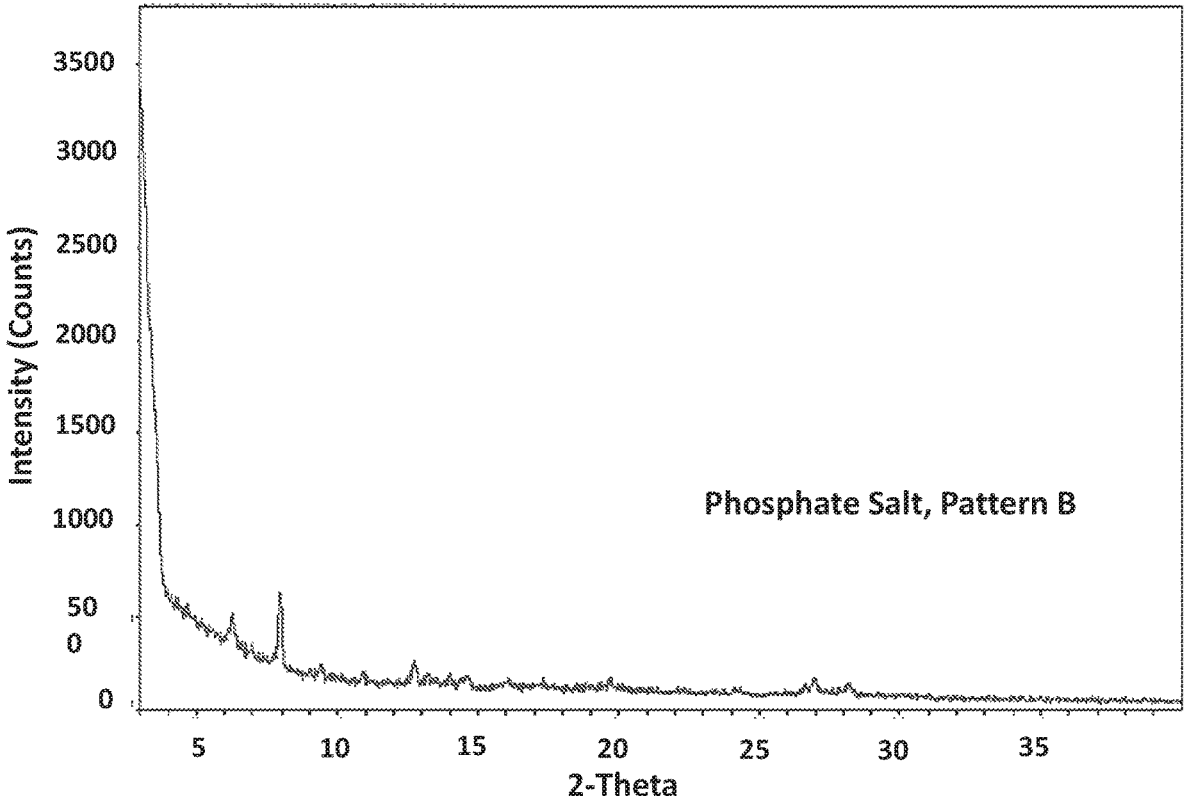
FIG. 3 illustrates an XRPD pattern for TPA023B Phosphate Pattern B
Figure 4:
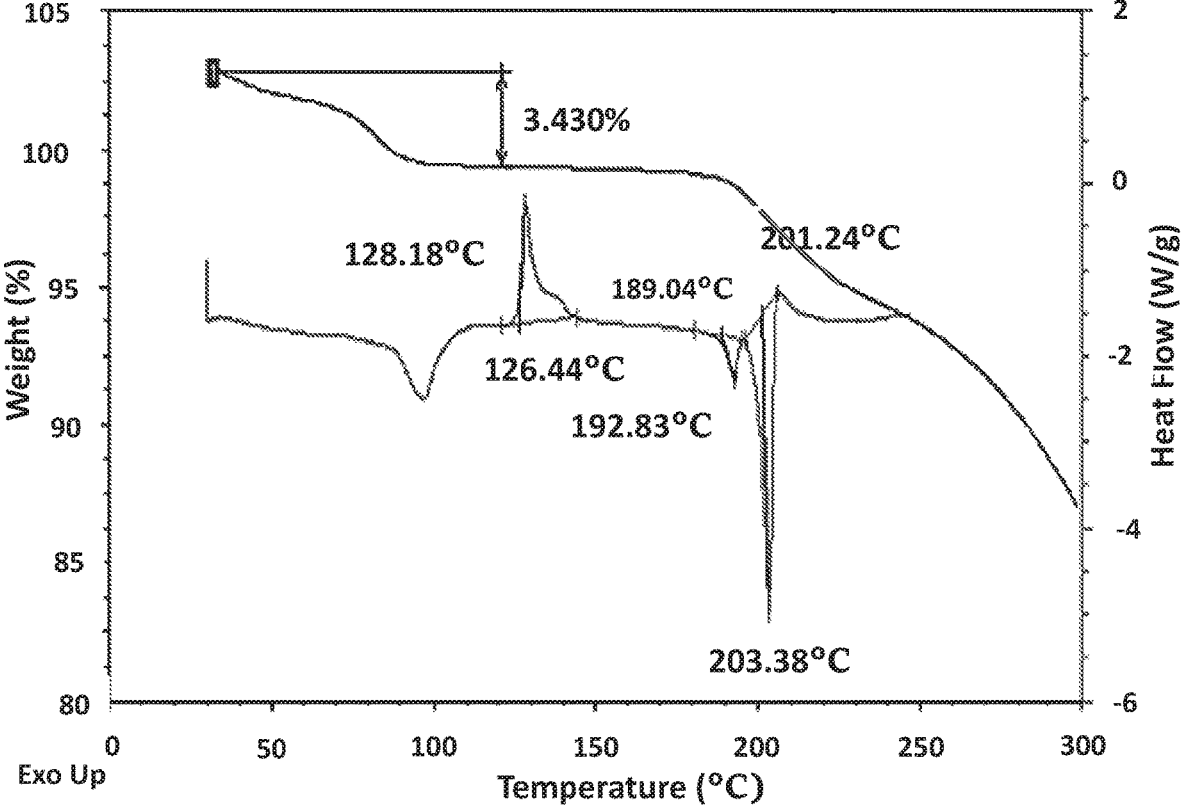
FIG. 4 illustrates an DSC/TGA thermogram for TPA023B phosphate Pattern B

An XRPD pattern of TPA023B Phosphate Polymorphic Pattern B is illustrated in FIG. 3. A DSC/TGA thermogram of TPA023B Phosphate Polymorphic Pattern B is illustrated in FIG. 4. As shown in FIG. 4, the DSC trace showed two endothermic peaks with onset temperatures of 189° C. (10.49 J/g) and 201° C. (76.46 J/g). The TGA result showed that the original form exhibits a three-step weight loss of 3.428% from 30° C. to 120° C., which could be attributed to removal of residual solvent.

Example 7

Preparation of Polymorphic Free Base Form C

The salt or cocrystal of 2',6-difluoro-5'-[3-(1-hydroxy-1-methylethyl)-imidazo[1,2-b][1,2,4]triazin-7-yl]biphenyl-2-carbonitrile with phosphoric acid (100 mg, 0.204 mmol) was transferred into a vial containing methanol (about 1.0 mL). The mixture was heated to about 60° C., stirred for about 4 hours, and then cooled to 20° C. to 25° C. This heat and cool cycle was repeated twice more. The resulting solid was collected by centrifugation and dried at about 30° C. in a vacuum oven to provide Free Base Form C.

Figure 5:
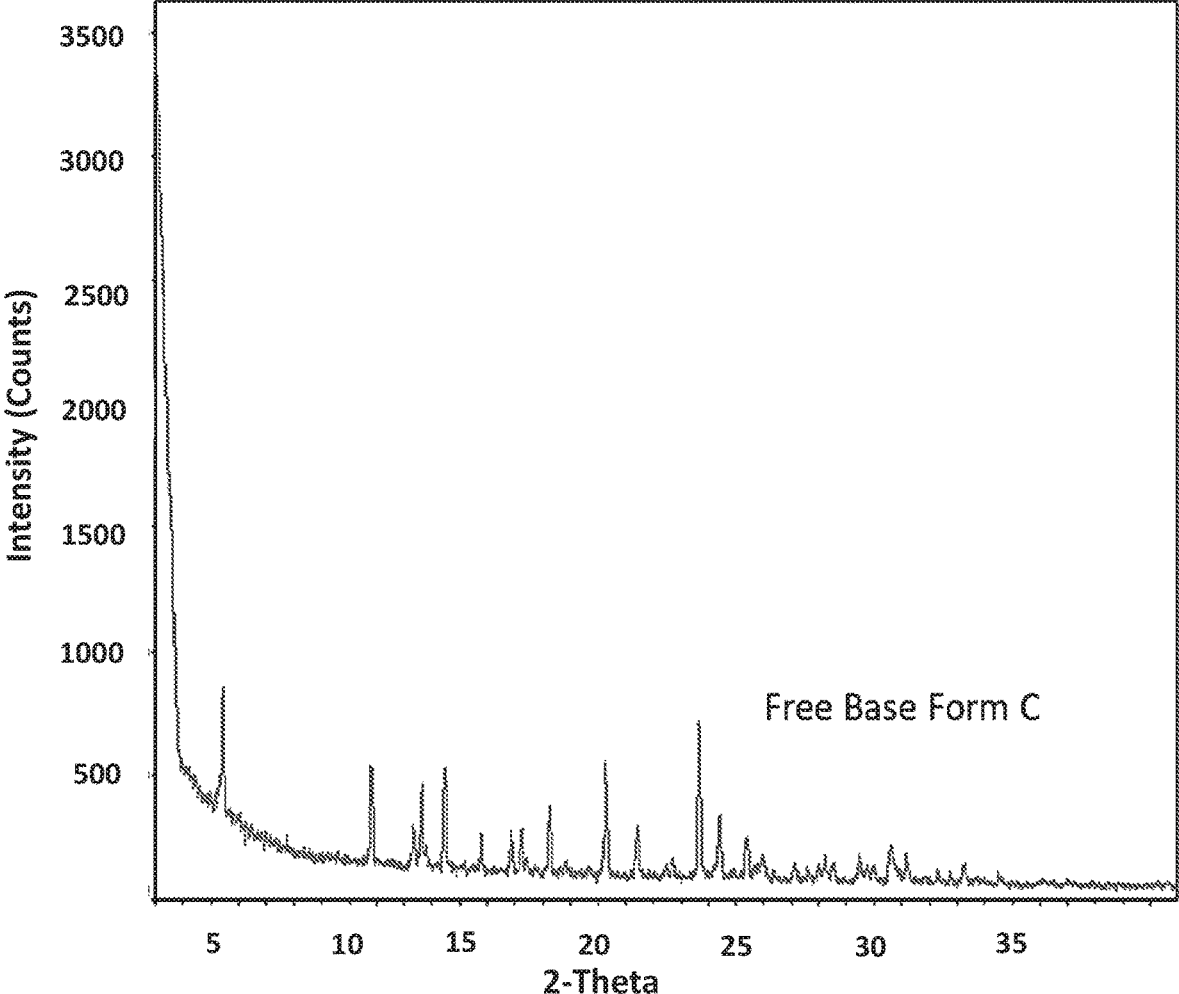
FIG. 5 illustrates an XRPD pattern for TPA023B free base Form C
Figure 6:
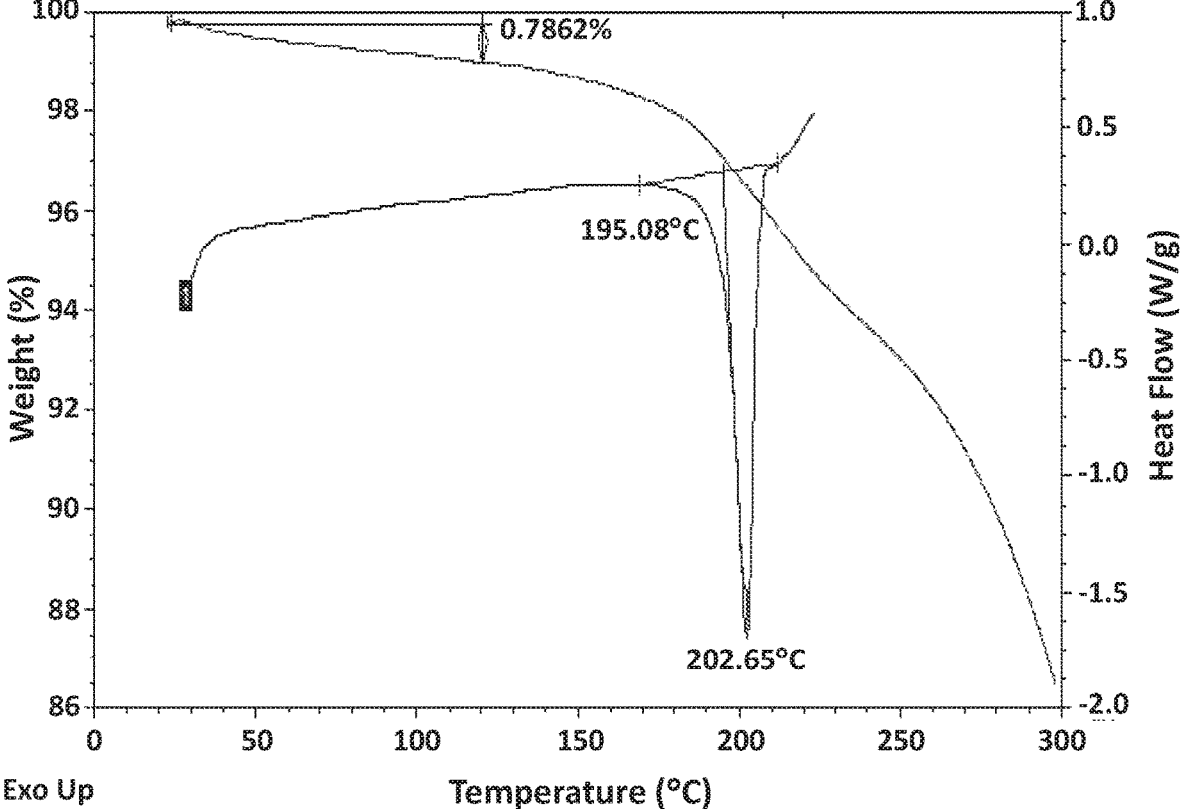
FIG. 6 illustrates a DSC/TGA thermogram for TPA023B free base Form C

An XRPD pattern of TPA023B Free Base Polymorphic Form C is illustrated in FIG. 5. A DSC/TGA thermogram of TPA023B Free Base Polymorphic Form C is illustrated in FIG. 6. As shown in FIG. 6, the DSC trace showed one endothermic peak with an onset temperature of 195° C. (96.04 J/g). Its TGA trace showed that a three-step weight loss of 0.7862% from 30° C. to 120° C., which could be attributed to removal of residual solvent.

Example 8

Preparation of Polymorphic Pattern E of the salt or cocrystal of 2',6-difluoro-5'-[3-(1-hydroxy-1-methylethyl)-imidazo[1,2-b][1,2,4]triazin-7-yl]biphenyl-2-carbonitrile with phosphoric acid

Phosphate Polymorphic Pattern E

Figure 7:
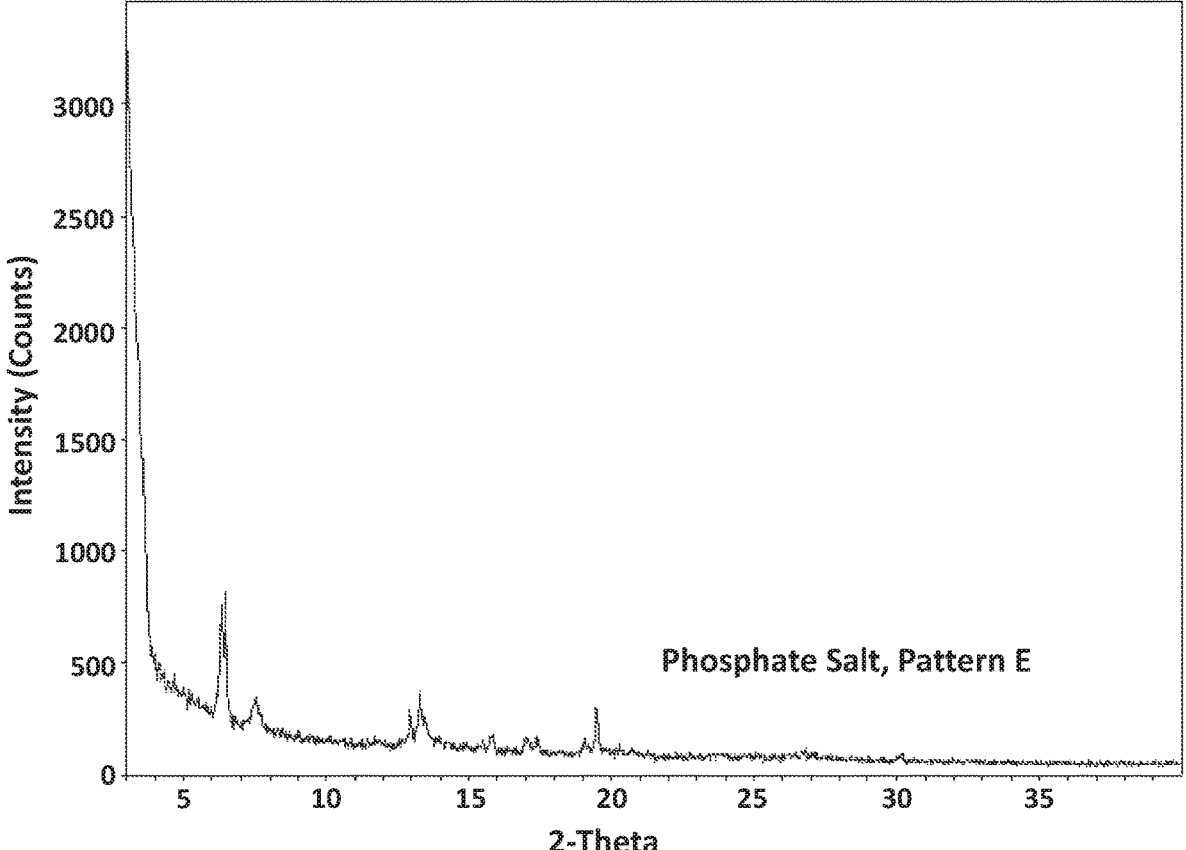
FIG. 7 illustrates an XRPD pattern for TPA023B phosphate mixture comprising TPA023B Phosphate Form A
Figure 8:
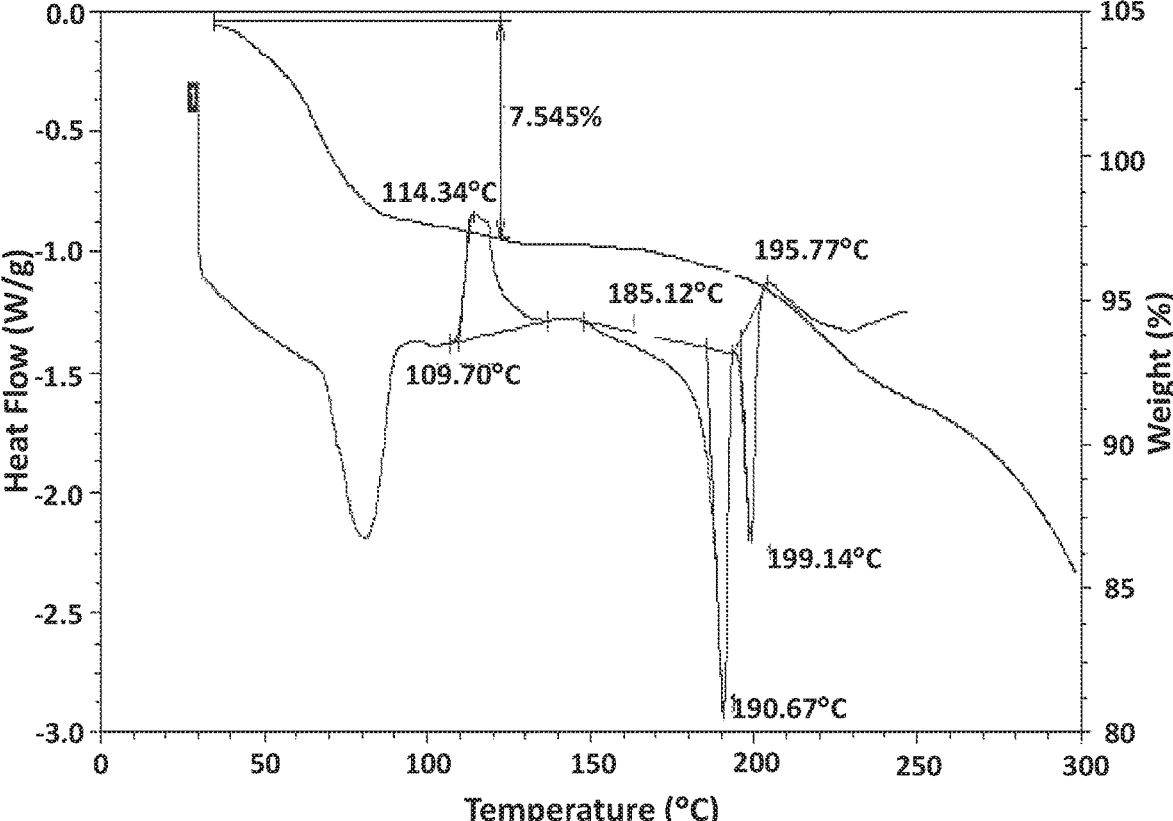
FIG. 8 illustrates a DSC/TGA thermogram for TPA023B phosphate mixture comprising TPA023B Phosphate Form A

Water (about 1.0 mL) was added dropwise to a vial containing 0.2 ml of a 100 mg/ml stock solution of the salt of 2',6-difluoro-5'-[3-(1-hydroxy-1-methylethyl)-imidazo[1,2-b][1,2,4]triazin-7-yl]biphenyl-2-carbonitrile with phosphoric acid (150 mg, 0.307 mmol) in dimethyl sulfoxide until precipitate formed. The precipitate was collected by centrifuge and dried overnight in a ~30° C. vacuum oven to provide Phosphate Polymorphic Pattern E. An XRPD pattern of TPA023B Phosphate Polymorphic Pattern E is illustrated in FIG. 7. A DSC/TGA thermogram of TPA023B Phosphate Polymorphic Pattern E is illustrated in FIG. 8. As shown in FIG. 8, the DSC pattern showed two endothermic peaks with onset temperatures of 185° C. (63.40 J/g) and 196° C. (19.60 J/g). It is believed that TPA023B Phosphate Pattern E likely comprises a mixture that comprises Phosphate Form A and another form.

Example 9

Preparation of Polymorphic Form A of the salt of 2',6-difluoro-5'-[3-(1-hydroxy-1-methylethyl)-imidazo[1,2-b][1,2,4]triazin-7-yl]biphenyl-2-carbonitrile with 4-methylbenzene sulfonic acid

Tosylate Polymorphic Form A

Figure 17B:
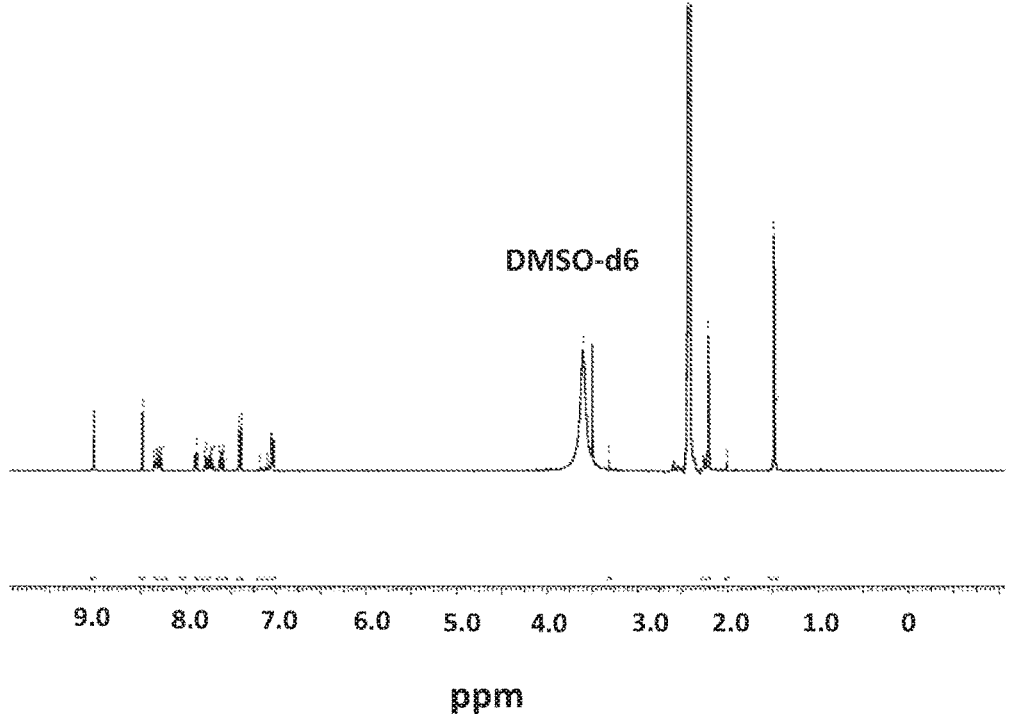

2',6-difluoro-5'-[3-(1-hydroxy-1-methylethyl)-imidazo[1,2-b][1,2,4]triazin-7-yl]biphenyl-2-carbonitrile (100 mg, 0.256 mmol) and toluene (1.5 ml) were heated to 110° C. and stirred vigorously for 15 min. The mixture was cooled to 95° C. and 1,4-dioxane (0.8 mL) was added slowly. A 0.5 M solution of 4-methylbenzene sulfonic acid in 1,4-dioxane (0.05 mL, 0.1 equivalents) was added, followed by ~1 mg of seed material. Additional 0.5M 4-methylbenzene sulfonic acid in 1,4-dioxane solution (0.49 mL, 0.95 Eq) was added over 30 min, and the resulting mixture was stirred at 95° C. for 30 min. The mixture was then allowed to cool to room temperature and the solids were collected by centrifugation (1000 rpm for 5 minutes). The isolated solid was washed with n-heptane and dried in a ~30° C. vacuum oven for 4 hrs to provide Tosylate Polymorphic Form A. An XRPD pattern of TPA023B tosylate Form A is provided in FIG. 17A, and an NMR spectrum of TPA023B tosylate is provided in FIG. 17B. TPA023B tosylate displays birefringence under polarized light.

Example 10

Preparation of Polymorphic Form A of 2',6-difluoro-5'-[3-(1-hydroxy-1-methylethyl)-imidazo[1,2-b][1,2,4]triazin-7-yl]biphenyl-2-carbonitrile

Free Base Polymorphic Form A

2',6-difluoro-5'-[3-(1-hydroxy-1-methylethyl)-imidazo[1,2-b][1,2,4]triazin-7-yl]biphenyl-2-carbonitrile (25 mg, 0.064 mmol) was added to a vial containing acetonitrile (0.5 ml). The mixture was mixed at about 20° C. to 25° C. for about 4 hours, then heated to about 50° C. overnight. The slurry was allowed to cool to ambient temperature. The resulting solids were isolated by centrifugation at about 14000 rpm for 5 minutes and dried in a vacuum oven at −35° C. to provide Free Base Polymorphic Form A. An XRPD pattern of TPA023B Free Base Polymorphic Form A is provided in FIG. 9. A DSC/TGA thermogram and an NMR spectrum of TPA023B Free Base Polymorphic Form A are provided in FIG. 10A and FIG. 10B, respectively.

Example 11

Preparation of Polymorphic Form B of 2',6-difluoro-5'-[3-(1-hydroxy-1-methylethyl)-imidazo[1,2-b][1,2,4]triazin-7-yl]biphenyl-2-carbonitrile

Free Base Polymorphic Form B

2',6-difluoro-5'-[3-(1-hydroxy-1-methylethyl)-imidazo[1,2-b][1,2,4]triazin-7-yl]biphenyl-2-carbonitrile (25 mg, 0.064 mmol) was added to a vial containing ethanol (0.5 ml). The mixture was mixed at about 20° C. to 25° C. for about 4 hours, then heated to −50° C. overnight. If the final mixture was clear solution, the solution would be evaporated by vacuum drying oven at −35° C. and the resulted solid was checked by XRPD. The resulting solid was isolated by centrifugation at about 14,000 rpm for ~5 minutes and dried by in a ~35° C. vacuum oven to provide Free Base Polymorphic Form B. Preliminary analysis suggests this is an Ethanol Solvate polymorph, which expunges Pd, and is a key intermediate.

Example 12

Preparation of Polymorphic Form C of 2',6-difluoro-5'-[3-(1-hydroxy-1-methylethyl)-imidazo[1,2-b][1,2,4]triazin-7-yl]biphenyl-2-carbonitrile

Free Base Polymorphic Form C

2',6-difluoro-5'-[3-(1-hydroxy-1-methylethyl)-imidazo[1,2-b][1,2,4]triazin-7-yl]biphenyl-2-carbonitrile (25 mg, 0.064 mmol) was added to a vial containing dichloromethane (0.5 ml) and the vial was sealed. The mixture was stirred at about 20° C. to ~25° C. for about 4 hours, then heated to ~50° C. overnight. The resulting slurry was allowed to cool to ambient, and the resulting solids were isolated by centrifugation at ~14000 rpm for ~5 minutes and dried by in a ~35° C. vacuum oven to provide Free Base Polymorphic Form C.

Example 13

Preparation of Polymorphic Pattern D of 2',6-difluoro-5'-[3-(1-hydroxy-1-methylethyl)-imidazo[1,2-b][1,2,4]triazin-7-yl]biphenyl-2-carbonitrile

Free Base Polymorphic Pattern D

2',6-difluoro-5'-[3-(1-hydroxy-1-methylethyl)-imidazo[1,2-b][1,2,4]triazin-7-yl]biphenyl-2-carbonitrile (25 mg, 0.064 mmol) was added to a vial containing 1,4-dioxane (0.5 ml) and the vial was sealed. The mixture was stirred at about 20° C. to 25° C. for ~4 hours, then heated to ~50° C. overnight. The resulting solution was cooled to about 20° C. to 25° C., and evaporated to dryness in a ~35° C. vacuum oven to provide Free Base Polymorphic Pattern D. Free Base Pattern D likely comprises a mixture that comprises Free Base Form A and a new form that may be a dioxane solvate.

Example 14

Competitive Slurry Experiment

Determining which polymorphic form is more thermodynamically stable may be experimentally determined by conventional methods known in the art. For example, a competitive slurry experiment in which a 1:1 mixture of polymorphic forms is stirred for a period of time in a solvent in which both polymorphic forms are partly soluble may be conducted. It is accepted by those skilled in the art that if the 1:1 mixture converts entirely to one polymorphic form, that form that results is more thermodynamically stable of the two, while the other form is metastable.

Example 15

Solubility of Free Base Polymorphic Form A and Phosphate Polymorphic Form A About 2 mg of test article was added to a 1.5 mL vials which contained ~1.0 mL of one medium listed in Table 7 and Table 8, which was then sealed. The mixtures were stirred at ~20-25° C. for ~24 hours. After that, the mixture was filtered by 0.45 μm filter membrane and then the supernatant was analyzed by HPLC. The results were showed in the Table 7 and Table 8. The results indicated that Phosphate Polymorphic Form A had higher solubility in simulated gastric fluid (SGF), Fasted-state simulated intestinal fluid (FaSSIF) and Fed-state simulated intestinal fluid (FeSSIF) than Free Base Polymorphic Form A.

TABLE 7

| solubility test result of Free Base Polymorphic Form A | | | | |
|---|---|---|---|---|
| Media | Target Conc. (mg/mL) | Measured Conc. (μg/mL) | Initial pH | pH value of supernatant |
| Purified water | 2 | 0.14 | 7.02 | 8.73 |
| pH 1.2 Hydrochloric Acid Buffer (50 mM) | | 9.77 | 1.17 | 1.12 |
| pH 3.0 citrate buffer (100 mM) | | <LOQ | 3.05 | 3.00 |
| pH 4.5 citrate buffer (100 mM) | | <LOQ | 4.44 | 4.45 |
| pH 7.4 PBS (50 mM) | | <LOQ | 7.40 | 7.42 |
| pH 9.0 USP Buffer (50 mM) | | <LOQ | 8.94 | 8.98 |
| SGF | | 1.38 | 1.80 | 1.86 |
| FaSSIF | | 2.11 | 6.51 | 6.50 |
| FeSSIF | | 9.63 | 5.00 | 5.02 |

TABLE 8

| Solubility Test results for Phosphate Polymorphic Form A | | | | |
|---|---|---|---|---|
| Media | Target Conc. (mg/mL) | Measured Conc. (μg/mL) | Initial pH | pH value of supernatant |
| Purified water | 2 | 0.40 | 7.02 | 2.62 |
| pH 1.2 Hydrochloric Acid Buffer (50 mM) | | 22.88 | 1.17 | 0.99 |
| pH 3.0 citrate buffer (100 mM) | | 0.16 | 3.05 | 2.96 |

TABLE 8-continued

| | Target Conc. (mg/mL) | Measured Conc. (µg/mL) | Initial pH | pH value of supernatant |
|---|---|---|---|---|
| Media | | | | |
| pH 4.5 citrate buffer (100 mM) | | <LOQ | 4.44 | 4.41 |
| pH 7.4 PBS (50 mM) | | <LOQ | 7.40 | 7.09 |
| pH 9.0 USP Buffer (50 mM) | | <LOQ | 8.94 | 8.46 |
| SGF | | 3.85 | 1.80 | 1.67 |
| FaSSIF | | 7.14 | 6.51 | 6.09 |
| FeSSIF | | 50.68 | 5.00 | 4.94 |

Solubility Test results for Phosphate Polymorphic Form A

LOQ: 0.1 µg/mL

Example 16

Intrinsic Dissolution Rate of Free Base Polymorphic Form A and Phosphate Polymorphic Form A About 100 mg of Free Base Polymorphic Form A or Phosphate Polymorphic Form A was weighed into the intrinsic dissolution apparatus and the sample compressed for 1 minute with a compression force of ~4 MPa to form a compacted pellet within the stainless-steel die. All loose powder was removed from the surface of the die. The intrinsic dissolution shaft was connected with the stainless-steel die and tightened so only one surface of the pellet was exposed (surface area=0.496 cm$^2$). The shaft in the spindle was adjusted to ensure the exposed surface of the compacted tablet was ~3.8 cm from the bottom of the vessel when lowered. The temperature of chamber water was set at 37° C.±0.5° C., the shaft rotation at 100 rpm and the sampling time points at 2, 5, 10, 15, 30, 45, 60, 120 min. SGF was used as dissolution medium (900 mL). At each time point, solution samples were filtered, and the supernatant was analyzed by HPLC-UV.

The intrinsic dissolution rate of Free Base Polymorphic Form A in SGF was $5 \times 10^{-5}$ mg·cm$^2$·min$^{-1}$ (linear scope within 2 to 120 min). The intrinsic dissolution rate of Phosphate Polymorphic Form A in SGF was 0.184 mg·cm$^{-2}$ min$^{-1}$. (linear scope within 2 to 120 min).

Example 17

Pharmacokinetics Experiments with Phosphate Polymorphic Form A in Rats

To evaluate the pharmacokinetics (PK) of Phosphate Polymorphic Form A, suspensions or solutions were dosed by either oral gavage (0.5% methyl cellulose) or IV (60% PEG400/40% saline) in normal, healthy, male Sprague-dawley rats with serial blood collection focused on the first 48 hours of exposure. Rats were dosed with vehicle or test compounds at 1 mg/kg (IV) or 2 mg/kg (PO). Approximately 0.2 mL blood was collected at each time point. All blood samples were collected jugular vein puncture. All blood samples were transferred into plastic microcentrifuge tubes containing 5 µL of EDTA-K$_2$ as anti-coagulant or pre-chilled commercial EDTA-K$_2$ tubes and placed on wet ice until centrifugation. Harvested blood samples were centrifuged within 30 min of collection at 7,000 rpm for 10 minutes. The extracts were analyzed for compound concentration by LC/MS/MS. Data were analyzed with Phoenix WinNonlin 6.3 using the IV-Noncompartmental model 201 (IV bolus input) and PO-Noncompartmental model 200 (extravascular input) methods.

TABLE 9

Results from Intravenously Administered Phosphate Polymorphic Form A

| PK Parameters | Mean IV |
|---|---|
| T$_{1/2}$ (h) | 12.4 |
| Vd$_{ss}$ (L/kg) | 1.49 |
| Cl (mL/min/kg) | 1.41 |
| AUC$_{0-last}$ (ng · h/mL) | 11260 |
| AUC$_{0-inf}$ (ng · h/mL) | 12097 |

TABLE 10

Results from Orally Administered Phosphate Polymorphic Form A

| PK Parameters | Mean PO |
|---|---|
| C$_{max}$ (ng/mL) | 794 |
| T$_{max}$ (h) | 7.00 |
| T$_{1/2}$ (h) | 11.1 |
| AUC$_{0-last}$ (ng · h/mL) | 14981 |
| AUC$_{0-inf}$ (ng · h/mL) | 15995 |
| AUC$_{Extra}$ (%) | 6.25 |
| Bioavailability(%)[a] | 66.1 |

Example 18

Canine Pharmacokinetics Experiment with Phosphate Polymorphic Form A

To evaluate the pharmacokinetics (PK) Phosphate Polymorphic Form A, suspensions or solutions were dosed by either oral gavage (0.5% methyl cellulose) or IV (60% PEG400/40% saline) in normal, healthy, male Beagle dogs with serial blood collection focused on the first 48 hours of exposure. Dogs were dosed with vehicle or test compounds at 1 mg/kg (IV) or 2 mg/kg (PO). Approximately 0.5 mL blood was collected at each time point. All blood samples were collected from a peripheral vein. Blood was collected into commercially available tubes (Jiangsu Kangjian medical supplies co., LTD) containing Potassium (K$_2$) EDTA*2H$_2$O and placed on wet ice until processed for plasma. Samples were centrifuged (3,000×g for 10 minutes at 2 to 8° C.) within one hour of collection. The extracts were analyzed for compound concentration by LC/MS/MS. Data were analyzed with Phoenix WinNonlin 6.3 using the IV-Noncompartmental model 201 (IV bolus input) and PO-Noncompartmental model 200 (extravascular input) methods.

TABLE 11

Results from Intravenously Administered Phosphate Polymorphic Form A

| PK Parameters | Mean IV |
|---|---|
| T$_{1/2}$ (h) | 12.8 |
| Vd$_{ss}$ (L/kg) | 1.93 |
| Cl (mL/min/kg) | 2.52 |
| AUC$_{0-last}$ (ng · h/mL) | 7846 |
| AUC$_{0-inf}$ (ng · h/mL) | 9167 |

TABLE 12

| Results from Orally Administered Phosphate Polymorphic Form A | |
| --- | --- |
| PK Parameters | Mean PO |
| $C_{max}$ (ng/mL) | 649 |
| $T_{max}$ (h) | 3.33 |
| $T_{1/2}$ (h) | 12.2 |
| $AUC_{0-last}$ (ng · h/mL) | 11725 |
| $AUC_{0-inf}$ (ng · h/mL) | 13943 |
| Bioavailability(%) | 74.7 |

The bioavailability of Phosphate Polymorphic Form A is over 3 times higher than the previously reported bioavailability of TPA023B in canines. This is highly adventitious for therapeutics meant to treat dogs, and significantly reduces the quantities of active pharmaceutical ingredient that need to be prepared for the completion of GLP toxicology studies.

Example 19

Preparation of Polymorphic Forms of TPA023B Salts or Co-Crystals

TPA023B and a pharmaceutically acceptable acid, and/or a previously prepared TPA023B salt or co-crystal, are combined and stirred for a period of time in one or more solvents, with or without heating and/or cooling steps; and/or are dissolved in a one or more solvents with or without heating and then some or all of the solvent(s) are removed; and/or are dissolved in one or more solvents the an anti-solvent, or combination of antisolvents, or a mixture of solvent and antisolvent are added; any other method known to one skilled in the art; and combinations of any or all of the above processes.

Example 20

Preparation of Polymorphic Forms of TPA023B Free Base

TPA023B is slurried for a period of time in one or more solvents, with or without heating; and/or dissolved in a one or more solvents with or without heating and then some or all of the solvent(s) are removed through a method such as evaporation or distillation; and/or dissolved in one or more solvents and an anti-solvent, combination of antisolvents, or a mixture of solvent and antisolvent is added; and/or dissolved in one or more solvents with or without heating and then allowing the solution is cooled, or actively cooled; and/or is heating in the absence of solvent; and/or is heated under atmospheric or reduced pressure until it sublimates and is collected on a cooled surface; and/or is melted and allowed it to cool; and/or is exposed to water vapor or the vapor of an solvent with or without heating; and/or any other method known to one skilled in the art; and by using combinations of any or all of the above processes.

Example 21

HPLC Protocols

Table 13 provides an exemplary set of parameters and conditions used in HPLC.

TABLE 13

| HPLC conditions and parameters | | | |
| --- | --- | --- | --- |
| Column: | Waters, Symmetry C18, 4.6* 150 mm 3.5-Micron | | |
| Column Temperature: | 40° C. | | |
| Flow rate: | 1 mL/min | | |
| Detection: | 266 nm | | |
| Injection volume: | 10.0 μL | | |
| Run time: | 20 minutes | | |
| Diluent | 50/50 ACN/H$_2$O | | |
| Mobile Phase A: | 0.1% TFA in water | | |
| Mobile Phase B: | ACN | | |
| | Time (min) | Mobile Phase A % | Mobile Phase B % |
| Gradient program | 0.0 | 80 | 20 |
| | 15 | 10 | 90 |
| | 15.1 | 80 | 20 |
| | 20 | 10 | 20 |

Example 22

Purity Test

Appropriately 2 mg of compounds were accurately weighed into a glass vial, then added diluents (ACN/water, 50/50) and sonicated for 2 minutes to dilute the target concentration of 0.2 mg/mL. The solution was equilibrated to room temperature and then the purity of the compounds was determined by HPLC.

Example 23 pKa Measurement 10 mg of TPA023B was used for the pKa measurement.
Solution Preparation:
ISA Water (Ionic Strength Adjusted Water, 0.15 M KCl): Accurately weigh 5.591 g KCl into a 500 mL volumetric flask, dissolve the sample with water, add to volume and mix well.
Cosolvent of 60% (v/v) DMSO: Dissolve 2.795 g potassium chloride in 100 mL distilled or deionised water and make up to 250 mL with analytical grade DMSO (Ionic strength adjusted DMSO solution).
Cosolvent of 80% (v/v) MeOH: Dissolve 2.795 g potassium chloride in 50 mL distilled or deionized water and make up to 250 mL with analytical grade MeOH (Ionic strength adjusted MeOH solution).
pKa Determination by pH Metric Method (with or without Co-Solvent):
About 1 mg of sample was weighed into a sample vial, about 1.5 mL of ISA water or 1.5 mL of co-solvent (80% MeOH or 60% DMSO) was added into the vial automatically. The sample solution pre-acidified to pH 2.0 with 0.5 M HCl by the instrument automatically, then titrated three times with base to get pKa value from pH 2 to pH 12, and then extrapolated to get aqueous pKa value. Using this method, the pKa of TPA023B was determined to be 2.19.

Example 24

Approximate Solubility Study of TPA023B in Organic Solvents

About 25 mg of compound (TPA023B) was added to a 2.0 mL vial containing 0.5 mL of each organic solvent in Table 14, which was then sealed. The mixtures were stirred-mixed at 800 rpm, RT (25° C.) for 4 hours. After that, if the compound was not completely dissolved in the solvent, the mixture was then stirred-mixed at 800 rpm, 50° C. overnight. If the final mixture was clear solution, the solution would be evaporated by vacuum drying oven at 35° C. and the resulted solid would be checked by XRPD. If the final mixture was slurry, the slurry would be centrifuged at 14000 rpm for 5 minutes and then the residues would be dried by vacuum drying oven at 35° C. and checked by XRPD.

Figure 27:
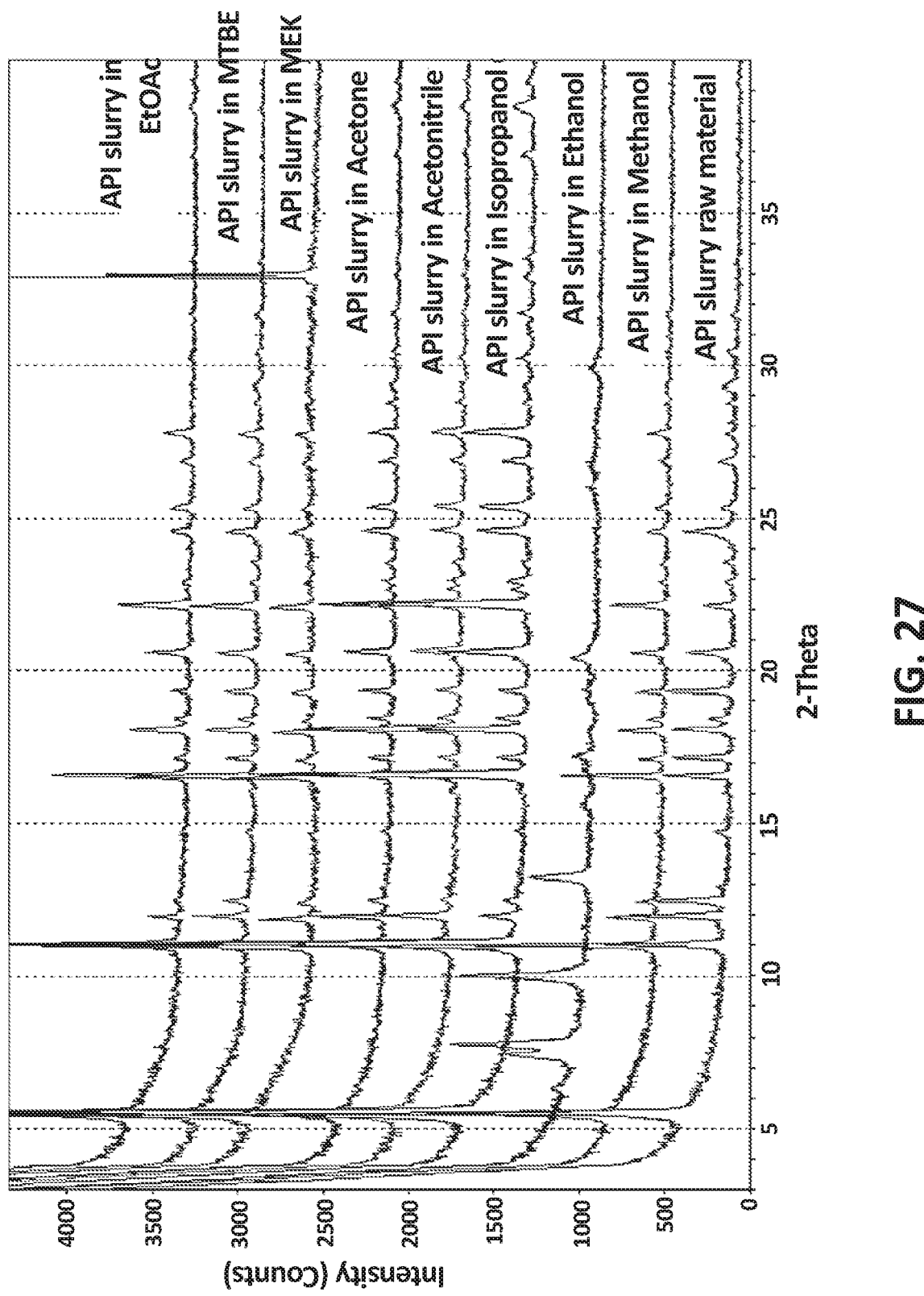
FIG. 27 illustrates an XRPD profile overlay of TPA023B slurry in solvents (I)
Figure 28:
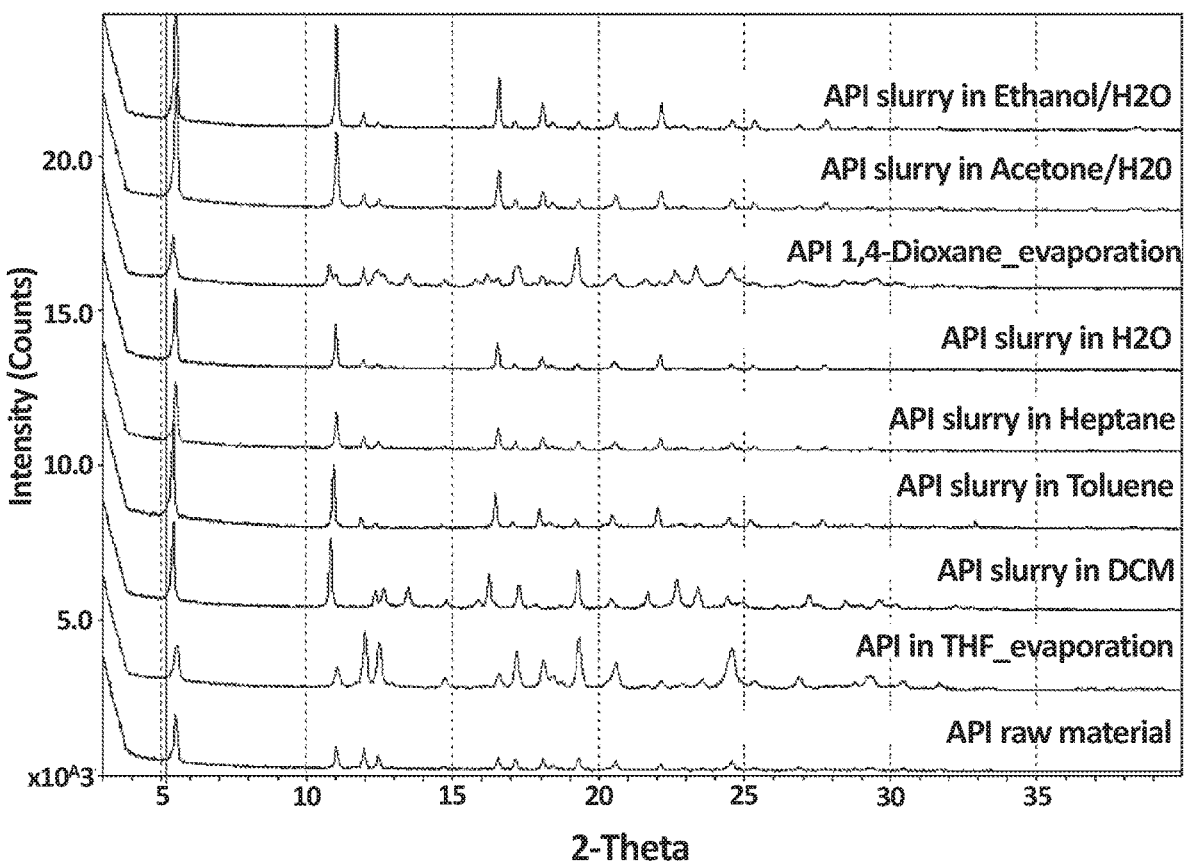
FIG. 28 illustrates an XRPD profile overlay of TPA023B slurry in solvents (II)

The form of TPA023B raw material was named as "Free-base Form A" and its corresponding XRPD pattern as "Pattern A." The characterization of solubility-test samples of TPA023B is provided in Table 15. The corresponding XRPD profile overlays of TPA023B slurry in solvents are provided in FIG. 27 and FIG. 28.

TABLE 14

Approximate Solubility Results of TPA023B in Solvents

| Solvent | Solubility (mg/mL) | | Solvent | Solubility (mg/mL) | |
|---|---|---|---|---|---|
| | RT | 50° C. | | RT | 50° C. |
| Methanol | N/A | <50 | DMF | >50 | N/A |
| Ethanol | N/A | <50 | DMSO | >50 | N/A |
| Isopropanol | N/A | <50 | DCM | N/A | <50 |
| Acetonitrile (ACN) | N/A | <50 | Toluene | N/A | <50 |
| Acetone | N/A | <50 | Heptane | N/A | <50 |
| MEK | N/A | <50 | H₂O | N/A | <50 |
| MTBE | N/A | <50 | 1,4-Dioxane | <50 | >50 |
| EtOAc | N/A | <50 | EtOH/H₂O (1/1, v/v) | N/A | <50 |
| THF | <50 | >50 | Acetone/H₂O (1/1, v/v) | N/A | <50 |

TABLE 15

Characterization of Solubility-Test Samples of TPA023B

| Solvent | Target conc. (mg/ml) | Visual Observation RT | Visual Observation 50° C. | Drying method and appearance | XRPD Results |
|---|---|---|---|---|---|
| Methanol | 50 | N/A | Slurry | Centrifugation/ Yellow powder | Pattern a |
| Ethanol | | N/A | Slurry | Centrifugation/ Yellow powder | Pattern b |
| Isopropanol | | N/A | Slurry | Centrifugation/ Yellow powder | Pattern a |
| Acetonitrile | | N/A | Slurry | Centrifugation/ Yellow powder | Pattern a |
| Acetone | | N/A | Slurry | Centrifugation/ Yellow powder | Pattern a |
| MEK | | N/A | Slurry | Centrifugation/ Yellow powder | Similar to Pattern a |
| MTBE | | N/A | Slurry | Centrifugation/ Yellow powder | Pattern a |
| EtOAc | | N/A | Slurry | Centrifugation/ Yellow powder | Pattern a |
| THF | | N/A | Clear | Evaporation/ Yellow powder | Pattern a |
| DCM | | N/A | Slurry | Centrifugation/ Yellow powder | Pattern c |
| DMSO | | Clear | N/A | Evaporation/ Yellow powder | N/A |

TABLE 15-continued

Characterization of Solubility-Test Samples of TPA023B

| Solvent | Target conc. (mg/ml) | Visual Observation RT | Visual Observation 50° C. | Drying method and appearance | XRPD Results |
|---|---|---|---|---|---|
| DMF | | Clear | N/A | Evaporation/ Yellow powder | N/A |
| Toluene | | N/A | Slurry | Centrifugation/ Yellow powder | Pattern a |
| Heptane | | N/A | Slurry | Centrifugation/ Yellow powder | Pattern a |
| H₂O | | N/A | Slurry | Centrifugation/ Yellow powder | Pattern a |
| 1,4-Dioxane | | N/A | Clear | Evaporation/ Yellow powder | Pattern d |
| EtOH/H₂O (1/1, v/v) | | N/A | Slurry | Centrifugation/ Yellow powder | Pattern a |
| Acetone/H₂O (1/1, v/v) | | N/A | Slurry | Centrifugation/ Yellow powder | Pattern a |

Example 25

Approximate Solubility Study of TPA023B Phosphate

Approximate 2 mg of TPA023B Phosphate Form A was weighed out into each 1.5 mL vial, and then solvent was added stepwise under stirring until no particles could be visually observed. The total amount of solvent was recorded to calculate the approximate solubility in these solvents. The solubility results are shown in Table 16. TPA023B phosphate showed relatively high solubility in DMF and DMSO.

TABLE 16

Approximate Solubility Results of TPA023B Phosphate in Solvents

| Solvent | Solubility (mg/mL) | | Solvent | Solubility (mg/mL) | |
|---|---|---|---|---|---|
| | RT | 50° C. | | RT | 50° C. |
| Methanol | 8-10 | 10-50 | DMF | >100 | N/A |
| Ethanol | <8 | 10-50 | DMSO | >100 | N/A |
| Isopropanol | <8 | 10-50 | DCM | 8-10 | 10-50 |
| Acetonitrile (ACN) | <2 | 2-10 | Toluene | <2 | <2 |
| Acetone | 6-10 | <10 | Heptane | <2 | <2 |
| MEK | 2-4 | <10 | H₂O | <2 | <2 |
| MTBE | <2 | <2 | 1,4-Dioxane | 20-25 | 20-25 |
| EtOAc | <2 | <2 | EtOH/H₂O (1/1, v/v) | <2 | <2 |
| THF | 20-50 | <50 | Acetone/H₂O (1/1, v/v) | <2 | 2-10 |

Example 26

Polymorph Screening of TPA023B Phosphate by Slurry Method

TPA023B phosphate (about 20 mg) was added in appropriate various solvents, respectively. The suspension was stirred at 500 rpm for 3 days at RT. The residues of the compound (TPA023B phosphate) were separated by centrifuge (5 min at 14000 rpm) and further dried overnight in the vacuum oven at 30° C. The dried solid was analyzed by XRPD. If XRPD was changed, the dried solids were then analyzed by PLM, DSC and TGA. Table 17 illustrates the results of the slurry screening methods using selected solvents. For example, when the form of TPA023B phosphate is named as "Form A," then its corresponding XRPD pattern is designated as "Pattern A."

TABLE 17

| | Polymorph Screening of TPA023B Phosphate by Slurry Method | | | |
|---|---|---|---|---|
| Solvent | TPA023B_phosphate weight (mg) | Solvent Volume (μL) | Appearance | XRPD pattern |
| Methanol | 20.88 | 200 | Yellow powder | Pattern B |
| Ethanol | 20.25 | 200 | Yellow powder | Pattern A |
| Isopropanol | 20.49 | 200 | Yellow powder | Pattern A |
| Acetone | 20.10 | 200 | Yellow powder | Pattern A |
| EtOAc | 19.98 | 200 | Yellow powder | Pattern A |
| MEK | 20.40 | 200 | Yellow powder | Pattern A |
| ACN | 20.70 | 200 | Yellow powder | Pattern A |
| Methyl tert-butyl ether (MTBE) | 19.95 | 200 | Yellow powder | Pattern A |
| EtOH/H$_2$O (1/1, v/v) | 20.57 | 200 | Yellow powder | Pattern B |
| Acetone/H$_2$O (1/1, v/v) | 20.45 | 200 | Yellow powder | Pattern A |

Example 27

Polymorph Screening of TPA023B Phosphate by Heat-Cooling Method

TPA023B phosphate (about 20 mg) was weighed and transferred into a vial containing of 200 μL of each selected solvent. The suspension was stirred at 700 rpm for 4 hours at 60° C., and the suspension was allowed to cool to room temperature. This cycle was repeated twice. Any resulting solids were collected by centrifugation and dried in a 30° C. vacuum oven. The samples were analyzed by XRPD. If XRPD pattern differed, the samples were analyzed by PLM, DSC and TGA. In addition to TPA023B Phosphate Pattern A, Free Base Pattern C and Phosphate pattern D were observed, as shown in Table 18 and FIG. 30.

Figure 31:
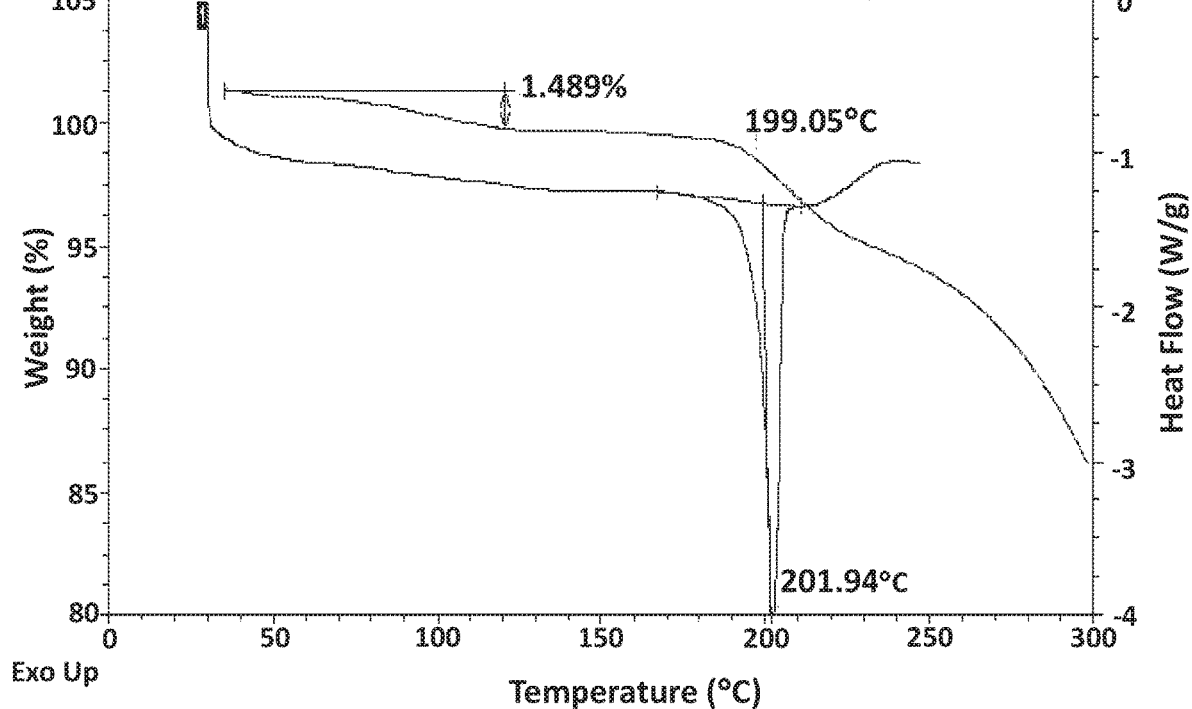
FIG. 31 illustrates a DSC/TGA thermogram for TPA023B phosphate Pattern D

A DSC/TGA thermogram of TPA023B Phosphate Polymorphic Pattern D is illustrated in FIG. 31. As shown in FIG. 31, the DSC trace showed a single endothermic peak with an onset temperature of 199° C. (95.92 J/g) and the TGA result showed that the original form exhibits a three-step weight loss of 1.489% from 30° C. to 150° C., which could be attributed to removal of residual solvent.

Example 28

Polymorph Screening of TPA023B Phosphate by Anti-Solvent Method

Figure 32:
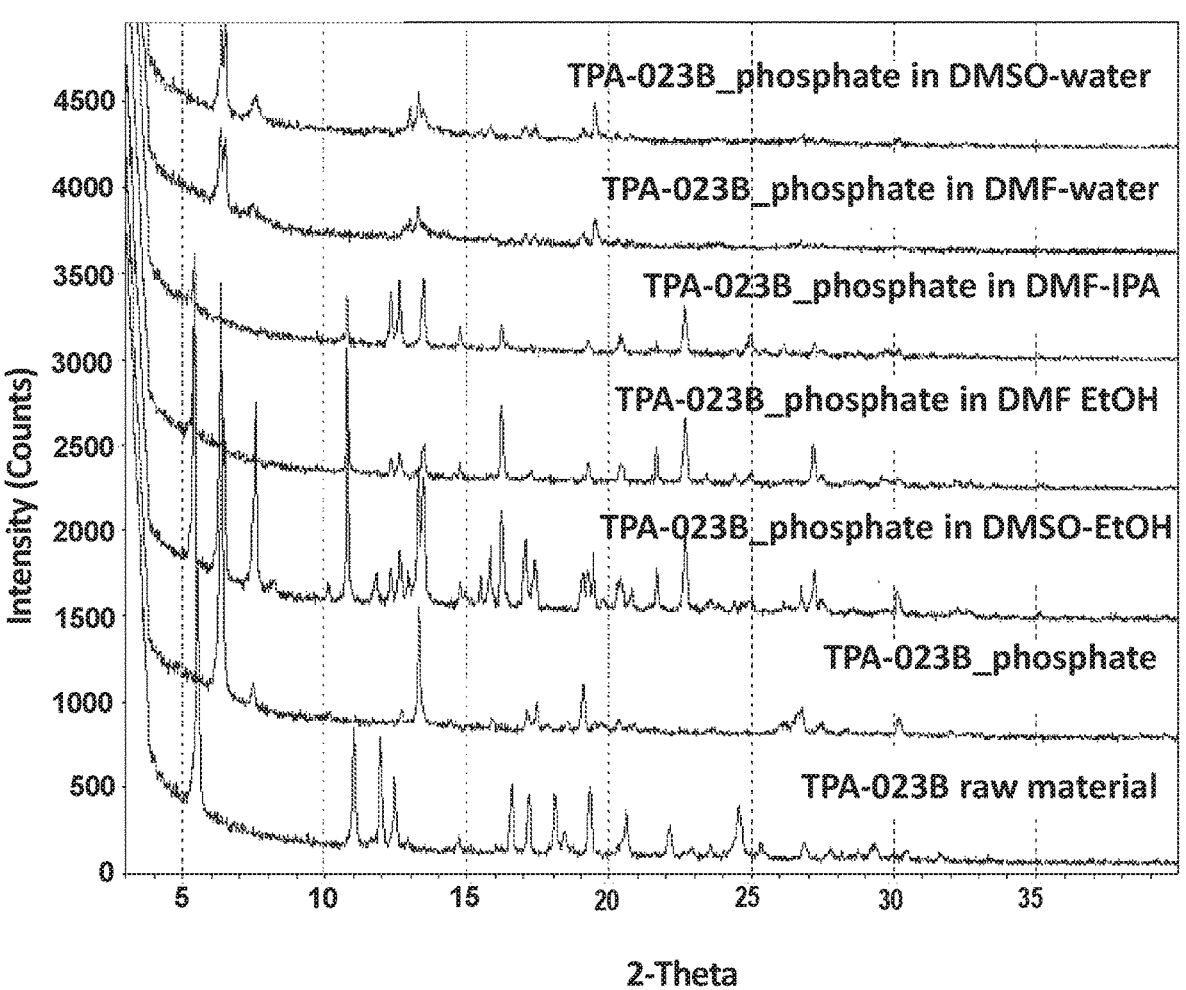
FIG. 32 illustrates XRPD patterns of TPA023B phosphate solids obtained by polymorph screening using the anti-solvent method

TPA023B phosphate (about 150 mg) was dissolved in 1.5 ml, of either DMSO or DMF to prepare stock solutions (100 mg/mL). Anti-solvent was added until either precipitation occurred, or the amount of anti-solvent added reached 5× of the amount of solvent. The precipitate was collected by centrifuge and dried overnight in a 30° C. vacuum oven. The obtained samples were analyzed by XRPD. If the XRPD pattern changed, the dried solids were analyzed by PLM, DSC and TGA. As shown in Table 19 and FIG. 32, TPA023B Free Base Form C and TPA023B Phosphate Pattern E (a mixture comprising Phosphate Form A) were observed.

TABLE 18

| | Polymorph Screening of TPA023B Phosphate by Heat-Cooling Method | | | |
|---|---|---|---|---|
| Solvent | TPA023B_phosphate weight (mg) | Solvent Volume (μL) | Appearance | XRPD pattern |
| Methanol | 20.08 | 200 | Yellow powder | Free Base Form C |
| Ethanol | 20.03 | 200 | Yellow powder | Phosphate Pattern A |
| Isopropanol | 20.71 | 200 | Yellow powder | Pattern D *(a mixture comprising Free Base Form C and Phosphate Form A) |
| THF | 20.77 | 200 | Yellow powder | Phosphate Pattern A |
| 1,4-Dioxane | 20.00 | 200 | Yellow powder | Phosphate Pattern A |
| DCM | 20.00 | 200 | Yellow powder | Phosphate Pattern A |
| ACN | 20.20 | 200 | Yellow powder | Phosphate Pattern A |
| Acetone/H$_2$O (1/1, v/v) | 20.40 | 200 | Yellow powder | Phosphate Pattern D (a mixture comprising Free Base Form C and Phosphate Form A) |

* Free Base Form C is obtained in a scale-up method, see example 29.

TABLE 19

| | | Anti-Solvent | | XRPD |
|---|---|---|---|---|
| Stock Solution | Anti-Solvent | Volume (mL) | Observation | pattern |
| 100 mg/mL of | ACN | 1.0 | Clear solution | N/A |
| TPA023B | Ethanol | 1.0 | Precipitate after | Free Base Form C |
| phosphate in | | | stored in 5° C. | |
| DMF (200 µL of | | | freezer overnight | |
| stock solution for | Isopropanol | 1.0 | precipitate | Free Base Form C |
| each anti-solvent) | | | immediately | |
| | Acetone | 1.0 | Clear solution | N/A |
| | Water | 1.0 | Precipitate | Pattern E |
| | | | immediately | (a mixture comprising |
| | | | | Phosphate Form A) |
| | EtOAc | 1.0 | Clear solution | N/A |
| 100 mg/mL of | ACN | 1.5 | Clear solution | N/A |
| TPA023B | Ethanol | 1.5 | Precipitate after | Pattern D |
| phosphate in | | | stored in 5° C. | (a mixture comprising |
| DMSO (300 µL of | | | freezer overnight | Free Base Form C and |
| stock solution for | | | | Phosphate Form A) |
| each anti-solvent) | Isopropanol | 1.5 | Clear solution | N/A |
| | Acetone | 1.5 | Clear solution | N/A |
| | Water | 1.5 | precipitate | Pattern E |
| | | | immediately | (a mixture comprising |
| | | | | Phosphate Form A) |
| | EtOAc | 1.5 | Clear solution | N/A |

Example 29

Scale-Up of Polymorph Screening of TPA023B Phosphate by Heat-Cooling Method

Figure 33:
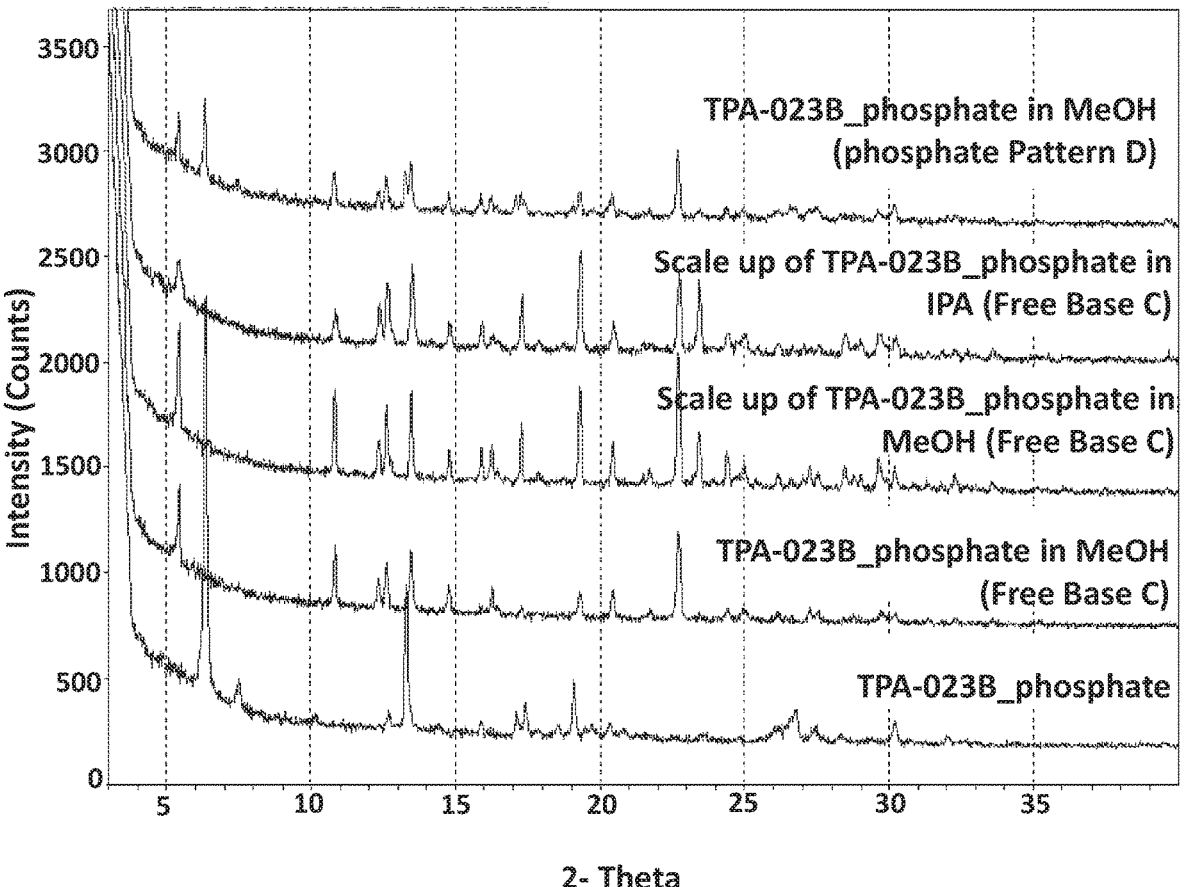
FIG. 33 illustrates additional XRPD patterns of TPA023B Polymorph screening by heat-cooling method

TPA023B phosphate (about 100 mg) was used in a scaled-up repeat of the experiments in Example 27 with solvents methanol and isopropanol, respectively. The solids obtained using methanol exhibited an XRPD pattern of Free Base Form C, the same pattern as shown in example 27. The solids obtained using isopropanol (IPA) also exhibited an XRPD pattern of Free Base Form C in the scale-up. The XRPD patterns of the obtained solids are illustrated in FIG. 33. The yield of the scale-up experiments is shown in Table 20.

Figure 34:
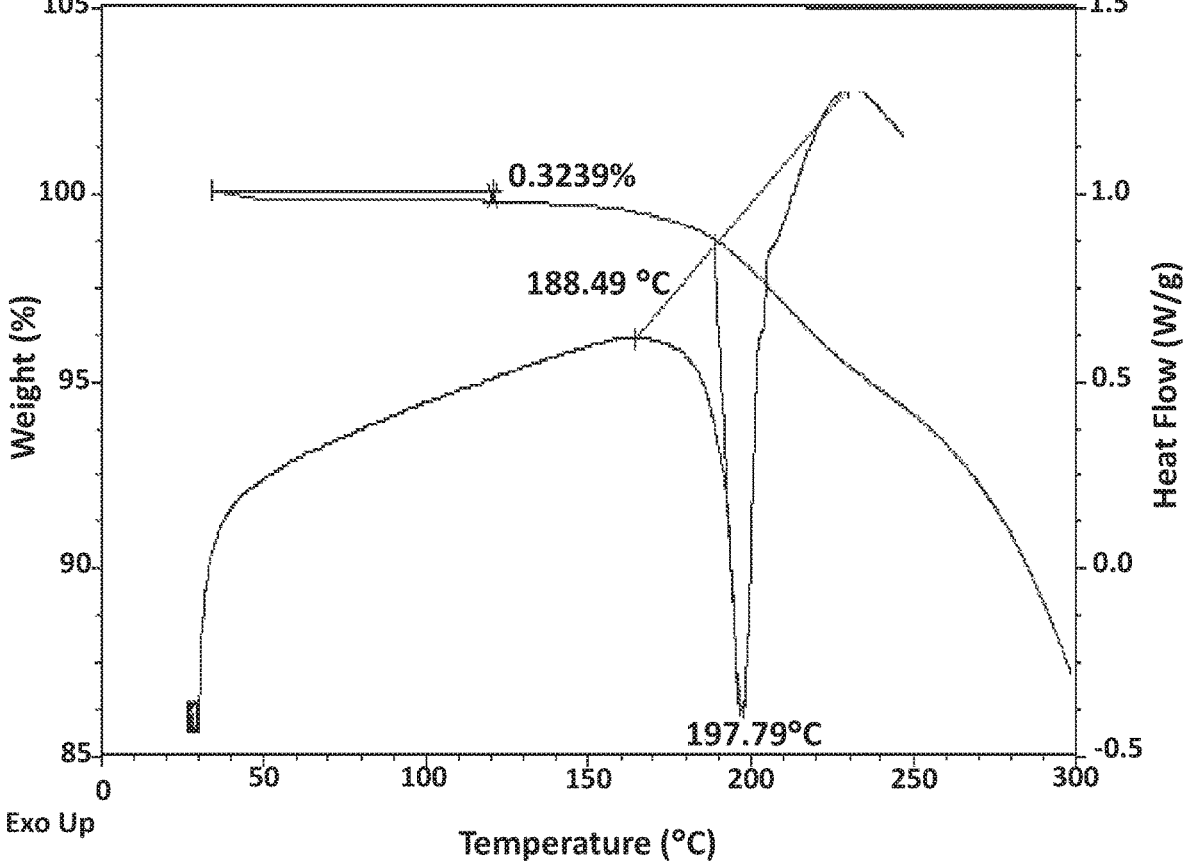
FIG. 34 illustrates an additional DSC/TGA thermogram of TPA023B Polymorph screening in IPA by the heat-cooling method

As shown in FIG. 34, the DSC/TGA thermogram of the TPA023B Phosphate produced in IPA by the heat-cooling method showed one endothermic peak with an onset temperature of 188° C. (112.9 J/g) by DSC. Its TGA trace showed a three-step weight loss of 0.32% from 30° C. to 120° C., which could be attributed to removal of residual solvent.

TABLE 20

Yield of scale-up of TPA023B phosphate with Heat-cooling method

| TPA023B_phosphate weight (mg) | Solvent | Solvent Volume (mL) | Product amount (mg) | Yield (%) |
|---|---|---|---|---|
| 100.39 | MeOH | 1.0 | 62.07 | 61.83 |
| 100.53 | IPA | 1.0 | 73.32 | 72.93 |

Additional Experiments to Prepare and Characterize TPA023B Phosphate

Additional experiments were conducted to prepare and characterize TPA023B Phosphate, the results of which are provided in Examples 31-37.

TPA023B Phosphate was prepared by reacting free base TPA023B with phosphoric acid. Four crystal form and patterns (phosphate Form A, Pattern F, Pattern G, and Pattern H) in total were identified during polymorph screening. TPA023B Phosphate Form A and H were anhydrates, Pattern F was a solvate (ethanol solvate), and Pattern G was a hydrate. Solvents THF, 2-Me-THF, IPAC, EA, Acetone, MTBE or ACN could be used to prepare TPA023B Phosphate Form A, which is stable in these solvents. Phosphate Pattern F and Pattern G were obtained by slurrying phosphate Form A in EtOH and EtOH-Water, respectively. Desolvation of Pattern F gave Pattern H.

The properties of the form and patterns are summarized in Table 21 below. Only phosphate Form A showed one single endothermic peak in DSC test. Competitive slurry showed that phosphate Form A is the most thermodynamically stable form. Form A shows slight hygroscopicity and no change after DVS test and grinding.

Figure 37A:
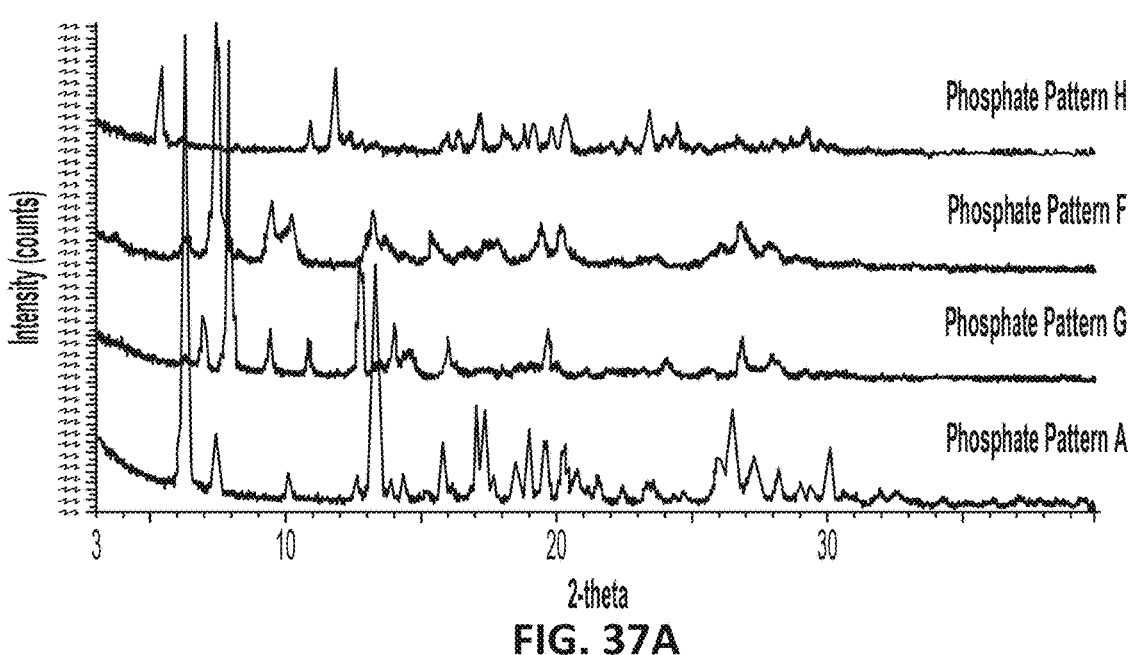
FIGS. 37A and 37B illustrate the XRPD patterns (FIG. 37A) and P-NMR spectra (FIG. 37B) of TPA023B phosphate Form A and several phosphate patterns
Figure 37B:
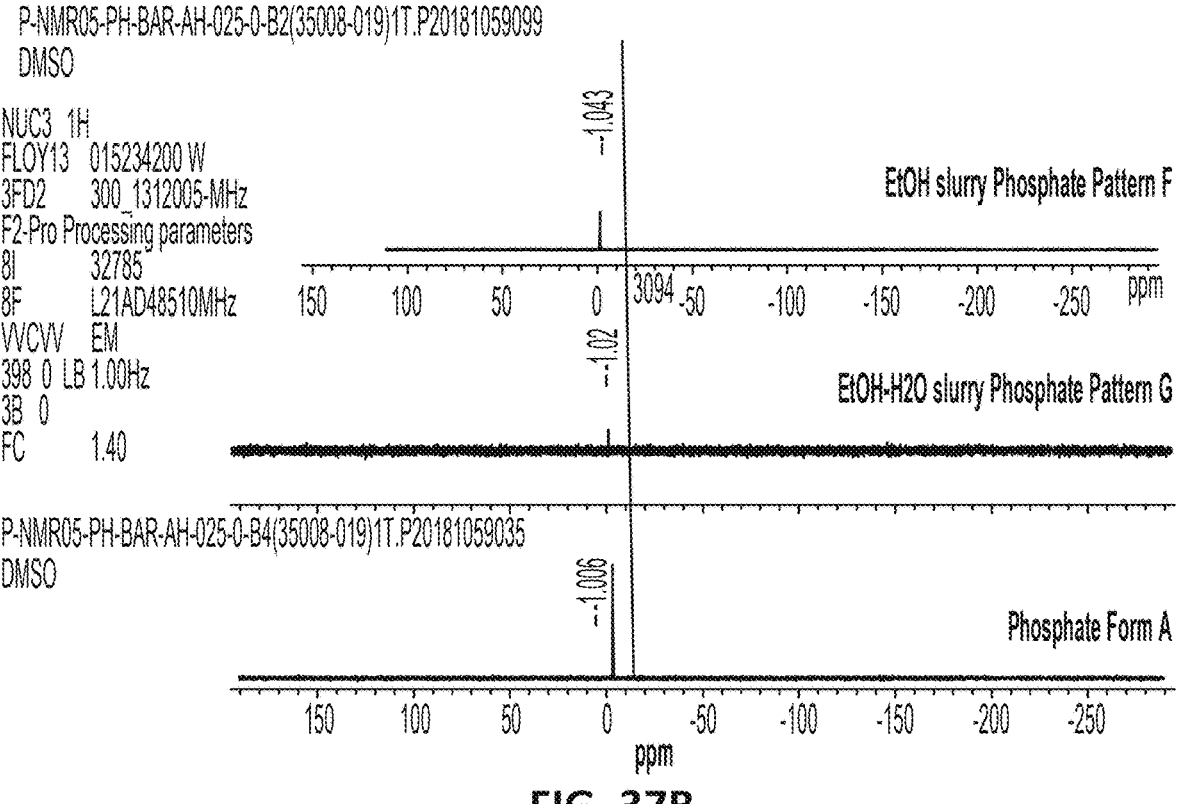

The XRPD patterns of the four crystal form and patterns are illustrated in FIG. 37A. FIG. 37B illustrates the P-NMR of Form A, Pattern F, and Pattern G. As shown in FIG. 38B, comparing the three NMR spectra, Phosphate Form A provides a phosphorus peak with the highest intensity and the intensity of the phosphorus peaks for Patterns F and G decreased significantly. It is believed that Phosphate Form A may have disassociated in EtOH or EtOH-Water, and Phosphate Patterns F and G comprise mainly TPA023B free base. Form A and Pattern H are needle-like crystals, and Pattern F and Pattern G are irregular crystals.

| Sample | XRPD | DSC (onset/peak; ΔH) | TGA | Remark |
|---|---|---|---|---|
| 35006-011-2 | Phosphate Form A | 204/206° C.; 109.7 J/g | 0.027% 175° C. | anhydrate |

-continued

| Sample | XRPD | DSC (onset/peak; ΔH) | TGA | Remark |
|---|---|---|---|---|
| 35006-013-2 | Phosphate Pattern F | Multi-peaks | 5.57%/120° C. | EtOH Solvate |
| 35006-013-3 | Phosphate Pattern G | Multi-peaks | 3.62%/115° C. | hydrate |
| 35006-016-1 | Phosphate Pattern H | 191.3/194.2° C.; 27.8 J/g 201.2/205.0° C.; 81.9 J/g | 0.046%/175° C. | anhydrate |

Additional Experiments 30.1 Freebase Polymorph Screening

About 100 mg of TPA023B freebase was weighed into certain amount of specific solvent or mixture solvents and stirred at RT or 50° C. for 3 days. The suspensions were filtered and characterized by XRPD.

30.2 Preparation of Phosphate Forms

TPA023B freebase (1000 mg) was dissolved in 16 ml THF. H₃PO₄ (0.25 mL) was added to the solution and stirred for 1 h at 35 TC. About 10 mL solvent was removed by rotary evaporator and solids crystallized out during evaporation. The suspension was further stirred after evaporation and more solids appeared. MTBE (10 mL) was added after 1 h, and the suspension was kept stirring for another 3 h and then filtered. The product obtained (1.1 g, 88% yield) was TPA023B Phosphate Form A.

30.3 Preliminary Solubility Study

TABLE 22

List of solvents

| No. | Solvent |
|---|---|
| 1 | methanol (MeOH) |
| 2 | ethanol (EtOH) |
| 3 | isopropanol (IPA) |
| 4 | ethyl acetate (EA) |
| 5 | dichloromethane (DCM) |
| 6 | tetrahydrofuran (THF) |
| 7 | acetonitrile (ACN) |
| 8 | methyl tert-butyl ether (MTBE) |
| 9 | 2-methyl tetrahydrofuran (2-Me THF) |
| 10 | water (W) |
| 11 | heptane |
| 12 | dimethyl formamide (DMF) |
| 13 | dimethyl sulfoxide (DMSO) |
| 14 | 1,4-Dioxane |
| 15 | acetone |

Figure 42:
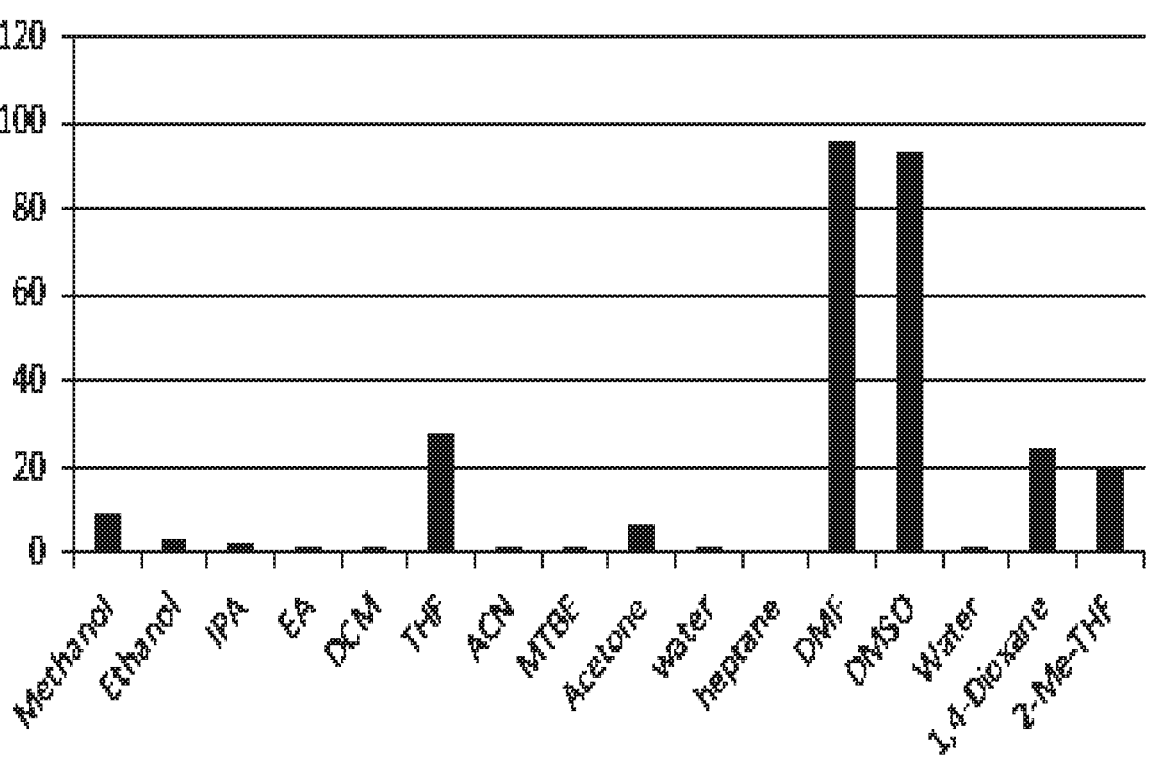
FIG. 42 illustrates the estimated solubility of TPA023B Phosphate Form A in various solvents

Preliminary solubility study of TPA023B Phosphate Form A was carried out. TPA023B Phosphate Form A solids (known amount) was added into a vial and the specific solvent was added. Then the mixture was agitated in a shaker block for at least 30 mins. Additional solvent was added in a stepwise manner until all solids were dissolved. The dissolution was checked by visual observation and the amount of solvent required to dissolve all the solids was recorded. The solvents used are listed in Table 22, and the results are shown in FIG. 42.

30.4. Slurry and Stability Study of Phosphate

About 50 mg of TPA023B Phosphate Form A was weighed into a predetermined amount of specific solvent and stirred at RT or 50° C. for 3 days. The suspensions were filtered and characterized by XRPD. When new forms were obtained, those that did not disproportionate were further analyzed by DSC and TGA.

30.5 Competitive Slurry Study

TPA023B Phosphate of mixed forms was added into specific solvents and stirred at RT or 50° C. for 1 day. The suspensions were filtered and characterized by XRPD.

30.6 Mechanical Treatment

Appropriate amount of TPA023B Phosphate Form A was ground for about 3 minutes using a mortar and pestle and then analyzed by XRPD.

Analysis Method and Conditions 30.7 X-Ray Powder Diffraction (XRPD)

Solid samples were examined using D8 ADVANCE X-ray diffractometer (Bruker) and D2 phaser X-ray power diffractometer (Bruker). The diffractometer was equipped with LynxEye detector. In XRPD analysis, samples were scanned from 3 to 40° 2θ at a step of 0.02° 2θ. The tube voltage and current were 40 KV and 40 mA, respectively. The XRPD parameters are provided in Table 26-4. The D2 phaser X-ray power diffractometer (Bruker) of samples were scanned from 3 to 40° 2θ, at a step of 0.02° 2θ. The tube voltage and current were 30 KV and 10 mA, respectively.

30.8 Polarized Light Microscope (PLM)

PLM analysis was conducted with a polarized light microscope ECLIPSE LV100POL (Nikon, JPN).

30.9 Thermogravimetric Analysis (TGA)

TGA was carried out on TGA Q500 or Discovery TGA 55 (TA Instruments, US). The sample was placed in an open tarred aluminum pan, automatically weighed, and inserted into the TGA furnace. The sample was heated at 10° C./min to the final temperature.

30.10 Differential Scanning Calorimeter (DSC)

DSC analysis was conducted with DSC Q200 or Discovery DSC 250 (TA Instruments, US). A weighted sample was placed into a DSC pinhole pan, and the weight was accurately recorded. The sample was heated at 10° C./min to the final temperature.

Example 31

Characterization of TPA023B Free Base

As shown below, two batches of TPA023B Free Base were used. Batch #AH-025-9-4 is an anhydrous form defined as freebase-pattern A, and batch AH-025-9-10 was found as a mixture:

| Batch 1: | AH-025-9-4, | Freebase-Pattern A, | 98.6% purity |
|---|---|---|---|
| Batch 2: | AH-025-9-10, | Mix pattern, | 97.8% purity |

Figure 35A:
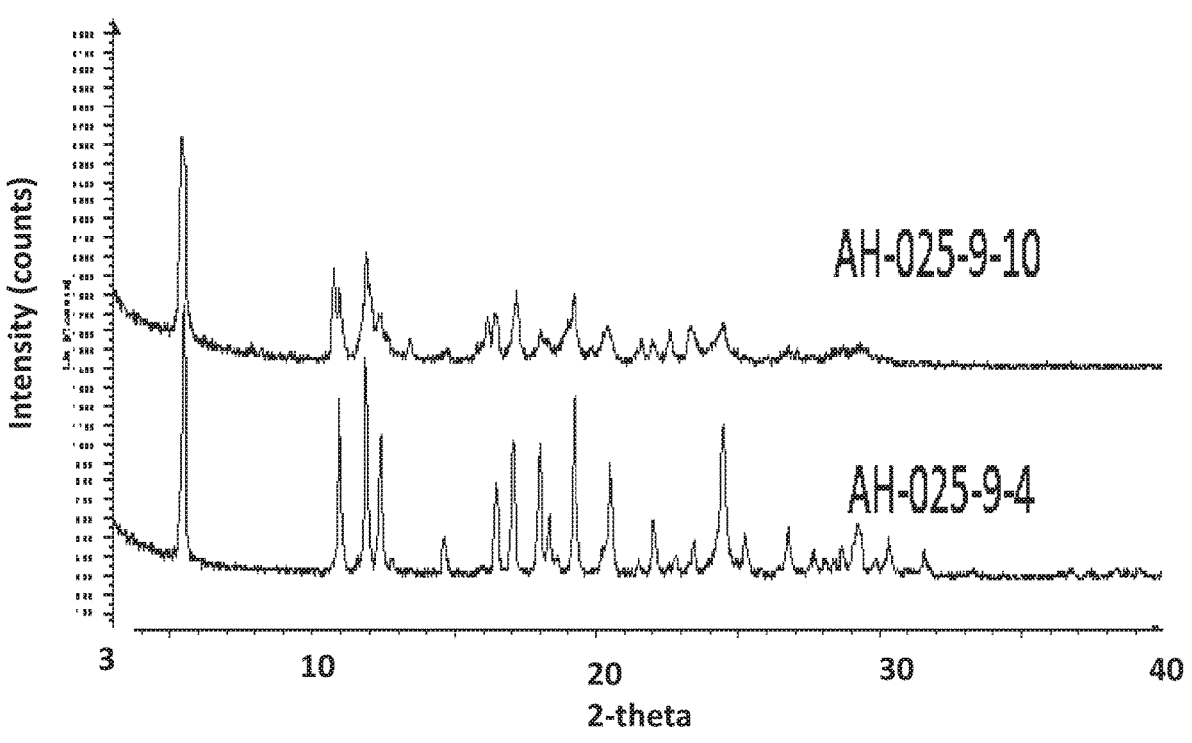
FIG. 35A and FIG. 35B illustrate the XRPD patterns (FIG. 35A) and the DSC diagrams (FIG. 35B) of two batches of TPA023B Free Base
Figure 35B:
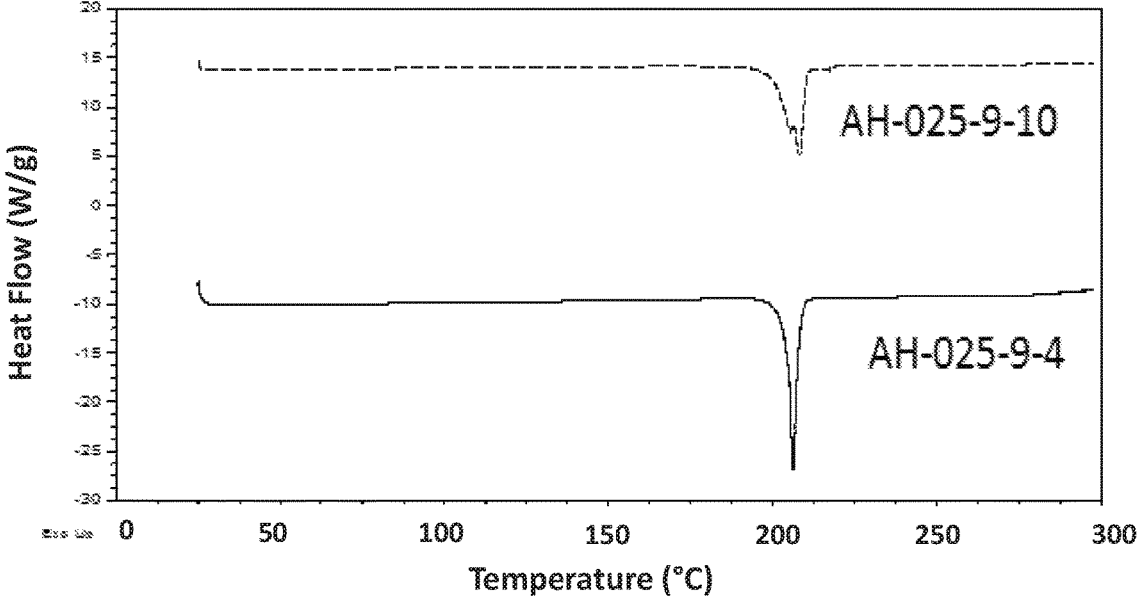

The XRPD patterns and the DSC diagrams of the two batches of Free Base are illustrated in FIG. 35A and FIG. 35B, respectively. The PLM images show AH-025-9-4 and AH-025-9-10 as irregular crystals. The DSC diagram of AH-025-9-4 shows one split peak, while the DSC diagram of AH-025-9-10 shows a single peak. According to the XRPD and DSC results, AH-025-9-4 is a pure form (form A) of TPA023B free base and AH-025-9-10 is a mixture of free base form A and form C.

Example 32

Identification of Additional TPA023B Free Base Forms

Figure 36A:
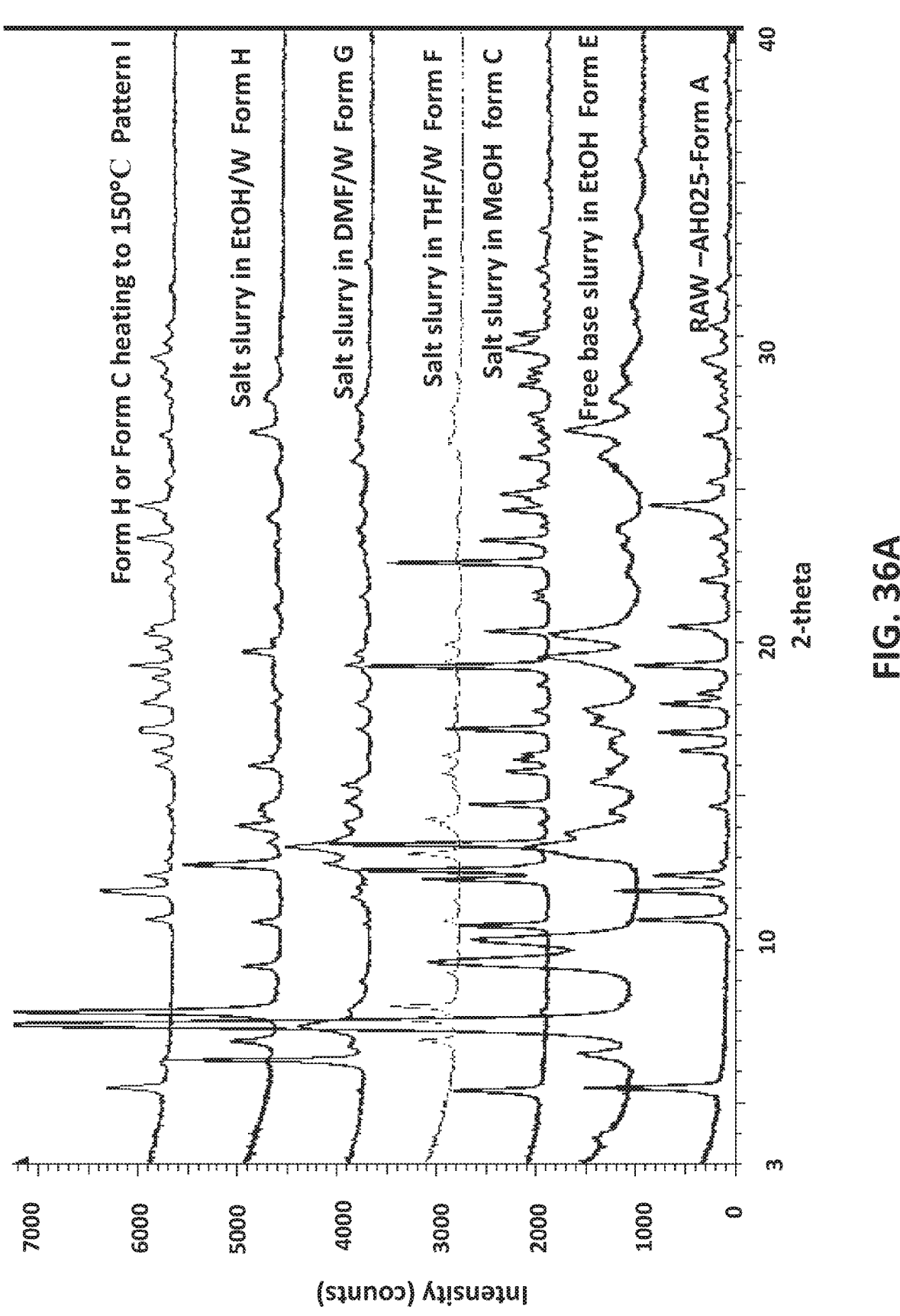
FIG. 36A-FIG. 36H illustrate the XRPD patterns of seven TPA023B free base forms (FIG. 36A); DSC and TGA profiles of TPA023B free base form A (FIG. 36B); DSC and TGA profiles of TPA023B free base form C (FIG. 36D); DSC and TGA profiles of TPA023B free base form E (FIG. 36C); DSC and TGA profiles of TPA023B free base form F (FIG. 36E); DSC and TGA profiles of TPA023B free base form G (FIG. 36F); DSC and TGA profiles of TPA023B free base form H (FIG. 36G); DSC and TGA profiles of TPA023B free base pattern I (FIG. 36H)
Figure 36B:
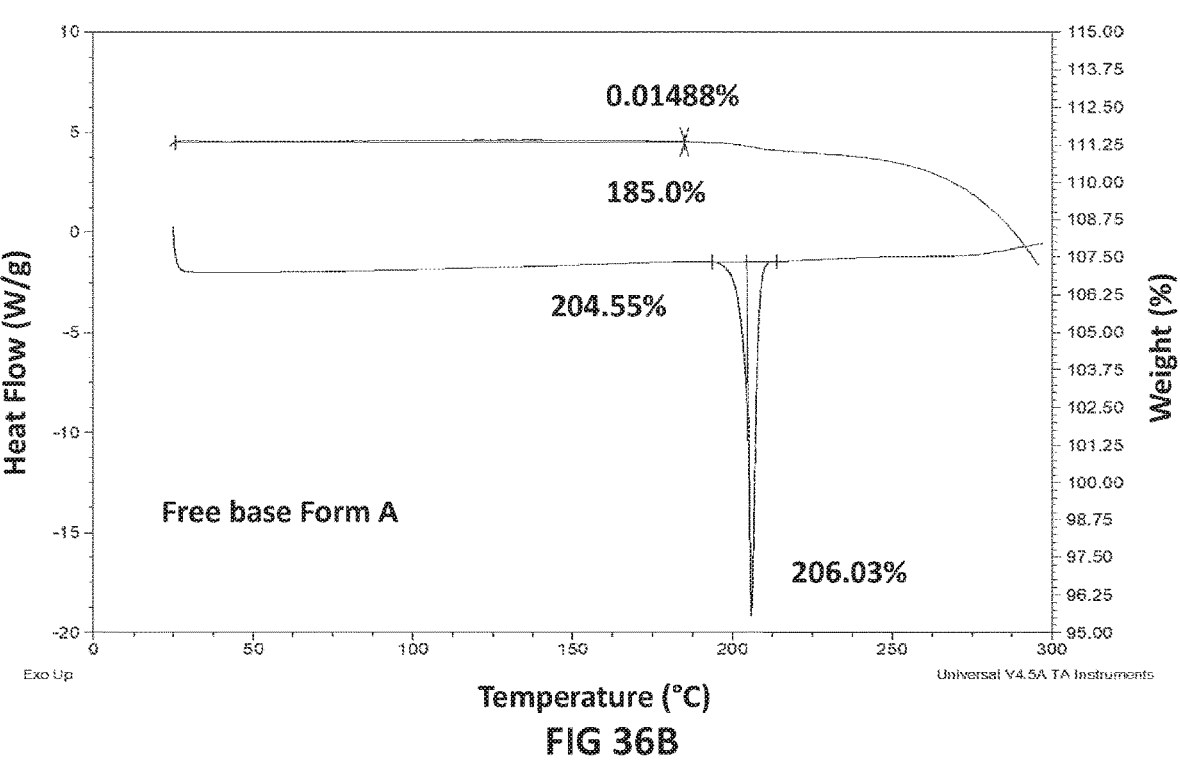
Figure 36C:
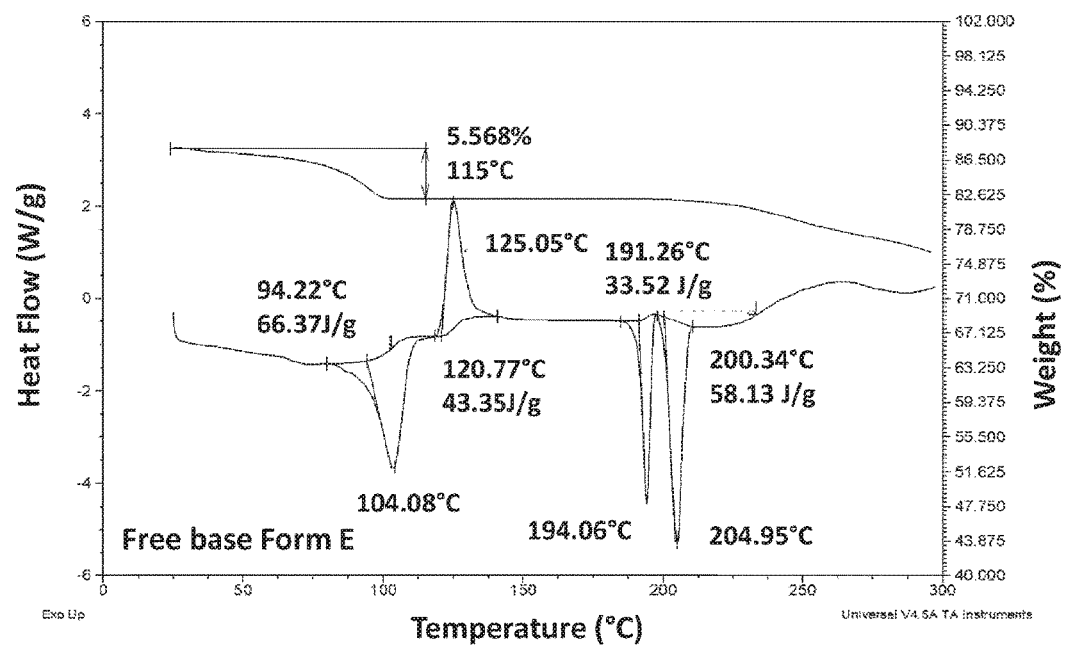
Figure 36D:
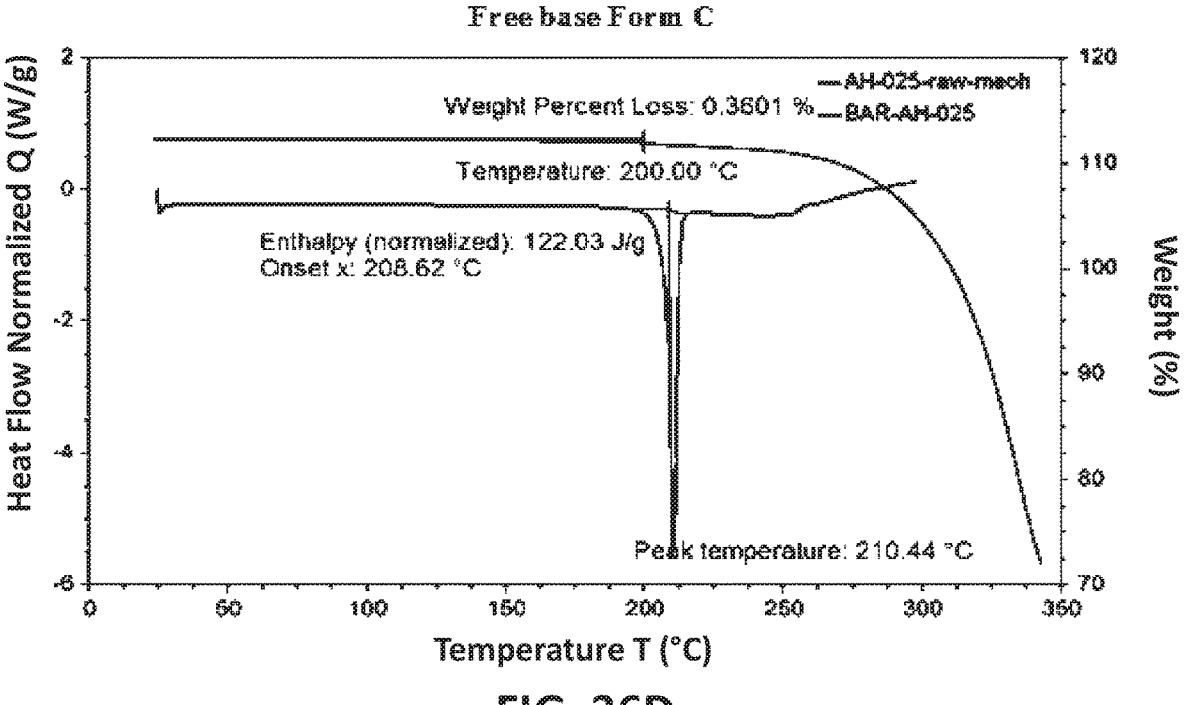
Figure 36E:
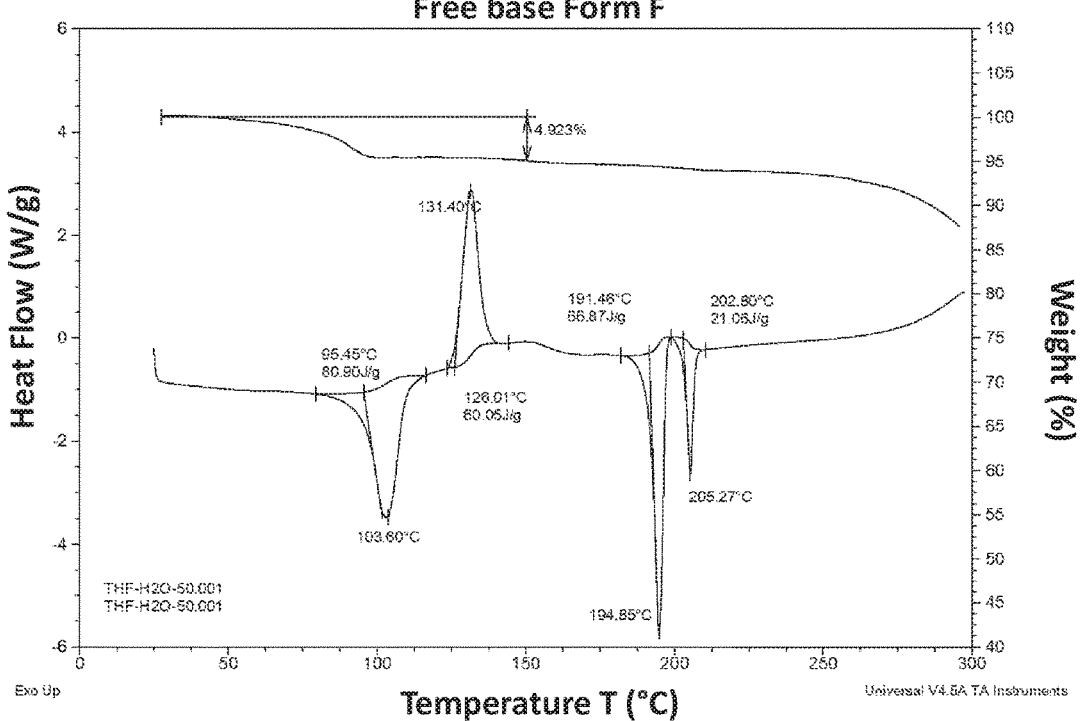
Figure 36F:
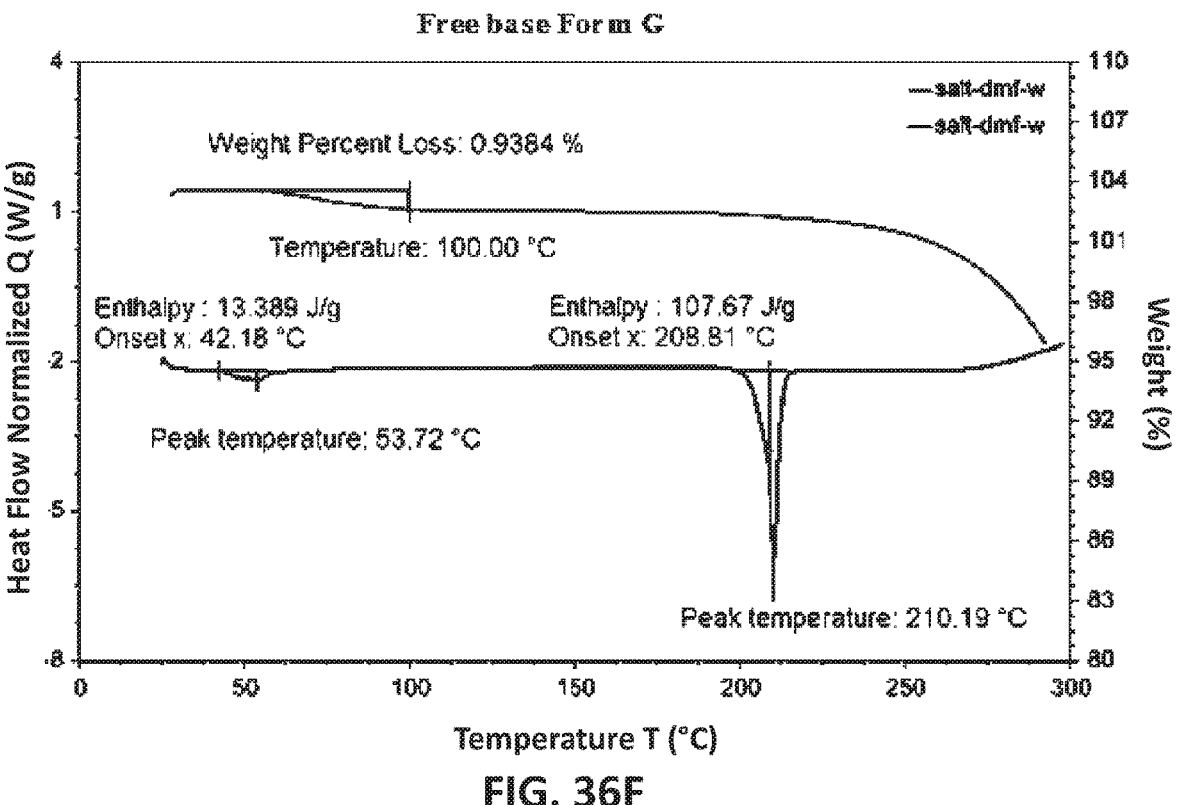
Figure 36G:
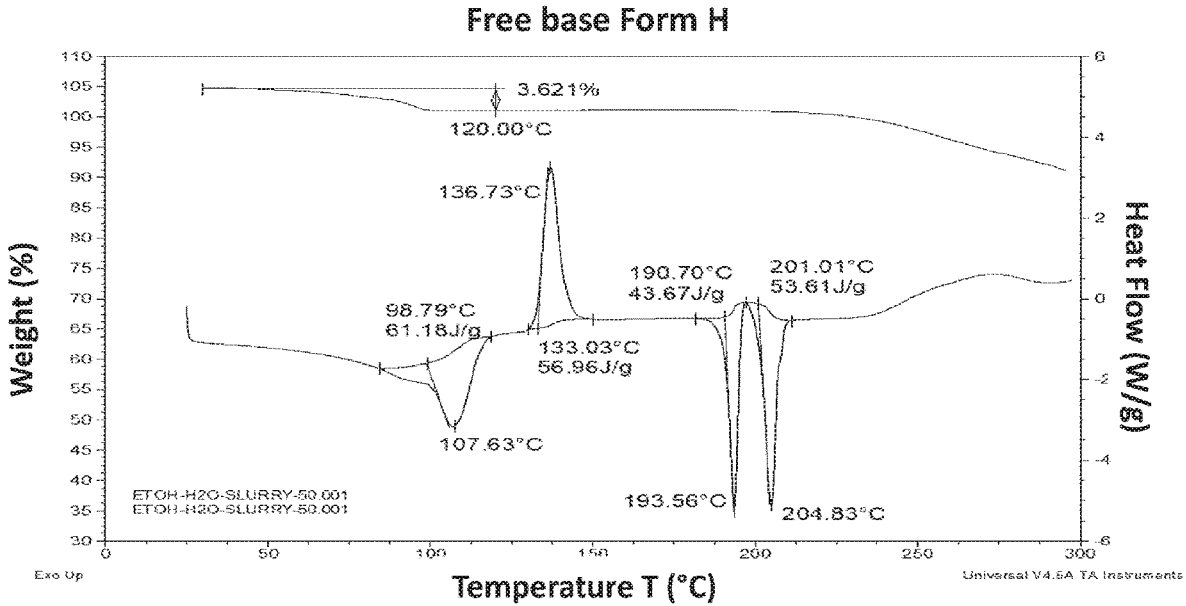
Figure 36H:
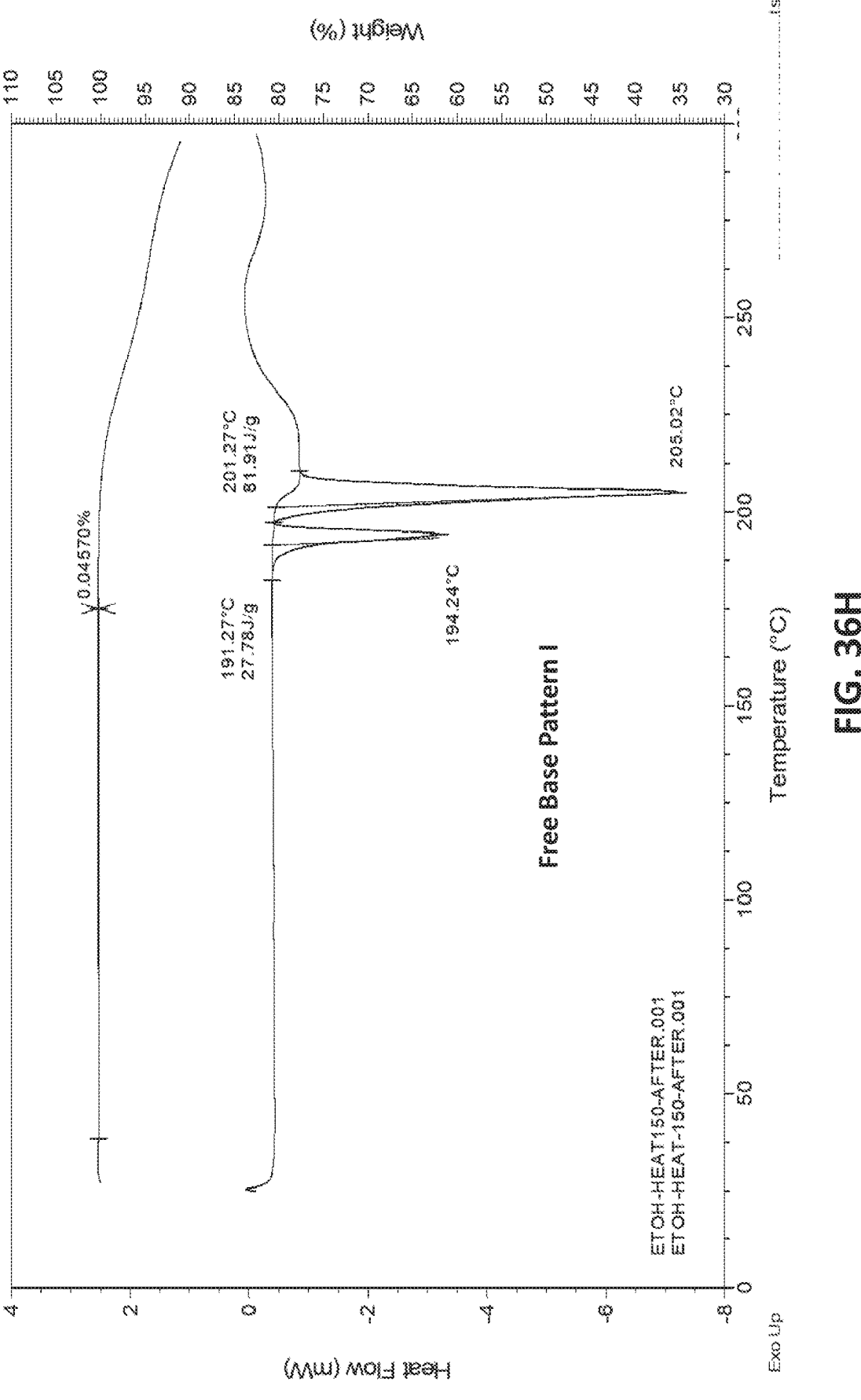

Polymorph screening was performed on Phosphate Form A, however TPA023B is a weak base and the phosphate formed readily dissociates to freebase in certain solvents. A total of six forms of TPA023B free base were identified with XRPD, which are illustrated in FIGS. 36A-36H and Table 23. The XRPD patterns of the TPA023B free base forms are shown in FIG. 36A, and the DSC/TGA profiles of the free base forms are shown in FIGS. 36B-36H.

Different freebase XRPD patterns could be used as standards to determine whether the phosphate is dissociated. Free Base Form E was obtained by slurrying either TPA023B freebase or phosphate in EtOH. Free Base Forms C, and F-H were obtained by dissociation of phosphate, and a new pattern (Pattern I) was obtained by heating Form C or Form H to 150° C. at 10° C./min by DSC. The DSC and TGA data of Forms A, C, and E-I are summarized in Table 23. The profiles are presented in FIGS. 36B-36H. Freebase Forms A and E were identified as anhydrates with Form C showing the highest melting point at 209° C., and Forms E, F, G and H are either hydrate or solvate.

TABLE 23

TPA023B Free Base Forms

| Freebase | DSC (onset/peak; ΔH) | TGA | Observations |
|---|---|---|---|
| Form A Anhydrate | 204/206° C.; 110 J/g | ~0/RT-185° C. | N/A |
| Form E Solvate | 94/104° C.; 67 J/g<br>Exo: 121/125° C.; 44 J/g<br>191/194° C.; 34 J/g<br>200/205° C.; 58 J/g | ~5.6%/RT-115° C. | Semi-EtOH solvate |
| Form C Anhydrate | 209/210° C.; 122 J/g | ~0/RT-150° C. | Highest melting point |
| Form F Solvate/ hydrate | 96/104° C.; 81 J/g<br>Exo: 126/131° C.; 60 J/g<br>192/195° C.; 67 J/g<br>203/205° C.; 21 J/g | ~4.9%/RT-150° C. | N/A |
| Form G Solvate/ hydrate | 42/54° C.; 14 J/g<br>209/210° C.; 108 J/g | ~1%/RT-100° C. | Converted to Form E upon heating |
| Form H Hydrate | 99/108° C.; 61 J/g<br>Exo: 133/137° C.; 57 J/g<br>191/194° C.; 44 J/g<br>201/205° C.; 54 J/g | ~3.6%/RT-120° C. | N/A |
| pattern I (Form A + Form J) | 191/194° C.; 28 J/g<br>201/205° C.; 82 J/g | ~0/RT-150° C. | Obtained by heating free base Form C or Form H to 150° C. |

Example 33

TPA023B Phosphate Forms

TPA023B Phosphate Form A is prepared by the following procedure: 1000 mg freebase was dissolved in 16 mL THF, followed by 0.25 mL $H_3PO_4$. The solution was stirred for 1 h at 35° C. ~10 mL solvent was removed by rotary evaporator and solid crystallized out during evaporation. The suspension was further stirred after evaporation and more solid appeared. 10 mL MTBE was added after 1 h, and the suspension was kept stirring for another 3 h and then filtered. TPA023B Phosphate Form A (1.1 g) was obtained with a yield of 88%. The crystals of TPA023B Phosphate Form A are needle-like crystals.

Figure 38A:
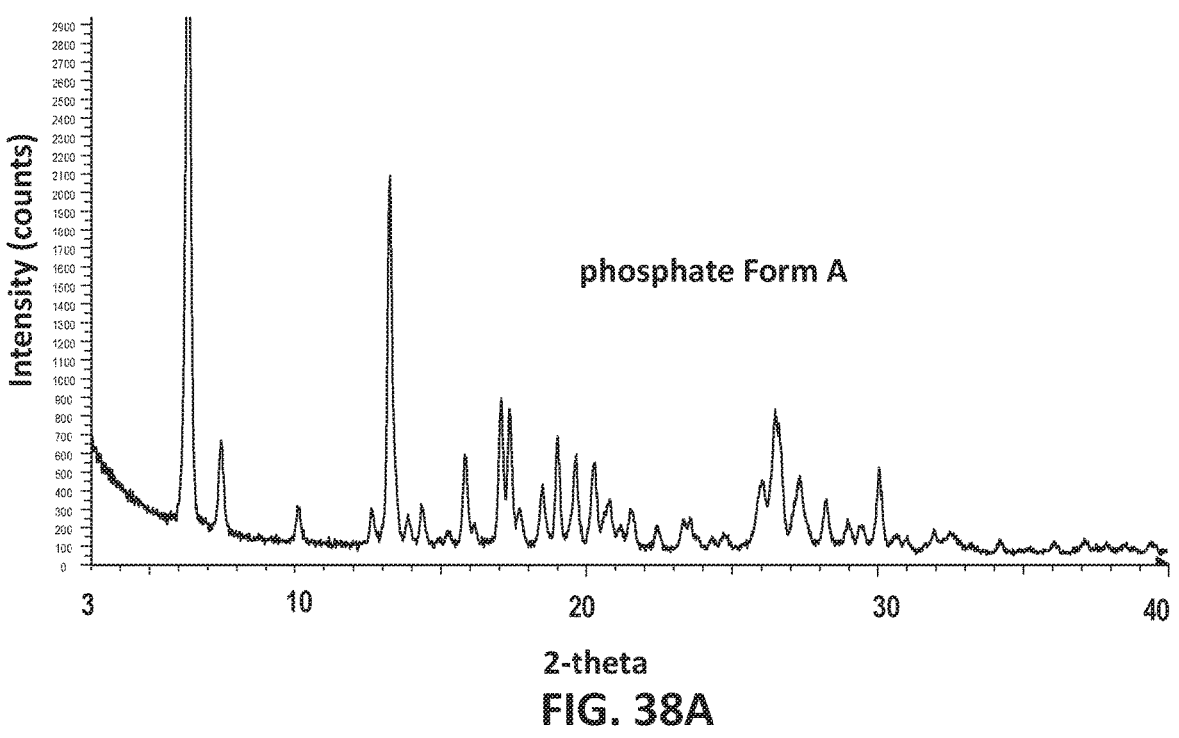
FIG. 38A-FIG. 38D illustrate an XRPD pattern (FIG. 38A), a DSC/TGA thermogram (FIG. 38B), a DVS result (FIG. 38C), and the XRPD patterns before and after DVS (FIG. 38D) for TPA023B Phosphate Form A
Figure 38B:
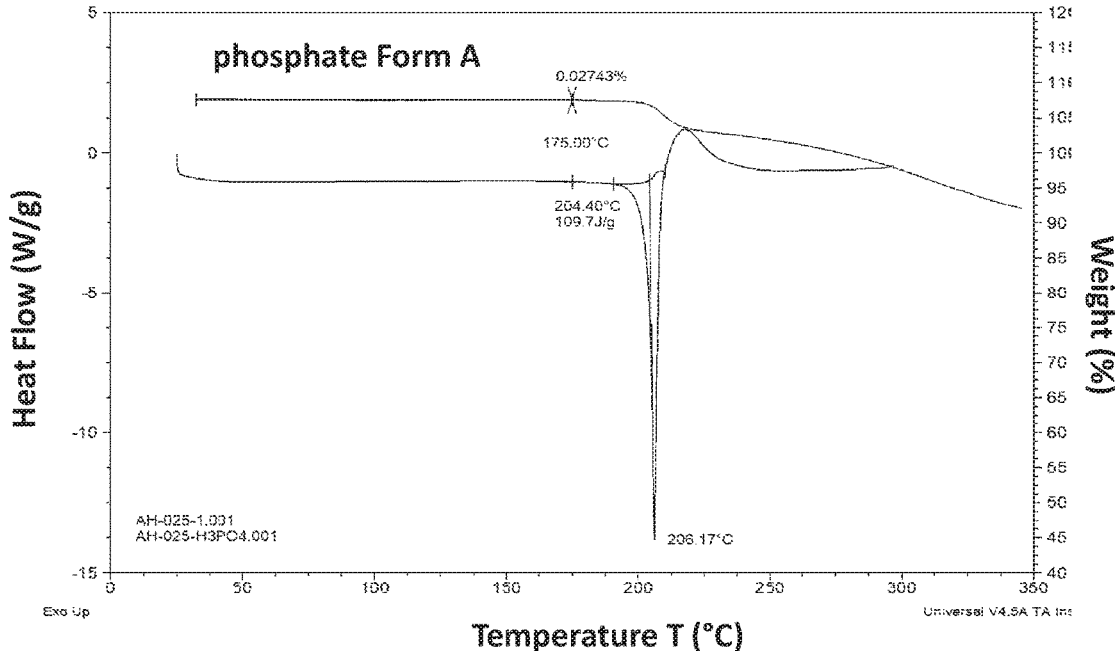
Figure 38C:
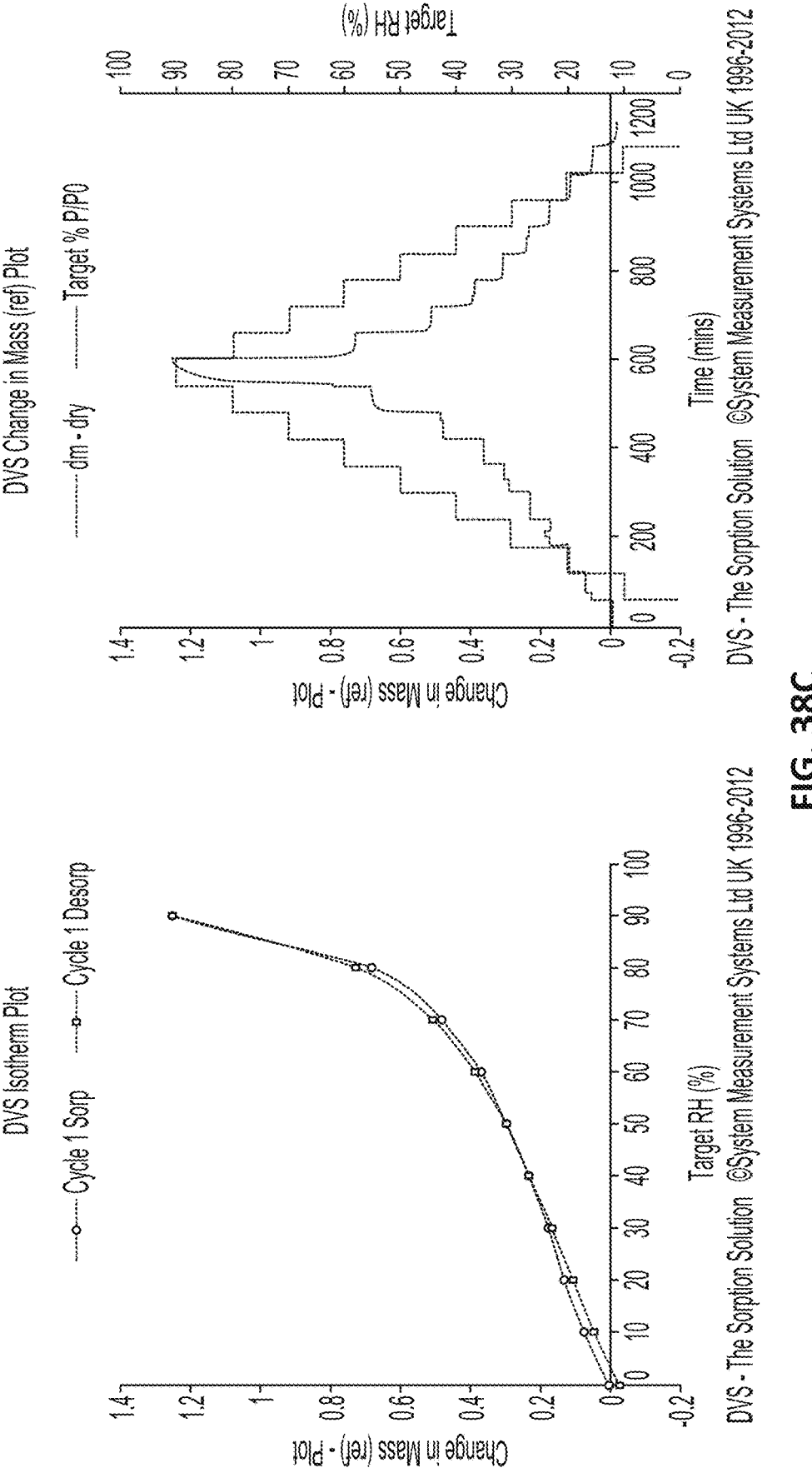
Figure 38D:
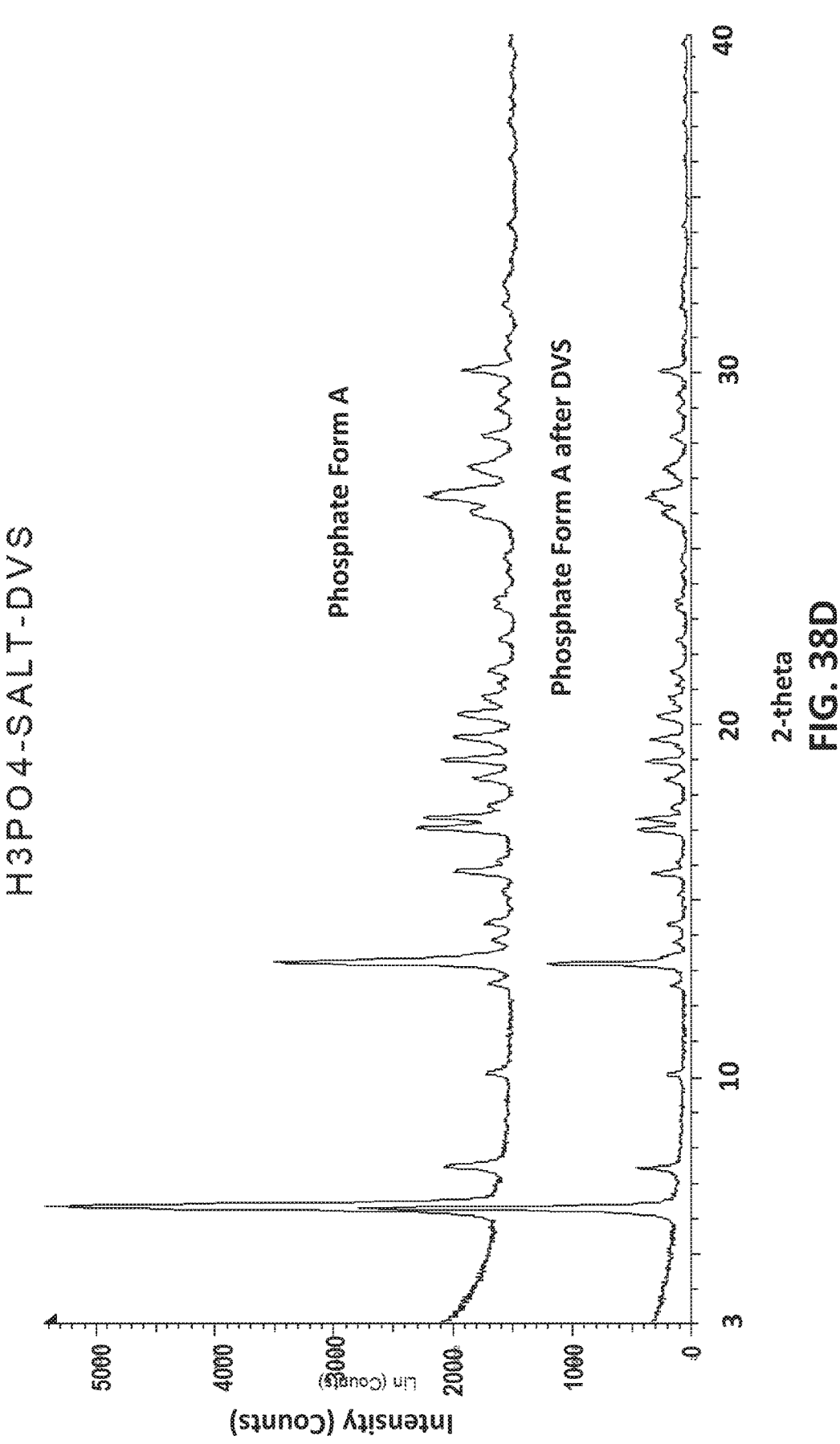

The XRPD pattern of TPA023B Phosphate Form A is shown in FIG. 38A. The thermal properties of TPA023B Phosphate Form A are illustrated in FIG. 38B. No significant weight loss was observed prior to 175° C. by TGA, suggesting that Phosphate Form A is an anhydrous form. The DSC thermogram shows one sharp endothermic peak at 206° C., which is due to melting of Phosphate Form A. An exothermic peak was observed right after melting accompanied by weight loss in TGA profile, which is because of decomposition of phosphate. DVS shows that Form A absorbed 0.68% of water from 0 to 80% RH, suggesting that Phosphate Form A can be slightly hygroscopic. The crystal form remained unchanged after DVS test (see FIG. 38C and FIG. 38D). The P-NMR spectrum of TPA023B Phosphate Form A (and other forms) is illustrated in FIG. 37B. Signal of phosphorus was detected by P-NMR and the ratio of freebase to $PO_4^{3-}$ was analyzed as 1:1 according to IC result.

Figure 39:
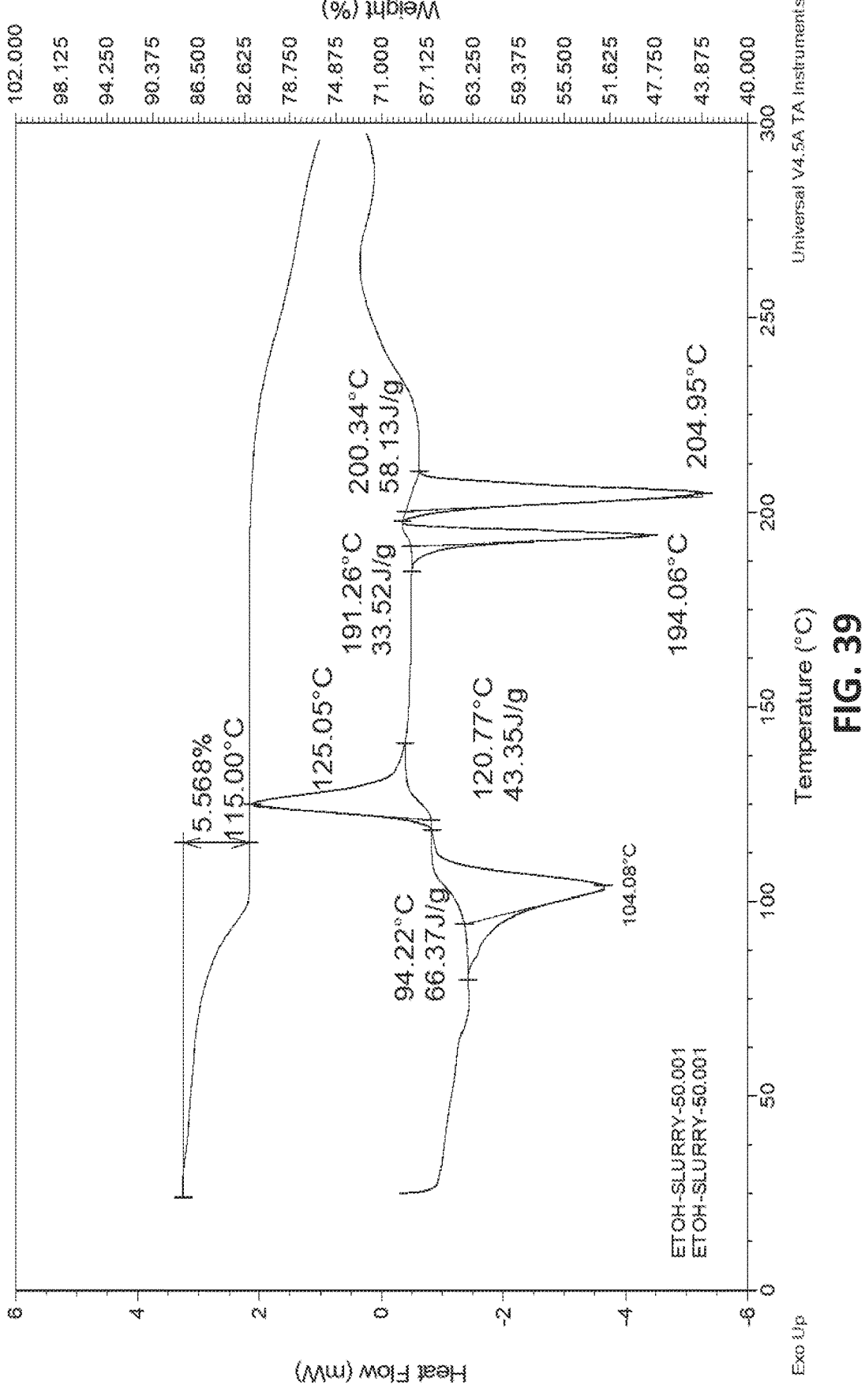
FIG. 39 illustrates a DSC/TGA thermogram of TPA023B Phosphate Pattern F

TPA023B Phosphate Pattern F was obtained by stirring form A in ethanol. The thermal properties of Pattern F are illustrated in FIG. 39. Pattern F has ~5.57% weight loss before 115° C., which could be caused by ethanol solvate. The DSC thermogram shows three endothermic peaks and one exothermic peak.

Figure 40:
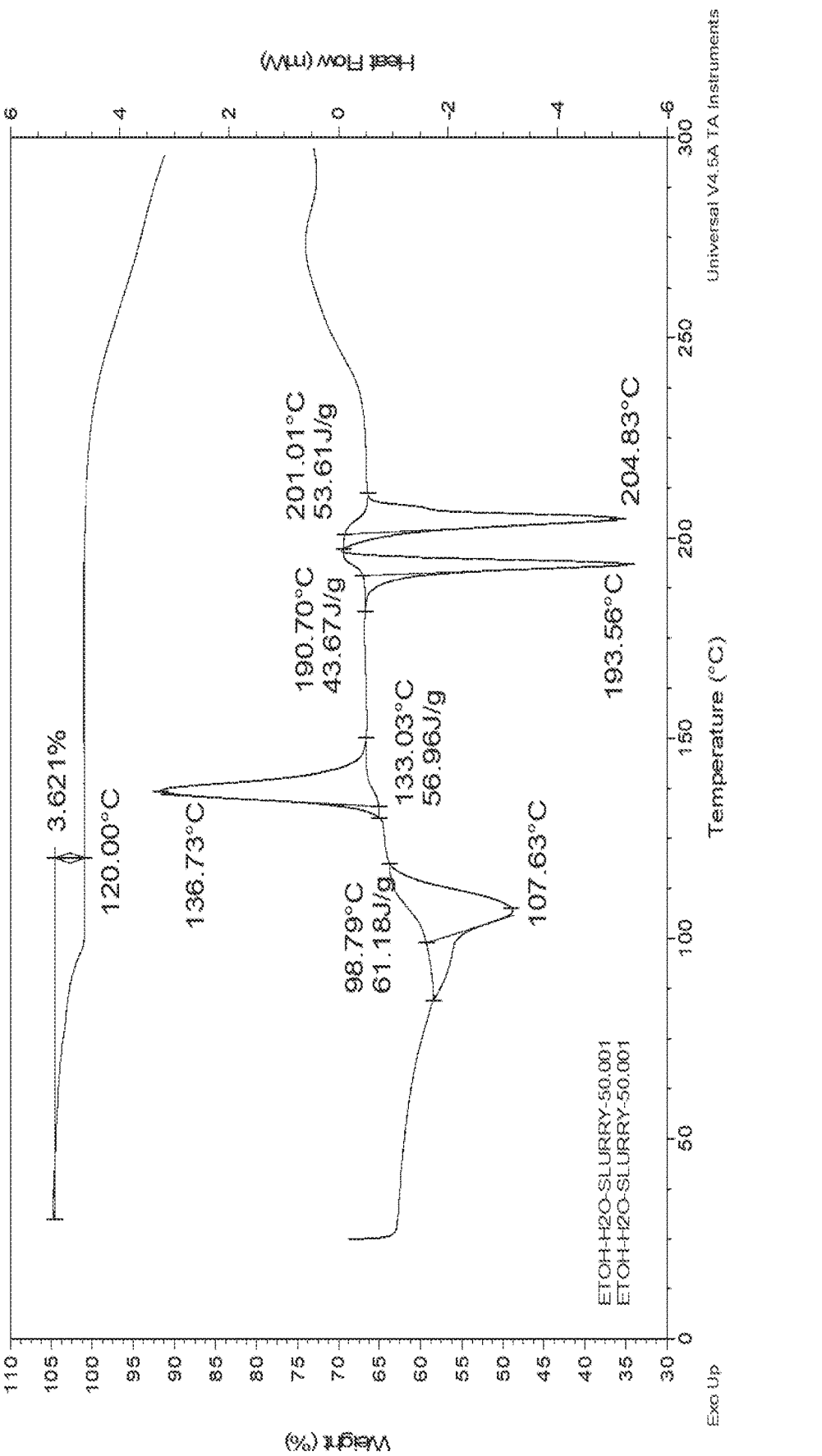
FIG. 40 illustrates a DSC/TGA thermogram of TPA023B Phosphate Pattern G

TPA023B Phosphate Pattern G was obtained by stirring form A in EtOH-Water. The thermal properties of TPA023B Phosphate Pattern G are illustrated in FIG. 40. A weight loss of about 3.6% was observed for Pattern G before 120° C. in TGA, together with three endothermic peaks in DSC (FIG. 40). Pattern G is therefore likely to be hydrate.

Figure 41:
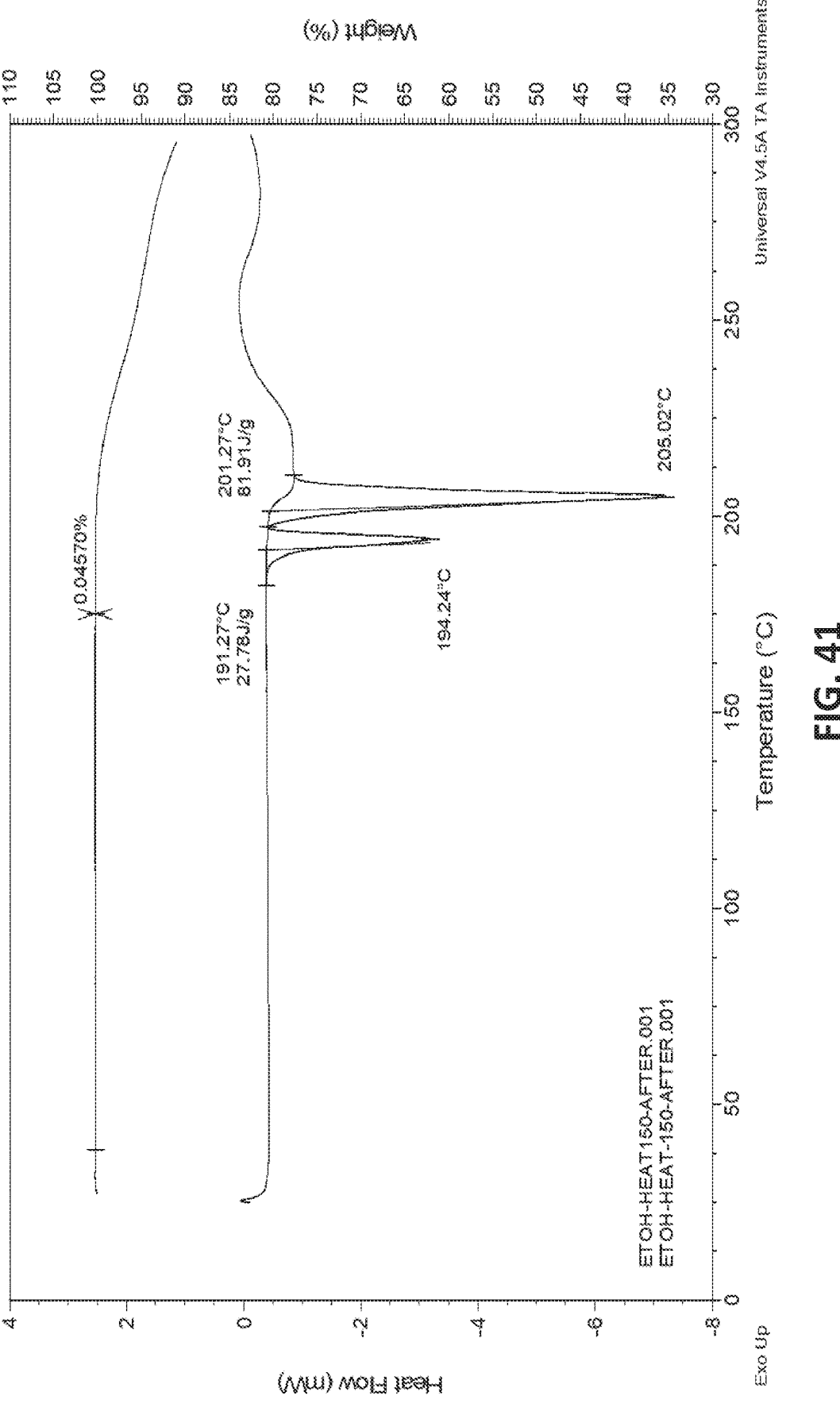
FIG. 41 illustrates a DSC/TGA thermogram of TPA023B Phosphate Pattern H

TPA023B Phosphate Pattern H was obtained by heating Phosphate Pattern F to 150° C. by TGA, thereby converting Pattern F to Pattern H. The thermal properties of TPA023B Phosphate Pattern H are illustrated in FIG. 41. As shown in FIG. 41, Pattern H has about 0.047% weight loss before 175° C., which could be due to solvent residue. Two endothermic peaks with peak temperatures at 194.2° C. and 205.0° C. were observed in the DSC thermogram.

Example 34

TPA023B Phosphate Preliminary Solubility Study

Solubility of TPA023B Phosphate Form A was measured in 16 solvents by visual observation and the results are summarized in Table 24 and FIG. 42. The solubility of Form A is high in DMF (96 mg/mL), DMSO (93 mg/mL), THF (28 mg/mL), 2-Me-THF (20 mg/mL), and 1,4-Dioxane (25 mg/mL). MTBE, EA, water and n-heptane could be used as anti-solvent due to the low solubility (<2 mg/mL) of TPA023B phosphate Form A in these solvents.

TABLE 24

| | Estimated solubility results | |
| --- | --- | --- |
| No. | Solvent | Solubility (mg/mL) |
| 1 | Methanol | 9.5 |
| 2 | Ethanol | 3 |
| 3 | IPA | 2.5 |
| 4 | EA | <2 |
| 5 | DCM | 2 |
| 6 | THF | 28 |
| 7 | ACN | <2 |
| 8 | MTBE | <1.5 |
| 9 | Acetone | 7 |
| 10 | Water | <2 |
| 11 | Heptane | <1 |
| 12 | DMF | 96 |
| 13 | DMSO | 93 |
| 14 | 1,4-Dioxane | 25 |
| 15 | 2-Me THF | 20 |
| 16 | | |

Example 35

Slurry and Stability Study of TPA023B Phosphate

Figure 43:
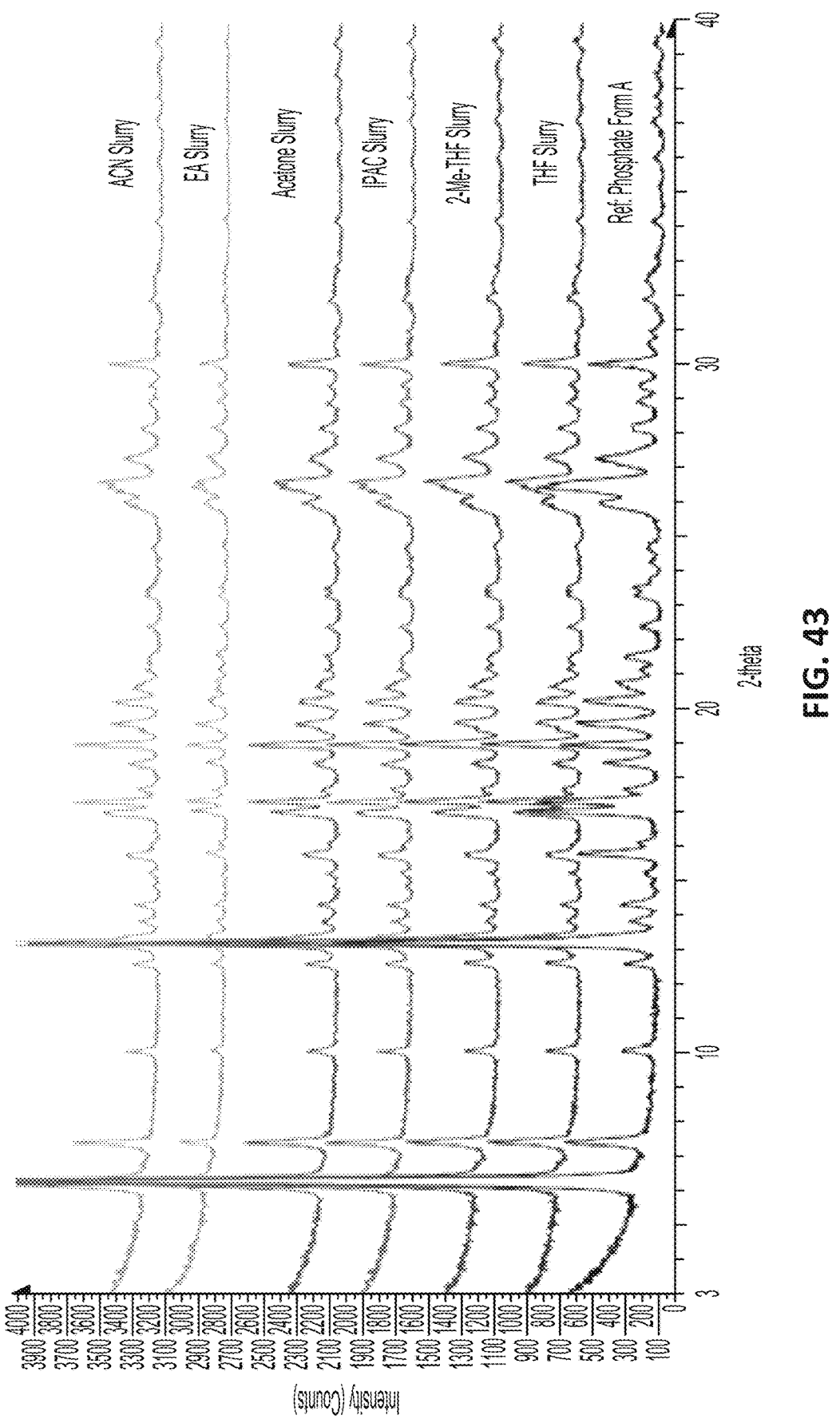
FIG. 43 illustrates the XRPD patterns of TPA023B Phosphate Form A slurried in single solvent
Figure 44:
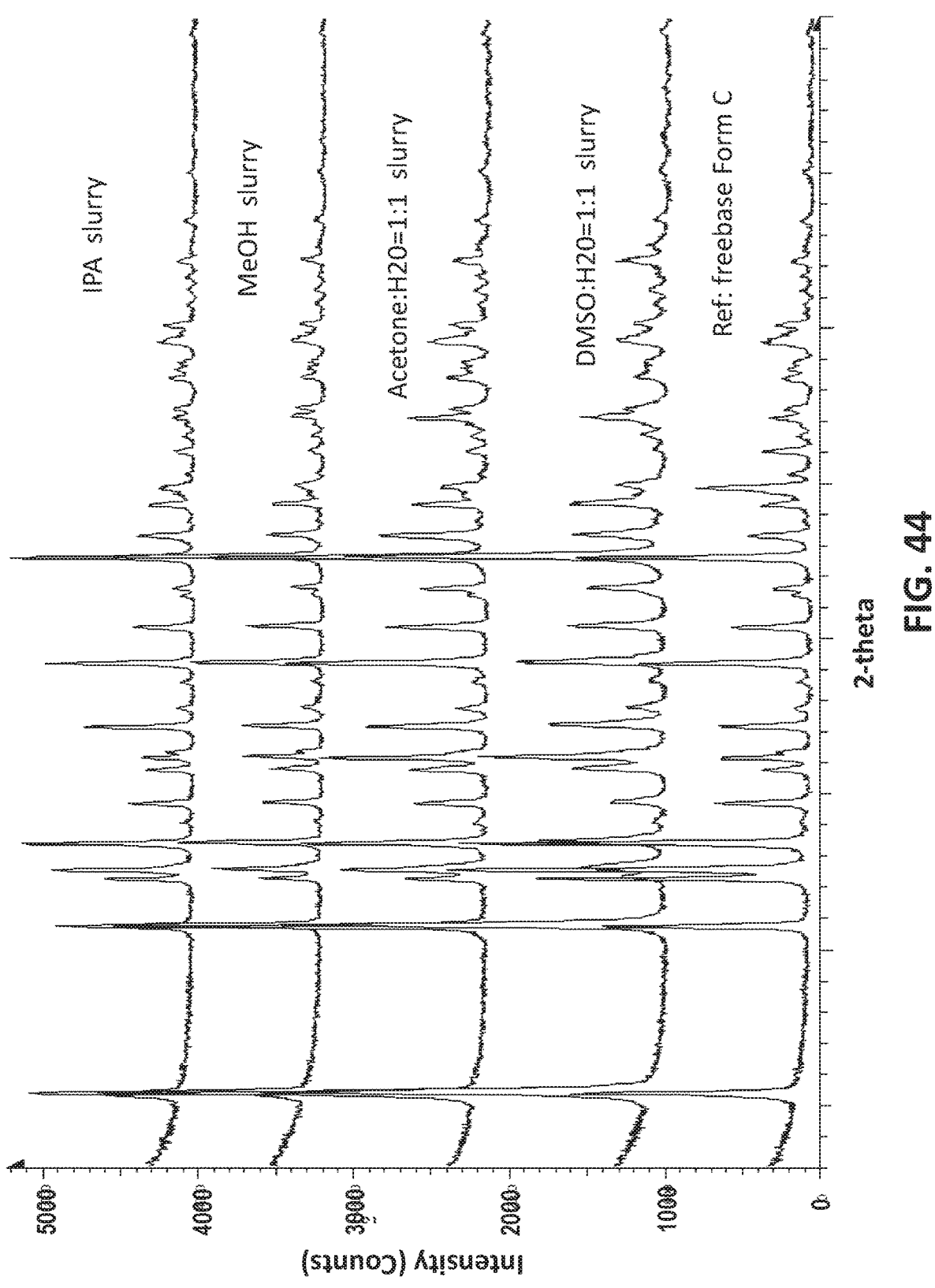
FIG. 44 illustrates the XRPD patterns of TPA023B Phosphate Form A converting to freebase form C
Figure 45:
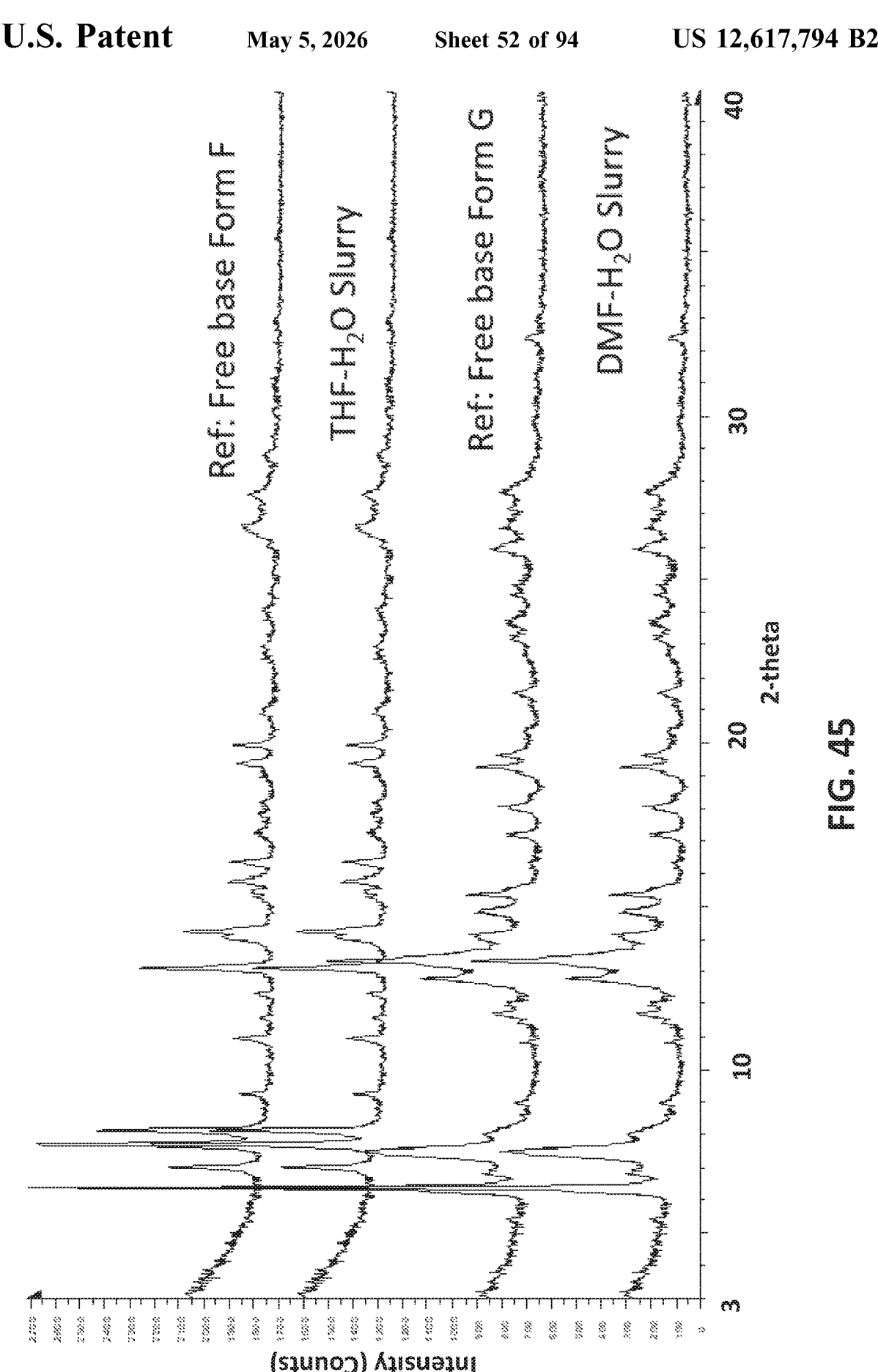
FIG. 45 illustrates the XRPD patterns of TPA023B Phosphate Form A converting to freebase forms F and G

TPA023B Phosphate Form A (100 mg) was slurried in 2 mL of various solvents (see FIGS. 43-45). In THF, 2-Me THF, IPAC, EA, acetone and ACN, Phosphate Form A remains unchanged at RT as shown in FIG. 43, suggesting it is physically stable in these solvents.

Figure 46A:
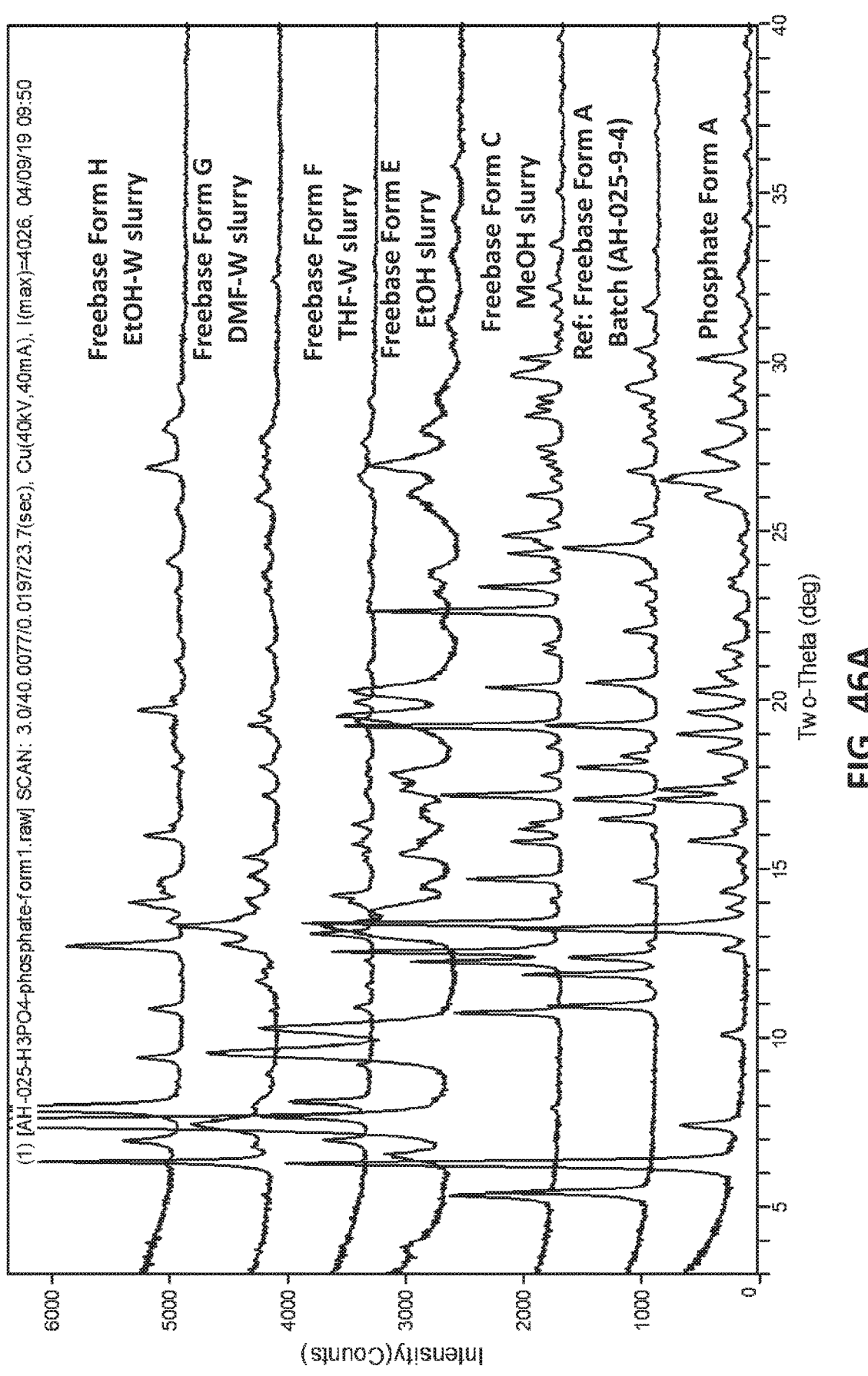
FIG. 46A and FIG. 46B illustrate the XRPD patterns of TPA023B freebase obtained by dissociation of TPA023B Phosphate (FIG. 46A); and the XRPD patterns of TPA023B freebase Form E, Form H and Pattern I (FIG. 46B)
Figure 46B:
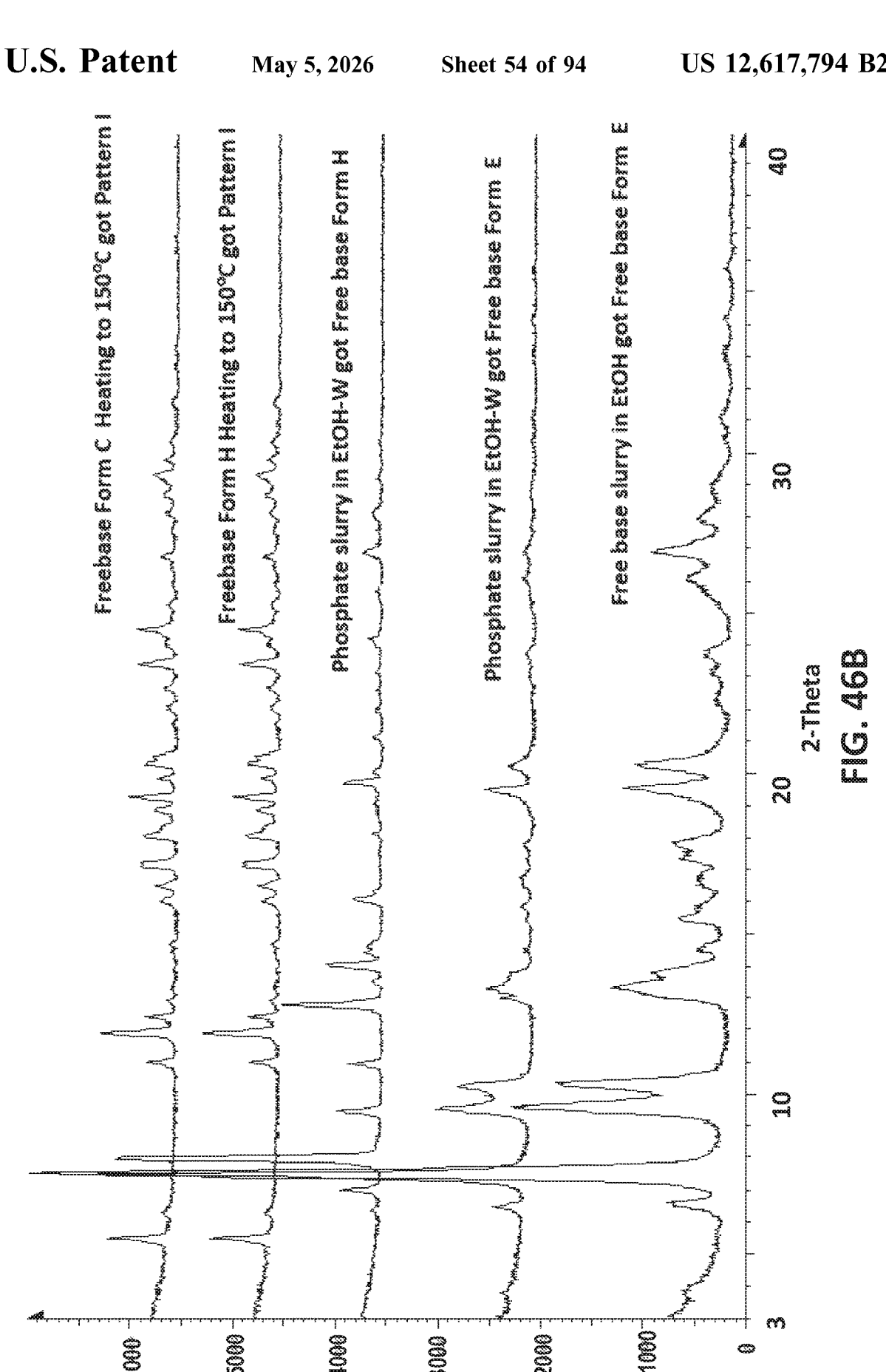

Slurry of Phosphate Form A in other solvents gave new XRPD patterns which were found to be freebase rather than salt. Five forms were obtained by dissociation of phosphate, which are TPA023B free base Forms C and Forms E-H as presented in Table 25. No P signal or $PO_4$; was detected by P-NMR or IC for Forms E-H. As slurry of phosphate in EtOH gave the same XRPD pattern (freebase Form C) as freebase in EtOH, phosphate was confirmed as dissociated into freebase in EtOH. A new pattern (Pattern I) was obtained by heating freebase Form C to 15° C., and the same applies to Form H. It was analyzed as a mixture of Form A and a new form (Form J). The XRPD patterns of freebase are shown in FIGS. 46A-46B. It was found that the presence of water or alcohols can lead to dissociation of phosphate into freebase.

TABLE 25

| | Freebase obtained by dissociation of phosphate |
| --- | --- |
| TPA023B Freebase Form | Experimental Details |
| Freebase Form E | 100 mg of phosphate was slurried in 2 mL EtOH at 50° C. for 3 days. The suspension was then filtered and dried at 50° C. overnight. |
| Freebase Form C | 100 mg of phosphate was slurried in 2 mL of MeOH, IPA, Acetone-W (1:1, v/v) or DMSO-W (1:1, v/v) at RT for 3 days. The suspension was then filtered and dried at 50° C. overnight. |
| Freebase Form F | 35 mg of phosphate was dissolved in 1 mL of THF at 50° C., followed by 0.5 mL of water. 0.5 mL of solvent was then removed by rotary evaporator, and the suspension was then stirred overnight and filtered. The solid obtained was dried at 50° C. overnight. |
| Freebase Form G | 100 mg of phosphate was added to 1 mL of DMF, followed by 1 mL of water, the suspension was stirred at 50° C. overnight and filtered. |
| Freebase Form H | 100 mg of phosphate was slurried in EtOH-W (2 mL, 1/1, v/v) at 50° C. for 3 days. The suspension was then filtered and the solid obtained was dried at 50° C. overnight. |
| Pattern I (Form A + Form J) | Heat freebase Form C or form H to 150° C. by DSC at 10° C./min |

Example 36

Stability Study of TPA023B Phosphate Form A

Figure 47:
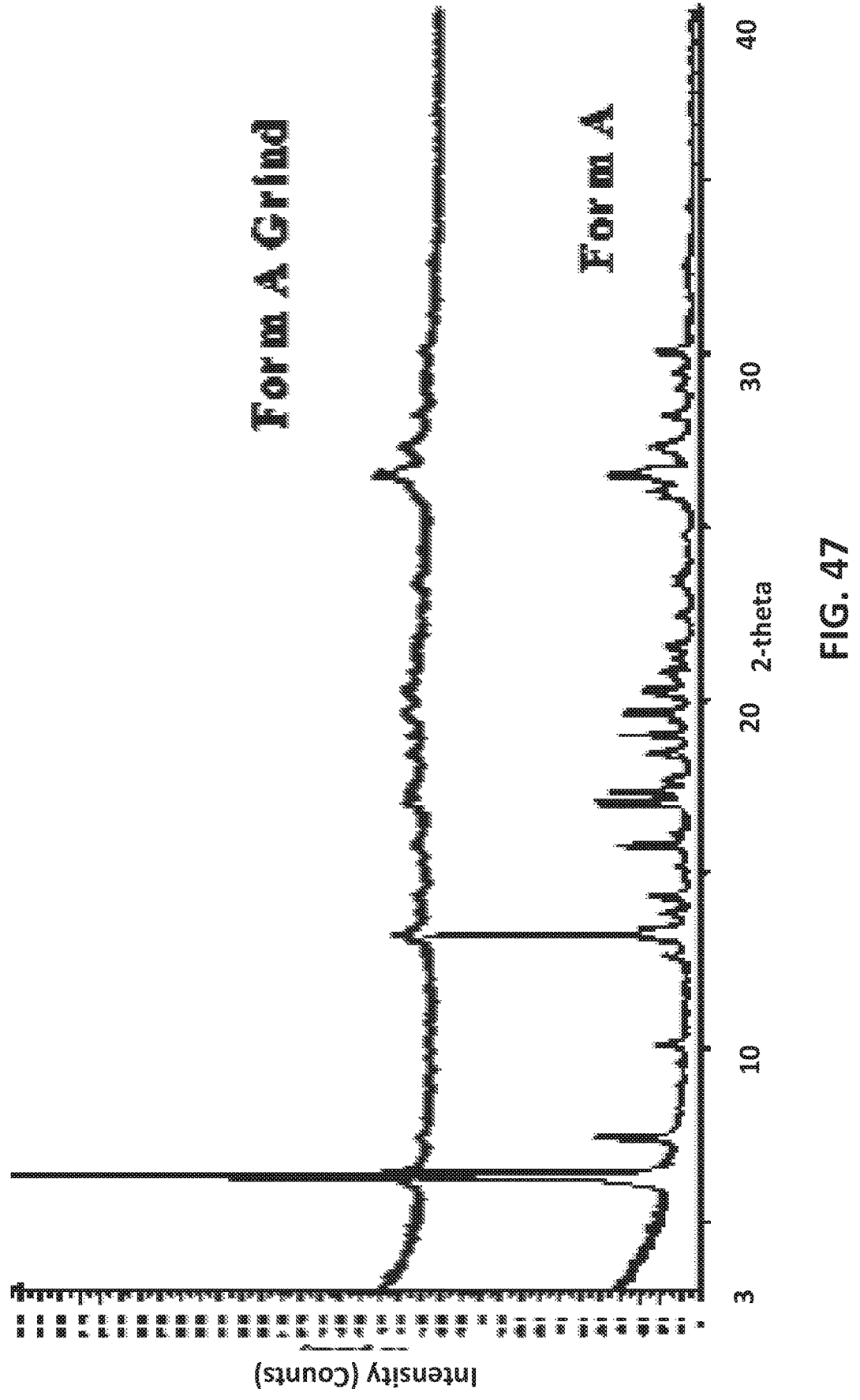
FIG. 47 illustrates the XRPD patterns of TPA023B Phosphate Form A before and after mechanical treatment

TPA023B Phosphate Form A was ground and analyzed by XRPD, as shown in FIG. 47. After grinding, the crystal form remained unchanged, but crystallinity decreased. Solid-state stability of Phosphate Form A was studied at 40° C./75% RH and 25° C./95% RH for up to two weeks. The crystal form remained unchanged (see FIG. 48).

Jet-milling study was performed for Phosphate Form A. The micronization was performed in a mini jet mill with the following conditions:

Instrument: Jet mill (Equipment number: PPD-OAJ-1)

Feeding speed: Manual addition according to the practical result.

Feeding pressure: 0.3-0.5 MPa

Milling One Pressure: 0.4-0.6 MPa

Milling Two Pressure: 0.4-0.6 MPa

The particle size of Phosphate Form A decreased after micronization. The D(0.1), D(0.5), and D(0.9) of Phosphate Form A before jet milling was 1.40 μm, 8.05 μm, and 27.90 μm, respectively. The D(0.1), D(0.5), and D(0.9) of Phosphate Form A after jet milling was 1.18 μm, 4.77 μm, and 10.80 μm, respectively. The TGA/DSC thermogram showed no significant change after the jet milling, e.g., the TGA/DSC thermogram after jet milling does not contain more peaks than the thermogram before the milling. The purity of the phosphate Form A did not change after the jet milling but the residual solvent and water content has decreased.

Example 37

Materials Used in Additional Salt Screening of TPA023B Free Base

Additional salt screenings were performed for TPA023B Free Base, the details and results of which are provided in Examples 37-48. As shown in Table 26-1, one batch of TPA023B Free Base was used for the screening. The acids and solvents used in the salt screening are provided in Tables 26-2 and 26-3, respectively.

TABLE 26-1

| Information of TPA023B Free Base | | |
| --- | --- | --- |
| Compound | Labelled Purity (HPLC) | XRD |
| TPA023B Free Base | 97.8% | Crystalline |

TABLE 26-2

| Acids for screening | |
| --- | --- |
| HCl | Methansulfonic acid |
| HBr | Benzenesulfonic acid |
| $H_2SO_4$ | Maleic acid |
| p-toluenesulfonic acid | Acetic acid |
| $H_3PO_4$ | N/A |

TABLE 26-3

| Solvents for screening | |
| --- | --- |
| 1,4-dioxane | EtOH (Ethanol) |
| IPA (Isopropanol) | Isopropyl ether |
| W (Water) | ACN (Acetonitrile) |
| Acetone | 2-butanone |
| Toluene | EA/EtOAc (Ethyl acetate) |
| MTBE (Methyl tert-butyl ether) | THF (Tetrahydrofuran) |
| MeOH (Methanol) | IPAc (Isopropyl acetate) |

Example 38

Additional Salt Screening of TPA023B Free Base

Additional salt screenings were performed for TPA023B Free Base, the details and results of which are provided in Examples 37-48.

Salt screening of TPA023B Free Base was conducted with 8 common acids in 96-well plates. Crystalline samples were obtained for three acids, HCl, $H_2SO_4$ and benzenesulfonic acid. TPA023B sulfate showed good crystallinity, low solvent residual, and light hygroscopicity. Physical and chemical stability of TPA023B free base, TPA023B chloride, TPA023B sulfate and TPA023B besylate were evaluated. The results showed that all samples were chemically stable at 60° C. and 40° C./75% RH for 7 days. TPA023B free base, TPA023B chloride and TPA023B sulfate were physically stable throughout the stability test (i.e., their respective crystalline forms did not change), while TPA023B besylate showed three extra peaks on XPRD pattern after kept at 40° C./75% RH for 7 days.

Salt Screening Experiments
38.1 Salt Preparation in 96-Well Plate

Acids (appropriate amount) were dissolved and diluted with MeOH (10 mL) to make 0.1 M solution. TPA023B Free Base (about 362 mg) was dissolved and diluted with THF (12 mL) to make 30 mg/mL solution (0.08 M).

The TPA023B Free Base solution in THF was distributed into 96-well plates. TPA023B Free Base solution (100 µL) and a single acid solution (80 µL, or 40 µL for $H_2SO_4$ solution) were added into each well. The resulting solution in each well was evaporated to dryness, and solvent (200 µL) was added into each well. The wells were covered with parafilm containing one pinhole over the opening. The solvents were allowed to evaporate under ambient conditions. One sample of each row was characterized by $^1$H NMR to confirm the formation of salts. Solid samples obtained in the plates were characterized by XRPD to determine whether they were crystalline. Acids and solvents used in the experiment are listed in Table 26-2 and 26-3.
38.2 Salt Preparation Based on the results of 96-well plate screening described above in 38.1, salt formation was repeated for solid samples on about 30-40 mg scale according to the above procedures.

An appropriate amount of TPA023B Free Base was dissolved in each solvent, and an acid solution (1 eq.) was added to form the salt. If no precipitation occurred, the reaction solution was concentrated or anti-solvent was added to induce precipitation.
38.3 Solid Stability of Free Base and Salts Samples of TPA023B Free Base, TPA023B chloride, TPA023B besylate, and TPA023B sulfate were mounted on stability at 60° C. and 40° C./75% RH for up to 7 days. At day-0, day-3 and day-7, the samples were dissolved in diluent to prepare solutions at 0.5 mg/mL for HPLC analysis. Solid samples were analyzed by XRPD to determine the crystal form.
Analysis Method and Conditions
38.4 $^1$H NMR

$^1$H NMR was performed using Bruker Advance 300 equipped with automated sampler (B-ACS 120).
38.5 X-Ray Powder Diffraction (XRPD)

Solid samples were examined using D8 ADVANCE X-ray diffractometer (Bruker). The diffractometer was equipped with LynxEye detector. In XRPD analysis, samples were scanned from 3 to 40° 2θ at a step of 0.02° 2θ. The tube voltage and current were 40 KV and 40 mA, respectively. The XRPD parameters are provided in Table 26-4.

TABLE 26-4

| XRPD Parameters | |
| --- | --- |
| Parameters | Settings/Values |
| X-Ray wavelength | Cu: K- Alpha ($\lambda$ = 1.54179 Å) |
| X-Ray tube setting | Voltage: 40 kV; Current: 40 mA |
| Scan scope | 3 to 40 deg |
| Sample rotation speed | 30 rpm |
| Scanning rate | 4 deg./min |

38.6 Polarized Light Microscope (PLM)

PLM analysis was conducted with a polarized light microscope ECLIPSE LV100POL (Nikon, JPN).
38.7 Thermogravimetric Analysis (TGA)

TGA was carried out on Discovery TGA 55 (TA Instruments, US). The sample was placed in an open tarred aluminum pan, automatically weighed, and inserted into the TGA furnace. The sample was heated at 10° C./min to the final temperature.
38.8 Differential Scanning Calorimeter (DSC)

DSC analysis was conducted with Discovery DSC 250 (TA Instruments, US). A weighted sample was placed into a DSC pinhole pan, and the weight was accurately recorded. The sample was heated at 10° C./min to the final temperature.
38.9 Dynamic Vapor Sorption (DVS)

DVS was determined using IGA Sorp (Hiden Isochema, UK). The sample was tested at a targeted RH of 0 to 90% full cycle in step mode. The analysis was performed in 10% RH increments.
38.10 HPLC Method HPLC method for solubility and stability testing was listed in Table 26-5.

TABLE 26-5

| HPLC Method | |
| --- | --- |
| Instrument | Agilent 1260 series |
| Column | XBrideg C18, 3.5 μm, 4.6*150 mm |
| Injection Volume | 3 μL |
| Wavelength | 266 nm |
| Injection Conc. | 0.5 mg/mL |
| Mobile Phase | A: 0.1% TFA in H₂O; B: ACN |
| T/B % | 0/20, 15/90, 15.1/20, 20/20 |
| Post time | 3 min |
| Temperature | 40° C. |
| Diluent | ACN:H₂O = 1:1 |

Example 39

Characterization of Starting Material (the TPA023B Free Base)

Figure 49:
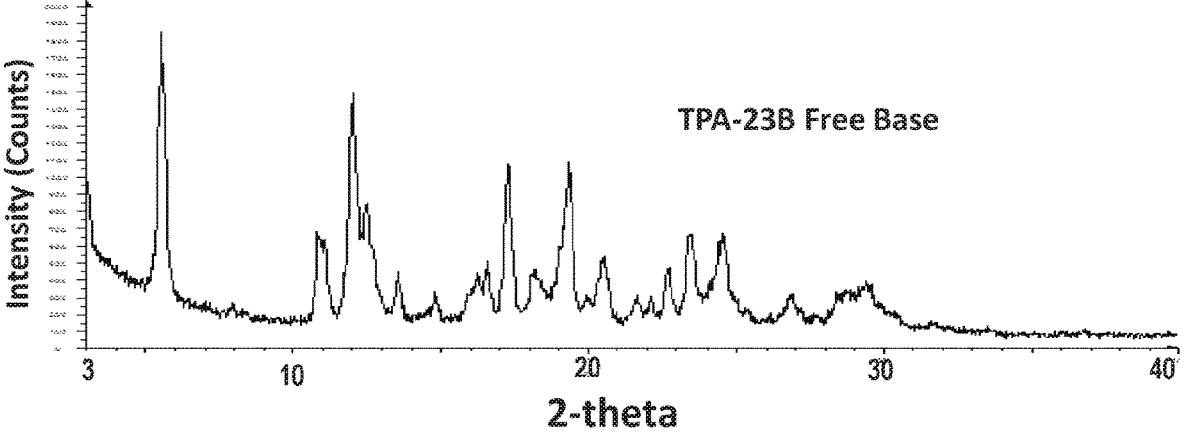
FIG. 49 illustrates an XRPD pattern of the TPA023B Free Base starting material
Figure 50:
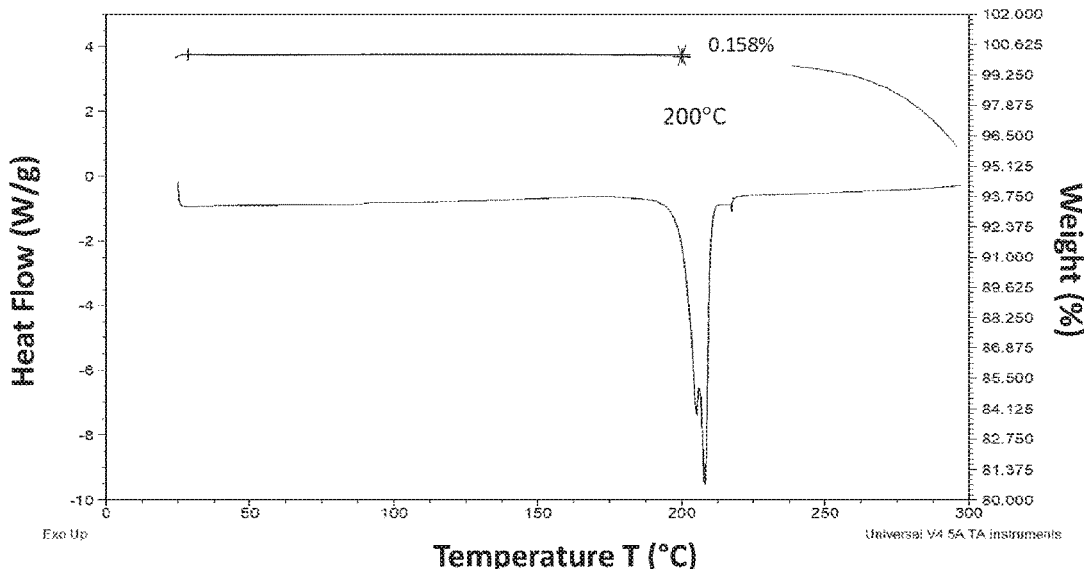
FIG. 50 illustrates a DSC/TGA diagram of the TPA023B Free Base starting material
Figure 49:
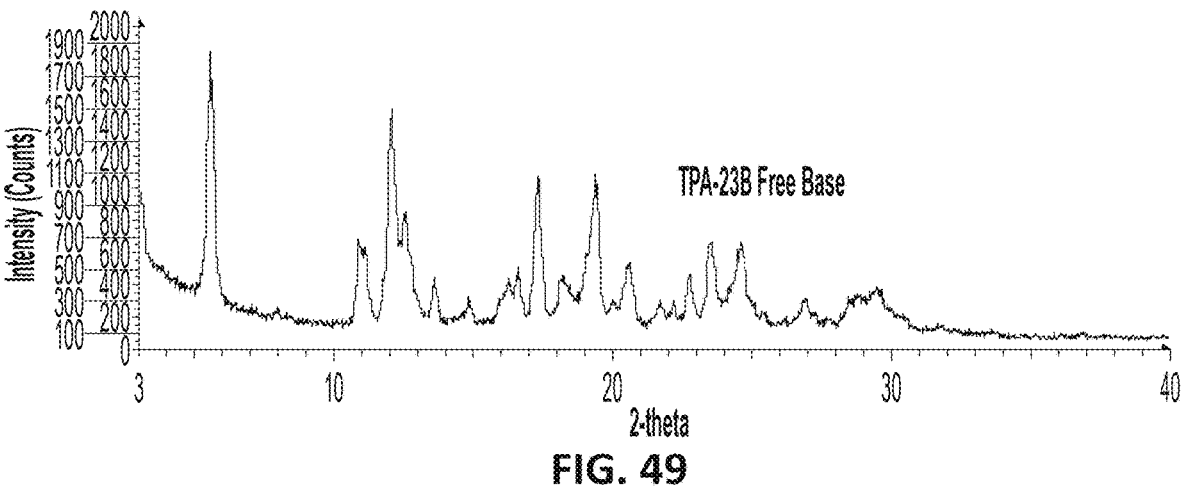
Figure 50:
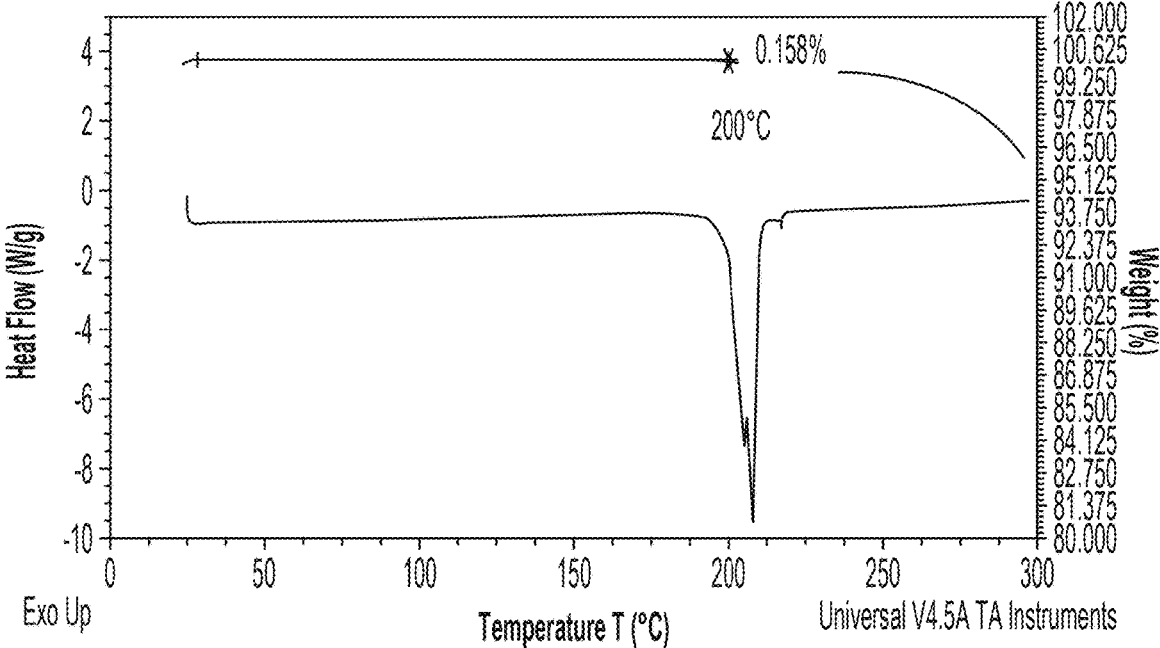

One batch of TPA023B Free base was used in examples 38-48. The characterization results are shown in FIG. 49 and FIG. 50. The XRPD pattern is shown on FIG. 49; the PLM image shows irregular crystals; the TGA profile shows 1.06% weight loss to 200° C.; the DSC thermogram shows two overlapping endothermic peaks@200-210° C.; and the purity of the free base is 97.8%. This batch of TPA023B is likely a mixture of free base Form A and free base Form C.

Example 40

Results of Salt Screening in 96-Well Plates

According to the procedure described in Example 38.1, 1 eq. or 0.5 eq. (for H₂SO₄ acid) of 0.1 M acid along with free base solution was added into a well on a 96-well plate. The solvents used are shown in Table 26-3. After drying, some solids appeared in the 96-well plate. One sample in each row of the 96-well plate was analyzed by ¹H NMR, and some solid samples were tested by PLM and XRPD.

Figure 51:
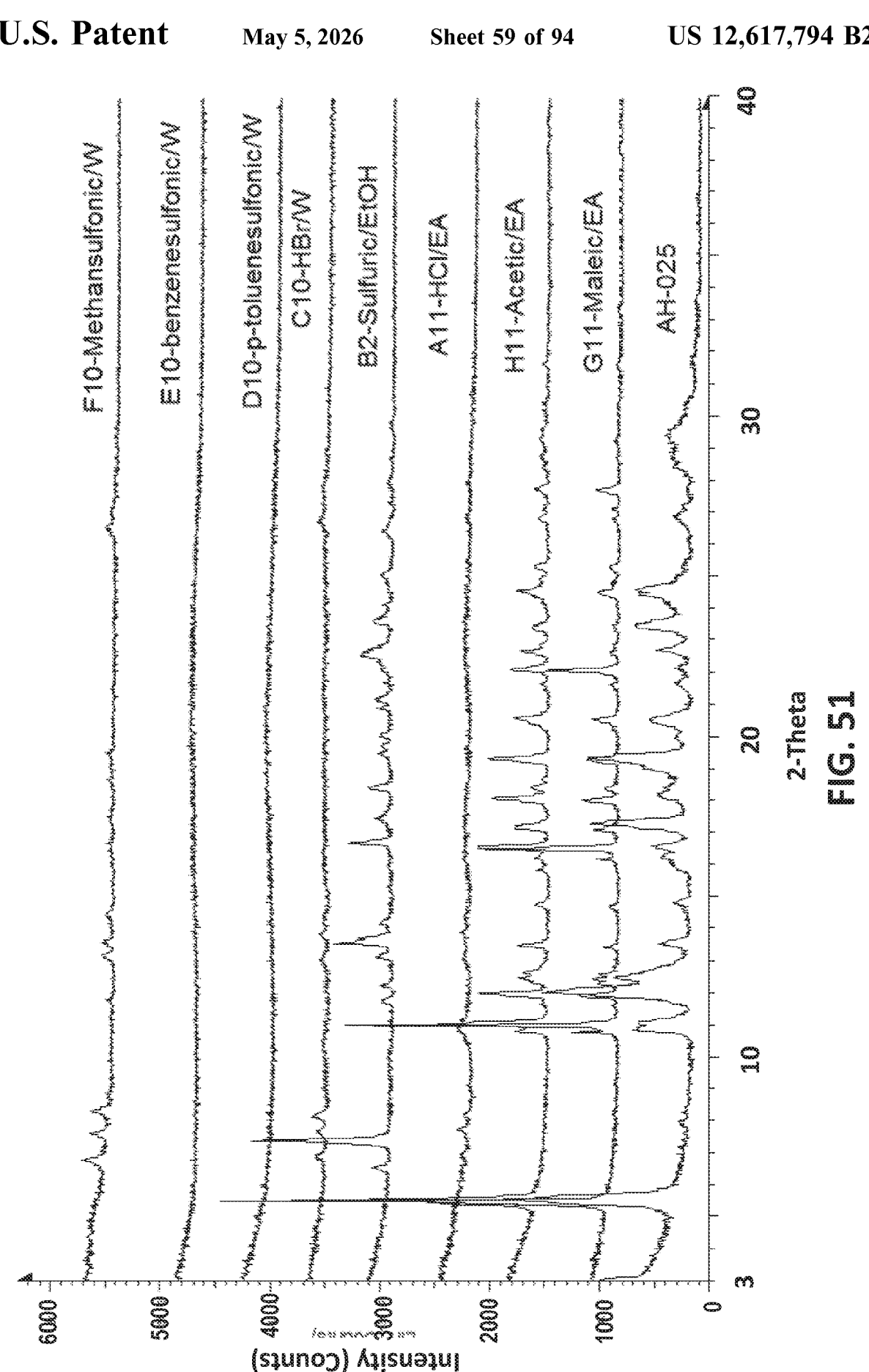
FIG. 51 illustrates the XRPD patterns of solid samples produced from reaction with acids in 96-well plate

The ¹H NMR spectra showed that, compared to the TPA023B free base, there were chemical shifts of the protons on the aromatic rings in the solid samples produced from reaction with HCl, H₂SO₄, HBr, methansulfonic acid, p-toluenesulfonic acid, or benzenesulfonic acid. The sulfate salt sample was in crystalline form. The chloride and mesylate salt samples were nearly amorphous. The crystal form of maleate and acetate salt samples were consistent with the TPA023B Free Base starting material. The other samples were amorphous. The XRPD results are shown in FIG. 51.

Example 41

Preparation of TPA023B Chloride

As shown in Table 27, seven experiments were conducted to prepare TPA023B chloride. The amount of HCl acid used in all of the seven experiments is 1 eq. compared to the TPA023B free base. The XRPD patterns, NMR spectra, DSC/TGA thermograms, and DVS profiles of the samples are illustrated in FIGS. 52A to 52F.

TABLE 27

| | Preparation of TPA023B chloride | |
| --- | --- | --- |
| Lot | Experimental details | Results |
| 1 | TPA023B free base (about 30 mg dissolved in THF) was reacted with 1 eq. of HCl at 50° C. Acetone was added as anti-solvent. Kept stirring at RT overnight. (THF/Acetone 1/1.5) | No solid |
| 2 | ~30 mg of free base was dissolved in THF and reacted with 1 eq. of HCl at 50° C. Kept stirring at RT overnight. | Nearly amorphous |
| 3 | ~30 mg of free base was dissolved in THF and reacted with 1 eq. of HCl at 50° C. 1,4-dioxane was added as anti-solvent. Kept stirring at RT overnight. (THF/Dioxane 2/1) | No solid |
| 4 | TPA023B free base (30 mg) was dissolved in 600 μL THF and reacted with 1 eq. of HCl acid (6.39 μL) diluted with 200 μL EtOH at 50° C. 1.6 mL of 1,4-dioxane was added as anti-solvent. The resultant mixture was stirred at RT overnight. (RT: 20° C.; humidity: 10% RH). | XRPD: Chloride Form B. NMR: 1,4-dioxane residue. TGA: 8.6%/150° C., DSC: T_endo: 143.62, 161.66, 193.38° C. DVS: 0-1.4691% absorption between 0% to 90% RH. No XRPD change after DVS. |
| 5 | TPA023B free base (200 mg) was dissolved in 3.5 mL THF and reacted with 1 eq. HCl acid (42.4 μL) diluted with 100 μL EtOH at 50° C. 3.6 mL of acetone was added as anti-solvent. The resultant mixture was stirred at RT overnight. (RT: 19° C.; humidity: 12% RH). | XRPD: Chloride Form C. NMR: THF and acetone residue. TGA: 4.6%/150° C. DSC: T_endo: 178.8° C. |
| 6 | Slurry 30 mg hydrochloride (Lot# 5) in EA at 50° C. overnight. | XRPD: Chloride Form C TGA: 6.0%/160° C., DSC: T_endo: 182.7 and 190.1° C. |
| 7 | Slurry 30 mg hydrochloride (Lot# 5) in heptane at 50° C. overnight. | XRPD: Chloride Form C TGA: 7.5%/160° C. DSC: T_endo: 185.0 and 199.8° C. |

Figure 52A:
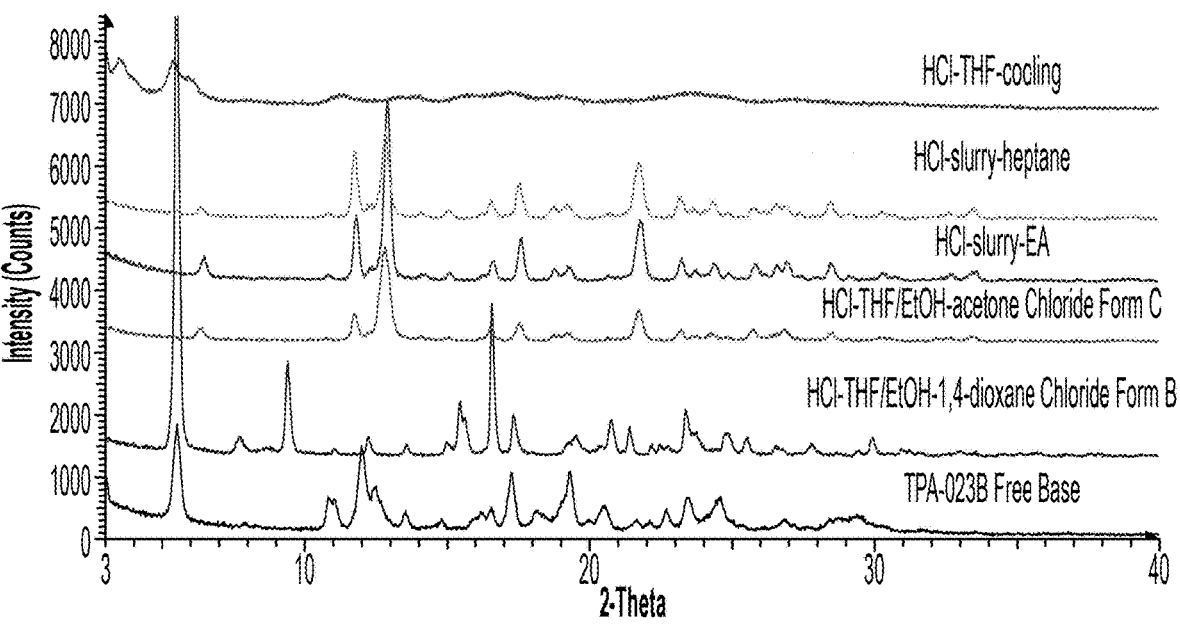
FIG. 52A-FIG. 52I illustrate the XRPD patterns of TPA023B Chloride (FIG. 52A), the XRPD patterns of TPA023B Chloride after performance of DVS testing (FIG. 52B), the NMR spectra of TPA023B Chloride prepared in THF/EtOH-acetone (FIG. 52C), the NMR spectra of the TPA023B Chloride sample prepared in THF/EtOH-1, 4-dioxane (FIG. 52D), the DSC/TGA thermogram of TPA023B Chloride Form B (FIG. 52E), the DSC/TGA thermogram of TPA023B Chloride Form C (FIG. 52F), the DSC/TGA thermogram of TPA023B Chloride Form C after being slurried in EA (FIG. 52G), the DSC/TGA thermogram of TPA023B Chloride Form C after being slurried in heptane (FIG. 52H), and the DVS profiles of TPA023B Chloride.
Figure 52B:
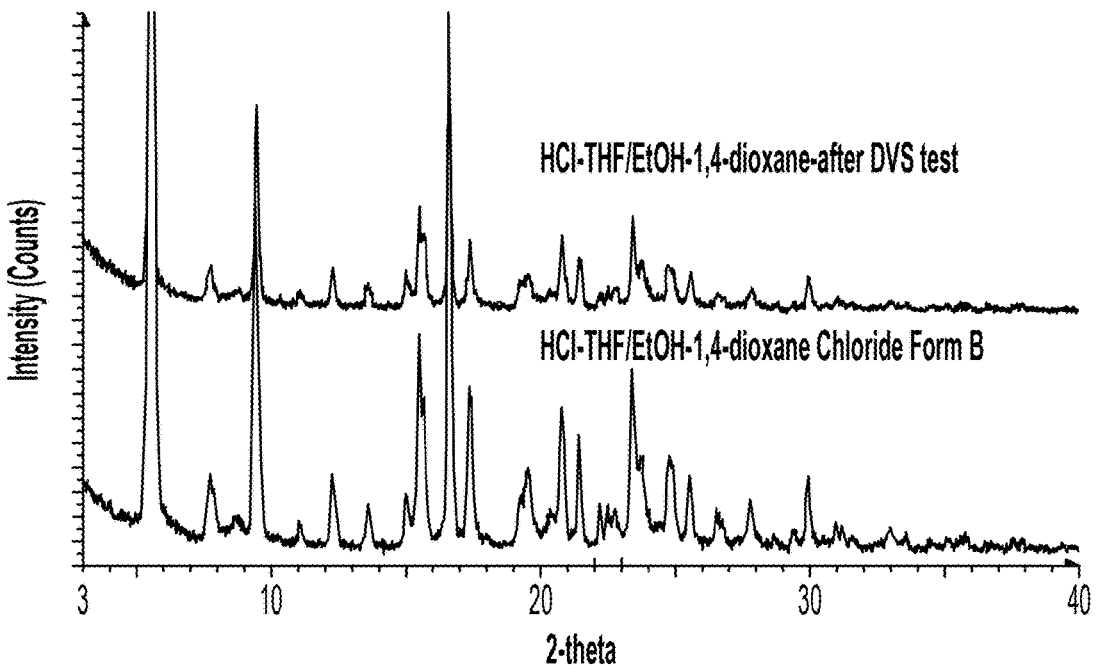
Figure 52C:
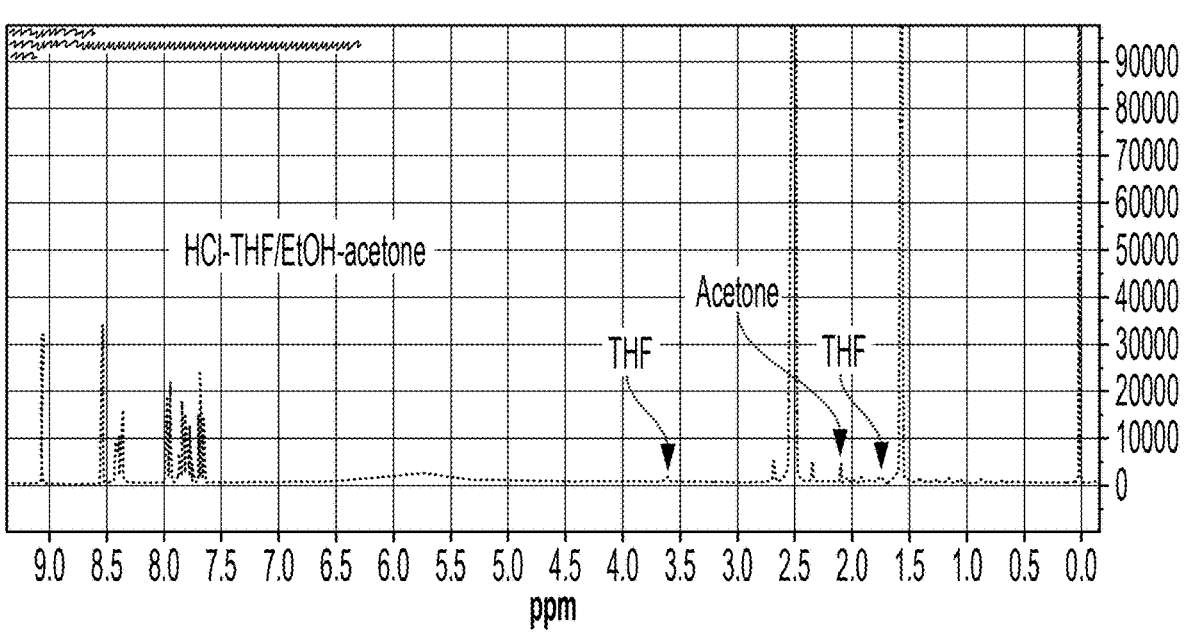
Figure 52D:
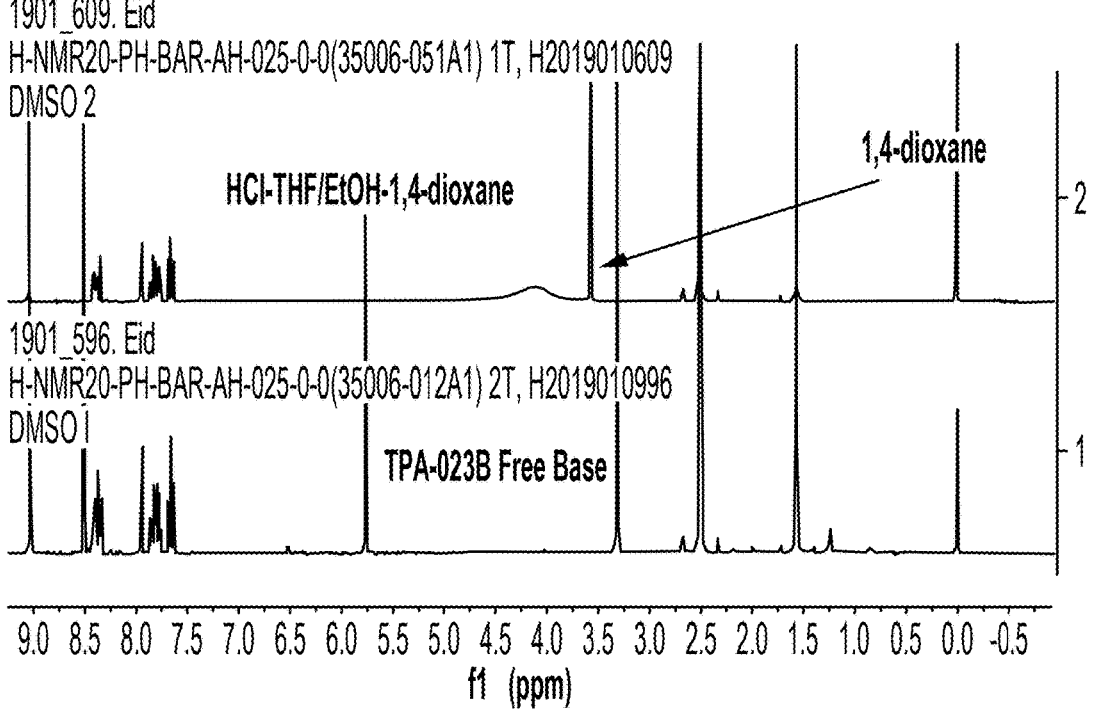
Figure 52E:
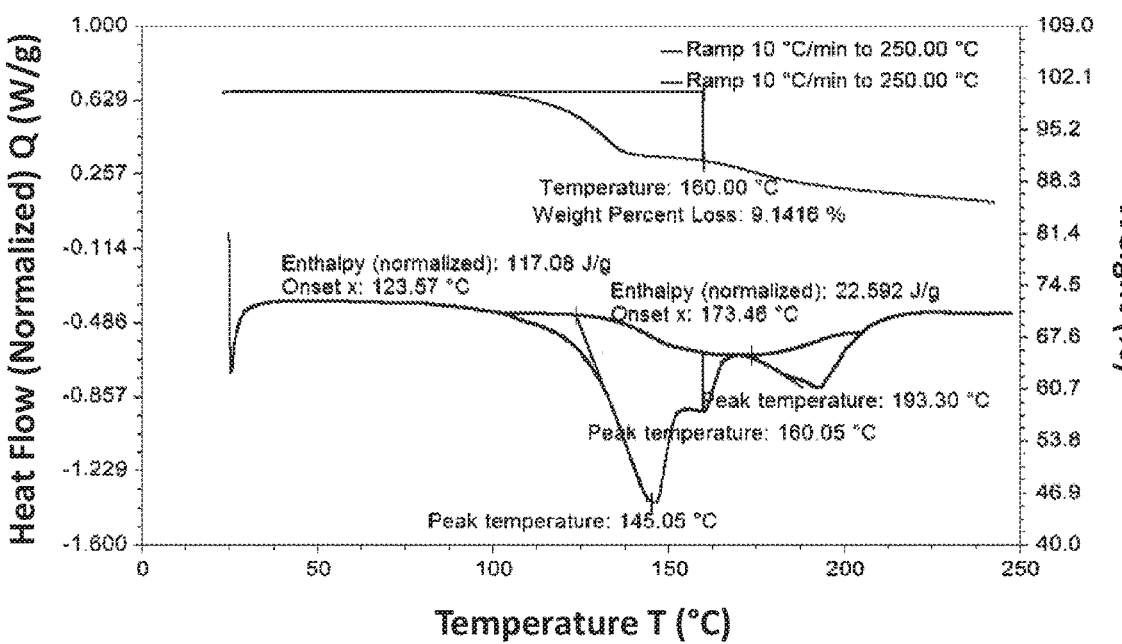

As illustrated in the XRPD patterns of FIG. 52A, the TPA023B chloride sample prepared in THF/EtOH-1, 4-dioxane exhibited XRPD pattern B (i.e., the sample is designated as TPA023B Chloride Form B), and the TPA023B chloride sample prepared in THF/EtOH-acetone exhibited XRPD pattern C (i.e., the sample is designated as TPA023B Chloride Form C).

NMR results (FIG. 52C-FIG. 52D) showed that TPA023B Chloride Form B and Form C had solvent residue. TGA (FIG. 52E-FIG. 52F) results showed that TPA023B Chloride Form B and Chloride Form C had about 8.6% and 4.6% weight loss prior to 15° C., respectively (DSC: before melting point). The weight loss below melting point indicated that the two crystal forms of TPA023B Chloride may be solvate. After being slurried in EA or heptane, TPA023B Chloride Form C remained unchanged (see FIG. 52G and FIG. 52H).

Example 42

Preparation of TPA023B Sulfate

As shown in Table 28, five experiments were conducted to prepare TPA023B sulfate. The sulfate salts were prepared with H₂SO₄ and TPA023B free base (1:1 molar ratio). The XRPD patterns, DSC/TGS thermograms, and DVS profiles of the samples are illustrated in FIGS. 53A to 53D.

TABLE 28

Preparation of TPA023B Sulfate

| Lot | Experimental details | Results |
|---|---|---|
| 1 | TPA023B free base (30 mg) was dissolved in 600 µL THF and reacted with 1 eq. of H₂SO₄ acid (2.08 µL) diluted at 50° C. 1.8 mL of acetone was added as anti-solvent. The resultant mixture was stirred at RT for 48 hours. (RT: 19° C.; humidity: 12% RH). (THF/Acetone, 1/3, v/v) | XRPD: Form A |
| 2 | TPA023B free base (30 mg) was dissolved in 600 µL THF and reacted with 1 eq. of H₂SO₄ acid (2.08 µL) diluted at 50° C. 300 µL of EA was added as anti-solvent. Kept stirring at RT overnight. (RT: 19° C.; humidity: 12% RH). (THF/EA, 2/1, v/v) | XRPD: Form A NMR: THF and EA residue. TGA: 0.18%/160° C. DSC: One endothermic peak at 192° C. |
| 3 | ~30 mg of free base was dissolved in THF and reacted with 1 eq. H₂SO₄ at 50° C. ACN was added as anti-solvent. Kept stirring at RT overnight. (THF/ACN, 1/3, v/v) | No solid |
| 4 | TPA023B free base (200 mg) was dissolved in 3.5 mL THF and reacted with 1 eq. of H₂SO₄ acid (13.87 µL) diluted with100 µL EtOH at 50° C. 3.6 mL of EA was added as anti-solvent. Kept stirring at RT for 2 hours. (RT: 19° C.; humidity: 12% RH). [(THF/EtOH)/EA, 1/1, v/v] | XRPD: Form A NMR: No residue. DVS: 0-1.206% moisture between 0% to 90% RH. No XRPD change after DVS test. |

XRPD results (FIG. 53A) showed that TPA023B Sulfate form A was produced in THF-acetone, THF-EA, and THF/EtOH-EA. NMR results showed that the TPA023B Sulfate form A prepared in THF-EA had THF and EA residue and form A prepared in THF/EtOH-EA had no residue. It was indicated that THF/EtOH was a good solvent for crystallization. TGA result (FIG. 53C) showed that form A had little weight loss prior to 150° C. DSC result (FIG. 53C) showed that form A had one endothermic peak at 192.27° C. It was indicated that form A can be anhydrate.

Example 43

Preparation of TPA023B Bromide

Figure 54:
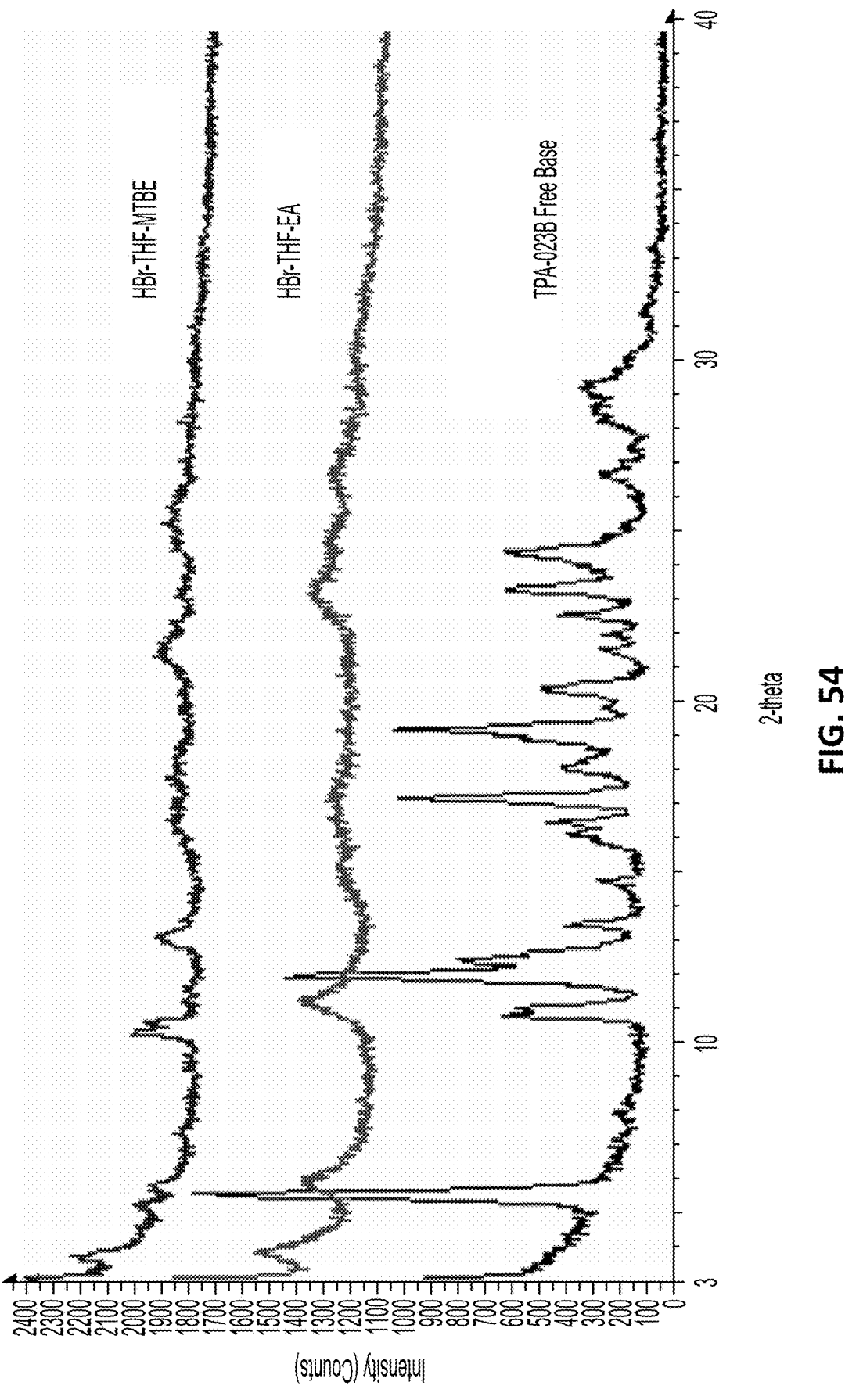
FIG. 54 illustrates the XRPD patterns of TPA023B Bromide with a free base reference

As shown in Table 29, three experiments were conducted to prepare TPA023B bromide. Salts were prepared with 1 eq. HBr to TPA023B free base. The XRPD patterns of the samples are illustrated in FIG. 54. TPA023B bromide salts in crystalline forms were not observed.

TABLE 29

Preparation of TPA023B Bromide

| Lot | Experimental details | Results |
|---|---|---|
| 1 | ~30 mg of free base was dissolved in THF and reacted with 1 eq. HBr at 50° C. Acetone was added as anti-solvent. Kept stirring at RT overnight. (THF/Acetone, 1/3, v/v) | No solid |
| 2 | TPA023B free base (30 mg) was dissolved in 600 µL THF and reacted with 1 eq. HBr acid (11.2 µL) at 50° C. 600 µL of MTBE was added as anti-solvent. The resultant mixture was stirred, at RT overnight. (RT: 20° C.; humidity: 10% RH). (THF/MTBE, 1/1, v/v) | Nearly amorphous |

TABLE 29-continued

Preparation of TPA023B Bromide

| Lot | Experimental details | Results |
|---|---|---|
| 3 | TPA023B free base (30 mg) was dissolved in 600 µL THF and reacted with 1 eq. HBr acid (11.2 µL) at 50° C. 1.8 mL of EA was added as anti-solvent. The resultant mixture was stirred at RT overnight. (RT: 20° C.; humidity: 10% RH). (THF/EA, 1/3, v/v) | Nearly amorphous |

Example 44

Preparation of TPA023B Tosylate

Figure 55:
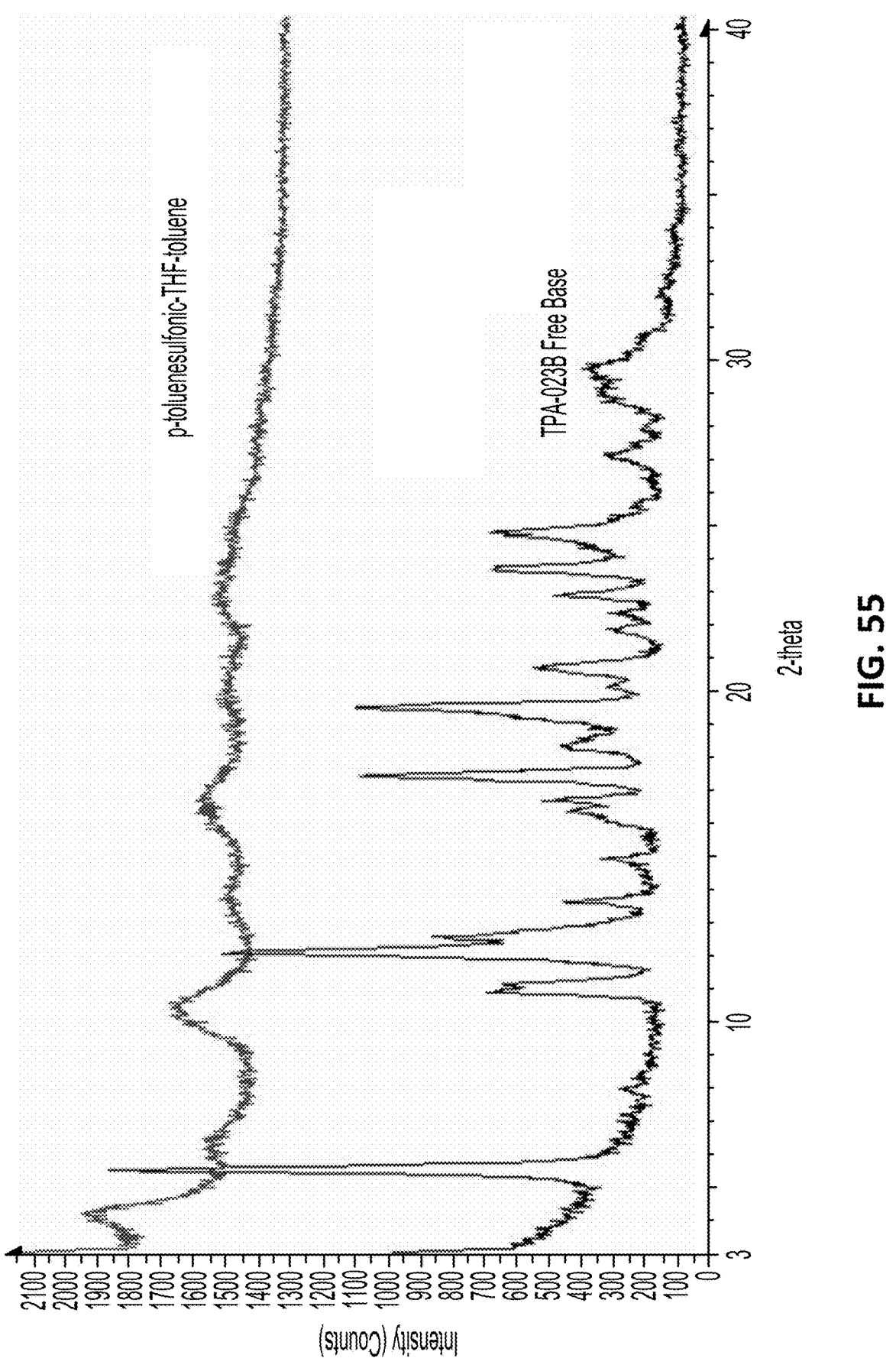
FIG. 55 illustrates an XRPD pattern of TPA023B Tosylate with a free base reference

As shown in Table 30, five experiments were conducted to prepare TPA023B tosylate. The tosylate salts were prepared with 1 eq. p-toluenesulfonic acid to TPA023B free base. The XRPD patterns of the samples are illustrated in FIG. 55. TPA023B tosylate salts in crystalline forms were not observed.

TABLE 30

Preparation of TPA023B Tosylate

| Lot | Experimental details | Results |
|---|---|---|
| 1 | ~30 mg of free base was dissolved in THF and reacted with 1 eq. toluenesulfonic at 50° C. Acetone was added as anti-solvent. Kept stirring at RT overnight. (THF/Acetone, 1/3, v/v) | No solid |
| 2 | TPA023B free base (30 mg) was dissolved in 600 µL THF and reacted with 1 eq. toluenesulfonic acid (13.2 mg) at 50° C. 900 µL of toluene was added as anti-solvent. The resultant mixture was stirred at RT overnight. (RT: 20° C.; humidity: 10% RH). (THF/toluene, 1/1.5, v/v) | Nearly amorphous |
| 3 | TPA023B free base (30 mg) was dissolved in 600 µL THF and reacted with 1 eq. toluenesulfonic acid (13.2 mg) at 50° C. 1.8 mL of IPAc was added as anti-solvent. The resultant mixture was stirred at RT overnight. (RT: 20° C.; humidity: 10% RH). (THF/IPAc, 1/3, v/v) | No birefringence |
| 4 | TPA023B free base (30 mg) was dissolved in 600 µL THF and reacted with 1 eq. toluenesulfonic acid (13.2 mg) at 50° C. 1.8 mL of MTBE was added as anti-solvent. The resultant mixture was stirred at RT overnight. (RT: 20° C.; humidity: 10% RH). (THF/MTBE, 1/3, v/v) | No birefringence |
| 5 | TPA023B free base (30 mg) was dissolved in THF and reacted with 1 eq. toluenesulfonic at 50° C. ACN was added as anti-solvent. The resultant mixture was stirred at RT overnight. (THF/ACN, 1/3, v/v) | No solid |

Example 45

Preparation of TPA023B Mesylate

Figure 56:
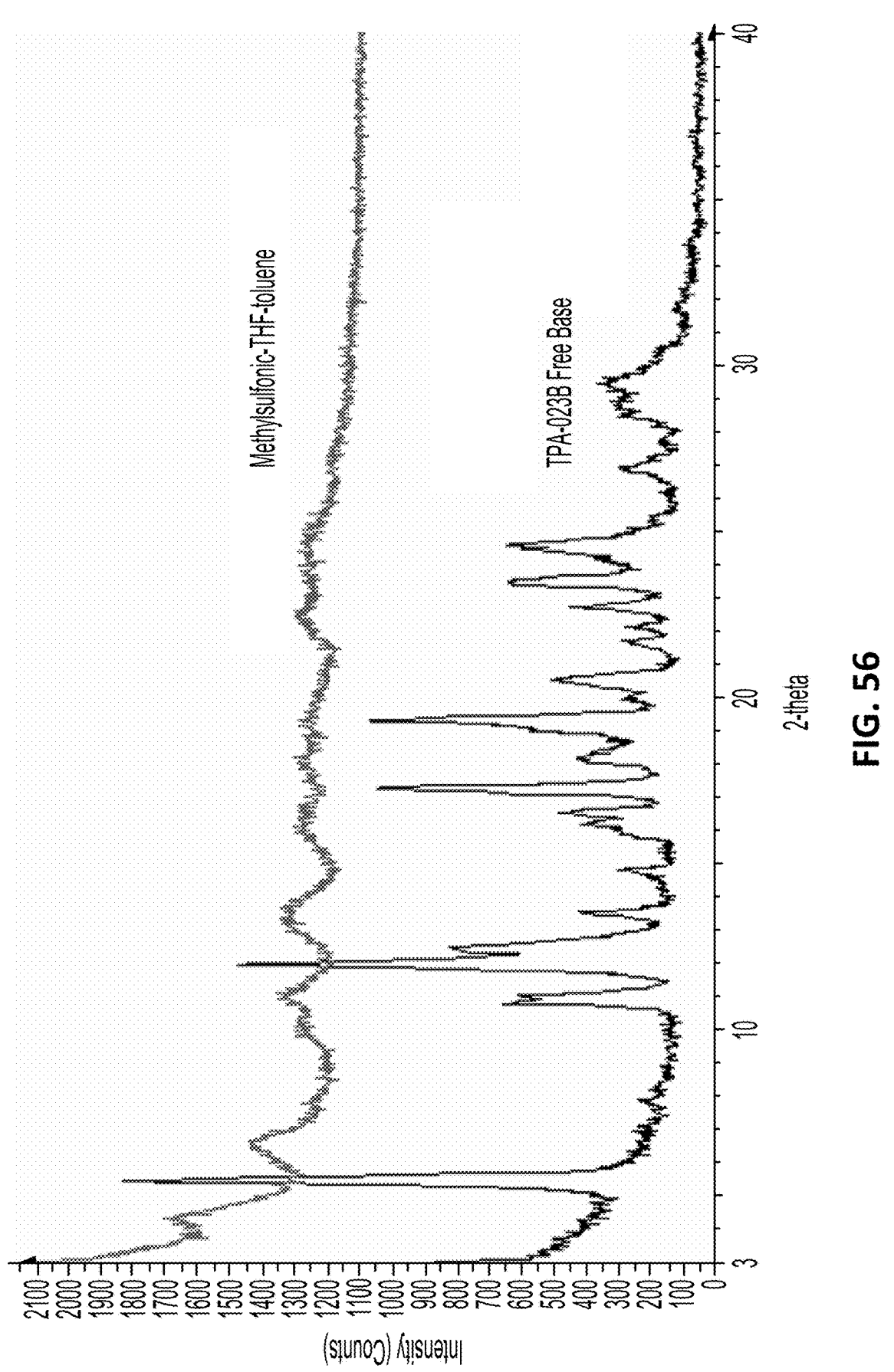
FIG. 56 illustrates an XRPD pattern of TPA023B Mesylate with a free base reference

As shown in Table 31, two experiments were conducted to prepare TPA023B mesylate. The mesylate salts were prepared with 1 eq. methylsulfonic acid to TPA023B free base. The XRPD patterns of the samples are illustrated in FIG. 56. TPA023B mesylate salts in crystalline forms were not observed.

TABLE 31

| | Preparation of TPA023B Mesylate | |
|---|---|---|
| Lot | Experimental details | Results |
| 1 | ~30 mg of free base was dissolved in THF and reacted with 1 eq. methylsulfonic at 50° C. Acetone was added as anti-solvent. Kept stirring at RT overnight. (THF/Acetone, 1/3, v/v) | No solid |
| 2 | TPA023B free base (30 mg) was dissolved in 600 μL THF and reacted with 1 eq. methylsulfonic acid (7.37 mg) at 50° C. 300 μL of toluene was added as anti-solvent. The resultant mixture was stirred at RT overnight. (THF/toluene, 2/1, v/v) | Nearly amorphous |

Example 46

Preparation of TPA023 D Besylate

As shown in Tale 32, five experiments were conducted to prepare TPA023 besylate. The besylate salts were prepared with 1 eq. benzenesulfonic acid to TPA023B free base. The XRPD patterns, NMR spectra, DSC/TGS thermograms and DVS profiles of the samples are illustrated in FIGS. 57A to 57G.

TABLE 32

| | Preparation of TPA023B Besylate | |
|---|---|---|
| Lot | Experimental details | Results |
| 1 | TPA023B free base (30 mg) was dissolved in 600 μL THF and reacted with 1 eq. benzenesulfonic acid (12.12 mg) at 50° C. 1.8 mL of acetone was added as anti-solvent. The resultant mixture was stirred at RT overnight. (RT: 20° C.; humidity: 10% RH). (THF/Acetone, 1/3, v/v) | XRPD: Besylate Form A NMR: THF and acetone residue. TGA: 5.15%/150° C. DVS: 0-1.047% moisture between 0% to 90% RH. No XRPD change after DVS test. |
| 2 | ~30 mg of free base was dissolved in THF and reacted with 1 eq. benzene-sulfonic acid at 50° C. Toluene was added as anti-solvent. Kept stirring at RT overnight. (THF/toluene, 2/1, v/v) | Nearly amorphous |
| 3 | ~200 mg of free base was dissolved in THF and reacted with 1 eq. benzene-sulfonic acid at 50° C. Acetone was added as anti-solvent. Kept stirring at RT overnight. (THF/Acetone, 1/3, v/v) | XRPD: Besylate Form A |
| 4 | Slurry 30 mg besylate (Lot# 3) in EA at 50° C. overnight. | XRPD: Besylate Form A TGA: 5.2%/160° C. DSC: $T_{endo}$: 148.24, 156.66, 188.15° C. |
| 5 | Slurry 30 mg besylate (Lot# 3) in heptane at 50° C. overnight. | XRPD: Besylate Form A TGA: 5.0%/160° C. DSC: $T_{endo}$: 144.40, 156.56, 188.25° C. |

The XRPD results (FIG. 57A) showed that the crystal forms of all samples were the same, and they are designated as TPA023B Besylate Form A. After being slurried in EA or heptane, Form A remained unchanged. The NMR results (FIG. 57C) showed that form A had solvent residue. The TGA result (FIG. 57D) showed that Form A has about 5.15% weight loss prior to 150° C. DSC result (FIG. 57D) showed that two endothermic peaks of form A stacked together. It is indicated that one crystal form of TPA023B besylate was produced and it may be a solvate.

Example 47

Preparation of TPA023B Phosphate

Figure 58:
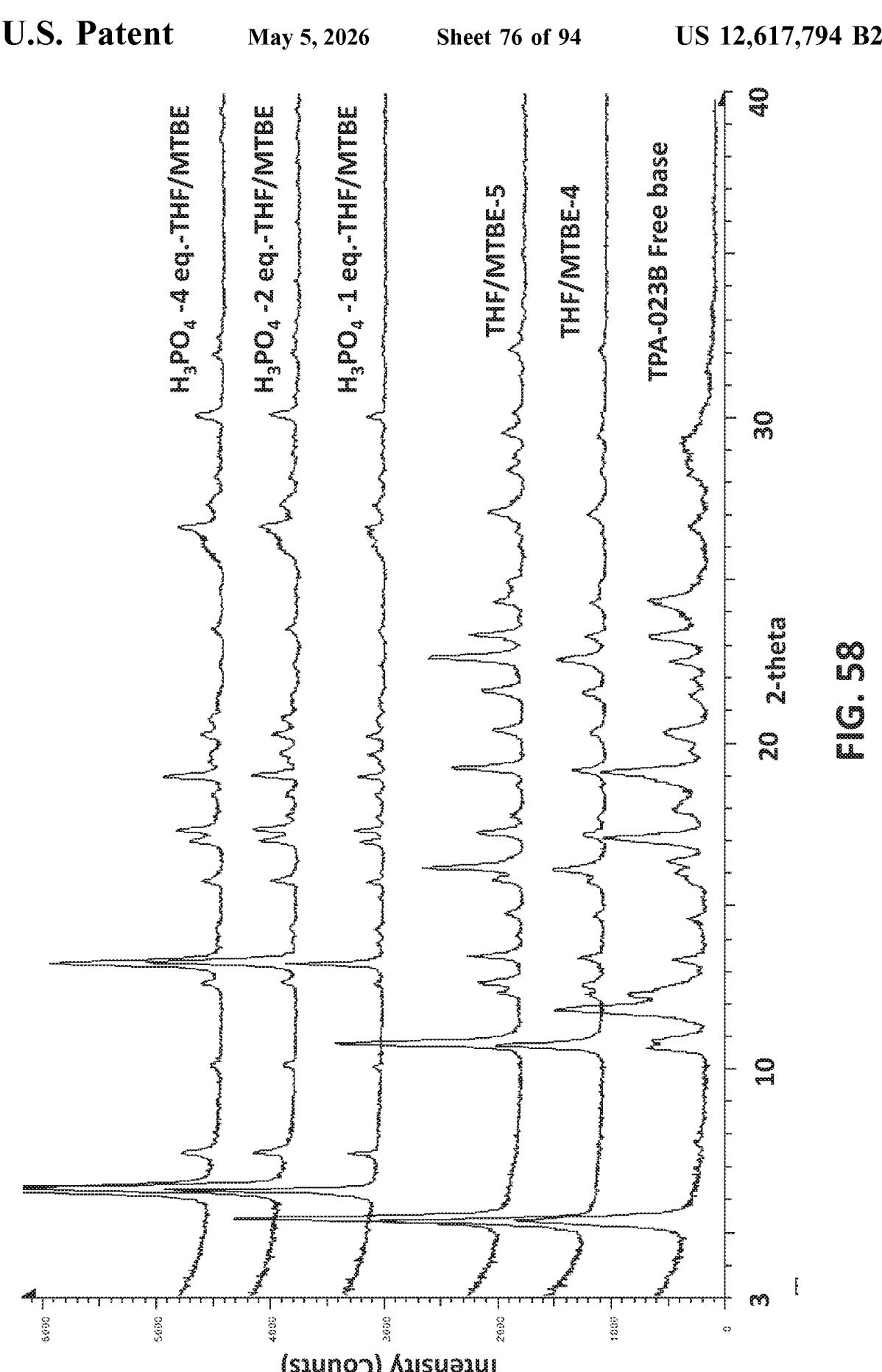
FIG. 58 illustrates the XRPD patterns of TPA023B phosphate

As shown in Table 33, five experiments were conducted to prepare TPA023B phosphate. All of the phosphate salts produced are in crystalline forms, and the crystalline forms of the phosphate salts were not affected by increasing the molar ratio of phosphoric acid to TPA023B (see FIG. 58).

TABLE 33

| | Preparation of TPA023B Phosphate | |
|---|---|---|
| Lot# | Experimental details | Results |
| 1 | ~30 mg of free base was dissolved in THF and reacted with 1 eq. $H_3PO_4$ at RT. MTBE was added as anti-solvent. Kept stirring at RT overnight. (THF/MTBE, 1/2, v/v) | XRPD: Phosphate Form A |
| 2 | ~30 mg of free base was dissolved in THF and reacted with 2 eq. $H_3PO_4$ at RT. MTBE was added as anti-solvent. Kept stirring at RT overnight. (THF/MTBE, 1/2, v/v) | XRPD Phosphate: Form A |
| 3 | ~30 mg of free base was dissolved in THF and reacted with 4 eq. $H_3PO_4$ at RT. MTBE was added as anti-solvent. Kept stirring at RT overnight. (THF/MTBE, 1/2, v/v) | XRPD: Phosphate Form A |
| 4 | ~30 mg of free base was dissolved in THF and MTBE was added as anti-solvent at RT. Kept stirring at RT overnight. (THF/MTBE, 1/2, v/v) | XRPD: free base Form C |
| 5 | ~50 mg of free base was dissolved in THF and MTBE was added as anti-solvent at RT. Kept stirring at RT overnight. (THF/MTBE, 1/2, v/v) | XRPD: free base Form C |

Example 48

Solid-State Stability Tests

Figure 59D:
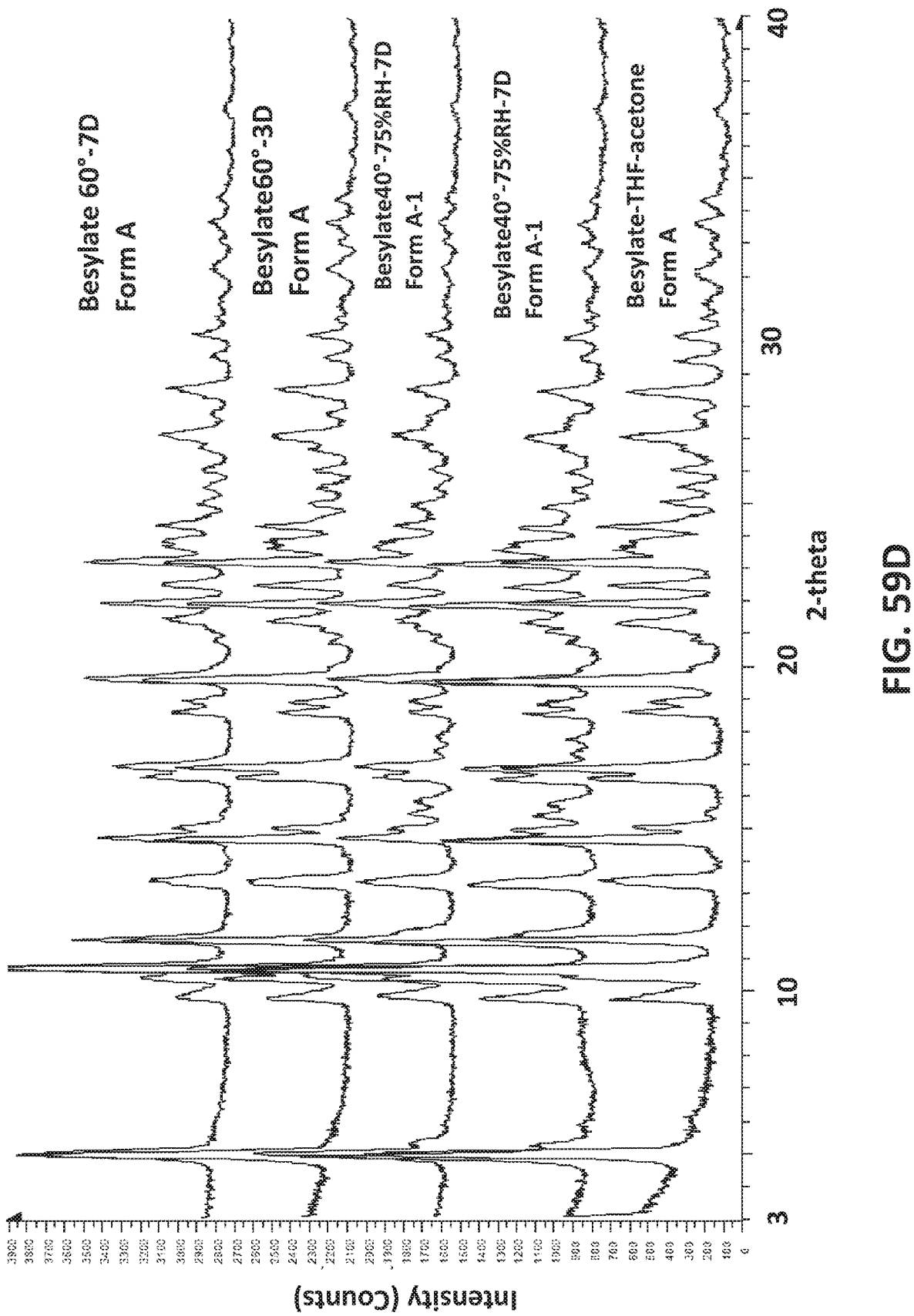

As illustrated in Table 34, TPA-23B free base (Form A), TPA-23B sulfate (Form A), TPA-23B chloride (Form C) and TPA-23B besylate (Form A) were chemically stable at test conditions. The purity of the TPA-23B chloride was improved at test conditions; it is possible that some impurities in the chloride salt were volatile, degraded into to non-UV absorbing or volatile impurities during the test, or were not homogenously distributed. The XRPD result (FIGS. 59A-59D) indicated that the crystal form of TPA-23B free base, TPA-23B chloride and TPA-23B sulfate remained unchanged during testing. There were three extra peaks at 15.8°, 17.4° and 17.8° (2θ) for TPA-23B besylate at 40° C.-75% RH after 7 days, which can be caused by impurities. The XRPD pattern of TPA-23B besylate with extra peaks was designated as TPA-23B besylate Form A-I (see, FIG. 59D).

TABLE 34

| | | Stability results in test conditions | | | | |
|---|---|---|---|---|---|---|
| Sample | Condition | HPLC Purity (%) day 0 | HPLC Purity (%) day 3 | Crystal form day 3 | HPLC Purity (%) day 7 | Crystal form day 7 |
| Free base (Form A) | 40° C./75% RH | 98.1% | 98.2% | Free base Form A | 98.2% | Free base Form A |
| | 60° C. | | 98.1% | Free base Form A | 98.3% | Free base Form A |
| TPA023B chloride (Form C) | 40° C./75% RH | 97.6% | 98.8% | Chloride Form C | 98.7% | Chloride Form C |
| | 60° C. | | 98.4% | Chloride Form C | 98.4% | Chloride Form C |
| TPA023B Sulfate (Form A) | 40° C./75% RH | 98.8% | 98.8% | Sulfate Form A | 98.8% | Sulfate Form A |
| | 60° C. | | 98.8% | Sulfate Form A | 98.8% | Sulfate Form A |
| TPA023B Besylate (Form A) | 40° C./75% RH | 98.8% | 98.8% | Besylate Form A-I | 98.8% | Besylate Form A-I |
| | 60° C. | | 98.8% | Besylate Form A | 98.8% | Besylate Form A |

Example 49

Annotated XRPD Patterns

Additional annotated XRPD patterns, when measured using the parameters described in Example 38, are illustrated in FIGS. 60-63.

Example 50

Kilogram-Scale Preparation Procedure for Phosphate Form A

Figure 65A:
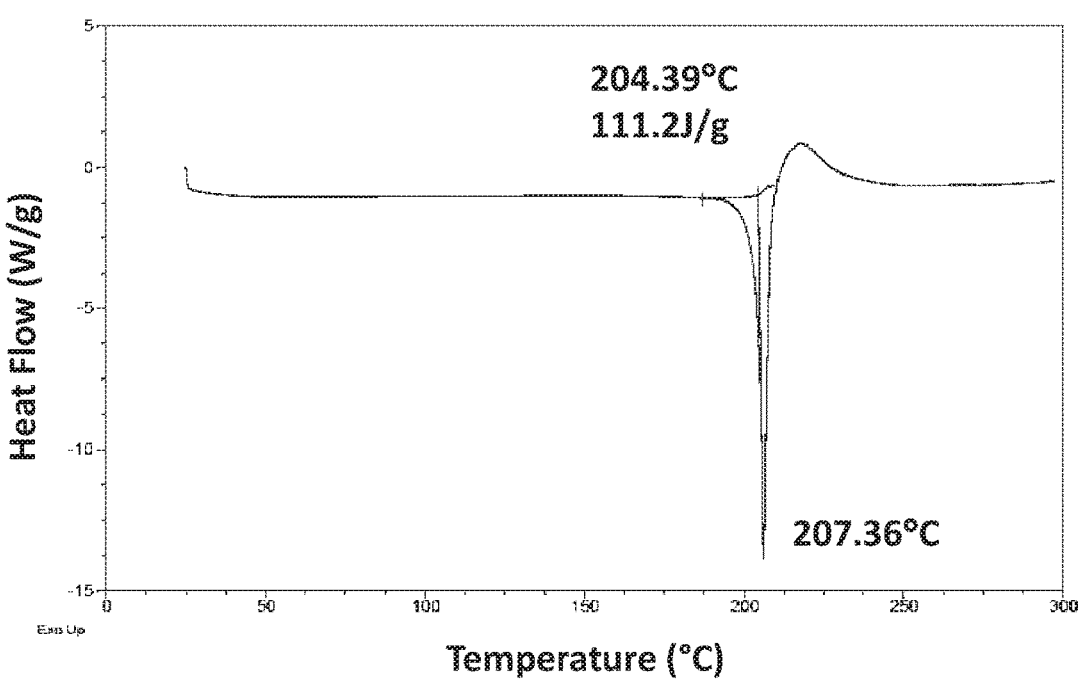
FIG. 65A and FIG. 65B illustrate the DSC (FIG. 65A) and TGA (FIG. 65B) thermograms of TPA023B phosphate Form A produced by the kilogram-Scale Preparation Procedure
Figure 65B:
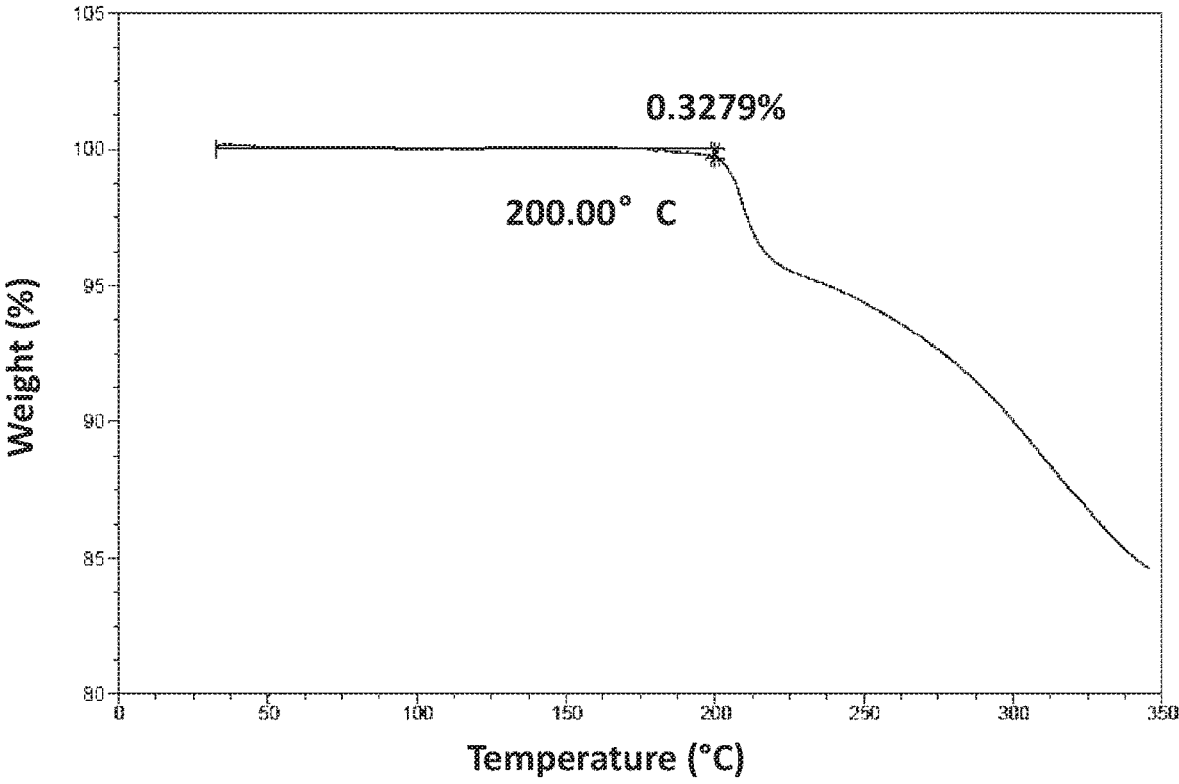

2',6-difluoro-5'-[3-(1-hydroxy-1-methylethyl)-imidazo[1,2-b][1,2,4]triazin-7-yl]biphenyl-2-carbonitrile (2.1 Kg, 5.4 moles, 1.0 Eq), acetone (42 L, 20 Vol.), and water (672 mL, 0.32 Vol.) were heated with stirring to 50±5° C. Concentrated phosphoric acid (85 wt %, 310 g, 2.7 moles, 0.50 eq.) was added over ~10 minutes. Additional concentrated phosphoric acid (85 wt %, 495 g, 4.3 moles, 0.80 eq.) was added over ~1 hour. The resulting mixture was stirred for ~1 hour at 50±5° C. resulting in a dark-colored, clear solution. The solution was filtered through a pad of diatomaceous earth (700 g) followed by an in-line, 0.2-micron filter. Acetone (8.5 L, 4.0 Vol.) was removed by distillation and anhydrous acetone (8.5 L, 4.0 Vol.) was added. This process was repeated an additional 2 times forming a slurry of yellow solid. Acetone (8.5 L, 4.0 Vol.) was removed by distillation and ethyl acetate (8.5 L, 4.0 Vol.) was added. This process was repeated an additional 2 times resulting in a slurry of about 20 Vol, which was heated to 50±5° C. The resulting slurry was slowly cooled to 20-25° C. and stirred for overnight. The slurry was cooled to 0~5° C. over 1 hour and stirred for 1 hour. The solids were collected by filtration, and the filter cake was washed with ethyl acetate (6.5 L, 3.0 Vol.). The filter cake was dried in vacuo at 25° C. under a $N_2$ stream for 5 hours, and at 70° C. in vacuo under a $N_2$ stream for 21 hours to provide Polymorphic Form A of the salt of 2',6-difluoro-5'-[3-(1-hydroxy-1-methylethyl)-imidazo[1,2-b][1,2,4]triazin-7-yl]biphenyl-2-carbonitrile with phosphoric acid (2.49 Kg, 94.7% Yield). The content of phosphoric acid in the product was determined by ion chromatography to be about 19.2%. The XRPD pattern and DSC/TGA curves, when measured using the parameters described in Example 38, are illustrated in FIG. 64, FIG. 65A, and FIG. 65B, respectively.

Example 51

51.0 Phosphate Polymorph Screening

Exemplary solvents and materials used in the polymorph screening include: ethanol (EtOH), isopropyl alcohol (IPA), methyl acetate (MAC), butyl acetate (BAC), trifluoroethanol, tetrahydrofuran (THF), acetonitrile (ACN), tert-butyl methyl ether (MTBE), diethyl ether (DEE), acetone, butanone (MEK), water, 1,4-dioxane (Diox), dichloromethane (DCM), ethyl acetate (EA), isopropyl acetate (IPAC), heptane (Hept), cyclohexane (CYH), dimethyl sulfoxide (DMSO), toluene, tert-amyl alcohol, 1-methyl-2-pyrrolidone (NMP), 4-methyl-2-pentanone (MIBK), cyclohexanane, polyethylene glycol 200 (PEG200), polypropylene glycol (PPG2000), polysorbate 80 (e.g., sold under the trade name Tween™ 80), propyl acetate, N,N-dimethylformamide (DMF), N-pentane, ethyl formate, anisole, xylene (mixed isomers), petroleum ether, dimethylacetamide (DMAC), 2-methyl tetrahydrofuran, methyl cyclohexane, butanol, isoamyl alcohol, and chloroform.

51.1 Slow Solvent Evaporation at RT

Phosphate Form A was dissolved in selected solvents. The solution was filtered, and the filtrate evaporated to dryness in an operating laboratory fume hood at room temperature (RT).

51.2 Fast Solvent Evaporation at RT

Phosphate Form A was dissolved in a solvent and evaporation crystallization was performed by $N_2$ purge at RT or removed by rotary evaporator. Solids were collected and analyzed.

51.3 Slurry in Single Solvent at RT

Phosphate Form A was added into single solvent to make suspension, which was then kept stirring at RT for 4-9 days. Solid samples were collected by filtration and analyzed.

51.4 Slurry in Mixed Solvent at RT

Phosphate Form A was added into mixed solvents to make a suspension. The suspensions were kept stirring at RT for 4-7 days. Solid samples were collected by filtration and analyzed.

51.5 Slurry in Single Solvent at 60° C.

Phosphate Form A was added into different solvents to make a suspension. The suspensions were kept stirring at 60° C. for 3-4 days. Solid samples were collected by filtration and analyzed after stirring.

51.6 Slurry in Mixed Solvent at 60° C.

Phosphate Form A was added into mixed solvents to make a suspension. The suspensions were kept stirring at 60° C. for 4-6 days. Solid samples were collected by filtration and analyzed after stirring.

51.7 Fast Cooling Crystallization

Phosphate Form A was weighed into vials and then selected solvents were added to make nearly clear solution with heating. The suspensions were filtered to obtain saturated solution which was cooled to final temperature (4° C. or −20° C.) immediately and characterized.

51.8 Slow Cooling Crystallization

Phosphate Form A was weighed into vials and then selected solvents were added to make nearly clear solution with heating. The suspensions were filtered to obtain saturated solution, and it was kept in an oil bath to cool to RT. The solids obtained were characterized.

51.9 Anti-Solvent Precipitation

Phosphate Form A was weighed into vials and the selected solvents were added to make a saturated solution. After filtration, filtrates were added into the anti-solvents gradually at RT or 50° C. (or reverse). If precipitation occurred, products were characterized.

51.10 Thermal Treatment

Amorphous salt of 2',6-difluoro-5'-[3-(1-hydroxy-1-methylethyl)-imidazo[1,2-b][1,2,4]triazin-7-yl]biphenyl-2-carbonitrile with phosphoric acid were prepared by fast evaporation of the saturated THF solution of Phosphate Form A. Thermal treatment of the amorphous salt of 2',6-difluoro-5'-[3-(1-hydroxy-1-methylethyl)-imidazo[1,2-b][1,2,4]triazin-7-yl]biphenyl-2-carbonitrile with phosphoric acid was performed by using DSC at a ramp rate of 10° C./min, from 25° C. to 160° C.

51.11 Liquid Vapor Diffusion

Phosphate Form A was dissolved in a solvent. After filtration, the filtrate in a small vial was put into a bigger vial containing anti-solvent. The bigger vial was left at RT for days. If precipitation occurred, solid was collected and characterized.

51.12 Solid Vapor Diffusion

Amorphous salt of 2',6-difluoro-5'-[3-(1-hydroxy-1-methylethyl)-imidazo[1,2-b][1,2,4]triazin-7-yl]biphenyl-2-carbonitrile with phosphoric acid was prepared by fast evaporation and was then added into a small vial which was put into a bigger vial containing selected solvent. The bigger vial was sealed and placed at RT for 1 day. The samples were analyzed.

51.13 Reactive Crystallization with Phosphoric Acid

About 25 mg of Free Base Form H was dissolved or suspended in ~1 mL of a selected solvent. Then 1.1 eq. of phosphoric acid was added, and the suspension was stirred at RT for 7 hours. The solid was isolated and characterized.

51.14 Reactive Crystallization with Excess Phosphoric Acid

About 30 mg of Free Base Form H was suspended in ~1 mL of acetone. Then excess phosphoric acid (2 eq., 3 eq. and 4 eq., respectively) was added and the suspension was stirred for 4 hours at RT. The products were characterized accordingly.

51.15 Polymer Induced Crystallization

About 15 mg of Phosphate Form A was dissolved in a selected solvent. Then ~10% of polymer was added into clear solution. The mixture was evaporated to dryness at RT. The solid was isolated and characterized.

51.16 Mechanical Treatment

Phosphate Form A was added to a mortar and ground at RT to find more crystal forms.

Amorphous salt of 2',6-difluoro-5'-[3-(1-hydroxy-1-methylethyl)-imidazo[1,2-b][1,2,4]triazin-7-yl]biphenyl-2-carbonitrile with phosphoric acid were ground manually with small amount of solvent for minutes, and then the samples were analyzed.

Analysis Method and Conditions 51.17 Dynamic Vapor Sorption (DVS)

Moisture sorption/desorption data was collected on a Vsorp Dynamic Moisture Sorption Analyzer (ProUmid GmbH & Co. KG, Germany). The sample was placed into a tared sample chamber and automatically weighed.

51.18 Differential Scanning Calorimeter (DSC)

DSC was performed using a Discovery DSC 250 (TA Instruments, US). The sample was placed into an aluminum pin-hole hermetic pan and the weight was accurately recorded. Then the sample was heated at a rate of 10° C./min from 25° C. to the final temperature.

51.19 Thermogravimetric Analysis (TGA)

TGA was carried out on a Discovery TGA 55 (TA Instruments, US). The sample was placed into an open tared aluminum pan, automatically weighed, and inserted into the TGA furnace. The sample was heated at a rate of 10° C./min from ambient temperature to the final temperature.

51.20 X-Ray Powder Diffraction (XRPD)

The solid samples were examined using X-ray diffractometer (PANalvtic Empyrean) equipped with PIXcel[1D] detector. The tube voltage and current were at 45 kV and 40 mA, respectively, and the samples were scanned from 3 to 40° 2θ at a step size of 0.0130°.

TABLE 35

| XRPD Parameters | |
|---|---|
| Parameters | Settings/Values |
| X-Ray wavelength | Cu: K- Alpha (λ = 1.54179 Å) |
| X-Ray tube setting | Voltage: 45 kV; Current: 40 mA |
| Scan scope | 3 to 40 deg |
| Sample rotation speed | 60 rpm |
| Scanning rate | 9.84 deg./min |

Example 52

Slow Solvent Evaporation at RT

Phosphate Form A was dissolved in selected solvents. The solution was filtered, and the filtrate evaporated to dryness in an operating laboratory fume hood at room temperature. Slow single solvent evaporative crystallization results are summarized in Table 36.

TABLE 36

| Results of Slow Single Solvent Evaporative Crystallization | |
|---|---|
| Solvent | Result |
| DCM | No solid |
| MEK | Phosphate Form A |
| Acetone | Free Base Form G |
| BAC (Butyl acetate) | No solid |
| MAC (Methyl acetate) | Phosphate Form A + Free Base Form F |

TABLE 36-continued

| Results of Slow Single Solvent Evaporative Crystallization | |
| --- | --- |
| Solvent | Result |
| EA | Phosphate Form A |
| ACN | Phosphate Form A |
| DMAC | Phosphate Form A + Free Base Form F |
| 2-methyl tetrahydrofuran | Phosphate Form A + Free Base Form F |
| Xylene | No solid |

Example 53

Slow Evaporative Crystallization in Mixed Solvent

Slow evaporative crystallization was also performed by using mixed solvents. No new phosphate form was discovered in solids produced by this method. Phosphate Form A dissociated into Free Base Form G in acetone-BAC, into Free Base Form A in acetone-isopropyl ether and acetone-DCM, and partially into Free Base Form F in ACN-MAC. The results are presented in Table 37.

TABLE 37

| Results of Mixed Solvent Evaporative Crystallization | | |
| --- | --- | --- |
| Solvent 1 | Solvent 2 | Result |
| CYH | THF | Phosphate Form A |
| MEK | MAC | Phosphate Form A |
| Acetone | BAC | Free Base Form G |
| Acetone | EA | Phosphate Form A |
| Acetone | ACN | Phosphate Form A |
| ACN | MAC | Phosphate Form A + Free Base Form F |
| ACN | THF | Phosphate Form A |
| THF | Trichloromethane | Phosphate Form A |
| THF | Toluene | Phosphate Form A |
| THF | MAC | Phosphate Form A |
| THF | EA | Phosphate Form A |
| THF | MTBE | Phosphate Form A |
| THF | Isopropyl ether | Phosphate Form A |
| Acetone | Isopropyl ether | Free Base Form A |
| Acetone | DCM | Free Base Form A |
| Acetone | Diox | Phosphate Form A |
| DMAC | MAC | No solid |
| DMAC | ACN | No solid |
| 2-methyl tetrahydrofuran | MEK | Phosphate Form A |
| 2-methyl tetrahydrofuran | MTBE | Phosphate Form A |

Example 54

Fast Solvent Evaporation at RT

Phosphate Form A was dissolved in a solvent and evaporation crystallization was performed by N$_2$ purge at RT or removed by rotary evaporator and solids were collected. No new phosphate form was obtained in fast evaporation. Phosphate partly dissociated into free base in DMAC, 2-methyl tetrahydrofuran, and DMAC-ACN in fast solvent evaporation. The results are summarized in Table 38.

TABLE 38

| Results of Fast Solvent Evaporative Crystallization | | |
| --- | --- | --- |
| Solvent 1 | Solvent 2 | Result |
| DMAC | N/A | Phosphate Form A + Free Base Form F |
| 2-methyl tetrahydrofuran | N/A | Phosphate Form A + Free Base form F |
| xylene | N/A | No solid |
| DMAC | MAC | No solid |
| DMAC | ACN | Phosphate Form A + Free Base Form F |
| 2-methyl tetrahydrofuran | MEK | Phosphate Form A |
| 2-methyl tetrahydrofuran | MTBE | Phosphate Form A |

Example 55

Slurry in Single Solvent at RT

Phosphate Form A was added into a single solvent to make a suspension, which was stirred at RT for 4-9 days. Solid samples were collected. No new phosphate form was obtained in solid prepared under this method. Phosphate Form A dissociated into Free Base Form E in DMSO and partially into Free Base Form A in tert-amyl alcohol. Phosphate Form A+Free Base Form E were obtained in butanol and isoamyl alcohol in the single solvent slurry at RT. The results are summarized in Table 39.

TABLE 39

| Results of Slurry in Single Solvent at RT | |
| --- | --- |
| Solvent | Result |
| Tert-amyl alcohol | Phosphate Form A + Free Base Form A |
| MEK | Phosphate Form A |
| CYH | Phosphate Form A |
| DCM | Phosphate Form A |
| MAC | Phosphate Form A |
| BAC | Phosphate Form A |
| Trichloromethane | Phosphate Form A |
| Diethylether | Phosphate Form A |
| Isopropyl ether | Phosphate Form A |
| MTBE | Phosphate Form A |
| Hept | Phosphate Form A |
| CYH | Phosphate Form A |
| Diox | Phosphate Form A |
| Toluene | Phosphate Form A |
| DMSO | Free Base Form E |
| Anisole | Phosphate Form A |
| xylene | Phosphate Form A |
| Petroleum ether | Phosphate Form A |
| 2-methyl tetrahydrofuran | Phosphate Form A |
| Methyl cyclohexane | Phosphate Form A |
| Butanol | Phosphate Form A + Free Base Form E |
| Isoamyl alcohol | Phosphate Form A + Free Base Form E |
| Chloroform | Phosphate Form A |

Example 56

Slurrying in Mixed Solvent at RT

Phosphate Form A was added into mixed solvents to make a suspension. The suspensions were stirred at RT for 4-7 days. Solid samples were collected by filtration. No new phosphate form was obtained under this method. Phosphate Form A dissociated into Free Base Form E in NMP-Ethyl formate and DMAC-anisole at RT. Free Base Form A was obtained in DMAC—methyl cyclohexane in at RT. The results are summarized in Table 40.

TABLE 40

| Results of Slurrying in Mixed Solvent at RT | | |
|---|---|---|
| Solvent 1 | Solvent 2 | Result |
| MEK | BAC | Phosphate Form A |
| MEK | EA | Phosphate Form A |
| MEK | ACN | Phosphate Form A |
| MEK | THF | Phosphate Form A |
| MEK | N-pentane | Phosphate Form A |
| MEK | CHY | Phosphate Form A |
| NMP | MAC | No solid |
| NMP | Ethyl formate | Free Base Form E |
| MIBK | MAC | Phosphate Form A |
| MIBK | EA | Phosphate Form A |
| MIBK | ACN | Phosphate Form A |
| MIBK | MTBE | Phosphate Form A |
| MIBK | N-pentane | Phosphate Form A |
| MIBK | Hept | Phosphate Form A |
| Anisole | 2-methyl tetrahydrofuran | Phosphate Form A |
| Anisole | Methyl Cyclohexane | Phosphate Form A |
| Anisole | Chloroform | Phosphate Form A |
| 2-methyl tetrahydrofuran | xylene | Phosphate Form A |
| 2-methyl tetrahydrofuran | Methyl cyclohexane | Phosphate Form A |
| DMAC | Anisole | Free Base Form E |
| DMAC | Methyl cyclohexane | Free Base Form A |

Example 57

Slurrying in Single Solvent 60° C.

Phosphate Form A was added into different solvents to make a suspension. The suspensions were stirred at 60° C. for 3-4 days. Solid samples were collected by filtration. No new phosphate forms were obtained. Phosphate Form A dissociated into Free Base Form E in tert-amyl alcohol, Butanol, Isoamylol, IPA, and PEG 200, and into Free Base Form C in EtOH. The results were summarized in Table 41.

TABLE 41

| Results of Slurry in Single Solvent at 60° C. | |
|---|---|
| Solvent | Result |
| Diox | No solid |
| MEK | Phosphate Form A |
| BAC | Phosphate Form A |
| Cyclohexanane | Phosphate Form A |
| CYH | Phosphate Form A |
| Hept | Phosphate Form A |
| Isopropyl ether | Phosphate Form A |
| MAC | Phosphate Form A |
| MTBE | Phosphate Form A |
| Tert-amyl alcohol | Free Base Form E |
| Toluene | Phosphate Form A |
| Trichloromethane | Phosphate Form A |
| EA | Phosphate Form A |
| Acetone | Phosphate Form A |
| EtOH | Free Base Form C |
| IPA | Free Base Form E |
| ACN | Phosphate Form A |
| PEG 200 | Free Base Form E |
| PPG 2000 | Phosphate Form A |
| polysorbate 80 | Phosphate Form A |
| Anisole | Phosphate Form A |
| xylene | Phosphate Form A |
| Petroleum ether | Phosphate Form A |
| 2-methyl tetrahydrofuran | Phosphate Form A |
| Methyl cyclohexane | Phosphate Form A |
| Butanol | Phosphate Form A + Free Base Form E |
| Isoamylol | Phosphate Form A + Free Base Form E |
| Chloroform | Phosphate Form A |

Example 58

Slurrying in Mixed Solvent at 60° C.

Phosphate Form A was added into mixed solvents to make a suspension. The suspensions were stirred at 60° C. for 4-6 days. The solid samples were collected by filtration and analyzed. No new phosphate form was obtained. Phosphate Form A dissociated into Free Base Form E in DMAC-anisole, and DMAC-methyl cyclohexane mixtures. The results are summarized in Table 42.

TABLE 42

| Results of Slurrying in Mixed Solvent at 60° C. | | |
|---|---|---|
| Solvent 1 | Solvent 2 | Result |
| MEK | BAC | Phosphate Form A |
| MEK | EA | Phosphate Form A |
| MEK | ACN | Phosphate Form A |
| MEK | THF | Phosphate Form A |
| MEK | N-pentane | Phosphate Form A |
| MEK | CYH | Phosphate Form A |
| NMP | MAC | No solid |
| NMP | Ethyl formate | No solid |
| MIBK | MAC | Phosphate Form A |
| MIBK | EA | Phosphate Form A |
| MIBK | ACN | Phosphate Form A |
| MIBK | MTBE | Phosphate Form A |
| MIBK | N-pentane | Phosphate Form A |
| MIBK | Hept | Phosphate Form A |
| Anisole | 2-methyl tetrahydrofuran | Phosphate Form A |
| Anisole | Methyl cyclohexane | Phosphate Form A |
| Anisole | chloroform | Phosphate Form A |
| 2-methyl tetrahydrofuran | xylene | Phosphate Form A |
| 2-methyl tetrahydrofuran | Methyl cyclohexane | Phosphate Form A |
| DMAC | Anisole | Free Base Form E |
| DMAC | Methyl cyclohexane | Free Base Form E |

Example 59

Anti-Solvent Precipitation at RT

Phosphate Form A was weighed into vials and the selected solvents were added to make saturated solutions. After filtration, filtrates were either added into their respective anti-solvents gradually at RT, then the procedure was reversed adding anti-solvents into the solutions. If precipitation occurred, the products were characterized. Solvents and anti-solvents were selected according to solubility test results. No new phosphate form was obtained in anti-solvent precipitation. Phosphate Form A dissociated into Free Base Form E in DMF and into Free Base Form A in NMP-MTBE (anti-solvent addition). Phosphate Form A with additional small peaks was obtained in Diox/CYH which might be due to dissociation of phosphate. The results were shown in Table 43.

TABLE 43

| Results of Anti-solvent Precipitation at RT | | | |
|---|---|---|---|
| Solvent | Anti-solvent | Anti-solvent Addition Result1 | Reverse Anti-solvent Addition Result2 |
| Acetone | DCM | No solid | No solid |
| | Isopropyl ether | Phosphate Form A | Phosphate Form A |
| DMF | N/A | Free Base Form E | |
| NMP | EA | No solid | No solid |
| | DCM | Phosphate Form A | Phosphate Form A |

TABLE 43-continued

| | | Results of Anti-solvent Precipitation at RT | |
|---|---|---|---|
| Solvent | Anti-solvent | Anti-solvent Addition Result1 | Reverse Anti-solvent Addition Result2 |
| | CYH | Phosphate Form A | NA |
| | MTBE | Free Base Form A | Phosphate Form A |
| | Hept | Phosphate Form A | NA |
| THF | CYH | Phosphate Form A | Phosphate Form A |
| Diox | DCM | Phosphate Form A | Phosphate Form A |
| | CYH | Phosphate Form A + Small Peaks | Phosphate Form A + Small Peaks |

Example 60

Anti-Solvent Precipitation at 50° C.

Phosphate Form A was weighed into vials and the selected solvents were added to make saturated solutions. After filtration, filtrates were added into the anti-solvents gradually at 50° C., then the procedure was reversed adding antisolvent to the solutions. If precipitation occurred, the products were characterized. No new phosphate form was obtained in anti-solvent precipitation at 50° C. under these conditions. Phosphate Form A dissociated or partly dissociated into Freebase Form A, Freebase Form E, and/or Freebase Form G in NMP-Hept, NMP/petroleum ether; THF-petroleum ether, and THF-methyl cyclohexane solvent systems depending on the order of operations as shown in Table 44.

TABLE 44

| | | Results of Anti-solvent Precipitation at 50° C. | |
|---|---|---|---|
| Solvent | Anti-solvent | Anti-solvent Addition Result 1 | Reverse Anti-solvent Addition Result 2 |
| DMAC | DCM | No solid | No solid |
| | Anisole | No solid | No solid |
| | xylene | No solid | No solid |
| 2-methyl tetrahy- | DCM | No solid | No solid |
| drofuran | xylene | Phosphate Form A | Phosphate Form A |
| | Methyl cyclohexane | Phosphate Form A | Phosphate Form A |
| NMP | Hept | Free Base Form A | Free Base Form A + E |
| | chloroform | Phosphate Form A | Not enough |
| | Petroleum ether | Free Base Form A | Free Base Form A |
| THF | Anisole | No solid | No solid |
| | Petroleum ether | Phosphate Form A + Free Base form G | Phosphate Form A + Free Base Form A |
| | Methyl cyclohexane | Phosphate Form A + Free Base form G | Phosphate Form A + Free Base Form A |

Example 61

Liquid Vapor Diffusion

Phosphate Form A was dissolved in solvent. After filtration, the filtrate was transferred into a small vial, which was then placed inside a bigger vial which contained anti-solvent. The bigger vial was left at RT for 6 days. If precipitation occurred, solid was collected and characterized. No new phosphate form was obtained. The results are summarized in Table 45.

TABLE 45

| | Results of Liquid Vapor Diffusion | |
|---|---|---|
| Solvent | Anti-solvent | Result |
| MEK | Cyclohexanone | Phosphate Form A |
| | MAC | No solid |
| | MTBE | No solid |
| | DCM | Phosphate Form A |
| | Trichloromethane | Phosphate Form A |
| Diox | ACN | No solid |
| | Heptane | Phosphate Form A |
| | BAC | Phosphate Form A |
| | Isopropyl ether | Phosphate Form A |
| | DCM | Phosphate Form A |
| THF | EA | Phosphate Form A |
| | ACN | No solid |
| | Trichloromethane | No solid |
| | Toluene | Phosphate Form A |
| | N-pentane | Phosphate Form A |
| 2-methyl tetrahydrofuran | xylene | Phosphate Form A |
| | Methyl cyclohexane | Phosphate Form A |
| | Chloroform | Phosphate Form A |
| NMP | MEK | No solid |
| | Chloroform | No solid |
| | Isopropyl ether | No solid |
| DMAC | DCM | No solid |
| | Isopropyl ether | No solid |
| | EA | No solid |

Example 62

Solid-Vapor Diffusion

Figure 71:
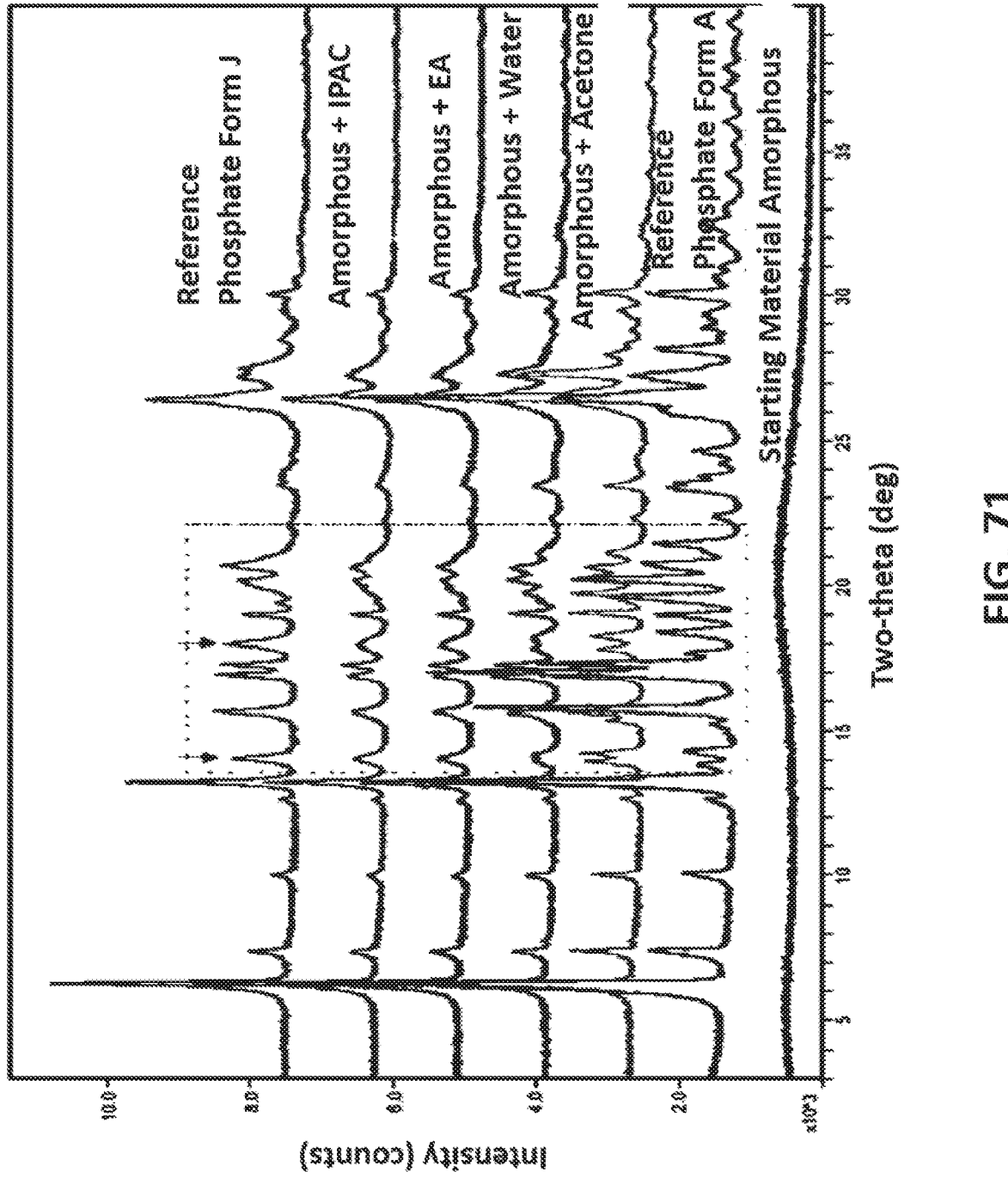
FIG. 71 illustrates the overlaid XRPD of converting amorphous salt of 2',6-difluoro-5'-[3-(1-hydroxy-1-methylethyl)-imidazo[1,2-b][1,2,4]triazin-7-yl]biphenyl-2-carbonitrile with phosphoric acid to Phosphate Form J and Phosphate Form A through solid-vapor diffusion.

Amorphous salt of 2',6-difluoro-5'-[3-(1-hydroxy-1-methylethyl)-imidazo[1,2-b][1,2,4]triazin-7-yl]biphenyl-2-carbonitrile with phosphoric acid was prepared by fast evaporation and then placed in a small vial which was placed inside a larger vial which contained selected solvent. The bigger vial was sealed and left undisturbed at RT for 1 day. The samples were analyzed. Phosphate Form J was identified when solvent IPAC or EA was used in solid-vapor diffusion as seen in FIG. 71. The results were presented in Table 46.

TABLE 46

| Vapor Diffusion of the amorphous salt of 2',6-difluoro-5'-[3-(1-hydroxyl-1-methylethyl)-imidazo[1,2-b][1,2,4]triazin-7-yl]biphenyl-2-carbonitrile with phosphoric acid | |
|---|---|
| Solvent | Result |
| IPAC | Phosphate Form J |
| EA | Phosphate Form J |
| Water | Phosphate Form J + A |
| Acetone | Phosphate Form A |

Example 63

Fast Cooling Crystallization

Phosphate Form A was added into vials and heated until nearly in solution. The suspensions were filtered to obtain saturated solutions which were immediately cooled to final temperature (4° C. or −20° C.). Any solids obtained were characterized. Either Phosphate Form A or clear solution was obtained from fast cooling crystallization. Phosphate Form A dissociated in butanol and isoamyl alcohol in cooling crystallization. A new Free Base pattern K was found in fast cooling crystallization in isoamyl alcohol. The results are summarized in Table 47.

TABLE 47

| Results of Fast Cooling Crystallization | |
|---|---|
| Solvent | Result |
| 4-methyl-2-pentanone | Phosphate Form A |
| Propyl acetate | Phosphate Form A |
| DMSO | No solid |
| 1,4-dioxane | No solid |
| BAC | Phosphate Form A |
| EA | Phosphate Form A |
| ACN | Phosphate Form A |
| MEK | Phosphate Form A |
| MAC | Phosphate Form A |
| Acetone | Phosphate Form A |
| THF | No solid |
| DMF | No solid |
| 1-methyl-2-pyrrolidone | No solid |
| Ethyl formate | Phosphate Form A |
| Anisole | No solid |
| 2-methyl tetrahydrofuran | No solid |
| Butanol | Freebase form A |
| Isoamyl alcohol | New Free Base pattern K |
| 2-butanone | Phosphate Form A |

Example 64

Slow Cooling Crystallization

Phosphate Form A was weighed into vials and selected solvents were added to make a nearly clear solution with heating. The suspensions were filtered to obtain a saturated solution, and it was kept in an oil bath which was allowed to cool to RT naturally. Any solids obtained were characterized. Phosphate Form A dissociated in butanol and isoamyl alcohol in slow cooling crystallization. No new phosphate Form was obtained. The results are summarized in Table 48.

TABLE 48

| Results of Slow Cooling Crystallization | |
|---|---|
| Solvent | Result |
| Anisole | No solid |
| 2-methyl tetrahydrofuran | No solid |
| Butanol | Free Base Form E |
| Isoamyl alcohol | Free Base Form E |
| EA | No solid |
| ACN | Phosphate Form A |
| 2-butanone | Phosphate Form A |
| BAC | Phosphate Form A |
| MAC | No solid |
| THF | No solid |

Example 65

Reactive Crystallization with 1.1 Eq Phosphoric Acid

Free Base Form H was dissolved or suspended in ~1 mL selected solvent. Then 1.1 eq. of phosphoric acid was added, and the suspension was stirred at RT for 7 hours. Solid was isolated and characterized. No new phosphate Form was obtained in reactive crystallization under this method. A mixture of Free Base Form H and Phosphate Form A was obtained from CYH and Hept which was likely due to very low solubility of Free Base Form H and phosphoric acid in CYH and Hept. The results are summarized in Table 49.

TABLE 49

| Results of Reactive Crystallization with 1 eq. Phosphoric Acid | |
|---|---|
| Solvent | Result |
| 1,4-dioxane | Phosphate Form A |
| MEK | Phosphate Form A |
| Acetone | Phosphate Form A |
| Cyclohexanone | Phosphate Form A |
| CYH | Phosphate Form A + Free Base Form E |
| Hept | Phosphate Form A+ Free Base Form E |
| N-pentane | Phosphate Form A |
| DEE | Phosphate Form A |
| MTBE | Phosphate Form A |
| DCM | Phosphate Form A |
| Trichloromethane | Phosphate Form A |
| IPAC | Phosphate Form A |
| EA | Phosphate Form A |
| BAC | Phosphate Form A |
| ACN | Phosphate Form A |
| polysorbate 80 | Phosphate Form A |
| PPG 2000 | Phosphate Form A |

Example 66

Reactive Crystallization with Excess Phosphoric Acid

Free Base Form H was suspended in ~1 mL of acetone. Then excess amounts of phosphoric acid was added and the suspension was stirred for 4 hours at RT. The products were characterized. Only Phosphate Form A was obtained. The results are presented in Table 50.

TABLE 50

| Results of Reactive Crystallization with Excess Phosphoric Acid | |
|---|---|
| Amount of Acid | Result |
| 2 eq. | Phosphate Form A |
| 3 eq. | Phosphate Form A |
| 4 eq. | Phosphate Form A |

Example 67

Polymer Induced Crystallization

Phosphate Form A was dissolved in a selected solvent and ~10% polymer was added, and then evaporative crystallization was performed at RT. No new phosphate form was obtained. Phosphate Form A dissociated in MEK which might be caused by adsorption of moisture during evaporation. The results are presented in Table 51.

TABLE 51

| Results of Polymer Induced Crystallization | | |
|---|---|---|
| Solvent | Polymer | Result |
| MEK | EC (Ethyl cellulose) | Phosphate Form A |
| | PAA Poly(acrylic acid) | Phosphate Form A |
| | PEG4000 | Phosphate Form A + Free Base Form F |

TABLE 51-continued

| Results of Polymer Induced Crystallization | | |
| --- | --- | --- |
| Solvent | Polymer | Result |
| | PVP-K30 (Polyvinyl pyrrolidone) | Phosphate Form A + Free Base Form F |
| THF | EC | Phosphate Form A |
| | PAA Poly | Phosphate Form A |
| | PEG4000 | Phosphate Form A |
| | PVP-K30 | Phosphate Form 1A |

Example 68

Slurry of Phosphate Form A in Different Water Content

Phosphate Form A was suspended in acetone with different water content. The suspension was stirred at RT for hours. The solid was isolated and analyzed. Phosphate Form A remained unchanged when water content was <3.5% wt. Phosphate dissociated when water content is >, 4% wt. in acetone at RT. The results are summarized in Table 52.

TABLE 52

| Results of Slurry of Phosphate Form A in Different Water Content | |
| --- | --- |
| Water Content (wt. %) | Result |
| 3 | Phosphate Form A |
| 3.5 | Phosphate Form A |
| 4 | Phosphate Form A + Free Base Form E |
| 4.5 | Phosphate Form A + Free Base Form E |
| 5 | Phosphate Form A + Free Base Form E |
| 5.5 | Phosphate Form A + Free Base Form E |
| 6 | Phosphate Form A + Free Base Form E |

Example 69

Mechanical Treatment

Phosphate Form A was ground manually for 5 mins and the sample was tested by XRPD. The crystal form was unchanged after grinding.

Figure 72:
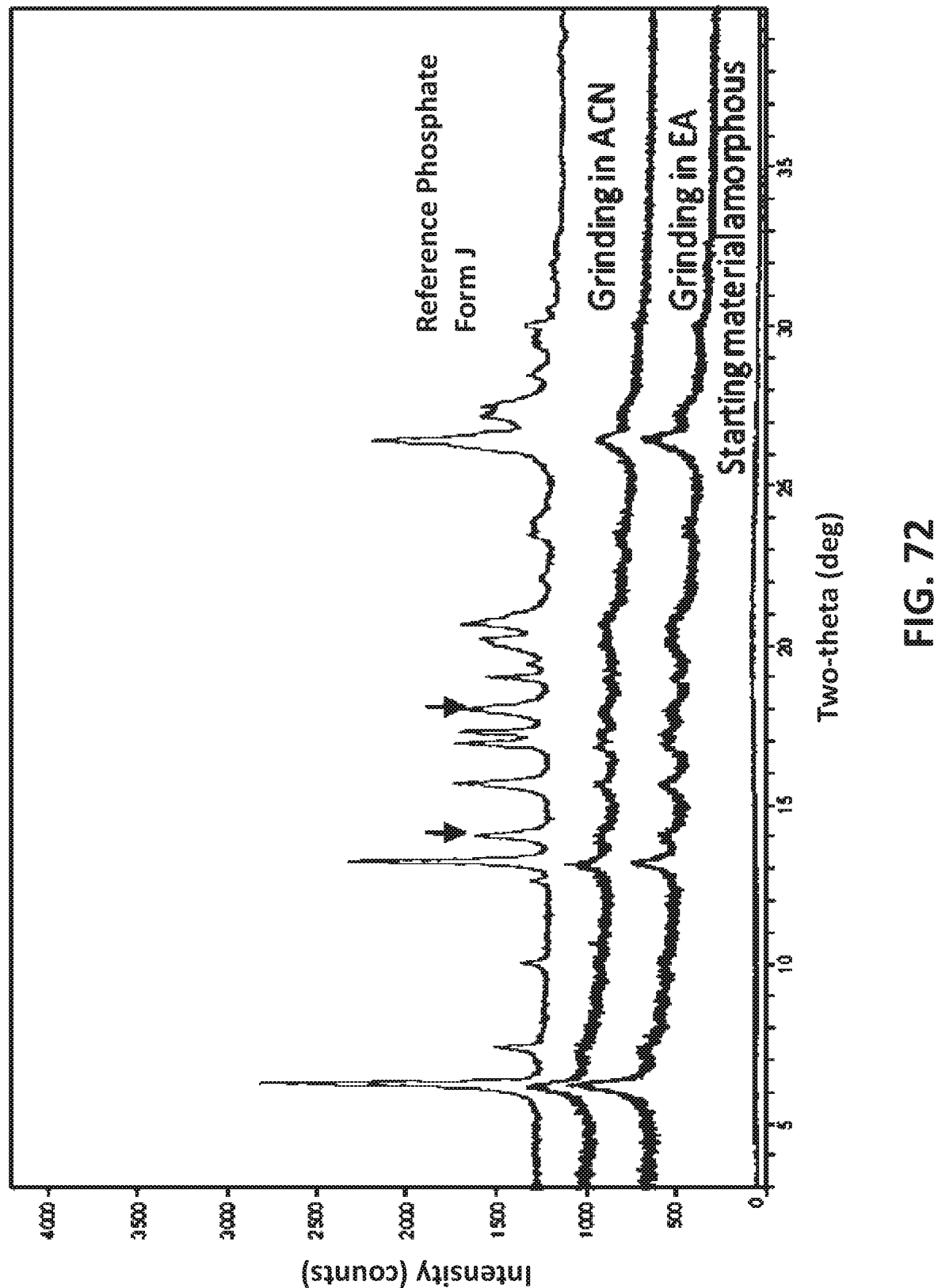
FIG. 72 illustrates the XRPD of converting the amorphous salt of 2',6-difluoro-5'-[3-(1-hydroxy-1-methylethyl)-imidazo[1,2-b][1,2,4]triazin-7-yl]biphenyl-2-carbonitrile with phosphoric acid to Phosphate Form J through mechanical grinding and fast evaporation of solvent.

Amorphous salt of 2',6-difluoro-5'-[3-(1-hydroxy-1-methylethyl)-imidazo[1,2-b][1,2,4]triazin-7-yl]biphenyl-2-carbonitrile with phosphoric acid was prepared by fast evaporation and ground manually for mins with a small amount of solvent, the resulting XPRD can be seen in FIG. 72. Phosphate Form J (low crystallinity) was obtained by grinding of amorphous sample with a small amount of ACN and EA, separately.

Example 70

Thermal Treatment

Amorphous salt of 2',6-difluoro-5'-[3-(1-hydroxy-1-methylethyl)-imidazo[1,2-b][1,2,4]triazin-7-yl]biphenyl-2-carbonitrile with phosphoric acid was prepared by fast evaporation for thermal treatment. The amorphous salt of 2',6-difluoro-5'-[3-(1-hydroxy-1-methylethyl)-imidazo[1,2-b][1,2,4]triazin-7-yl]biphenyl-2-carbonitrile with phosphoric acid sample was heated to 160° C. by DSC. No obvious glass transition was observed, and a recrystallization peak was observed at ~120° C. The sample was analyzed and revealed Phosphate Form A was obtained. Therefore, amorphous salt of 2',6-difluoro-5'-[3-(1-hydroxy-1-methylethyl)-imidazo[1,2-b][1,2,4]triazin-7-yl]biphenyl-2-carbonitrile with phosphoric acid crystallized to Phosphate Form A after thermal treatment.

Example 71

Phosphate salt of TPA023B was dissolved in THF and subsequently evaporated by rotary evaporator resulted in an amorphous salt of TPA023B with phosphoric acid. The amorphous salt was recrystallized at room temperature in a desiccator resulting in Phosphate Form J.

Figures 53C, 53D:
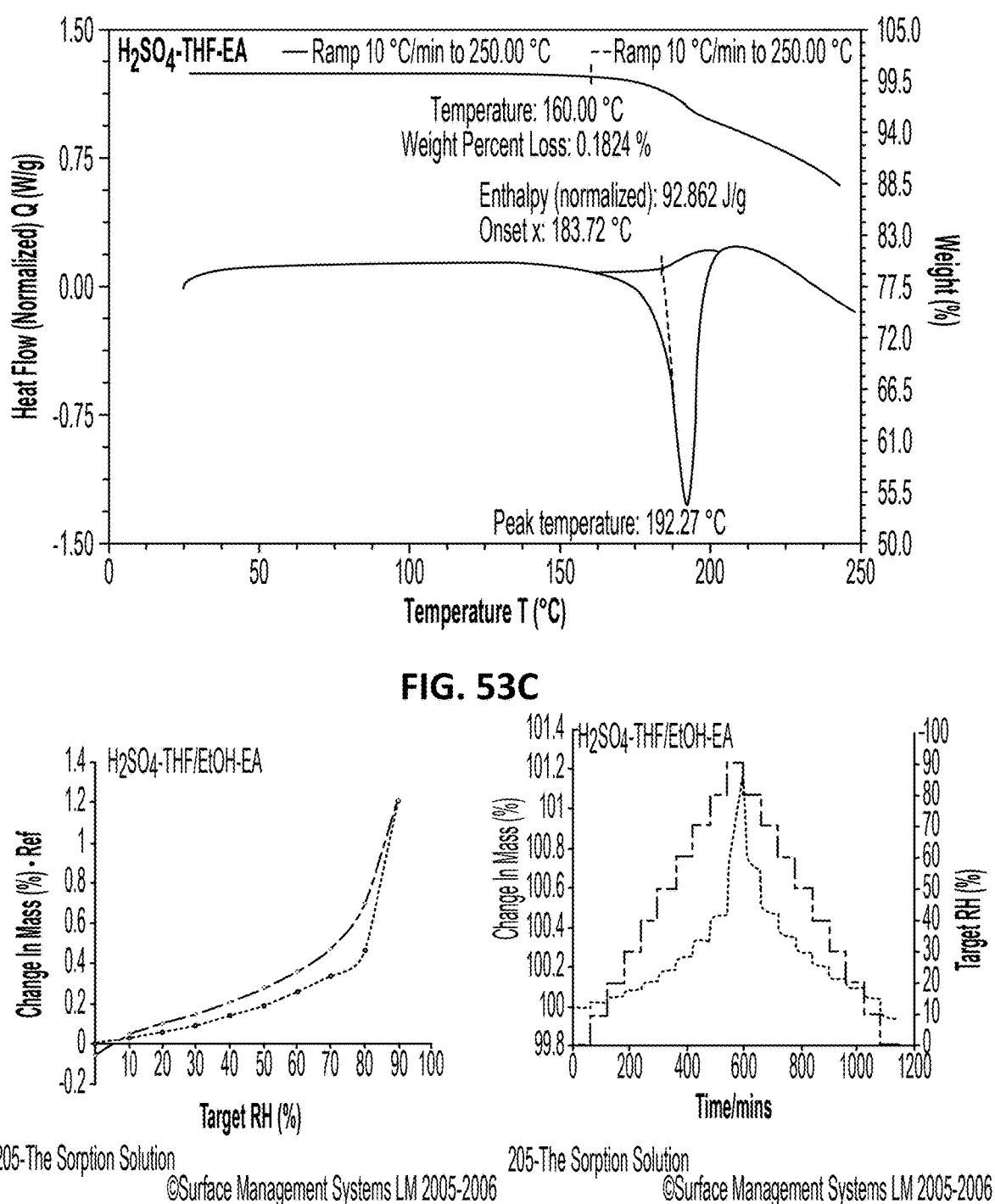
Figure 61:
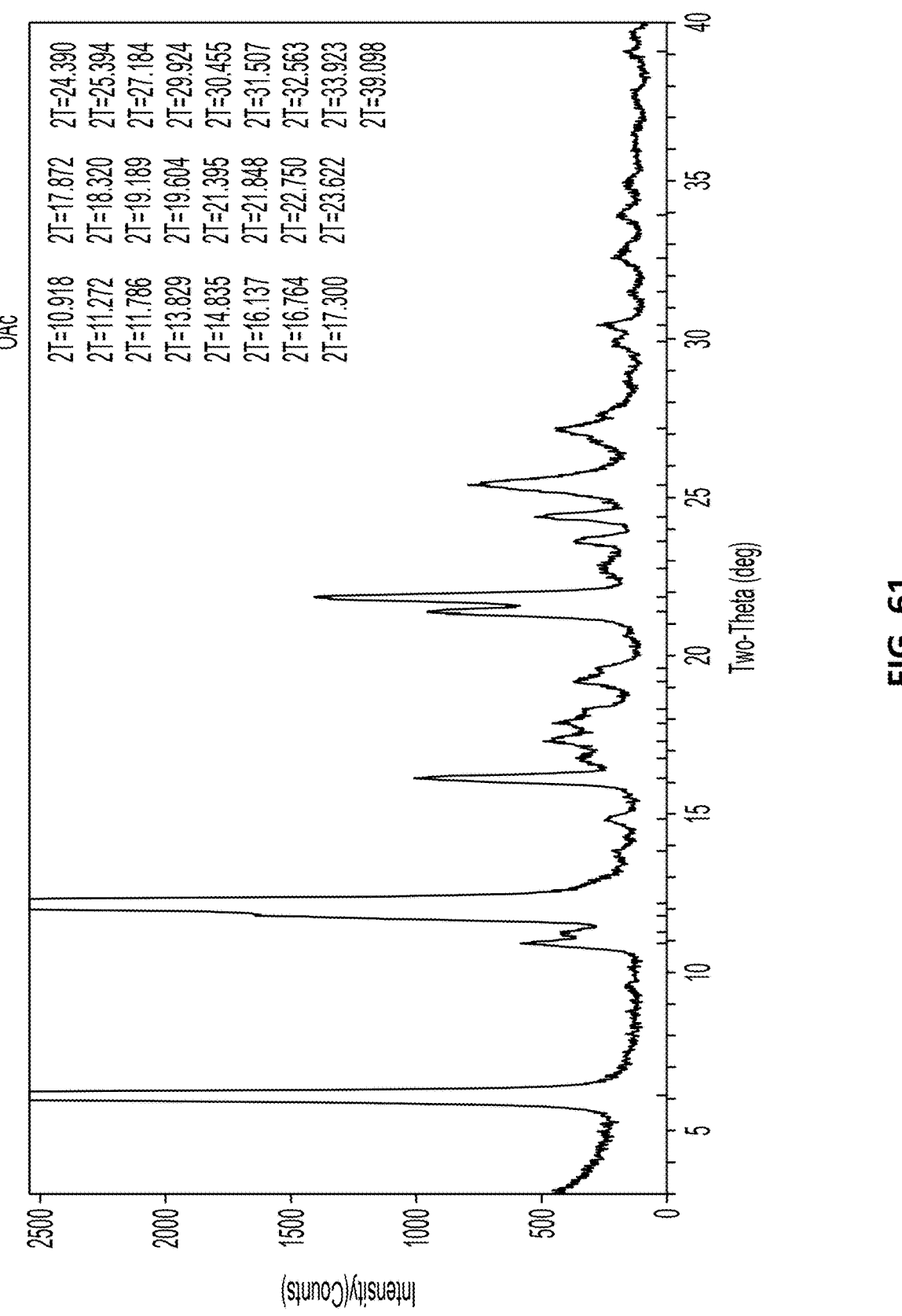
FIG. 61 illustrates an annotated XRPD pattern of TPA023B sulfate Form A

What is claimed is:

1. A crystalline form of 2',6-difluoro-5'-[3-(1-hydroxy-1-methylethyl)-imidazo [1,2-b][1,2,4]triazin-7-yl]biphenyl-2-carbonitrile with sulfuric acid, wherein the crystalline form has at least one of the following properties:
   (a) an X-ray powder diffraction (XRPD) pattern the same as shown in FIG. 61, when measured using X-Ray wavelength of Cu: K-Alpha;
   (b) an XRPD pattern having at least three characteristic peak locations, in terms of 2-Theta, selected from 6.1±0.2 degrees, 10.9±0.2 degrees, 11.3±0.2 degrees, 11.8±0.2 degrees, 12.2±0.2 degrees, 13.8±0.2 degrees, 14.8±0.2 degrees, 16.1±0.2 degrees, 16.8±0.2 degrees, 17.3±0.2 degrees, 17.9±0.2 degrees, 18.3±0.2 degrees, 19.2±0.2 degrees, 19.6±0.2 degrees, 21.4±0.2 degrees, 21.8±0.2 degrees, 22.8±0.2 degrees, 23.6±0.2 degrees, 24.4±0.2 degrees, 25.4±0.2 degrees, 27.2±0.2 degrees, 29.9±0.2 degrees, 30.5±0.2 degrees, 31.5±0.2 degrees, 32.6±0.2 degrees, 33.9±0.2 degrees, or 39.1±0.2 degrees when measured using X-Ray wavelength of Cu: K-Alpha;
   (c) a differential scanning calorimetry (DSC) thermogram the same as shown in FIG. 53C;
   (d) a DSC thermogram with an endothermic peak at about 192° C.;
   (e) stable for at least 3 days at about 40° C.; or
   (f) stable for at least 3 days at about 60° C.

2. The crystalline form of claim 1, wherein the crystalline form provides an XRPD pattern having at least three characteristic peak locations, in terms of 2-Theta, selected from 6.1±0.2 degrees, 12.2±0.2 degrees, 16.1±0.2 degrees, 21.8±0.2 degrees, 24.4±0.2 degrees, or 25.4±0.2 degrees, when measured using X-Ray wavelength of Cu: K-Alpha.

3. The crystalline form of claim 1, wherein the crystalline form provides an XRPD pattern having characteristic peak locations, in terms of 2-Theta, of 6.1±0.2 degrees, 12.2±0.2 degrees, and 21.8±0.2 degrees when measured X-Ray wavelength of Cu: K-Alpha.

4. The crystalline form of claim 1, wherein the crystalline form is a salt or a co-crystal.

Figure 52F:
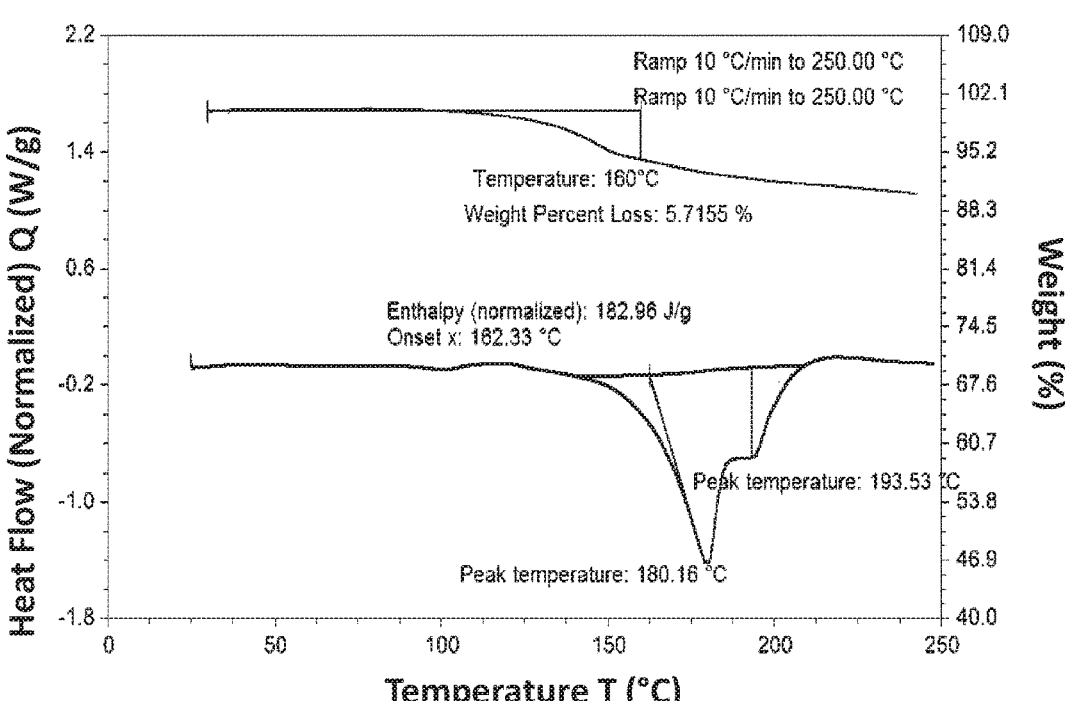
Figure 52G:
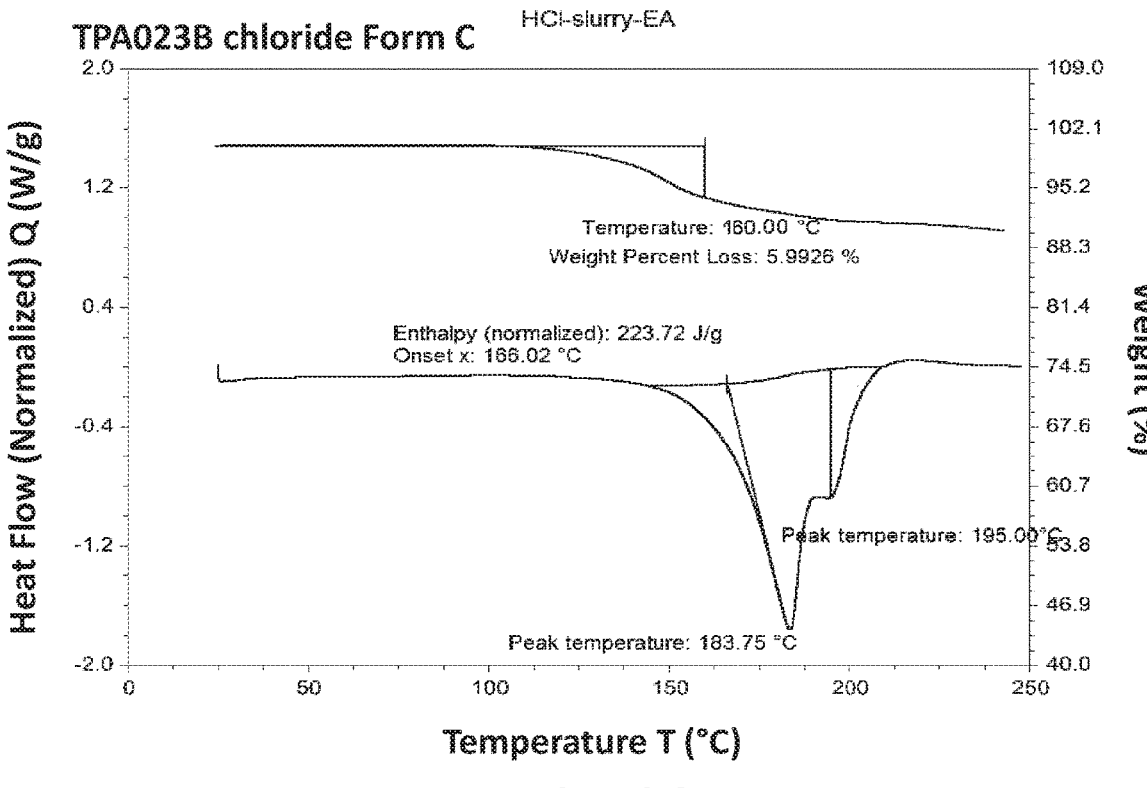
Figure 52H:
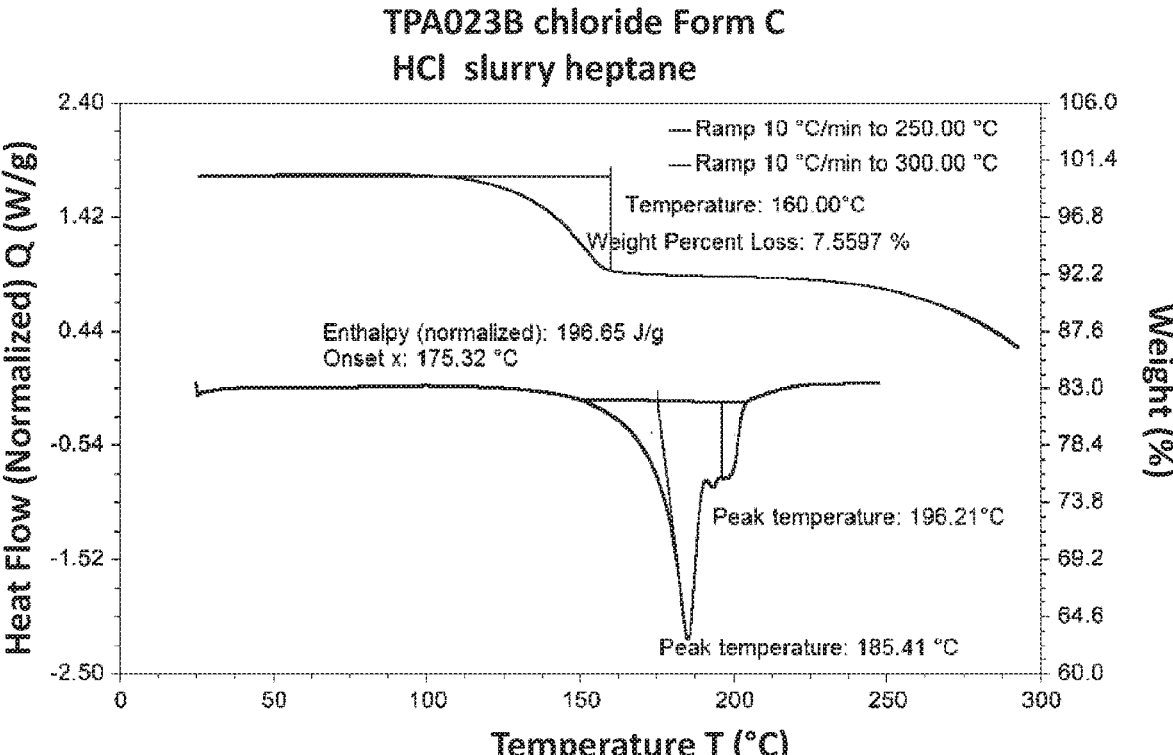
Figure 52I:
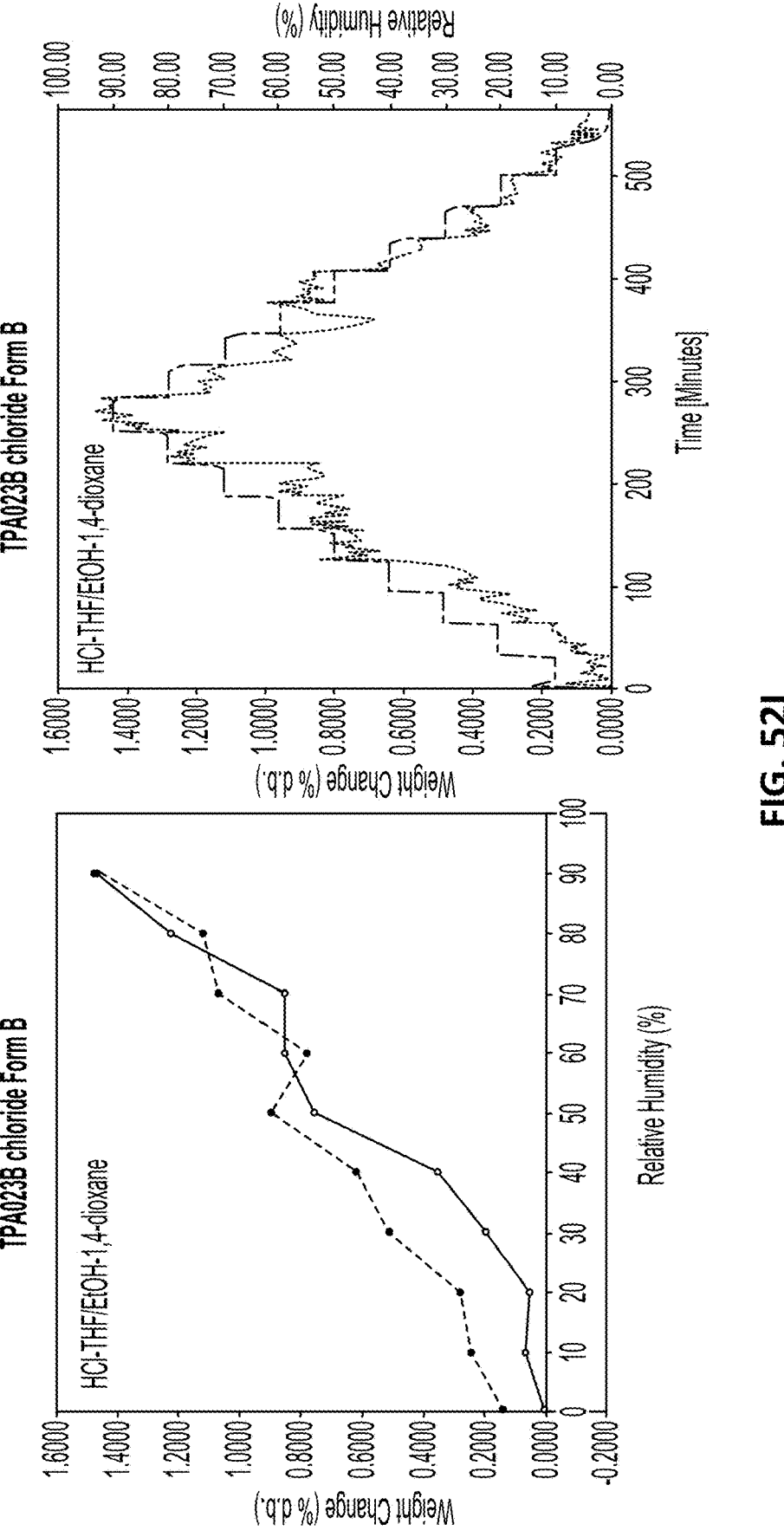
Figure 57A:
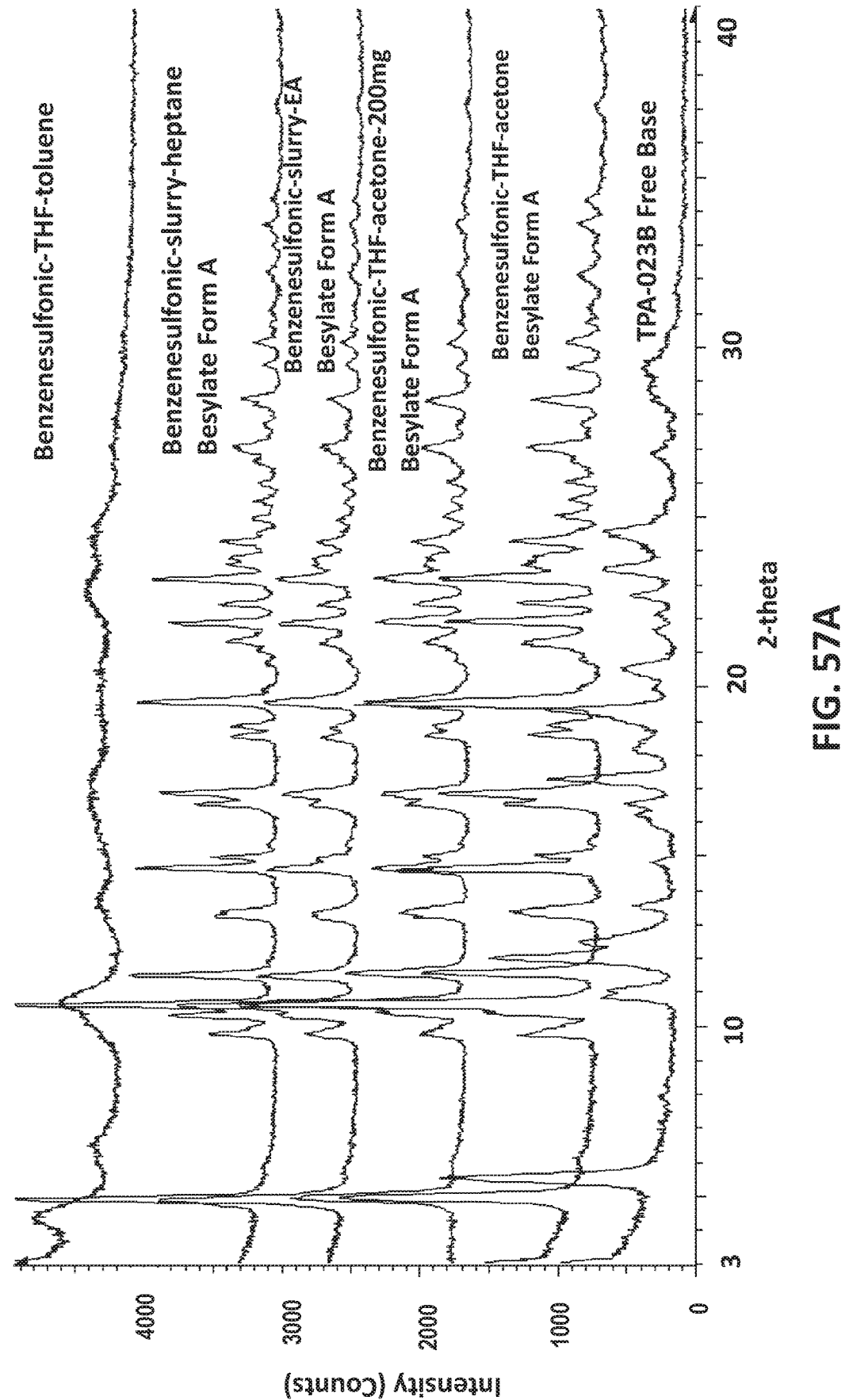
FIG. 57A-FIG. 57G illustrate the XRPD patterns (FIG. 57A), the XRPD patterns of TPA023B Besylate after performance of DVS testing (FIG. 57B), the NMR spectra (FIG. 57C), the DSC/TGA thermogram (FIG. 57D-FIG. F), and DVS profiles of TPA023B Besylate (FIG. 57G).
Figures 57B, 57C:
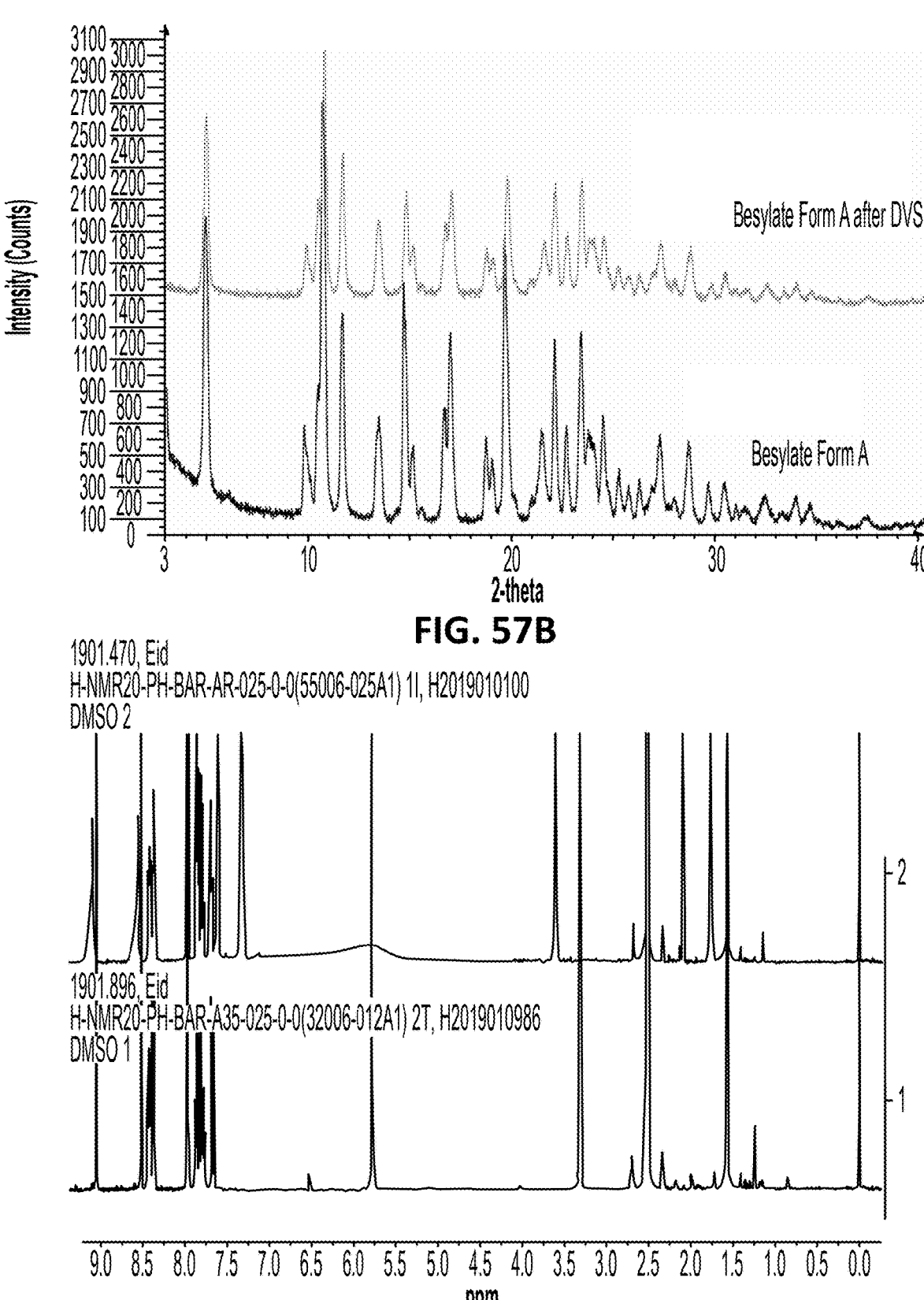
Figure 57B:
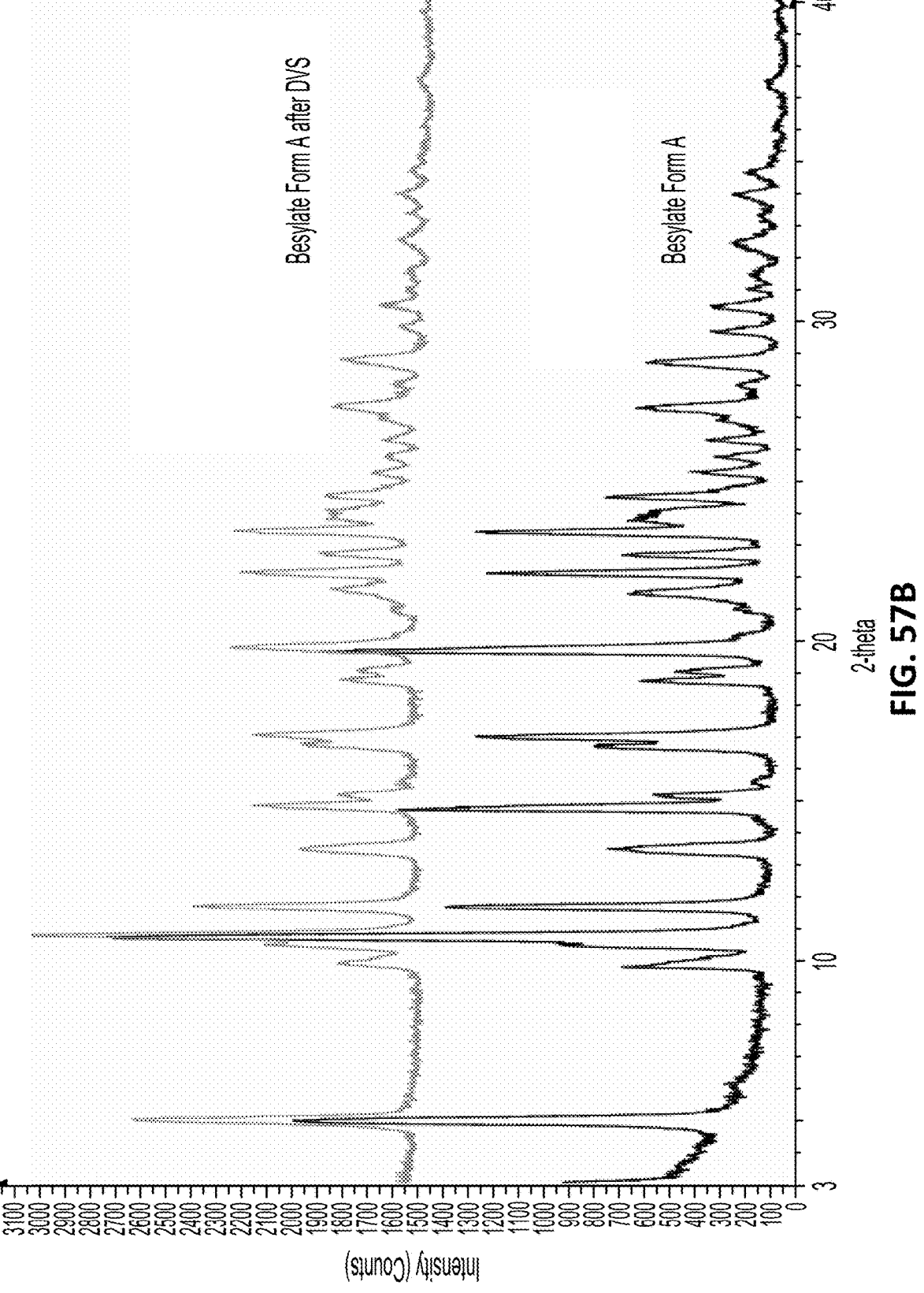
Figures 57D, 57E:
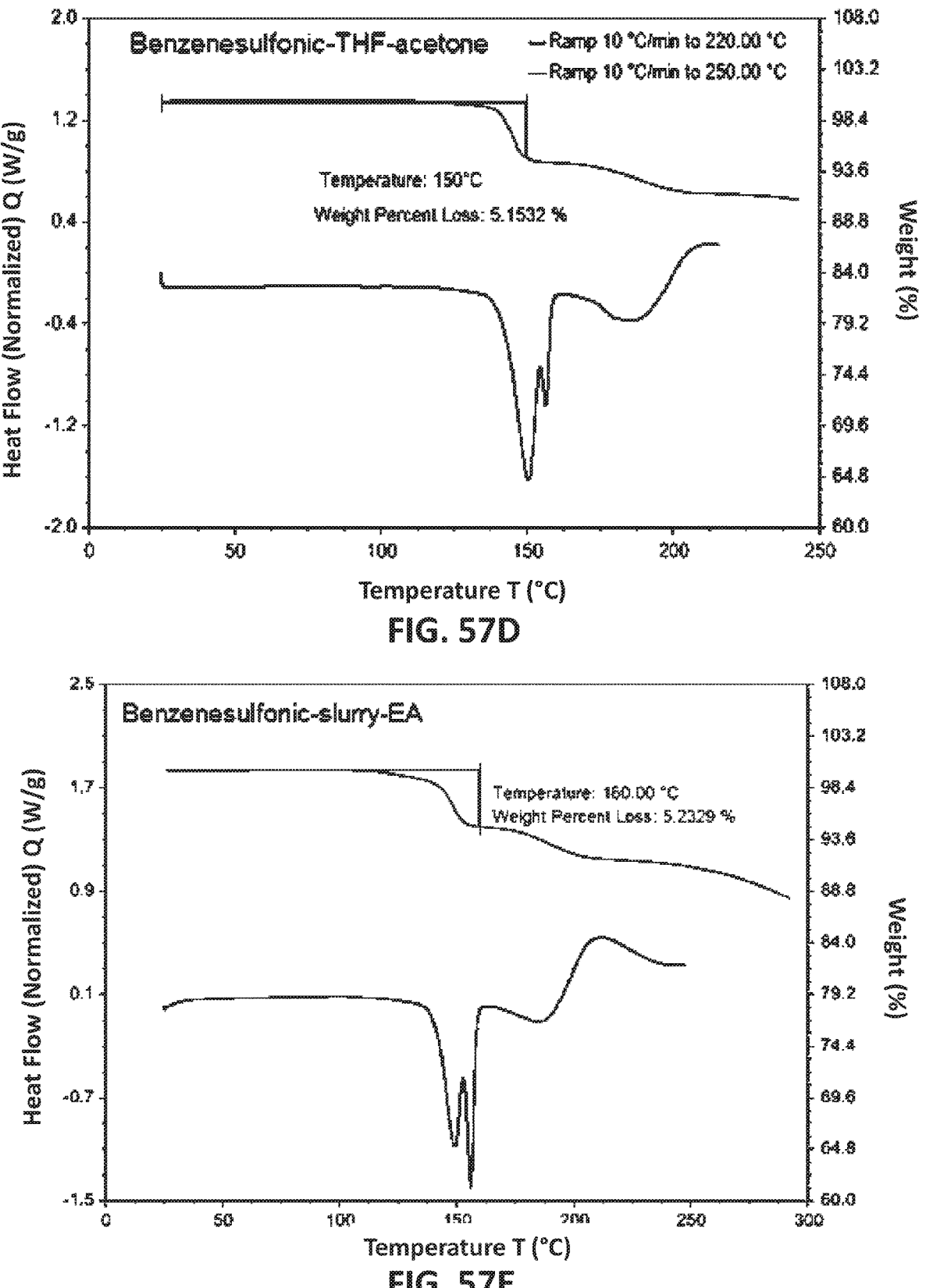
Figure 57F:
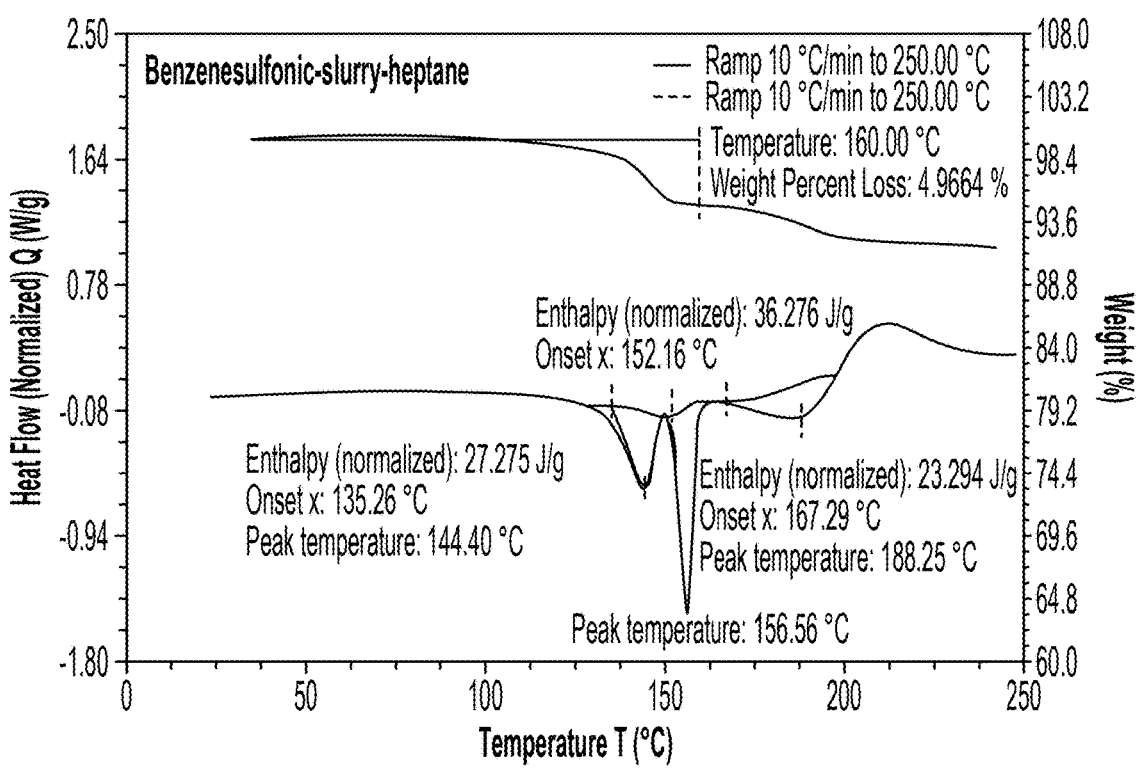
Figure 57G:
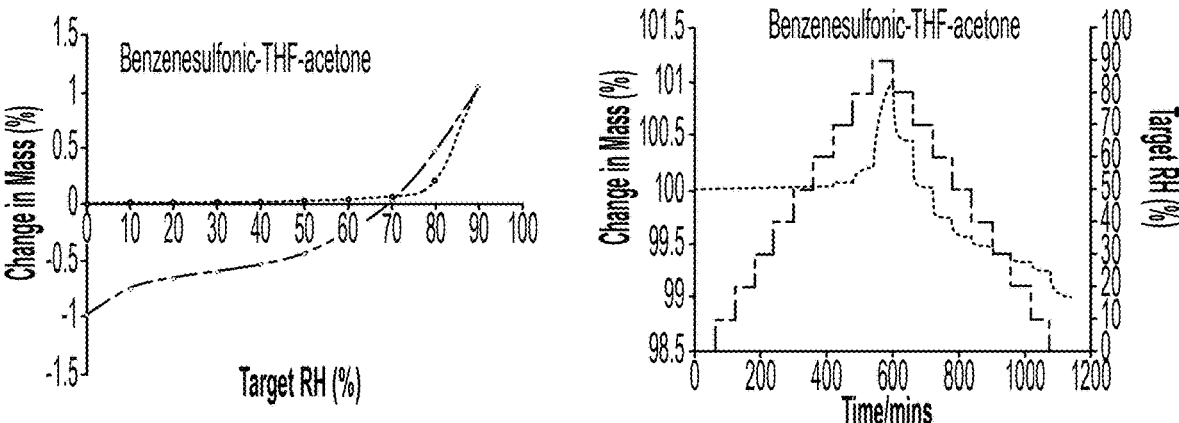
Figure 57G:
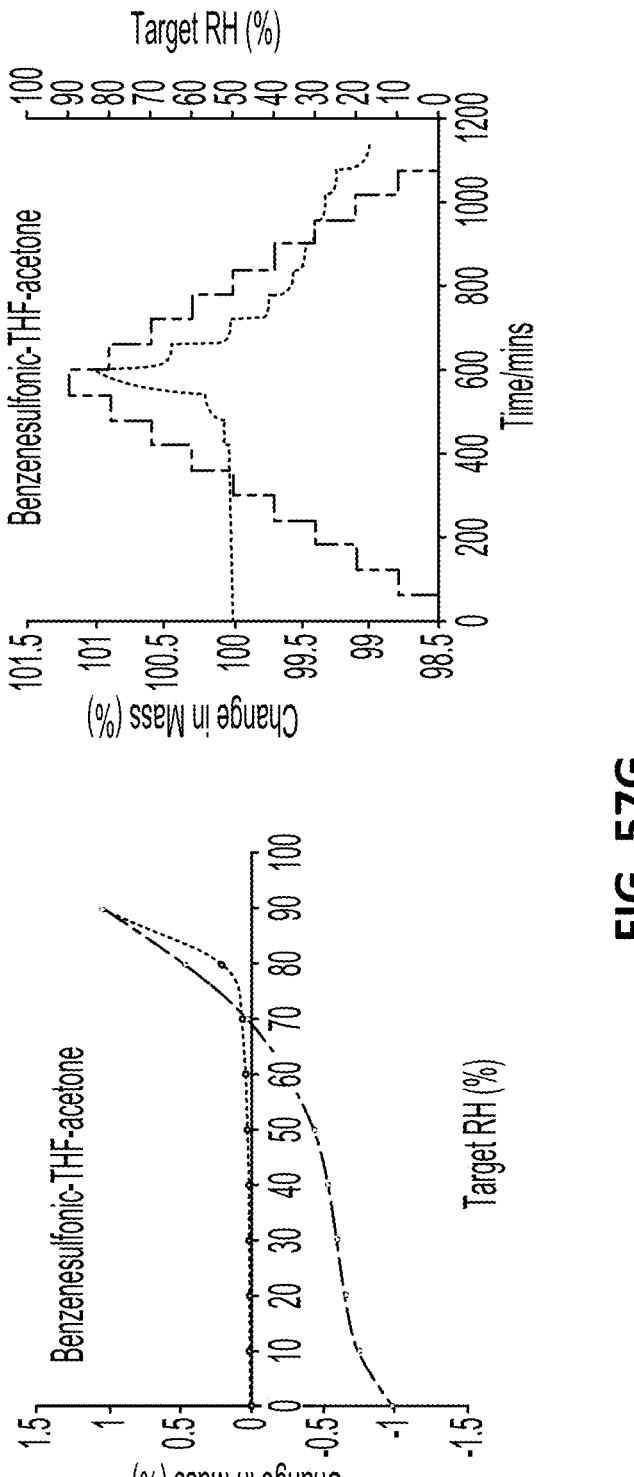
Figure 62:
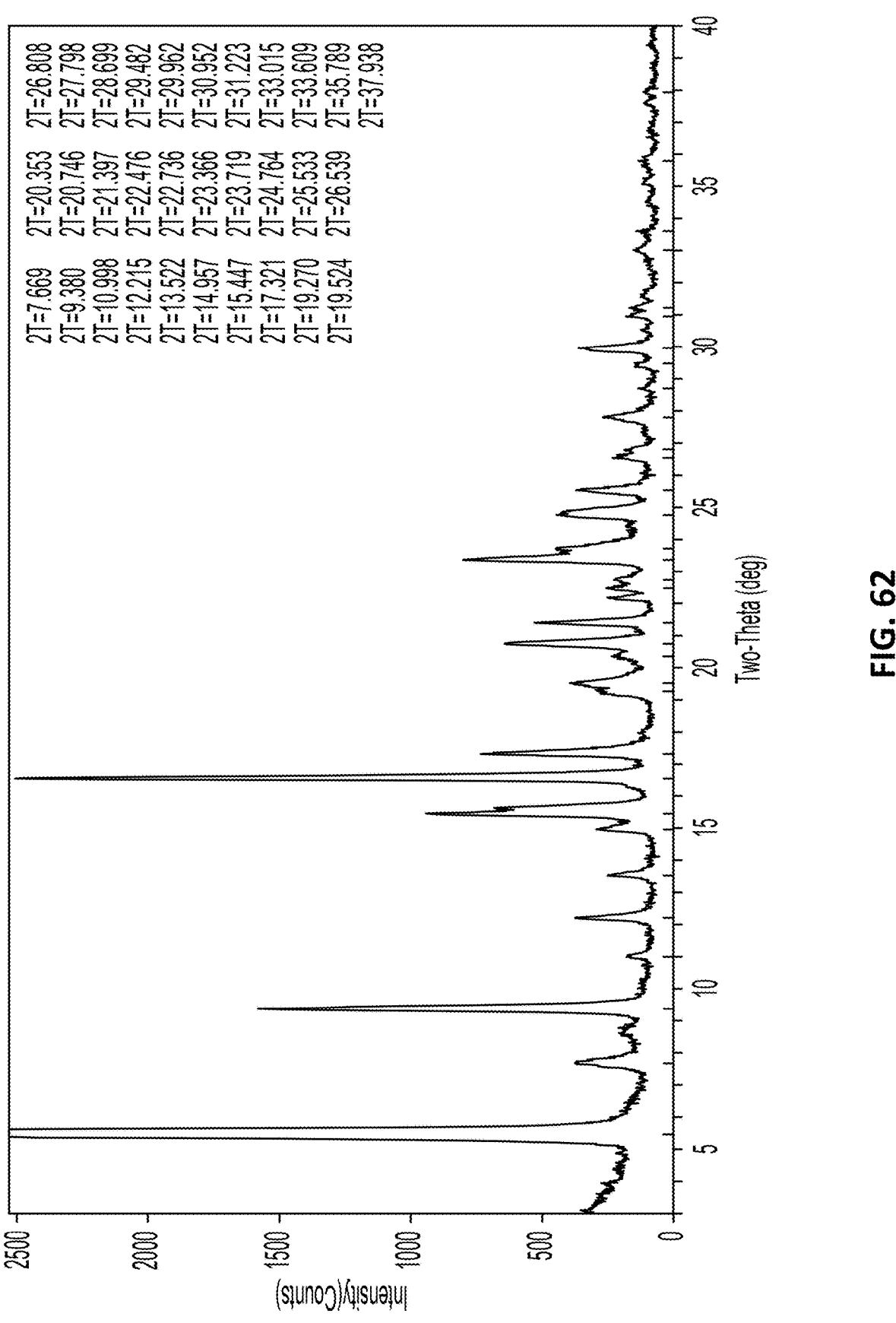
FIG. 62 illustrates an annotated XRPD pattern of TPA023B chloride Form B
Figure 63:
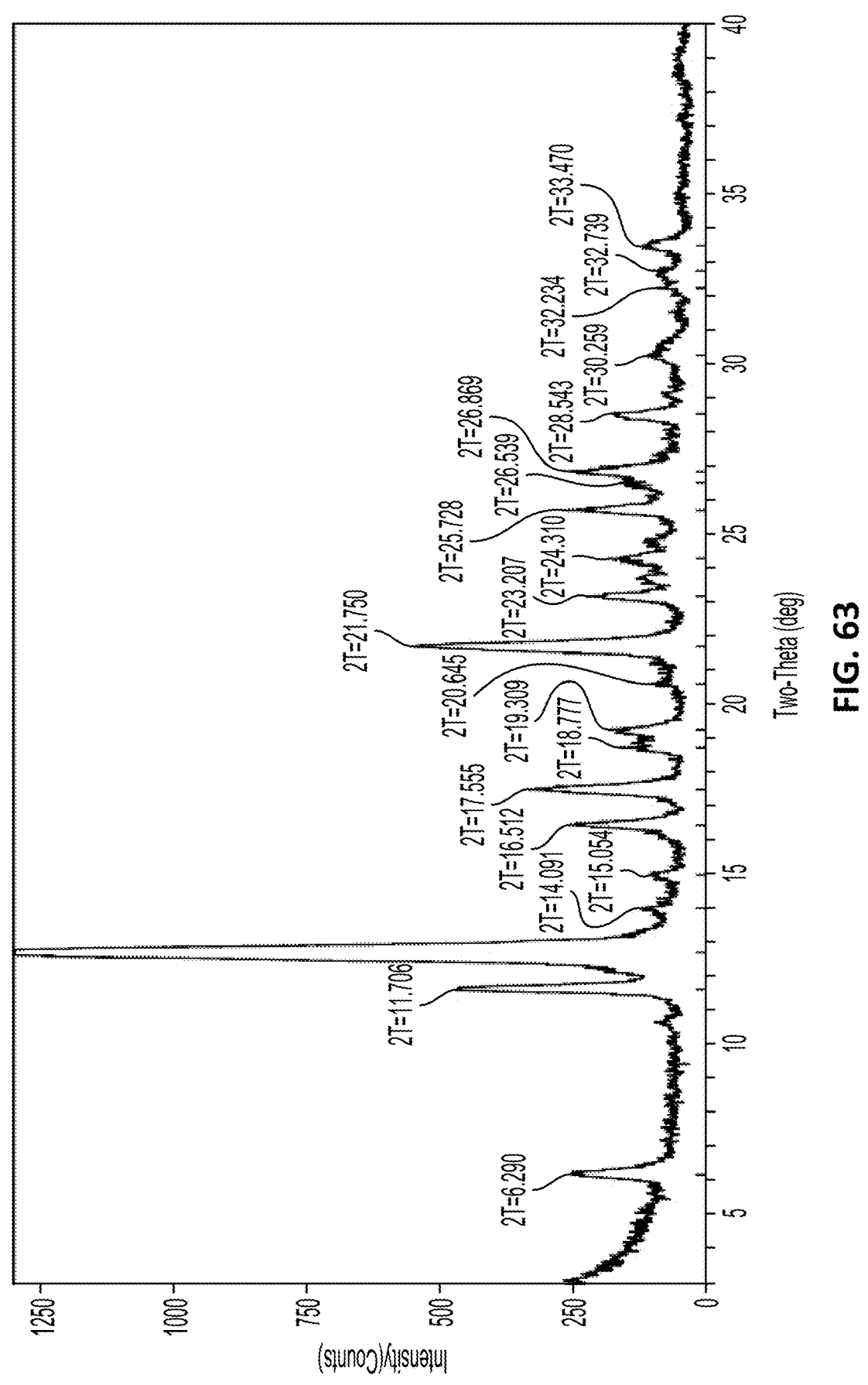
FIG. 63 illustrates an annotated XRPD pattern of TPA023B chloride Form C

5. A crystalline form of 2',6-difluoro-5'-[3-(1-hydroxy-1-methylethyl)-imidazo [1,2-b][1,2,4]triazin-7-yl]biphenyl-2-carbonitrile selected from:
   (i) a salt with hydrochloric acid, wherein the crystalline form has at least one of the following properties:
      (a) an X-ray powder diffraction (XRPD) pattern the same as shown in FIG. 63, when measured using X-Ray wavelength of Cu: K-Alpha;
      (b) an XRPD pattern having at least three characteristic peak locations, in terms of 2-Theta, selected from 6.3 ±0.2 degrees, 11.7±0.2 degrees, 12.8±0.2 degrees, 14.1±0.2 degrees, 15.1±0.2 degrees, 16.5±0.2 degrees, 17.6±0.2 degrees, 18.8±0.2 degrees, 19.3±0.2 degrees, 20.6±0.2 degrees, 21.8±0.2 degrees, 23.2±0.2 degrees, 24.3±0.2 degrees, 25.7±0.2 degrees, 26.5±0.2 degrees, 26.9±0.2 degrees, 28.5±0.2 degrees, 30.3±0.2 degrees, 32.2±0.2 degrees, 32.7±0.2 degrees, or 33.5±0.2 degrees, when measured using X-Ray wavelength of Cu: K-Alpha;

(c) a differential scanning calorimetry (DSC) thermo-gram substantially the same as one labelled Chloride Form C in FIG. 52F;

(d) a DSC thermogram with an endothermic peak at about 179° C.;

(e) the same XRPD pattern post-storage at 40° C. and 75% RH for at least 3 days; and (f) the same XRPD pattern post-storage at 60° C. and 75% RH for at least 3 days;

(ii) a chloride salt, which provides the same XRPD pattern as shown in FIG. 62; or (iii) a besylate salt, which provides the same XRPD pattern as an XRPD pattern labelled Besylate Form A shown in FIG. 57A.

6. The crystalline form of claim 5, wherein the crystalline form provides an XRPD pattern having at least three char-acteristic peak locations, in terms of 2-Theta, selected from 6.3±0.2 degrees, 11.7±0.2 degrees, 12.8±0.2 degrees, 16.5±0.2 degrees, 17.6±0.2 degrees, or 21.8±0.2 degrees when measured using X-Ray wavelength of Cu: K-Alpha.

7. The crystalline form of claim 5, wherein the crystalline form provides an XRPD pattern having characteristic peak locations, in terms of 2-Theta, of 11.7±0.2 degrees, 12.8±0.2 degrees, and 21.8±0.2 degrees when measured using X-Ray wavelength of Cu: K-Alpha.

8. A crystalline polymorph of 2',6-difluoro-5'-[3-(1-hy-droxy-1-methylethyl)-imidazo[1,2-b][1,2,4]triazin-7-yl]bi-phenyl-2-carbonitrile, wherein the crystalline polymorph, which is Form E, provides an XRPD pattern having char-acteristic peak locations, in terms of 2-Theta, of 7.5±0.2 degrees, 9.6±0.2 degrees, and 10.3±0.2 degrees when mea-sured using X-Ray wavelength of Cu: K-Alpha.

9. A crystalline polymorph of 2',6-difluoro-5'-[3-(1-hy-droxy-1-methylethyl)-imidazo[1,2-b][1,2,4]triazin-7-yl]bi-phenyl-2-carbonitrile, wherein the crystalline polymorph, which is Form F, provides an XRPD pattern having char-acteristic peak locations, in terms of 2-Theta, of 7.7±0.2 degrees, 8.1±0.2 degrees, and 13.1±0.2 degrees when mea-sured using X-Ray wavelength of Cu: K-Alpha.

10. A crystalline polymorph of 2',6-difluoro-5'-[3-(1-hy-droxy-1-methylethyl)-imidazo[1,2-b][1,2,4]triazin-7-yl]bi-phenyl-2-carbonitrile, wherein the crystalline polymorph, which is Form G, provides an XRPD pattern having char-acteristic peak locations, in terms of 2-Theta, of 6.3±0.2 degrees, 8.0±0.2 degrees, and 13.3±0.2 degrees when mea-sured using X-Ray wavelength of Cu: K-Alpha.

11. A crystalline polymorph of 2',6-difluoro-5'-[3-(1-hy-droxy-1-methylethyl)-imidazo[1,2-b][1,2,4]triazin-7-yl]bi-phenyl-2-carbonitrile, wherein the crystalline form, which is Form H, provides an XRPD pattern having characteristic peak locations, in terms of 2-Theta, of 7.9±0.2 degrees, 12.7 ±0.2 degrees, and 14.0±0.2 degrees when measured using X-Ray wavelength of Cu: K-Alpha.

12. A crystalline form of 2',6-difluoro-5'-[3-(1-hydroxy-1-methylethyl)-imidazo [1,2-b][1,2,4]triazin-7-yl]biphenyl-2-carbonitrile with phosphoric acid, Form J, wherein the crystalline form has at least one of the following properties:

a) an XRPD pattern having characteristic peak locations, in terms of 2-Theta, of 6.3±0.2 degrees, 13.2±0.2 degrees, 14.0±0.2 degrees, 15.7±0.2 degrees, 17.0±0.2 degrees, 17.3±0.2 degrees, 18.0±0.2 degrees, 19.0±0.2 degrees, 20.2±0.2 degrees, 20.7±0.2 degrees, and 26.4±0.2 degrees when measured using X-Ray wave-length of Cu: K-Alpha;

b) a DSC thermogram with an endothermic peak at about 200° C.; or c) a DSC thermogram with an endothermic peak having an onset temperature at about 197° C.

13. The crystalline form of claim 12, wherein the crys-talline form provides an XRPD pattern having characteristic peak locations, in terms of 2-Theta, of 6.3±0.2 degrees, 7.4±0.2 degrees, 10.1 ±0.2 degrees, 12.6±0.2 degrees, 13.2±0.2 degrees, 14.0±0.2 degrees, 15.7±0.2 degrees, 17.0±0.2 degrees, 17.3±0.2 degrees, 18.0±0.2 degrees, 19.0±0.2 degrees, 20.2±0.2 degrees, 20.7±0.2 degrees, 26.4±0.2 degrees, 27.2±0.2 degrees, and 27.5±0.2 degrees, when measured using X-Ray wavelength of Cu: K-Alpha.

14. The crystalline form of claim 12, wherein the crys-talline form is a salt or a co-crystal.

15. A therapeutic or prophylactic composition comprising the compound of claim 1.

16. A method of treating a condition or a disorder asso-ciated with GABA receptors in a subject in need thereof, the method comprising administering a therapeutically effective amount of the compound of claim 1 to said subject.

17. The method of claim 16, wherein the condition or disorder is associated with a2/a3 GABAA receptor.

18. The method of claim 16, wherein the condition or disorder is selected from: pain, anxiety, epilepsies, muscle spasms, pruritus, itch, cognitive impairment, alcohol depen-dence, drug addiction, schizophrenia, depression, autism, panic disorder, or generalized anxiety disorder.

19. A method of administering a compound to a subject, wherein the compound is the compound of claim 1.

\* \* \* \* \*